(12) United States Patent
Kellar et al.

(10) Patent No.: US 12,173,167 B2
(45) Date of Patent: Dec. 24, 2024

(54) STABLE INOCULANT COMPOSITIONS AND METHODS FOR PRODUCING SAME

(71) Applicant: NOVOZYMES BIOAG A/S, Bagsvaerd (DK)

(72) Inventors: Kenneth Edmund Kellar, Fuquay-Varina, NC (US); Yaowei Kang, Durham, NC (US); Claire Pelligra, Raleigh, NC (US); Emily Barnett, Bedford, VA (US); Caitlin Burklew, Salem, VA (US); Anna Wysinski, Roanoke, VA (US); Jarrod E. Leland, Blacksburg, VA (US); Ben Doughan, Salem, VA (US); Michael Harrison Fethe, Raleigh, NC (US); Ashley Delanie Trahan, Hillsborough, NC (US); David Greenshields, Saskatchewan (CA); Kristi Woods, Blacksburg, VA (US)

(73) Assignee: NOVOZYMES BIOAG A/S, Bagsvaerd (DK)

( * ) Notice: Subject to any disclaimer, the term of this patent is extended or adjusted under 35 U.S.C. 154(b) by 0 days.

(21) Appl. No.: 17/830,445

(22) Filed: Jun. 2, 2022

(65) Prior Publication Data
US 2022/0380620 A1 Dec. 1, 2022

Related U.S. Application Data

(63) Continuation of application No. 15/758,828, filed as application No. PCT/US2016/050529 on Sep. 7, 2016, now Pat. No. 11,472,981.

(60) Provisional application No. 62/343,250, filed on May 31, 2016, provisional application No. 62/296,766, filed on Feb. 18, 2016, provisional application No. 62/273,054, filed on Dec. 30, 2015, provisional application No. 62/217,250, filed on Sep. 11, 2015.

(51) Int. Cl.
| C09D 105/00 | (2006.01) |
| A01C 1/06 | (2006.01) |
| A01N 25/10 | (2006.01) |
| A01N 25/14 | (2006.01) |
| A01N 25/26 | (2006.01) |
| A01N 43/16 | (2006.01) |
| A01N 63/20 | (2020.01) |
| A01N 63/36 | (2020.01) |
| C09D 105/02 | (2006.01) |
| C12N 1/00 | (2006.01) |
| C12N 1/04 | (2006.01) |

(52) U.S. Cl.
CPC ............ *C09D 105/00* (2013.01); *A01C 1/06* (2013.01); *A01N 25/10* (2013.01); *A01N 25/14* (2013.01); *A01N 25/26* (2013.01); *A01N 43/16* (2013.01); *A01N 63/20* (2020.01); *A01N 63/36* (2020.01); *C09D 105/02* (2013.01); *C12N 1/00* (2013.01); *C12N 1/04* (2013.01)

(58) Field of Classification Search
None
See application file for complete search history.

(56) References Cited

U.S. PATENT DOCUMENTS

| 5,104,437 | A | ‡ | 4/1992 | Hadwiger | A01N 43/16 47/57.6 |
| 5,358,863 | A | ‡ | 10/1994 | Quimby, Jr. | A01N 63/30 435/177 |
| 5,484,464 | A | ‡ | 1/1996 | Gleddie | A01C 1/06 435/252.4 |
| 5,527,760 | A | ‡ | 6/1996 | Rensing | B01J 2/006 47/57.6 |
| 5,586,411 | A | ‡ | 12/1996 | Gleddie | A01C 1/06 435/252.4 |
| 5,695,541 | A | ‡ | 12/1997 | Kosanke | A01N 63/20 71/7 |
| 5,804,208 | A | ‡ | 9/1998 | Andersch | A01N 63/30 424/407 |
| 5,916,029 | A | ‡ | 6/1999 | Smith | A01C 1/06 435/252.4 |
| 5,928,469 | A | ‡ | 7/1999 | Franks | C12N 11/02 159/48.1 |
| 6,426,210 | B1 | ‡ | 7/2002 | Franks | C12N 9/96 424/93.4 |
| 6,569,425 | B2 | ‡ | 5/2003 | Drahos | A01N 63/22 435/252.4 |

(Continued)

FOREIGN PATENT DOCUMENTS

| CN | 102433287 A | ‡ | 2/2012 |
| CN | 103421693 A | ‡ | 4/2013 |

(Continued)

OTHER PUBLICATIONS

Lal et al.(Development of a fast-dissolving tablet formulation of a live attenuated enterotoxigenic *E. coli* vaccine candidate(Vaccine 31, 2013, pp. 4759-4764). (Year: 2013).*

(Continued)

*Primary Examiner* — Alton N Pryor
(74) *Attorney, Agent, or Firm* — Adam Rucker

(57) ABSTRACT

The present disclosure provides stable inoculant compositions and methods for enhancing the survival and/or stability of microorganisms in an inoculant composition. In some embodiments, the microorganisms in an inoculant compositions are stabilized by the presence of one or more maltodextrins having a dextrose equivalent value of about 15 to about 20.

20 Claims, 20 Drawing Sheets

(56) References Cited

U.S. PATENT DOCUMENTS

| | | | | |
|---|---|---|---|---|
| 6,808,917 B1 ‡ | 10/2004 | Johnson | ............... | A01C 1/06 435/252.4 |
| 6,824,772 B2 ‡ | 11/2004 | Drahos | ............... | A01N 63/22 424/93.46 |
| 7,037,708 B1 ‡ | 5/2006 | Runge | ............... | C12N 1/04 424/93.4 |
| 7,037,709 B2 ‡ | 5/2006 | Blumenfeld | ......... | C12N 9/0073 435/189 |
| 7,429,477 B2 ‡ | 9/2008 | Johnson | ............... | A01N 63/30 435/252.4 |
| 8,011,132 B2 ‡ | 9/2011 | Pearce | ............... | A01C 1/06 47/57.6 |
| 8,148,138 B2 ‡ | 4/2012 | Johnson | ............... | A01N 63/30 435/252.4 |
| 8,278,247 B2 ‡ | 10/2012 | Hnatowich | ............ | A01N 63/36 504/117 |
| 8,445,256 B2 ‡ | 5/2013 | Woods | ............... | C05F 11/08 504/117 |
| 8,883,679 B2 ‡ | 11/2014 | Woods | ............... | C05G 5/20 504/117 |
| 8,921,089 B2 ‡ | 12/2014 | Kang | ............... | A01H 3/00 435/252.1 |
| 8,940,510 B2 ‡ | 1/2015 | Subramanian | ....... | C12N 9/0006 435/254.2 |
| 8,999,698 B2 ‡ | 4/2015 | Kang | ............... | C12N 1/205 504/117 |
| 9,017,442 B2 ‡ | 4/2015 | Johnson | ............... | C12N 1/20 71/7 |
| 9,055,746 B2 ‡ | 6/2015 | Smith | ............... | C05F 11/00 |
| 9,090,884 B2 ‡ | 7/2015 | Harman | ............... | C12N 1/14 |
| 9,101,088 B2 ‡ | 8/2015 | Hnatowich | ............ | A01N 63/30 |
| 9,102,893 B2 ‡ | 8/2015 | Custis | ............... | C10M 113/02 |
| 9,234,251 B2 ‡ | 1/2016 | Snyder | ............... | A01N 63/22 |
| 9,340,464 B2 ‡ | 5/2016 | Hnatowich | ............ | C05F 11/08 |
| 10,820,594 B2 ‡ | 11/2020 | Kellar | ............... | C12N 1/00 |
| 2002/0015988 A1 ‡ | 2/2002 | Enzmann | ............... | C12N 9/58 435/252.1 |
| 2003/0012819 A1 ‡ | 1/2003 | Ko | ............... | A23K 40/30 424/93.1 |
| 2003/0138936 A1 ‡ | 7/2003 | Mizuguchi | ............... | C12N 1/04 435/254.2 |
| 2004/0022860 A1 ‡ | 2/2004 | Johson | ............... | A61K 47/36 424/488 |
| 2004/0038825 A1 ‡ | 2/2004 | Leland | ............... | A01N 25/22 504/117 |
| 2006/0229203 A1 ‡ | 10/2006 | Peltonen | ............... | A01N 25/24 504/100 |
| 2007/0254353 A1 ‡ | 11/2007 | Stavnsbjerg | ............. | C12N 1/20 435/243 |
| 2008/0132411 A1 ‡ | 6/2008 | Watt | ............... | A01N 63/20 504/100 |
| 2009/0142303 A1 ‡ | 6/2009 | Edwards | ............... | A61P 43/00 424/93.4 |
| 2010/0160160 A1 ‡ | 6/2010 | Hewlett | ............... | A01C 1/06 504/100 |
| 2012/0039956 A1 ‡ | 2/2012 | Harel | ............... | A23K 20/142 426/62 |
| 2012/0135017 A1 ‡ | 5/2012 | Harel | ............... | A61K 47/38 435/235.1 |
| 2013/0061645 A1 ‡ | 3/2013 | Smith | ............... | A01C 1/06 71/23 |
| 2013/0323362 A1 ‡ | 12/2013 | Penhasi | ............... | A61K 9/5042 426/61 |
| 2014/0143909 A1 ‡ | 5/2014 | Greenshields | .......... | C05F 17/00 800/298 |
| 2015/0230478 A1 ‡ | 8/2015 | Vujanovic | ............... | A01N 25/00 504/100 |
| 2016/0298201 A1 ‡ | 10/2016 | Siepe | ............... | C07C 59/46 |

FOREIGN PATENT DOCUMENTS

| | | | |
|---|---|---|---|
| CN | 103911314 A | ‡ | 9/2014 |
| CN | 106190929 A | ‡ | 12/2016 |
| EP | 0203708 A1 | ‡ | 12/1986 |
| EP | 0906951 A2 | ‡ | 4/1999 |
| SU | 922104 | ‡ | 9/1979 |
| SU | 922104 A1 | | 4/1982 |
| UA | 40992078 A | | 10/2007 |
| WO | WO-2009/010561 A1 | ‡ | 1/2009 |
| WO | WO-2009/049747 A2 | ‡ | 4/2009 |
| WO | WO-2010/037228 A1 | ‡ | 4/2010 |
| WO | 2013/044208 A2 | | 3/2013 |
| WO | WO-2013/044214 A1 | ‡ | 3/2013 |
| WO | WO-2013/096883 A2 | ‡ | 6/2013 |
| WO | WO-2014/138490 A1 | ‡ | 9/2014 |
| WO | WO-2015/003908 A1 | ‡ | 1/2015 |
| WO | WO-2015/063090 A2 | ‡ | 5/2015 |
| WO | WO-2017/044473 A1 | ‡ | 3/2017 |
| WO | WO-2017/116837 A1 | ‡ | 7/2017 |
| WO | WO-2017/116846 A1 | ‡ | 7/2017 |
| WO | 2017131971 A1 | | 8/2017 |

OTHER PUBLICATIONS

Rong et al, 2009, J Food Sci 74(1), C33-C40.‡
A-Cunningham et al, 1990, Can J Bot 68(10), 2270-2274.‡
Diange et al, 2013, Curr Microbiol 66(6), 599-605.‡
Friesen et al, 2005, Appl Microbiol Biotechnol 68(3), 397-404.‡
Fu et al, 2011, Food Res Int 44(5), 1127-1149.‡
Anonymous, 2013, Jumpstart LCO Extended Label, Internet website.‡
Colaco et al, 1992, Biotechnology 10(9), 1007-1011.‡
Cunningham et al, 1990, Can J Bot, vol. 68, No. 10, pp. 2270-2274.‡
Schoebitz et al, 2013, Agronomy for Sustainable Development 33(4), 751-765.‡
Oldenhof et al, 2005, Biotechnol Progr 21(3), 885-892.‡
Streeter, 2003, J Appl Microbiol 95(3), 484-491.‡
Shahidi et al, 1993, Crit Rev Food Sci Nutri 33(6), 501-547.‡
Behboudi-Jobbehdar et al, 2013, Drying Technology 31(11), 1274-1283.‡
Mary et al, 1994, Soil Biol Biochem 26(9), 1125-1132.‡
Campos et al, 2014, World J Microbiol Biotechnol 30(9), 2371-2378.‡
Rinaudo, 2006, Progress in Polymer Science, vol. 31, No. 7, pp. 603-632.‡
Scarmeas et al, 2018, The lancet neurology, vol. 17, pp. 1006-1015.‡
Ibatsam et al, 2012, African journal of food, vol. 12, No. 3, pp. 1-10.‡
Hofman et al, 2016, Crit Rev Food Sci Nutri, vol. 56, No. 12, pp. 2091-2100.‡
Zhao(Ed) et al, 1988, Beijing Agricultural University Press, p. 228.‡
Zhao(Ed), 1986, Agricultural Press, pp. 497-499.‡
Zhang(Ed) et al, 2009, China Light Industry Press, pp. 291.‡
Yao et al, 2007, China traditional Chinese Medicine Press, pp. 232-234.‡
Harti et al, 2015, International journal of pharma medicine and biological sciences, vol. 4, No. 3, pp. 204-208.‡
Gaucher, 2020, 5 Benefits of Lactobacillus bacteria, pp. 1-7.‡
Hewitt et al, 2013, Food and bioproducts processing, vol. 91, pp. 362-369.‡
Haytowitz et al, 2007, USDA, pp. 280S-281S.‡
Diange et al, 2013, Curr Microbiol, vol. 66, No. 6, pp. 599-605.‡
Fu et al, 2008, China traditional Chinese Medicine Press, pp. 109-112.‡
Cruz et al, 2012, Structure and function of food engineering, vol. 2, pp. 21-42.‡
Boos et al, 1998, Microbiol Mol Biol Revs, vol. 62, No. 1, pp. 204-229.‡
Pispan, S., C. J. Hewitt, and A. G. F. Stapley. "Comparison of cell survival rates of *E. coli* K12 and *L. acidophilus* undergoing spray drying." Food and Bioproducts Processing 91.4 (2013): 362-369.‡

(56) References Cited

OTHER PUBLICATIONS

Semyonov, David, Ory Ramon, and Eyal Shimoni. "Using ultrasonic vacuum spray dryer to produce highly viable dry probiotics." LWT-Food Science and Technology 44.9 (2011): 1844-1852.‡

Kawai, Kiyoshi, et al. "Comparative investigation by two analytical approaches of enthalpy relaxation for glassy glucose, sucrose, maltose, and trehalose." Pharmaceutical research 22.3 (2005): 490-495.‡

Anonymous, 2013, Extended Label, Internet website.

Fu et al, 2008, China traditional Chinese Medicine Press, pp. 109-112 and Translation.

Fu et al, 2011, Food Res Int vol. 44, No. 5, pp. 1127-1149.

Yao et al, 2007, China traditional Chinese Medicine Press, pp. 232-234 and Translation.

Zhang(Ed) et al, 2009, China Light Industry Press, p. 291 and Translation.

Chi et al., Appl Environ Microbiol, 2005, 7271-7278, 71(11).

Behboudi-Jobbehdar; 2013, Drying technology, vol. 31, No. 11, pp. 1274-1283.

Campos; 2014, World J Microbiol Biotechnol, vol. 30, No. 9, pp. 2371-2378.

Colaco; 1992, Biotechnology, vol. 10, No. 9, pp. 1007-1011.

Cunningham; 1990, Can J Bot, vol. 68, No. 10, pp. 2270-2274.

Friesen; 2005, Appl Microbiol Biotechnol, vol. 68, No. 3, pp. 397-404.

Ibatsam; 2012, African journal of food, vol. 12, No. 3, pp. 1-10.

Kawai; 2005, Pharmaceutical research, vol. 22, No. 3, pp. 490-495.

Mary et al; 1994, Soil Biol. Biochem, vol. 26, No. 9, pp. 1125-1132.

Oldenhof; 2005, Biotechnol Progr, vol. 21, No. 3, pp. 885-892.

Pispan; 2013, Food and bioproducts processing, vol. 91, No. 4, pp. 362-369.

Rong; 2009, J Food Sci, vol. 74, No. 1, pp. C33-C40.

Schoebitz; 2013, Agronomy for Sustainable Development, vol. 33, No. 4, pp. 751-765.

Semyonov; 2011, LWT-Food science and technology, vol. 44, No. 9, pp. 1844-1852.

Shahidi; 1993, Crit Rev Food Sci Nutri, vol. 33, No. 6, pp. 501-547.

Streeter; 2003, J Appl Microbiol, vol. 95, No. 3, pp. 484-491.

Zhao(Ed); 1988, Beijing Agricultural University Press 228 Tr, 228.

Zhao(Ed); 1988, Beijing Agricultural University Press 228.

\* cited by examiner

‡ imported from a related application

STABLE INOCULANT COMPOSITIONS AND METHODS FOR PRODUCING SAME

CROSS-REFERENCE TO RELATED APPLICATIONS

The present application is a continuation of U.S. application Ser. No. 15/758,828, filed Mar. 9, 2018, which is a 35 U.S.C. 371 national application of international application no. PCT/US2016/050529, filed Sep. 7, 2016, which claims priority or the benefit under 35 U.S.C. 119 of U.S. provisional application Nos. 62/217,250; 62/273,054; 62/296,766; and 62/343,250, filed Sep. 11, 2015, Dec. 30, 2015, Feb. 18, 2016, and May 31, 2016, respectively. The contents of each of the aforementioned applications are fully incorporated herein by reference.

FIELD OF THE INVENTION

The present disclosure relates to compositions and methods for enhancing the stability and survival of microorganisms in inoculant compositions.

BACKGROUND OF THE INVENTION

Inoculant compositions comprising agriculturally beneficial microorganisms are well known in the art. See, e.g., U.S. Pat. Nos. 5,484,464; 5,586,411; 5,695,541; 5,804,208; 5,916,029; 6,569,425; 6,808,917; 6,824,772; 7,429,477; 8,148,138; 8,278,247; 8,445,256; 8,883,679; 8,921,089; 8,999,698; 9,017,442; 9,101,088; 9,234,251; 9,340,464.

Because the effectiveness of such inoculant compositions generally depends on the ability of the microorganisms therein to survive and propagate following application, much effort has been made to increase the stability of agriculturally beneficial microorganisms in inoculant compositions. See, e.g., U.S. Pat. No. 8,011,132 (describing a method of adding trehalose, sucrose or glycerol to the substantially stationary phase of fermentation) and U.S. Pat. No. 9,090,884 (describing the microencapsulation of microorgnaisms in a water-soluble encapsulating material).

Nevertheless, there remains a need for improved compositions and methods for enhancing the stability and survival of microorganisms in inoculant compositions.

SUMMARY OF THE CLAIMED INVENTION

The present disclosure provides compositions and methods for enhancing the survival and/or stability of microorganisms in inoculant compositions.

A first aspect of the present disclosure is an inoculant composition comprising one or more maltodextrins, one or more disaccharides and one or more microorganisms. In some embodiments, the inoculant composition further comprises one or more monosaccharides, one or more oligosaccharides, one or more pesticides, one or more lipo-chitooligosaccharides, one or more chitooligosaccharides, one or more chitinous compounds, one or more flavonoids, one or more oxidation control components, one or more surfactants and/or one or more drying agents.

A second aspect of the present disclosure is a kit comprising an inoculant composition of the present disclosure and a container housing the inoculant composition.

A third aspect of the present disclosure is a coated plant propagation material comprising a plant propagation material and a coating that covers at least a portion of an outer surface of the plant propagation material, said coating comprising an inoculant composition of the present disclosure.

A fourth aspect of the present disclosure is a kit comprising a coated plant propagation material of the present disclosure and a container housing the coated plant propagation material.

A fifth aspect of the present disclosure is a plant germinated from a coated plant propagation material of the present disclosure.

A sixth aspect of the present disclosure is a plant part harvested from a plant that was germinated from a coated plant propagation material of the present disclosure.

A seventh aspect of the present disclosure is a processed product derived from a plant that was germinated from a coated plant propagation material of the present disclosure.

An eighth aspect of the present disclosure is a crop comprising a plurality of plants germinated from coated plant propagation materials of the present disclosure.

A ninth aspect of the present disclosure is a method that comprises applying an inoculant composition of the present disclosure to a plant propagation material.

A tenth aspect of the present disclosure is a method that comprises, consists essentially of or consisting of planting a coated plant propagation material of the present disclosure.

DETAILED DESCRIPTION

Figure 1:
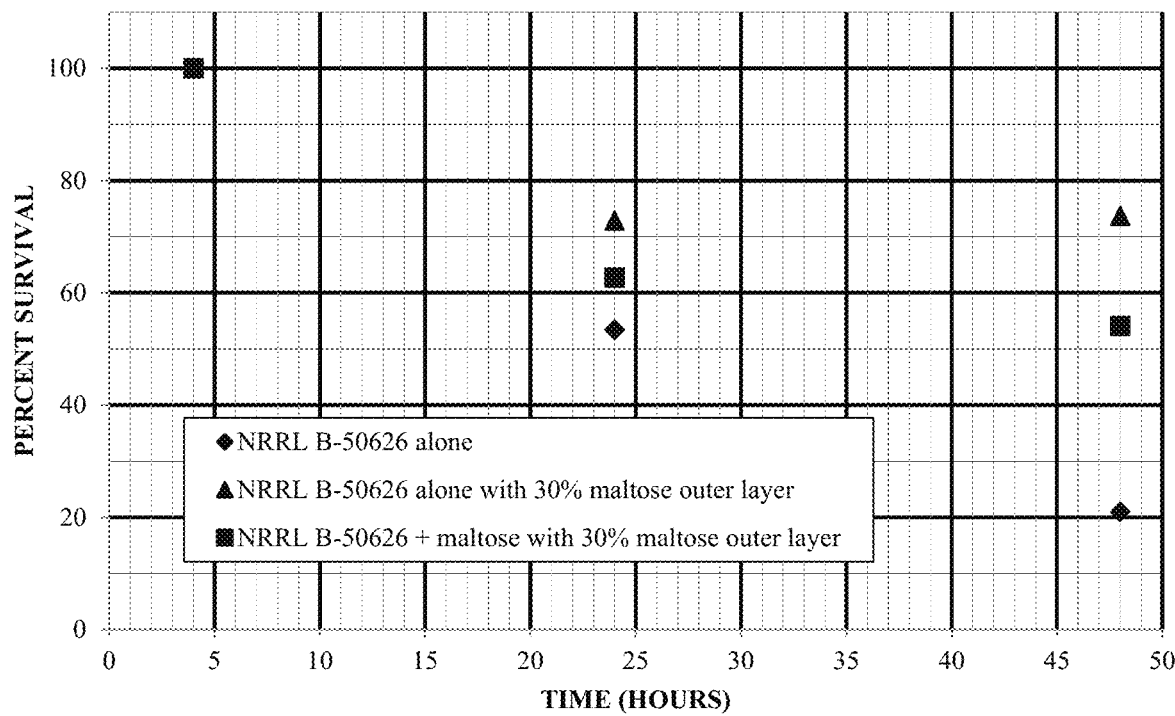
FIGS. 1-3 are graphs showing the survivability of desiccated *Bradyrhizobium japonicum* NRRL B-50626 on soybean seeds stored at room temperature and less than 20%, 35-40% or 70-75% relative humidity, respectively. Diamonds=soybeans coated with 300 µl *Bradyrhizobium japonicum* NRRL B-50626 suspension. Triangles=soybeans coated with 300 µl *Bradyrhizobium japonicum* NRRL B-50626 suspension; 300 µl deionized water containing maltose monohydrate (30% w/w). Squares=soybeans coated with 300 µl *Bradyrhizobium japonicum* NRRL B-50626 suspension containing maltose monohydrate (30% w/w); 300 µl deionized water containing maltose monohydrate (30% w/w).

The present disclosure is explained in greater detail below. This description is not intended to be a detailed catalog of all the different ways in which the invention may be implemented or of all the features that may be added to the instant invention. For example, features illustrated with respect to one embodiment may be incorporated into other embodiments and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following specification is intended to illustrate some particular embodiments of the invention and not to exhaustively specify all permutations, combinations and variations thereof.

The terminology used herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. For the sake of brevity and/or clarity, well-known functions or constructions may not be described in detail.

As used herein, the singular forms "a," "an," and "the" are intended to include the plural forms as well, unless the context clearly indicates otherwise. Thus, unless the context clearly indicates otherwise, "a maltodextrin" is to be interpreted as "one or more maltodextrins," "a microorganism" is to be interpreted as "one or more microorganisms," "a lipo-chitooligosaccharide" is to be interpreted as "one or more lipo-chitooligosaccharides," etc.

As used herein, the term "about," when used in reference to a measurable value such as an amount of mass, dose, time, temperature and the like, is meant to encompass variations of 0.1%, 0.25%, 0.5%, 0.75%, 1%, 2%, 3%, 4%, 5%, 6%, 7%, 8%, 9%, 10%, 11%, 12%, 13%, 14%, 15%, 16%, 17%, 18%, 19% or 20% of the specified amount. Unless otherwise indicated, all numerical values in the specification are to be understood as being modified by the term "about."

As used herein, the term "agriculturally beneficial agent" refers to any agent (e.g., chemical or biological agent) or combination of agents the application of which causes or provides a beneficial and/or useful effect in agriculture including, but not limited to, agriculturally beneficial microorganisms, biostimulants, nutrients, pesticides (e.g., acaricides, fungicides, herbicides, insecticides, and nematicides) and plant signal molecules.

As used herein, the term "agriculturally beneficial microorganism" refers to a microorganism having at least one agriculturally beneficial property (e.g., the ability to fix nitrogen, the ability to solubilize phosphate and/or the ability to produce an agriculturally beneficial agent, such as a plant signal molecule).

As used herein, the term "agriculturally acceptable carrier" refers to a material that can be used to deliver an agriculturally beneficial agent to a plant, plant part or plant growth medium (e.g., soil). As used herein, the term "soil-compatible carrier" refers to a material that can be added to a soil without causing/having an unduly adverse effect on plant growth, soil structure, soil drainage, or the like. As used herein, the term "seed-compatible carrier" refers to a material that can be added to a seed without causing/having an unduly adverse effect on the seed, the plant that grows from the seed, seed germination, or the like. As used herein, the term "foliar-compatible carrier" refers to a material that can be added to a plant or plant part without causing/having an unduly adverse effect on the plant, plant part, plant growth, plant health, or the like.

As used herein, the term "and/or" is intended to include any and all combinations of one or more of the associated listed items, as well as the lack of combinations when interpreted in the alternative ("or").

As used herein, the term "aqueous" refers to a composition that contains more than a trace amount of water (i.e., more than 0.5% water by weight, based upon the total weight of the composition).

As used herein, the term "biostimulant" refers to an agent or combination of agents the application of which enhances one or more metabolic and/or physiological processes of a plant or plant part (e.g., carbohydrate biosynthesis, ion uptake, nucleic acid uptake, nutrient delivery, photosynthesis and/or respiration).

As used herein, the term "BRADY" is to be interpreted as a shorthand substitute for the phrase "*Bradyrhizobium elkanii* SEMIA 501, *Bradyrhizobium elkanii* SEMIA 587, *Bradyrhizobium elkanii* SEMIA 5019, *Bradyrhizobium japonicum* NRRL B-50586 (also deposited as NRRL B-59565), *Bradyrhizobium japonicum* NRRL B-50587 (also deposited as NRRL B-59566), *Bradyrhizobium japonicum* NRRL B-50588 (also deposited as NRRL B-59567), *Bradyrhizobium japonicum* NRRL B-50589 (also deposited as NRRL B-59568), *Bradyrhizobium japonicum* NRRL B-50590 (also deposited as NRRL B-59569), *Bradyrhizobium japonicum* NRRL B-50591 (also deposited as NRRL B-59570), *Bradyrhizobium japonicum* NRRL B-50592 (also deposited as NRRL B-59571), *Bradyrhizobium japonicum* NRRL B-50593 (also deposited as NRRL B-59572), *Bradyrhizobium japonicum* NRRL B-50594 (also deposited as NRRL B-50493), *Bradyrhizobium japonicum* NRRL B-50608, *Bradyrhizobium japonicum* NRRL B-50609, *Bradyrhizobium japonicum* NRRL B-50610, *Bradyrhizobium japonicum* NRRL B-50611, *Bradyrhizobium japonicum* NRRL B-50612, *Bradyrhizobium japonicum* NRRL B-50726, *Bradyrhizobium japonicum* NRRL B-50727, *Bradyrhizobium japonicum* NRRL B-50728, *Bradyrhizobium japonicum* NRRL B-50729, *Bradyrhizobium japonicum* NRRL B-50730, *Bradyrhizobium japonicum* SEMIA 566, *Bradyrhizobium japonicum* SEMIA 5079, *Bradyrhizobium japonicum* SEMIA 5080, *Bradyrhizobium japonicum* USDA 6, *Bradyrhizobium japonicum* USDA 110, *Bradyrhizobium japonicum* USDA 122, *Bradyrhizobium japonicum* USDA 123, *Bradyrhizobium japonicum* USDA 127, *Bradyrhizobium japonicum* USDA 129 and/or *Bradyrhizobium japonicum* USDA 532C."

As used herein, the term "colony forming unit" refers to a microbial cell/spore capable of propagating on or in a substrate (e.g., a soil) when conditions (e.g., temperature, moisture, nutrient availability, pH, etc.) are favorable for microbial growth.

As used herein, the terms "comprise," "comprises," "comprising," "include," "includes" and "including" specify the presence of stated features, steps, operations, elements and/or components, but do not preclude the presence or addition of one or more other features, steps, operations, elements, components and/or groups thereof.

As used herein, the term "consists essentially of" (and grammatical variants thereof), as applied to the compositions and methods of the present disclosure, means that the compositions/methods may contain additional components so long as the additional components do not materially alter the composition/method. The term "materially alter," as applied to a composition/method, refers to an increase or decrease in the effectiveness of the composition/method of at least about 20% or more. For example, a component added to an inoculant composition of the present disclosure "materially alters" the composition if it increases or decreases the composition's ability to enhance microbial survival by at least about 50%.

As used herein, the terms "effective amount," "effective concentration," and "effective dosage" (and grammatical variants thereof) refer to an amount, concentration or dosage that is sufficient to cause a desired effect (e.g., enhanced microbial survival). The absolute value of the amount/concentration/dosage that is sufficient to cause the desired effect may be affected by factors such as the type and magnitude of effect desired, the type, size and volume of seeds to which the inoculant composition will be applied, the type(s) of microorganisms in the composition, the number of microorganisms in the composition, the stability of the microorganisms in the inoculant composition and the storage conditions (e.g., temperature, relative humidity, duration). Those skilled in the art will understand how to select an effective amount/concentration/dosage using routine dose-response experiments.

As used herein, the term "enhanced dispersion" refers to an improvement in one or more characteristics of microbial dispersion as compared to one or more controls (e.g., a control composition that is identical to an inoculant composition of the present disclosure except that it lacks one or more of the components found in the inoculant composition of the present disclosure). Exemplary microbial dispersion characteristics include, but are not limited to, the percentage of microbes that exist as single cells/spores when the inoculant composition is diluted in water. An inoculant composition that improves one or more microbial dispersion characteristics of the microorganism(s) contained therein as compared to a control composition (e.g., a control composition that is identical to the inoculant composition except that it lacks one or more of the components found in the inoculant composition) provides enhanced dispersion and can be referred to as a "readily dispersable inoculant composition."

As used herein, the terms "enhanced growth" and "enhanced plant growth" refer to an improvement in one or more characteristics of plant growth and/or development as compared to one or more control plants (e.g., a plant germinated from an untreated seed or an untreated plant). Exemplary plant growth/development characteristics include, but are not limited to, biomass, carbohydrate biosynthesis, chlorophyll content, cold tolerance, drought tolerance, height, leaf length, leaf mass, leaf number, leaf surface area, leaf volume, nutrient uptake (e.g., calcium, magnesium, nitrogen, phosphorous and/or potassium uptake), rate(s) of photosynthesis, root area, root diameter, root length, root mass, root nodulation (e.g., nodule mass, nodule number, nodule volume), root number, root surface area, root volume, salt tolerance, seed germination, seedling emergence, shoot diameter, shoot length, shoot mass, shoot number, shoot surface area, shoot volume, spread, stomatal conductance and survival rate. Unless otherwise indicated, references to enhanced plant growth are to be interpreted as meaning that compositions and methods of the present disclosure may be capable of enhancing plant growth by enhancing nutrient availability, improving soil characteristics, etc. and are not to be interpreted as suggesting that compositions and methods of the present disclosure act as plant growth regulators.

As used herein, the term "enhanced stability" refers to an improvement in one or more characteristics of microbial stability as compared to one or more controls (e.g., a control composition that is identical to an inoculant composition of the present disclosure except that it lacks one or more of the components found in the inoculant composition of the present disclosure). Exemplary microbial stability characteristics include, but are not limited to, the ability to germinate and/or propagate after being coated on a seed and/or stored for a defined period of time and the ability to cause a desired effect (e.g., enhanced plant yield and/or increased pesticidal activity) after being coated on a seed and/or stored for a defined period of time. A microorganism that exhibits improvement in one or more microbial stability characteristics as compared to a control microorganism when each is subjected to the same conditions (e.g., seed coating and storage conditions) displays enhanced stability and can be referred to as a "stable microorganism." An inoculant composition that improves one or more microbial stability characteristics of the microorganism(s) contained therein as compared to a control composition (e.g., a control composition that is identical to the inoculant composition except that it lacks one or more of the components found in the inoculant composition) provides enhanced stability and can be referred to as a "stable inoculant composition."

As used herein, the term "enhanced survival" refers to an improvement in the survival rate of one or more microorganisms in an inoculant composition as compared to one or more microorganisms in a control composition (e.g., a control composition that is identical to an inoculant composition of the present disclosure except that it lacks one or more of the components found in the inoculant composition of the present disclosure). An inoculant composition that improves the survival rate of one or more of the microorganisms contained therein as compared to a control composition (e.g., a control composition that is identical to the inoculant composition except that it lacks one or more of the components found in the inoculant composition) provides enhanced survival and can be referred to as a stable inoculant composition.

As used herein, the terms "enhanced yield" and "enhanced plant yield" refer to an improvement in one or more characteristics of plant yield as compared to one or more control plants (e.g., a control plant germinated from an untreated seed). Exemplary plant yield characteristics include, but are not limited to, biomass; bushels per acre; grain weight per plot (GWTPP); nutritional content; percentage of plants in a given area (e.g., plot) that fail to produce grain; yield at standard moisture percentage (YSMP), such as grain yield at standard moisture percentage (GYSMP); yield per plot (YPP), such as grain weight per plot (GWTPP); and yield reduction (YRED). Unless otherwise indicated, references to enhanced plant yield are to be interpreted as meaning that compositions and methods of the present disclosure may be capable of enhancing plant yield by enhancing nutrient availability, improving soil characteristics, etc. and are not to be interpreted as suggesting that compositions and methods of the present disclosure act as plant growth regulators. As used herein, the term "foliage" refers to those portions of a plant that normally grow above the ground, including, but not limited to, leaves, stalks, stems, flowers, fruiting bodies and fruits.

As used herein, the terms "foliar application," "foliarly applied" and grammatical variations thereof, refer to the application of one or more active ingredients to the foliage of a plant (e.g., to the leaves of the plant). Application may be effected by any suitable means, including, but not limited to, spraying the plant with a composition comprising the active ingredient(s). In some embodiments, the active ingredient(s) is/are applied to the leaves, stems and/or stalk of the plant and not to the flowers, fruiting bodies or fruits of the plant.

As used herein, the term "glass transition temperature" and its abbreviation "Tg" refer to the midpoint of the temperature range over which a composition transitions from a glassy state to a rubbery state.

As used herein, the term "glassy state" refers to an amorphous solid.

As used herein, the terms "inoculant composition" and "inoculum" refer to compositions comprising microbial cells and/or spores, said cells/spores being capable of propagating/germinating on or in a substrate (e.g., a soil) when conditions (e.g., temperature, moisture, nutrient availability, pH, etc.) are favorable for microbial growth.

As used herein, the term "isomer" includes all stereoisomers of the compounds and/or molecules to which it refers, including enantiomers and diastereomers, as well as all conformers, roatmers and tautomers, unless otherwise indicated. Compounds and/or molecules disclosed herein include all enantiomers in either substantially pure levorotatory or dextrorotatory form, or in a racemic mixture, or in any ratio of enantiomers. Where embodiments disclose a (D)-enantiomer, that embodiment also includes the (L)-enantiomer; where embodiments disclose a (L)-enantiomer, that embodiment also includes the (D)-enantiomer. Where embodiments disclose a (+)-enantiomer, that embodiment also includes the (−)-enantiomer; where embodiments disclose a (−)-enantiomer, that embodiment also includes the (+)-enantiomer. Where embodiments disclose a (S)-enantiomer, that embodiment also includes the (R)-enantiomer; where embodiments disclose a (R)-enantiomer, that embodiment also includes the (S)-enantiomer. Embodiments are intended to include any diastereomers of the compounds and/or molecules referred to herein in diastereomerically pure form and in the form of mixtures in all ratios. Unless stereochemistry is explicitly indicated in a chemical structure or chemical name, the chemical structure or chemical name is intended to embrace all possible stereoisomers, conformers, rotamers and tautomers of compounds and/or molecules depicted.

As used herein, the term "modified microbial strain" refers to a microbial strain that is modified from a strain isolated from nature. Modified microbial strains may be produced by any suitable method(s), including, but not limited to, chemical or other form of induced mutation to a polynucleotide within any genome within the strain; the insertion or deletion of one or more nucleotides within any genome within the strain, or combinations thereof; an inversion of at least one segment of DNA within any genome within the strain; a rearrangement of any genome within the strain; generalized or specific transduction of homozygous or heterozygous polynucleotide segments into any genome within the strain; introduction of one or more phage into any genome of the strain; transformation of any strain resulting in the introduction into the strain of stably replicating autonomous extrachromosomal DNA; any change to any genome or to the total DNA composition within the strain isolated from nature as a result of conjugation with any different microbial strain; and any combination of the foregoing. The term modified microbial strains includes a strain with (a) one of more heterologous nucleotide sequences, (b) one or more non-naturally occurring copies of a nucleotide sequence isolated from nature (i.e., additional copies of a gene that naturally occurs in the microbial strain from which the modified microbial strain was derived), (c) a lack of one or more nucleotide sequences that would otherwise be present in the natural reference strain by for example deleting nucleotide sequence, and (d) added extrachromosomal DNA. In some embodiments, modified microbial strains comprise a combination of two or more nucleotide sequences (e.g., two or more naturally occurring genes that do not naturally occur in the same microbial strain) or comprise a nucleotide sequence isolated from nature at a locus that is different from the natural locus.

As used herein, the term "nitrogen fixing organism" refers to an organism capable of converting atmospheric nitrogen ($N_2$) into a form that may be utilized by a plant or plant part (e.g., ammonia ($NH_3$), ammonium ($NH_4+$), etc.).

As used herein, the term "non-aqueous" refers to a composition that comprises no more than a trace amount of water (i.e., no more than 0.5% water by weight, based upon the total weight of the composition).

As used herein, the term "nutrient" refers to a compound or element useful for nourishing a plant (e.g., vitamins, macrominerals, micronutrients, trace minerals, organic acids, etc. that are necessary for plant growth and/or development).

As used herein, the term "onset temperature" refers to the temperature at which a composition begins the transition from a glassy state to a rubbery state.

As used herein, the term "PENI" is to be interpreted as a shorthand substitute for the phrase "*Penicillium bilaiae* ATCC 18309, *Penicillium bilaiae* ATCC 20851, *Penicillium bilaiae* ATCC 22348, *Penicillium bilaiae* NRRL 50162, *Penicillium bilaiae* NRRL 50169, *Penicillium bilaiae* NRRL 50776, *Penicillium bilaiae* NRRL 50777, *Penicillium bilaiae* NRRL 50778, *Penicillium bilaiae* NRRL 50777, *Penicillium bilaiae* NRRL 50778, *Penicillium bilaiae* NRRL 50779, *Penicillium bilaiae* NRRL 50780, *Penicillium bilaiae* NRRL 50781, *Penicillium bilaiae* NRRL 50782, *Penicillium bilaiae* NRRL 50783, *Penicillium bilaiae* NRRL 50784, *Penicillium bilaiae* NRRL 50785, *Penicillium bilaiae* NRRL 50786, *Penicillium bilaiae* NRRL 50787, *Penicillium bilaiae* NRRL 50788, *Penicillium bilaiae* RS7B-SD1, *Penicillium brevicompactum* AgRF18, *Penicillium canescens* ATCC 10419, *Penicillium expansum* ATCC 24692, *Penicillium expansum* YT02, *Penicillium fellatanum* ATCC 48694, *Penicillium gaestrivorus* NRRL 50170, *Penicillium glabrum* DAOM 239074, *Penicillium glabrum* CBS 229.28, *Penicillium janthinellum* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* N93/47267 and/or *Penicillium raistrickii* ATCC 10490."

As used herein, the term "*Penicillium bilaiae*" is intended to include all iterations of the species name, such as "*Penicillium bilaji*" and "*Penicillium bilaii*."

As used herein, the term "pest" includes any organism or virus that negatively affects a plant, including, but not limited to, organisms and viruses that spread disease, damage host plants and/or compete for soil nutrients. The term "pest" encompasses organisms and viruses that are known to associate with plants and to cause a detrimental effect on the plant's health and/or vigor. Plant pests include, but are not limited to, arachnids (e.g., mites, ticks, spiders, etc.), bacteria, fungi, gastropods (e.g., slugs, snails, etc.), invasive plants (e.g., weeds), insects (e.g., white flies, thrips, weevils, etc.), nematodes (e.g., root-knot nematode, soybean cyst nematode, etc.), rodents and viruses (e.g., tobacco mosaic virus (TMV), tomato spotted wilt virus (TSWV), cauliflower mosaic virus (CaMV), etc.).

As used herein, the terms "pesticide" and "pesticidal" refer to agents or combinations of agents the application of which is toxic to a pest (i.e., kills a pest, inhibits the growth of a pest and/or inhibits the reproduction of a pest). Non-limiting examples of pesticides include acaricides, fungicides, herbicides, insecticides, and nematicides, etc.

As used herein, the term "phosphate-solubilizing microorganism" refers to a microorganism capable of converting insoluble phosphate into a soluble form of phosphate.

As used herein, the term "plant" includes all plant populations, including, but not limited to, agricultural, horticultural and silvicultural plants. The term "plant" encompasses plants obtained by conventional plant breeding and optimization methods (e.g., marker-assisted selection) and plants obtained by genetic engineering, including cultivars protectable and not protectable by plant breeders' rights.

As used herein, the term "plant cell" refers to a cell of an intact plant, a cell taken from a plant, or a cell derived from a cell taken from a plant. Thus, the term "plant cell" includes cells within seeds, suspension cultures, embryos, meristematic regions, callus tissue, leaves, shoots, gametophytes, sporophytes, pollen and microspores.

As used herein, the term "plant part" refers to any part of a plant, including cells and tissues derived from plants. Thus, the term "plant part" may refer to any of plant components or organs (e.g., leaves, stems, roots, etc.), plant tissues, plant cells and seeds. Examples of plant parts, include, but are not limited to, anthers, embryos, flowers, fruits, fruiting bodies, leaves, ovules, pollen, rhizomes, roots, seeds, shoots, stems and tubers, as well as scions, rootstocks, protoplasts, calli and the like.

As used herein, the term "plant propagation material" refers to a plant part from which a whole plant can be generated. Examples of plant propagation materials include, but are not limited to, cuttings (e.g., leaves, stems), rhizomes, seeds, tubers and cells/tissues that can be cultured into a whole plant.

As used herein, the term "protectant" refers to an agent or combination of agents the application of which enhances the survival and/or stability of a microorganism in an inoculant composition.

As used herein, the term "rubbery state" refers to an amorphous, visoelastic liquid.

As used herein, the terms "signal molecule" and "plant signal molecule" refer to an agent that, when applied to a plant or plant part, results in enhanced growth and/or development as compared to untreated plants or plant parts (e.g., seeds and plants harvested from untreated seeds). Non-limiting examples of signal molecules include lipo-chitooligosaccharides, chitooligosaccharides, chitinous compounds, flavonoids, jasmonic acid or derivatives thereof, linoleic acid or derivatives thereof, linolenic acid or derivatives thereof, karrikins, etc.

As used herein, the terms "spore" and "microbial spore" refer to a microorganism in its dormant, protected state.

As used herein with respect to inoculant compositions, the term "stable" refers to an inoculant composition in which microorganisms exhibit enhanced stability and/or enhanced survival. In general, an inoculant composition may be labeled "stable" if it improves the survival rate and/or at least one microbial stability characteristic of at least one microorganism contained therein.

As used herein with respect to microbial spores, the term "survival rate" refers to the percentage of microbial spores that are viable (i.e., capable of propagating on or in a substrate (e.g., on a seed and/or in a soil) when conditions (e.g., temperature, moisture, nutrient availability, pH, etc.) are favorable for microbial growth) at a given period of time.

While certain aspects of the present disclosure will hereinafter be described with reference to embodiments thereof, it will be understood by those of ordinary skill in the art that various changes in form and details may be made therein without departing from the spirit and scope of the present disclosure as defined by the claims.

All publications, patent applications, patents and other references mentioned herein are incorporated by reference in their entirety, except insofar as they contradict any disclosure expressly set forth herein.

The present disclosure provides inoculant compositions and methods for enhancing the stability and/or survival of microorganisms.

Inoculant compositions of the present disclosure comprise, consist essentially of, or consist of one or more microorganisms in a stabilizing medium.

In some embodiments, inoculant compositions of the present disclosure comprise one or more agriculturally beneficial microorganisms such as diazotrophs, phosphate-solubilizing microorganisms and biopesticides.

In some embodiments, inoculant compositions of the present disclosure comprise one or more Gram-negative bacteria.

In some embodiments, inoculant compositions of the present disclosure comprise one or more Gram-positive bacteria.

Non-limiting examples of bacteria that may be useful in inoculant compositions of the present disclosure include *Azospirillum brasilense* INTA Az-39, *Bacillus amyloliquefaciens* D747, *Bacillus amyloliquefaciens* NRRL B-50349, *Bacillus amyloliquefaciens* TJ1000, *Bacillus amyloliquefaciens* FZB24, *Bacillus amyloliquefaciens* FZB42, *Bacillus amyloliquefaciens* IN937a, *Bacillus amyloliquefaciens* IT-45, *Bacillus amyloliquefaciens* TJ1000, *Bacillus amyloliquefaciens* MB1600, *Bacillus amyloliquefaciens* BS27 (deposited as NRRL B-5015), *Bacillus amyloliquefaciens* BS2084 (deposited as NRRL B-50013), *Bacillus amyloliquefaciens* 15AP4 (deposited as ATCC PTA-6507), *Bacillus amyloliquefaciens* 3AP4 (deposited as ATCC PTA-6506), *Bacillus amyloliquefaciens* LSSA01 (deposited as NRRL B-50104), *Bacillus amyloliquefaciens* ABP278 (deposited as NRRL B-50634), *Bacillus amyloliquefaciens* 1013 (deposited as NRRL B-50509), *Bacillus amyloliquefaciens* 918 (deposited as NRRL B-50508), *Bacillus amyloliquefaciens* 22CP1 (deposited as ATCC PTA-6508) and *Bacillus amyloliquefaciens* BS18 (deposited as NRRL B-50633), *Bacillus cereus* 1-1562, *Bacillus firmus* I-1582, *Bacillus licheniformis* BA842 (deposited as NRRL B-50516), *Bacillus licheniformis* BL21 (deposited as NRRL B-50134), *Bacillus mycoides* NRRL B-21664, *Bacillus pumilus* NRRL B-21662, *Bacillus pumilus* NRRL B-30087, *Bacillus pumilus* ATCC 55608, *Bacillus pumilus* ATCC 55609, *Bacillus pumilus* GB34, *Bacillus pumilus* KFP9F, *Bacillus pumilus* QST 2808, *Bacillus subtilis* ATCC 55078, *Bacillus subtilis* ATCC 55079, *Bacillus subtilis* MBI 600, *Bacillus subtilis* NRRL B-21661, *Bacillus subtilis* NRRL B-21665, *Bacillus subtilis* CX-9060, *Bacillus subtilis* GB03, *Bacillus subtilis* GB07, *Bacillus subtilis* QST-713, *Bacillus subtilis* FZB24, *Bacillus subtilis* D747, *Bacillus subtilis* 3BP5 (deposited as NRRL B-50510), *Bacillus thuringiensis* ATCC 13367, *Bacillus thuringiensis* GC-91, *Bacillus thuringiensis* NRRL B-21619, *Bacillus thuringiensis* ABTS-1857, *Bacillus thuringiensis* SAN 4011, *Bacillus thuringiensis* ABG-6305, *Bacillus thuringiensis* ABG-6346, *Bacillus thuringiensis* AM65-52, *Bacillus thuringiensis* SA-12, *Bacillus thuringiensis* SB4, *Bacillus thuringiensis* ABTS-351, *Bacillus thuringiensis* HD-1, *Bacillus thuringiensis* EG 2348, *Bacillus thuringiensis* EG 7826, *Bacillus thuringiensis* EG 7841, *Bacillus thuringiensis* DSM 2803, *Bacillus thuringiensis* NB-125, *Bacillus thuringiensis* NB-176, *Bradyrhizobium elkanii* SEMIA 501, *Bradyrhizobium elkanii* SEMIA 587, *Bradyrhizobium elkanii* SEMIA 5019, *Bradyrhizobium japonicum* NRRL B-50586 (also deposited as NRRL B-59565), *Bradyrhizobium japonicum* NRRL B-50587 (also deposited as NRRL B-59566), *Bradyrhizobium japonicum* NRRL B-50588 (also deposited as NRRL B-59567), *Bradyrhizobium japonicum* NRRL B-50589 (also deposited as NRRL B-59568), *Bradyrhizobium japonicum* NRRL B-50590 (also deposited as NRRL B-59569), *Bradyrhizobium japonicum* NRRL B-50591 (also deposited as NRRL B-59570), *Bradyrhizobium japonicum* NRRL B-50592 (also deposited as NRRL B-59571), *Bradyrhizobium japonicum* NRRL B-50593 (also deposited as NRRL B-59572), *Bradyrhizobium japonicum* NRRL B-50594 (also deposited as NRRL B-50493), *Bradyrhizobium japonicum* NRRL B-50608, *Bradyrhizobium japonicum* NRRL B-50609, *Bradyrhizobium japonicum* NRRL B-50610, *Bradyrhizobium japonicum* NRRL B-50611, *Bradyrhizobium japonicum* NRRL B-50612, *Bradyrhizobium japonicum* NRRL B-50726, *Bradyrhizobium japonicum* NRRL B-50727, *Bradyrhizobium japonicum* NRRL B-50728, *Bradyrhizobium japonicum* NRRL B-50729, *Bradyrhizobium japonicum* NRRL B-50730, *Bradyrhizobium japonicum* SEMIA 566, *Bradyrhizobium japonicum* SEMIA 5079, *Bradyrhizobium japonicum* SEMIA 5080, *Bradyrhizobium japonicum* USDA 6, *Bradyrhizobium japonicum* USDA 110, *Bradyrhizobium japonicum* USDA 122, *Bradyrhizobium japonicum* USDA 123, *Bradyrhizobium japonicum* USDA 127, *Bradyrhizobium japonicum* USDA 129, *Bradyrhizobium japonicum* USDA 532C, *Pseudomonas jessenii* PS06, *Rhizobium leguminosarum* SO12A-2 (IDAC 080305-01), *Sinorhizobium fredii* CCBAU114, *Sinorhizobium fredii* USDA 205 and combinations thereof, as well as microorganisms having at least at least 75%, 80%, 85%, 90%, 95%, 96%, 97%, 98%, 99% or more identical to any of the aforementioned strains on the basis of 16S rDNA sequence identity.

In some embodiments, inoculant compositions of the present disclosure comprise one or more fungi.

Non-limiting examples of fungi that may be useful in inoculant compositions of the present disclosure include *Gliocladium virens* ATCC 52045, *Gliocladium virens* GL-21, *Glomus intraradices* RTI-801, *Metarhizium anisopliae* F52, *Penicillium bilaiae* (formerly known as *P. bilaiae* and *P. bilaji*) ATCC 18309, *Penicillium bilaiae* ATCC 20851, *Penicillium bilaiae* ATCC 22348, *Penicillium bilaiae* NRRL 50162, *Penicillium bilaiae* NRRL 50169, *Penicillium bilaiae* NRRL 50776, *Penicillium bilaiae* NRRL 50777, *Penicillium bilaiae* NRRL 50778, *Penicillium bilaiae* NRRL 50777, *Penicillium bilaiae* NRRL 50778, *Penicillium bilaiae* NRRL 50779, *Penicillium bilaiae* NRRL 50780, *Penicillium bilaiae* NRRL 50781, *Penicillium bilaiae* NRRL 50782, *Penicillium bilaiae* NRRL 50783, *Penicillium bilaiae* NRRL 50784, *Penicillium bilaiae* NRRL 50785, *Penicillium bilaiae* NRRL 50786, *Penicillium bilaiae* NRRL 50787, *Penicillium bilaiae* NRRL 50788, *Penicillium bilaiae* RS7B-SD1, *Penicillium brevicompactum* AgRF18, *Penicillium canescens* ATCC 10419, *Penicillium expansum* ATCC 24692, *Penicillium expansum* YT02, *Penicillium fellatanum* ATCC 48694, *Penicillium gaestrivorus* NRRL 50170, *Penicillium glabrum* DAOM 239074, *Penicillium glabrum* CBS 229.28, *Penicillium janthinellum* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* N93/47267, *Penicillium raistrickii* ATCC 10490, *Trichoderma asperellum* SKT-1, *Trichoderma asperellum* ICC 012, *Trichoderma atroviride* LC52, *Trichoderma atroviride* CNCM 1-1237, *Trichoderma fertile* JM41R, *Trichoderma gamsii* ICC 080, *Trichoderma hamatum* ATCC 52198, *Trichoderma harzianum* ATCC 52445, *Trichoderma harzianum* KRL-AG2, *Trichoderma harzianum* T-22, *Trichoderma harzianum* TH-35, *Trichoderma harzianum* T-39, *Trichoderma harzianum* I00012, *Trichoderma reesi* ATCC 28217, *Trichoderma virens* ATCC 57678, *Trichoderma virens* GI-3, *Trichoderma virens* GL-21, *Trichoderma virens* G-41, *Trichoderma viridae* ATCC 52440, *Trichoderma viridae* ICC080, *Trichoderma viridae* TV1 and combinations thereof, as well as microorganisms having at least at least 75%, 80%, 85%, 90%, 95%, 96%, 97%, 98%, 99% or more identical to any of the aforementioned strains on the basis of internal transcribed spacer (ITS) and/or cytochrome c oxidase (C01) sequence identity.

In some embodiments, inoculant compositions of the present disclosure comprise one or more mycorrhizal fungi (e.g., one or more endomycorrhizal fungi, one or more ectomycorrhizal fungi and/or one or more ericoid mycorrhizal fungi).

Non-limiting examples of mycorrhizal strains that may be useful in inoculant compositions of the present disclosure include mycorrhizal strains such as *Gigaspora margarita*, *Glomus aggregatum*, *Glomus brasilianum*, *Glomus clarum*, *Glomus deserticola*, *Glomus etunicatum*, *Glomus intraradices*, *Glomus monosporum*, *Glomus mosseae*, *Laccaria bicolor*, *Laccaria laccata*, *Paraglomus brazilianum*, *Pisolithus tinctorius*, *Rhizopogon amylopogon*, *Rhizopogon fulvigleba*, *Rhizopogon luteolus*, *Rhizopogon villosuli*, *Scleroderma cepa* and *Scleroderma citrinum* and combinations thereof.

In some embodiments, inoculant compositions of the present disclosure comprise one or more biopesticides (e.g., one or more biofungicides, bioherbicides, bioinsectides and/or bionematicides). See generally Burges, Formulation of Microbial Biopesticides: Beneficial Microorganisms, Nematodes and Seed Treatments (Springer Science & Business Media) (2012); Hall & Menn, Biopesticides: Use and Delivery (Humana Press) (1998); McCoy, et al., Entomogenous fungi, in CRC Handbook of Natural Pesticides. Microbial Pesticides, Part A. Entomogenous Protozoa and Fungi (C. M. Inoffo, ed.), Vol. 5:151-236 (1988); Samson, et al., Atlas of Entomopathogenic Fungi (Springer-Verlag, Berlin) (1988); deFaria and Wraight, *Mycoinsecticides and Mycoacaricides: A comprehensive list with worldwide coverage and international classification of formulation types*, Biol. Control (2007), doi: 10.1016/j.biocontrol.2007.08.001; and WO 2016/096821.

Non-limiting examples of biopesticidal strains that may be useful in compositions of the present disclosure include *Ampelomyces quisqualis* AQ 10® (Intrachem Bio GmbH & Co. KG, Germany), *Aspergillus flavus* AFLA-GUARD® (Syngenta Crop Protection, Inc., CH), *Aureobasidium pullulans* BOTECTOR® (bio-ferm GmbH, Germany), *Bacillus* AQ175 (ATCC 55608), *Bacillus* AQ177 (ATCC 55609), *Bacillus amyloliquefaciens* FZB24, *Bacillus amyloliquefaciens* FZB42, *Bacillus amyloliquefaciens* NRRL B-50349, *Bacillus amyloliquefaciens* TJ1000 (also known as 1BE, isolate ATCC BAA-390), *Bacillus firmus* 1-1582, *Bacillus mycoides* AQ726 (NRRL B-21664); *Bacillus pumilus* AQ717 (NRRL B-21662), *Bacillus pumilus* NRRL B-30087, *Bacillus subtilis* AQ713 (NRRL B-21661), *Bacillus subtilis* AQ743 (NRRL B-21665), *Bacillus subtilis* ATCC 55078, *Bacillus subtilis* ATCC 55079, *Bacillus thuringiensis* AQ52 (NRRL B-21619), *Beauveria bassiana* ATCC-74040, *Beauveria bassiana* ATCC-74250, *Burkholderia* sp. A396 sp. nov. *rinojensis*, NRRL B-50319, *Candida oleophila* 1-182 (e.g., ASPIRE® from Ecogen Inc., USA), *Candida saitoana* BIOCURE® (in mixture with lysozyme; BASF, USA) and BIOCOAT® (ArystaLife Science, Ltd., Cary, N.C.), *Chromobacterium subtsugae* NRRL B-30655, *Chromobacterium vaccinii* NRRL B-50880, *Clonostachys rosea* f. *catenulata* (also referred to as *Gliocladium catenulatum*) J1446 (PRESTOP®, Verdera, Finland), *Coniothyrium minitans* CONTANS® (Prophyta, Germany), *Cryphonectria parasitica* (CNICM, France), *Cryptococcus albidus* YIELD PLUS® (Anchor Bio-Technologies, South Africa), *Flavobacterium* H492, NRRL B-50584, *Fusarium oxysporum* BIOFOX® (from S.I.A.P.A., Italy) and FUSACLEAN® (Natural Plant Protection, France), *Metarhizium anisopliae* F52 (also known as *Metarhizium anisopliae* strain 52, *Metarhizium anisopliae* strain 7, *Metarhizium anisopliae* strain 43 and *Metarhizium anisopliae* BIO-1020, TAE-001; deposited as DSM 3884, DSM 3885, ATCC 90448, SD 170 and ARSEF 7711), *Metschnikowia fructicola* SHEMER® (Agrogreen, Israel), *Microdochium dimerum* ANTIBOT® (Agrauxine, France), *Muscodor albus* NRRL 30547, *Muscodor roseus* NRRL 30548, *Paecilomyces fumosoroseus* FE991, *Phlebiopsis gigantea* ROTSOP® (Verdera, Finland), *Pseudozyma flocculosa* SPORODEX® (Plant Products Co. Ltd., Canada), *Pythium oligandrum* DV74 (POLYVERSUM®, Remeslo SSRO, Biopreparaty, Czech Rep.), *Reynoutria sachlinensis* (e.g., REGALIA® from Marrone Biolnnovations, USA), *Streptomyces* NRRL B-30145, *Streptomyces* M1064, *Streptomyces galbus* NRRL 30232, *Streptomyces lydicus* WYEC 108 (ATCC 55445), *Streptomyces violaceusniger* YCED 9 (ATCC 55660; DE-THATCH-9®, DECOMP-9® and THATCH CON- TROL®, Idaho Research Foundation, USA), *Streptomyces* WYE 53 (ATCC 55750; DE-THATCH-9®, DECOMP-9® and THATCH CONTROL®, Idaho Research Foundation, USA), *Talaromyces flavus* V117b (PROTUS®, Prophyta, Germany), *Trichoderma asperellum* SKT-1 (ECO-HOPE®, Kumiai Chemical Industry Co., Ltd., Japan), *Trichoderma atroviride* LC52 (SENTINEL®, Agrimm Technologies Ltd, NZ), *Trichoderma harzianum* T-22 (PLANTSHIELD®, der Firma BioWorks Inc., USA), *Trichoderma harzianum* TH-35 (ROOT PRO®, from Mycontrol Ltd., Israel), *Trichoderma harzianum* T-39 (TRICHODEX®, Mycontrol Ltd., Israel; *TRICHODERMA* 2000®, Makhteshim Ltd., Israel), *Trichoderma harzianum* ICC012 and *Trichoderma viride* TRICHOPEL (Agrimm Technologies Ltd, NZ), *Trichoderma harzianum* ICC012 and *Trichoderma viride* ICC080 (REMEDIER® WP, Isagro Ricerca, Italy), *Trichoderma polysporum* and *Trichoderma harzianum* (BINAB®, BINAB Bio-Innovation AB, Sweden), *Trichoderma stromaticum* TRICOVAB® (C.E.P.L.A.C., Brazil), *Trichoderma virens* GL-21 (SOILGARD®, Certis LLC, USA), *Trichoderma virens* G1-3 (ATCC 57678), *Trichoderma virens* G1-21 (Thermo Trilogy Corporation, Wasco, Calif.), *Trichoderma virens* G1-3 and *Bacillus amyloliquefaciens* FZB24, *Trichoderma virens* G1-3 and *Bacillus amyloliquefaciens* NRRL B-50349, *Trichoderma virens* G1-3 and *Bacillus amyloliquefaciens* TJ1000, *Trichoderma virens* G1-21 and *Bacillus amyloliquefaciens* FZB24, *Trichoderma virens* G1-21 and *Bacillus amyloliquefaciens* NRRL B-50349, *Trichoderma virens* G1-21 and *Bacillus amyloliquefaciens* TJ 1000, *Trichoderma viride* TRIECO® (Ecosense Labs. (India) Pvt. Ltd., India, BIO-CURE® F from T. Stanes & Co. Ltd., Indien), *Trichoderma viride* TV1 (Agribiotec srl, Italy), *Trichoderma viride* ICC080, *Ulocladium oudemansii* HRU3 (BOTRY-ZEN®, Botry-Zen Ltd, NZ) and combinations thereof.

In some embodiments, inoculant compositions of the present disclosure comprise one or more modified microbial strains.

In some embodiments, inoculant compositions of the present disclosure comprise one or more microorganisms selected from the genera and species listed in Appendix A.

Microorganisms may be incorporated into inoculant compositions of the present disclosure in any suitable amount(s)/concentration(s).

In some embodiments, the microorganism(s) is/are present in an amount ranging from about $1\times10^1$ to about $1\times10^{20}$ colony-forming units (cfu) per gram and/or milliliter of inoculant composition. For example, inoculant compositions of the present disclosure may comprise about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^13$, $1\times10^{14}$, $1\times10^{15}$ cfu/g or more of agriculturally beneficial microorganisms (e.g., about $1\times10^2$ to about $1\times10^6$ cfu per g/ml of *Bradyrhizobium japonicum* SEMIA 587, *Bradyrhizobium japonicum* SEMIA 5019, *Bradyrhizobium japonicum* SEMIA 5079 and/or *Bradyrhizobium japonicum* SEMIA 5080).

In some embodiments, the amount/concentration of microorganisms is an amount effective to enhance the yield of the plant or plant part to which the inoculant composition is applied.

In some embodiments, the amount/concentration of microorganisms is $1\times10^4$, $1\times10^5$, $1\times10^6$, $1\times10^7$, $1\times10^8$, $1\times10^9$, $1\times10^{10}$, $1\times10^{11}$, $1\times10^{12}$ or more cfu per gram/milliliter of inoculant composition.

It is to be understood that microorganisms may be incorporated into inoculant compositions of the present disclosure in any suitable form, including vegetative form, spore form and combinations thereof. In some embodiments, inoculant compositions of the present disclosure comprise are devoid of spores. In some embodiments, inoculant compositions of the present disclosure comprise are devoid of vegetative cells.

In some embodiments, microbial spores comprise about 0.1 to about 50% (by weight) of the inoculant composition. For example, inoculant compositions of the present disclosure may comprise about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% or more (by weight) of one or more microbial spores. In some embodiments, the microbial spore amount/concentration is about 1, 2, 3, 4 or 5 to about 5, 6, 7, 8, 9, 10, 11, 12, 13, 14, 15, 16, 17, 18, 19, 20, 21, 22, 23, 24 or 25% (by weight) of the inoculant composition.

In some embodiments, microbial spores are present in an amount ranging from about $1\times10^1$ to about $1\times10^{20}$ colony-forming units (cfu) per gram and/or milliliter of inoculant composition. For example, inoculant compositions of the present disclosure may comprise about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ or more microbial spores per gram and/or milliliter of inoculant composition (e.g., about $1\times10^4$ to about $1\times10^9$ *Bacillus amyloliquefaciens* TJ1000 (also known as 1 BE, isolate ATCC BAA-390), *Metarhizium anisopliae* F52, *Penicillium bilaiae* ATCC 20851, *Penicillium bilaiae* RS7B-SD1 and/or *Trichoderma virens* GI-3 spores per gram/milliliter).

In some embodiments, the amount/concentration of spores is that amount/concentration which is effective to enhance the yield of the plant or plant part to which the inoculant composition is applied.

Microorganisms included in inoculant compositions of the present disclosure may be produced using any suitable method(s), including, but not limited to, liquid state fermentation and solid state fermentation. See, generally, Cunningham et al., CAN. J. BOT. 68:2270 (1990); Friesen et al., APPL. MICROBIOL. BIOTECH. 68:397 (2005).

Microorganisms included in inoculant compositions of the present disclosure may be harvested and/or concentrated using any suitable method(s), including, but not limited to, centrifugation (e.g., density gradient centrifugation, disc stack centrifugation, tubular bowl centrifugation), coagulation, decanting, felt bed collection, filtration (e.g., drum filtration, sieving, ultrafiltration), flocculation, impaction and trapping (e.g., cyclone spore trapping, liquid impingement).

Microorganisms may be harvested and incorporated into inoculant compositions of the present disclosure during any suitable growth phase. In general, microorganisms are allowed to reach the stationary growth phase before they are harvested and incorporated into inoculant compositions of the present disclosure.

The stabilizing medium may comprise, consist essentially of or consist of one or more maltodextrins, one or more monosaccharides, one or more disaccharides, one or more oligosaccharides, one or more malt extracts, one or more peat extracts, one or more betaines, one or more prolines, one or more sarcosines, one or more peptones, one or more skim milks, one or more oxidation control components, and/or one or more hygroscopic polymers.

In some embodiments, the stabilizing medium comprises, consists essentially of or consists of one or more maltodextrins.

In some embodiments, the stabilizing medium comprises, consists essentially of or consists of one or more monosaccharides.

In some embodiments, the stabilizing medium comprises, consists essentially of or consists of one or more disaccharides.

In some embodiments, the stabilizing medium comprises, consists essentially of or consists of one or more maltodextrins and one or more monosaccharides.

In some embodiments, the stabilizing medium comprises, consists essentially of or consists of one or more maltodextrins and one or more disaccharides.

In some embodiments, the stabilizing medium comprises, consists essentially of or consists of one or more maltodextrins, one or more monosaccharides and one or more disaccharides.

Inoculant compositions of the present disclosure may comprise any suitable maltodextrin(s), including, but not limited to, maltodextrins having a dextrose equivalent value (DEV) of about 3, 4, 5, 6, 7, 8, 9, 10, 11, 12, 13, 14, 15, 16, 17, 18, 19, 20, 21, 22, 23, 24, or 25. In some embodiments, inoculant compositions of the present disclosure comprise one or more maltodextrins having a DEV of about 5 to about 6, 7, 8, 9, 10, 11, 12, 14, 15, 16, 17, 18, 19 or 20, about 10 to about 11, 12, 14, 15, 16, 17, 18, 19 or 20, or about 15 to about 16, 17, 18, 19 or 20. In some embodiments, inoculant compositions of the present disclosure comprise a combination of maltodextrins having a DEV of about 5 to about 6, 7, 8, 9, 10, 11, 12, 14, 15, 16, 17, 18, 19 or 20, about 10 to about 11, 12, 14, 15, 16, 17, 18, 19 or 20, or about 15 to about 16, 17, 18, 19 or 20. In some embodiments, inoculant compositions of the present disclosure comprise one or more maltodextrins having a DEV of about 10 to about 20 (e.g., one or more maltodextrins having a DEV of about 15 to about 20). In some embodiments, inoculant compositions of the present disclosure comprise a combination of maltodextrins having a DEV of about 10 to about 20 (e.g., a combination of maltodextrins having a DEV of about 15 to about 20).

In some embodiments, inoculant compositions of the present disclosure comprise one or more maltodextrins having a glass transition temperature (Tg) of at least 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity. In some embodiments, inoculant compositions of the present disclosure comprise a combination of maltodextrins having a collective glass transition temperature (Tg) of at least 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity.

In some embodiments, inoculant compositions of the present disclosure comprise one or more maltodextrins having an onset temperature of at least 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity. In some embodiments, inoculant compositions of the present disclosure comprise a combination of maltodextrins having a collective onset temperature of at least 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity.

Non-limiting examples of maltodextrins that may be useful in compositions of the present disclosure include MALTRIN® M040 (DEV=5; molecular weight=3600; Grain Processing Corporation, Muscatine, Iowa), MALTRIN® M100 (DEV=10; molecular weight=1800; Grain Processing Corporation, Muscatine, Iowa), MALTRIN® M150 (DEV=15; molecular weight=1200; Grain Processing Corporation, Muscatine, Iowa), MALTRIN® M180 (DEV=18; molecular weight=1050; Grain Processing Corporation, Muscatine, Iowa), MALTRIN® M200 (DEV=20; molecular weight=900; Grain Processing Corporation, Muscatine, Iowa), MALTRIN® M250 (DEV=25; molecular weight=720; Grain Processing Corporation, Muscatine, Iowa); GLOBE® Plus 15 DE (Ingredion Inc., Westchester, Ill.); and combinations thereof. In some embodiments, the maltodextrin (or combination of maltodextrins) has a DEV of 15 to 20 and/or a Tg and/or onset temperature at the relative humidity at which the inoculant composition is to be stored that is at least 5, 10, 15, 20, 25, 30, 35, 40, 45, or 50° C. higher than the temperature at which the inoculant composition is to be stored.

Maltodextrins may be incorporated into inoculant compositions of the present disclosure in any suitable form. In some embodiments, the maltodextrin(s) included in inoculant compositions of the present disclosure is/are at least 70, 75, 80, 85, 90, 91, 92, 93, 94, 95, 96, 97, 98, 99, 99.5% or more pure.

Inoculant compositions of the present disclosure may comprise any suitable monosaccharide(s), including, but not limited to, allose, altrose, arabinose, fructose, galactose, glucose, gulose, iodose, lyxose, mannose, ribose, talose, threose and/or xylose. In some embodiments, inoculant compositions of the present disclosure comprise gluscose. In some embodiments, inoculant compositions of the present disclosure do not comprise glucose.

Inoculant compositions of the present disclosure may comprise any suitable disaccharide(s), including, but not limited to, cellobiose, chitobiose, gentiobiose, gentiobiulose, isomaltose, kojibiose, lactose, lactulose, laminaribiose, maltose (e.g., maltose monohydrate, anhydrous maltose), maltulose, mannobiose, melibiose, melibiulose, nigerose, palatinose, rutinose, rutinulose, sophorose, sucrose, trehalose, turanose and/or xylobiose. In some embodiments, inoculant compositions of the present disclosure comprise maltose. In some embodiments, inoculant compositions of the present disclosure do not comprise maltose. In some embodiments, inoculant compositions of the present disclosure comprise trehalose. In some embodiments, inoculant compositions of the present disclosure do not comprise trehalose.

Inoculant compositions of the present disclosure may comprise any suitable oligosaccharide(s), including, but not limited to, fructo-oligosaccharides, galacto-oligosaccharides, mannon-oligosaccharides and/or raffinose.

Mono-, di- and/or oligosaccharides may be incorporated into inoculant compositions of the present disclosure in any suitable form. In some embodiments, the mono-, di- and/or oligosaccharide(s) (e.g., maltose) included in inoculant compositions of the present disclosure is/are at least 70, 75, 80, 85, 90, 91, 92, 93, 94, 95, 96, 97, 98, 99, 99.5% or more pure.

Inoculant compositions of the present disclosure may comprise any suitable betaine(s), including, but not limited to, trimethylglycine.

Betaines may be incorporated into inoculant compositions of the present disclosure in any suitable form. In some embodiments, the betaine(s) included in inoculant compositions of the present disclosure is/are at least 70, 75, 80, 85, 90, 91, 92, 93, 94, 95, 96, 97, 98, 99, 99.5% or more pure.

Proline may be incorporated into inoculant compositions of the present disclosure in any suitable form. In some embodiments, the proline(s) included in inoculant compositions of the present disclosure is/are at least 70, 75, 80, 85, 90, 91, 92, 93, 94, 95, 96, 97, 98, 99, 99.5% or more pure.

Sarcosine may be incorporated into inoculant compositions of the present disclosure in any suitable form. In some embodiments, the sarcosine(s) included in inoculant compositions of the present disclosure is/are at least 70, 75, 80, 85, 90, 91, 92, 93, 94, 95, 96, 97, 98, 99, 99.5% or more pure.

Inoculant compositions of the present disclosure may comprise any suitable peptone(s), including, but not limited to, bacterial peptones, meat peptones, milk peptones, vegetable peptones and yeast peptones.

Peptones may be incorporated into inoculant compositions of the present disclosure in any suitable form. In some embodiments, the peptone(s) included in inoculant compositions of the present disclosure is/are at least 70, 75, 80, 85, 90, 91, 92, 93, 94, 95, 96, 97, 98, 99, 99.5% or more pure.

Inoculant compositions of the present disclosure may comprise any suitable oxidation control component(s), including, but not limited to, antioxidants and/or oxygen scavengers. In some embodiments, the oxidation control component is/comprises ascorbic acid and/or glutathione.

In some embodiments, inoculant compositions comprise one or more antioxidants. For example, in some embodiments, inoculant compositions of the present disclosure comprise ascorbic acid, ascorbyl palmitate, ascorbyl stearate, calcium ascorbate, carotenoids, lipoic acid, phenolic compounds (e.g., flavonoids, flavones, flavonols), potassium ascorbate, sodium ascorbate, thiols (e.g., glutathione, lipoic acid, N-acetyl cysteine), tocopherols, tocotrienols, ubiquinone and/or uric acid.

Non-limiting examples of antioxidants that may be useful in compositions of the present disclosure include those that are soluble in the cell membrane (e.g., alpha tocopherol (vitamin E), ascorbyl palmitate) and those that are soluble in water (e.g., ascorbic acid and isomers or ascorbic acid, sodium or potassium salts of ascorbic acid or isomers or ascorbic acid, glutathione, sodium or potassium salts of glutathione). In some embodiments, use of a membrane-soluble antioxidant necessitates the addition of one or more surfactants to adequately disperse the antioxidant within the inoculant composition.

In some embodiments, inoculant compositions of the present disclosure comprise one or more commercial antioxidants used in accordance with the manufacturer's recommended amounts/concentrations.

In some embodiments, inoculant compositions comprise one or more oxygen scavengers. For example, in some embodiments, inoculant compositions of the present disclosure comprise ascorbic acid, ascorbate salts, catechol and/or sodium hydrogen carbonate.

Inoculant compositions of the present disclosure may comprise any suitable hygroscopic polymer, including, but not limited to, hygroscopic agars, albumins, alginates, carrageenans, celluloses, gums (e.g., cellulose gum, guar gum, gum arabic, gum combretum, xantham gum), methyl celluloses, nylons, pectins, polyacrylic acids, polycaprolactones, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches.

Non-limiting examples of polymers that may be useful in compositions of the present disclosure include AGRIMER™ polymers (e.g., 30, AL-10 LC, AL-22, AT/ATF, VA 3E, VA 31, VA 5E, VA 51, VA 6, VA 6E, VA 7E, VA 71, VEMA AN-216, VEMA AN-990, VEMA AN-1200, VEMA AN-1980, VEMA H-815MS; Ashland Specialty Ingredients, Wilmington, Del.), EASYSPERSE™ polymers (Ashland Specialty Ingredients, Wilmington, Del.); DISCO™ AG polymers (e.g., L-250, L-280, L-285, L-286, L-320, L-323, L-517, L-519, L-520, L800; Incotec Inc., Salinas, Calif.), KELZAN® polymers (Bri-Chem Supply Ltd., Calgary, Alberta, CA), SEEDWORX™ polymers (e.g., Bio 200; Aginnovation, LLC, Walnut Groove, Calif.), TICAXAN® xanthan powders, such as PRE-HYDRATED® TICAXAN® Rapid-3 Powder (TIC Gums, White Marsh, Md.) and combinations thereof.

Additional examples of polymers that may be included in inoculant compositions of the present disclosure may be found in Pouci, et al. AM. J. AGRIC. BIOL. SCI. 3(1):299 (2008).

Hygroscopic polymers may be incorporated into inoculant compositions of the present disclosure in any suitable form. In some embodiments, the hygroscopic polymer(s) included in inoculant compositions of the present disclosure is/are at least 70, 75, 80, 85, 90, 91, 92, 93, 94, 95, 96, 97, 98, 99, 99.5% or more pure.

In some embodiments, inoculant compositions of the present disclosure comprise one or more stabilizing components (e.g., one or more maltodextrins, monosaccharides and/or disaccharides) that raise the Tg of the inoculant composition until it is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity. In some embodiments, the stabilizer(s) raise(s) the Tg of the inoculant composition until it is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity.

In some embodiments, inoculant compositions of the present disclosure comprise one or more stabilizing components (e.g., one or more maltodextrins, monosaccharides and/or disaccharides) that raise the Tg of the inoculant composition at the relative humidity at which the inoculant composition is to be stored until it is at least 5, 10, 15, 20, 25, 30, 35, 40, 45, 50° C. or more higher than the temperature at which the inoculant composition is to be stored. In some embodiments, the stabilizer(s) raise(s) the Tg of the inoculant composition at the relative humidity at which the inoculant composition is to be stored until it is at least 5, 10, 15, 20, 25, 30, 35, 40, 45, 50° C. or more higher than the temperature at which the inoculant composition is to be stored.

In some embodiments, inoculant compositions of the present disclosure comprise one or more stabilizing components (e.g., one or more maltodextrins, monosaccharides and/or disaccharides) that raise the onset temperature of the inoculant composition until it is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity. In some embodiments, the stabilizer(s) raise(s) the onset temperature of the inoculant composition until it is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity.

In some embodiments, inoculant compositions of the present disclosure comprise one or more stabilizing components (e.g., one or more maltodextrins, monosaccharides and/or disaccharides) that raise the onset temperature of the inoculant composition at the relative humidity at which the inoculant composition is to be stored until it is at least 5, 10, 15, 20, 25, 30, 35, 40, 45, 50° C. or more higher than the temperature at which the inoculant composition is to be stored. In some embodiments, the stabilizer(s) raise(s) the onset temperature of the inoculant composition at the relative humidity at which the inoculant composition is to be stored until it is at least 5, 10, 15, 20, 25, 30, 35, 40, 45, 50° C. or more higher than the temperature at which the inoculant composition is to be stored.

Stabilizing compounds, such as maltodextrins, monosaccharides, disaccharides, oligosaccharides, malt extracts, peat extracts, betaines, prolines, sarcosines, peptones, skim milks, oxidation control components and hygroscopic polymers, may be incorporated into inoculant compositions of the present disclosure in any suitable amount(s)/concentration(s). The absolute value of the amount/concentration/dosage of stabilizing compound(s) that is/are sufficient to cause the desired effect(s) may be affected by factors such as the type, size and volume of material to which the composition will be applied, the type(s) of microorganisms in the composition, the number of microorganisms in the composition, the stability of the microorganisms in the composition and storage conditions (e.g., temperature, relative humidity, duration). Those skilled in the art will understand how to select an effective amount/concentration/dosage using routine dose-response experiments.

In some embodiments, the stabilizing compound(s) comprise(s) about 1 to about 95% or more (by weight) of the inoculant composition. In some embodiments, the stabilizing compound(s) (e.g., maltodextrins, monosaccharides and/or disaccharides) comprise about 1 to about 65%, about 10% to about 30%, about 20% to about 40%, about 20% to about 50%, or about 30 to about 60% (by weight) of the inoculant composition. For example, inoculant compositions of the present disclosure may comprise about 5, 10, 15, 20, 25, 30, 35, 40, 45, 50, 55, 60, 65, 70, 75, 80, 85, 90, 95% or more (by weight) of one or more stabilizing compounds (e.g., one or more maltodextrins (each and/or collectively) having a DEV value of about 15 to about 20 and/or maltose).

In some embodiments, peat extract(s) comprise(s) about 0.1 to about 25% (by weight) of the inoculant composition. For example, inoculant compositions of the present disclosure may comprise about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of one or more peat extracts. In some embodiments, the peat extract amount/concentration is about 0.5 to about 10% (by weight) of the inoculant composition.

In some embodiments, betaine(s) comprise(s) about 0.001 to about 50% (by weight) of the inoculant composition. For example, inoculant compositions of the present disclosure may comprise about 0.01, 0.05, 0.1, 0.5, 1, 2, 3, 4, 5, 10, 15, 20, 25, 30, 35, 40, 45, 50% or more (by weight) of one or more betaines.

In some embodiments, proline(s) comprise(s) about 0.001 to about 50% (by weight) of the inoculant composition. For example, inoculant compositions of the present disclosure may comprise about 0.01, 0.05, 0.1, 0.5, 1, 2, 3, 4, 5, 10, 15, 20, 25, 30, 35, 40, 45, 50% or more (by weight) of one or more prolines.

In some embodiments, sarcosine(s) comprise(s) about 0.001 to about 50% (by weight) of the inoculant composition. For example, inoculant compositions of the present disclosure may comprise about 0.01, 0.05, 0.1, 0.5, 1, 2, 3, 4, 5, 10, 15, 20, 25, 30, 35, 40, 45, 50% or more (by weight) of one or more sarcosines.

In some embodiments, peptone(s) comprise(s) about 0.1 to about 25% (by weight) of the inoculant composition. For example, inoculant compositions of the present disclosure may comprise about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of one or more peptones. In some embodiments, the peptone amount/concentration is about 0.5 to about 10% (by weight) of the inoculant composition.

In some embodiments, skim milk(s) comprise(s) about 0.1 to about 25% (by weight) of the inoculant composition. For example, inoculant compositions of the present disclosure may comprise about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of skim milk. In some embodiments, the skim milk amount/concentration is about 0.5 to about 10% (by weight) of the inoculant composition.

In some embodiments, oxidation control component(s) comprise(s) about 0.0001 to about 5% or more (by weight) of the composition. For example, inoculant compositions of the present disclosure may comprise about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more of one or more oxidation control components. In some embodiments, the amount/concentration of oxidation control components is about 0.005 to about 2% (by weight) of the composition.

In some embodiments, oxidation control component(s) is/are present in a concentration ranging from about $1\times10^{-20}$ M to about $1\times10^{-1}$ M. For example, one or more oxidation control components may be added at a concentration of $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more.

In some embodiments, inoculant compositions of the present disclosure comprise one or more commercial oxygen scavengers used in accordance with the manufacturer's recommended amounts/concentrations.

In some embodiments, hygroscopic polymer(s) comprise(s) about 0.1 to about 95% (by weight) of the inoculant composition. For example, inoculant compositions of the present disclosure may comprise about 5, 10, 15, 20, 25, 30, 35, 40, 45, 50, 55, 60, 65, 70, 75, 80, 85, 90, 95% or more (by weight) of one or more hygroscopic polymers. In some embodiments, the hygroscopic polymer amount/concentration is about 1 to about 65%, about 5% to about 20%, about 10% to about 25%, about 20% to about 50%, or about 30 to about 60% (by weight) of the inoculant composition.

In some embodiments, inoculant compositions of the present disclosure comprise one or more commercial polymers used in accordance with the manufacturer's recommended amounts/concentrations.

In some embodiments, the stabilizing compound(s) is/are present in an amount/concentration sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microorganisms in the inoculant composition remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when the inoculant composition is desiccated by about 5, 10, 15, 20, 25, 30, 35, 40, 45, 50, 55, 60, 65, 70, 75, 80, 85, 90, 95% or more.

In some embodiments, the stabilizing compound(s) is/are present in an amount/concentration sufficient to ensure that microorganisms remain viable in inoculant compositions of the present disclosure for at least 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more (e.g., at least 12, 16, 20, 24, 28, 32, 36, 40, 44, 48, 52, 56, 60, 64, 68, 72, 76, 80, 84, 88, 92, 96, 100, 104 weeks or more when stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity).

In some embodiments, the stabilizing compound(s) is/are present in an amount/concentration sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microorganisms in the inoculant composition survive following storage at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are present in an amount/concentration sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microorganisms in the inoculant composition survive following desiccation (of about 5, 10, 15, 20, 25, 30, 35, 40, 45, 50, 55, 60, 65, 70, 75, 80, 85, 90, 95% or more) and storage at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are present in an amount/concentration sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microorganisms in the inoculant composition survive following cryopreservation at or below −80° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are present in an amount/concentration sufficient to ensure that at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microbial spores therein survive when the inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are present in an amount/concentration sufficient to ensure that at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microbial spores therein survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are present in an amount/concentration sufficient to ensure that at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microbial spores therein survive when the inoculant composition is desiccated (by about 5, 10, 15, 20, 25, 30, 35, 40, 45, 50, 55, 60, 65, 70, 75, 80, 85, 90, 95% or more) stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are present in an amount/concentration sufficient to ensure that at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microbial spores therein survive following cryopreservation at or below −80° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are present in an amount/concentration sufficient to ensure that at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microbial spores therein survive when the inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing medium comprises two or more stabilizers that synergistically enhance the stability and/or survival of one or more microorganisms in the inoculant composition.

Stablizing compounds may be incorporated into inoculant compositions of the present disclosure in any suitable ratio(s). In some embodiments, inoculant compositions of the present disclosure comprise a maltodextrin:additional stabilizing compound ratio of about 1:99 to about 99:1 (by weight, based upon the respective weight percentages of the maltodextrin(s) and the additional stabilizing compound(s) in the inoculant composition). For example, inoculant compositions of the present disclosure may comprise a maltodextrin:additional stabilizing compound ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more, preferably about 45:55, 50:50, 55:45, 60:40, 65:35, 70:30, 75:25, 80:20, 85:15, 90:10, 95:5 or more. In some embodiments, the maltodextrin:additional stabilizing compound ratio is about 15:85 to about 85:15, optionally about 65:35. In some embodiments, inoculant compositions of the present disclosure comprise one or more maltodextrins (e.g., one or more maltodextrins (each and/or collectively) having a DEV of about 15 to about 20) and one or more disaccharides (e.g., maltose) in a maltodextrin: disaccharide ratio of about 15:85, about 35:65, about 65:35 or about 85:15.

In the interest of maximizing the teaching of the present application and without intending to be limited by any particular theory, applicants submit that maltodextrins may enhance the stability and survival of microorganisms in an inoculant composition by binding to the surfaces of the microorganisms and causing/allowing the cell membranes of the microorganisms to remain in a fluid state whilst the surrounding composition is in a glassy or rubbery state. The stabilizing effects of maltodextrins may be particularly beneficial in those instances in which an inoculant composition is desiccated (e.g., when an inoculant composition is coated on a seed and dried).

In such instances, maltodextrins may enhance the stability and survival of the microorganisms by two simultaneous mechanisms: 1) replacing membrane-bound water molecules as they are lost during the desiccation process, thereby allowing the cell membranes of the microorganisms to remain in a fluid state when the inoculant composition is desiccated; and 2) causing/allowing the composition surrounding the microorganisms to adopt a glassy or rubbery state when the inoculant composition is desiccated. The stabilizing effects of maltodextrins may be particularly beneficial when the inoculant composition is to be stored under high relative humidity (e.g., when a seed coated with an inoculant composition of the present disclosure is to be stored at 25, 30, 35, 40, 45, 50, 55, 60, 65, 70, 75, 80, 85% or more relative humidity).

In the interest of maximizing the teaching of the present application and without intending to be limited by any particular theory, applicants submit that the inclusion of additional stabilizing compounds, such as monosaccharides, disaccharides, oligosaccharides, malt extracts, peat extracts, betaines, prolines, sarcosines, peptones, oxidation control components and hygroscopic polymers, may further enhance the stability and/or survival of microorganisms in inoculant compositions comprising one or more maltodextrins. Thus, in some embodiments, inoculant compositions of the present disclosure comprise one or more maltodextrins as well as one or more monosaccharides, one or more disaccharides, one or more oligosaccharides, one or more malt extracts, one or more peat extracts, one or more betaines, one or more prolines, one or more sarcosines, one or more peptones, one or more oxidation control components and/or one or more hygroscopic polymers. In some embodiments, inoculant compositions of the present disclosure comprise one or more maltodextrins (e.g., one or more maltodextrins (each and/or collectively) having a DEV of about 15 to about 20); one or more disaccharides (e.g., maltose); and one or more microorganisms (e.g., one or more strains of *Bradyrhizobium*, such as BRADY; and/or one or more strains of *Penicillium*, such as PENI).

As noted above, maltodextrins may enhance the stability and survival of microorganisms in an inoculant composition by binding to the surfaces of the microorganisms and causing/allowing the cell membranes of the microorganisms to remain in a fluid state whilst the surrounding composition is in a glassy or rubbery state. Other constituents (and combinations of constituents) capable of replacing membrane-bound water molecules and stabilizing the inoculant composition in a glass or rubbery state may be used to achieve similar results.

In the interest of maximizing the teaching of the present application and without intending to be limited by any particular theory, applicants submit that betaines, proline and sarcosine may enhance the stability and survival of microorganisms in an inoculant composition by intercalating into the surfaces of the microorganisms and causing/allowing the cell membranes of the microorganisms to remain in a fluid state whilst the surrounding composition is in a glassy or rubbery state. The stabilizing effects of betaines, proline and sarcosine may be particularly beneficial in those instances in which an inoculant composition is desiccated (e.g., when an inoculant composition is coated on a seed and dried).

In some embodiments, the microorganism(s) and the stabilizing compound(s) are incorporated into one or more agriculturally acceptable carriers.

Inoculant compositions of the present disclosure may comprise any suitable agriculturally acceptable carrier(s), including, but not limited to, seed-compatible carriers, foliar-compatible carriers and soil-compatible carriers.

In some embodiments, inoculant compositions of the present disclosure comprise one or more liquid and/or gel carriers. For example, in some embodiments, inoculant compositions of the present disclosure comprise an aqueous solvent and/or a nonaqueous solvent.

In some embodiments, inoculant compositions of the present disclosure comprise one or more inorganic solvents, such as decane, dodecane, hexylether and nonane; one or more organic solvents, such as acetone, dichloromethane, ethanol, hexane, methanol, propan-2-ol and trichloroethylene; and/or water.

Non-limiting examples of liquid/gel carriers that may be useful in compositions of the present disclosure include oils (e.g., mineral oil, olive oil, peanut oil, soybean oil, sunflower oil), polyethylene glycols (e.g., PEG 200, PEG 300, PEG 400, etc.), propylene glycols (e.g., PPG-9, PPG-10, PPG-17, PPG-20, PPG-26, etc.), ethoxylated alcohols (e.g., TOMADOL® (Air Products and Chemicals, Inc., Allentown, Pa.), TERGITOL™ 15-S surfactants such as TERGITOL™15-S-9 (The Dow Chemical Company, Midland, Mich.), etc.), polysorbates (e.g. polysorbate 20, polysorbate 40, polysorbate 60, polysorbate 80, etc.), silicones (siloxanes, trisiloxanes, etc.) and combinations thereof.

Additional examples of solvents that may be included in inoculant compositions of the present disclosure may be found in BURGES, FORMULATION OF MICROBIAL BIOPESTICIDES: BENEFICIAL MICROORGANISMS, NEMATODES AND SEED TREATMENTS (Springer Science & Business Media) (2012); Inoue & Horikoshi, J. FERMENTATION BIOENG. 71(3):194 (1991).

In some embodiments, inoculant compositions of the present disclosure comprise one or more solid carriers. For example, in some embodiments, inoculant compositions of the present disclosure comprise one or more powders (e.g., wettable powders) and/or granules.

Non-limiting examples of solid carriers that may be useful in compositions of the present disclosure include clays (e.g., attapulgite clays, montmorillonite clay, etc.), peat-based powders and granules, freeze-dried powders, spray-dried powders, spray-freeze-dried powders and combinations thereof.

Additional examples of solid carriers that may be included in inoculant compositions of the present disclosure may be found in BURGES, FORMULATION OF MICROBIAL BIOPESTICIDES: BENEFICIAL MICROORGANISMS, NEMATODES AND SEED TREATMENTS (Springer Science & Business Media) (2012).

Carriers incorporated into inoculant compostions of the present disclosure may comprise a growth medium suitable for culturing one or more of the microorganisms in the inoculant composition. For example, in some embodiments, inoculant compositions of the present disclosure comprise Czapek-Dox medium, glycerol yeast extract, mannitol yeast extract, potato dextrose broth and/or YEM media.

Selection of appropriate carrier materials will depend on the intended application(s) and the microorganism(s) present in the inoculant composition. In some embodiments, the carrier material(s) will be selected to provide an inoculant composition in the form of a liquid, gel, slurry, or solid.

Carriers may be incorporated into inoculant compositions of the present disclosure in any suitable amount(s)/concentration(s). The absolute value of the carrier amount/concentration/dosage may be affected by factors such as the type, size and volume of material to which the composition will be applied, the type(s) of microorganisms in the composition, the number of microorganisms in the composition, the stability of the microorganisms in the composition and storage conditions (e.g., temperature, relative humidity, duration). Those skilled in the art will understand how to select an effective amount/concentration/dosage using routine dose-response experiments.

In some embodiments, inoculant compositions of the present disclosure comprise one or more commercial carriers used in accordance with the manufacturer's recommended amounts/concentrations.

As noted above, inoculant compositions of the present disclosure may comprise agriculturally beneficial microorganisms, such as diazotrophs, phosphate-solubilizing microorganisms and biopesticides. It is to be understood that other agriculturally beneficial constituents, such as biostimulants, microbial extracts, nutrients, pesticides and plant signal molecules, may also be included in inoculant compostions of the present disclosure.

Inoculant compositions of the present disclosure may comprise any suitable biostimulant(s), including, but not limited to, seaweed extracts (e.g., *Ascophyllum nodosum* extracts, such as alginate, *Ecklonia maxima* extracts, etc.), humic acids (e.g., potassium humate), fulvic acids, myo-inositol, glycine and combinations thereof.

Biostimulants may be incorporated into inoculant compositions of the present disclosure in any suitable amount(s)/concentration(s). The absolute value of the amount/concentration/dosage of biostimulant(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

In some embodiments, the biostimulant(s) comprise(s) about 0.001 to about 5% (by weight) of the inoculant composition. For example, inoculant compositions of the present disclosure may comprise about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more biostimulants. In some embodiments, the biostimulant(s) comprise(s) about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition.

Inoculant compositions of the present disclosure may comprise any suitable microbial extract(s), including, but not limited to, bacterial extracts, fungal extracts and combinations thereof. In some embodiments, inoculant compositions of the present disclosure comprise one or more extracts of media comprising one or more diazotrophs, phosphate-solubilizing microorganisms and/or biopesticides. In some embodiments, inoculant compositions of the present disclosure comprise one or more *Azospirillum* extracts (e.g., an extract of media comprising *A. brasilense* INTA Az-39), one or more *Bradyrhizobium* extracts (e.g., an extract of media comprising *B. elkanii* SEMIA 501, *B. elkanii* SEMIA 587, *B. elkanii* SEMIA 5019, *B. japonicum* NRRL B-50586 (also deposited as NRRL B-59565), *B. japonicum* NRRL B-50587 (also deposited as NRRL B-59566), *B. japonicum* NRRL B-50588 (also deposited as NRRL B-59567), *B. japonicum* NRRL B-50589 (also deposited as NRRL B-59568), *B. japonicum* NRRL B-50590 (also deposited as NRRL B-59569), *B. japonicum* NRRL B-50591 (also deposited as NRRL B-59570), *B. japonicum* NRRL B-50592 (also deposited as NRRL B-59571), *B. japonicum* NRRL B-50593 (also deposited as NRRL B-59572), *B. japonicum* NRRL B-50594 (also deposited as NRRL B-50493), *B. japonicum* NRRL B-50608, *B. japonicum* NRRL B-50609, *B. japonicum* NRRL B-50610, *B. japonicum* NRRL B-50611, *B. japonicum* NRRL B-50612, *B. japonicum* NRRL B-50726, *B. japonicum* NRRL B-50727, *B. japonicum* NRRL B-50728, *B. japonicum* NRRL B-50729, *B. japonicum* NRRL B-50730, *B. japonicum* SEMIA 566, *B. japonicum* SEMIA 5079, *B. japonicum* SEMIA 5080, *B. japonicum* USDA 6, *B. japonicum* USDA 110, *B. japonicum* USDA 122, *B. japonicum* USDA 123, *B. japonicum* USDA 127, *B. japonicum* USDA 129 and/or *B. japonicum* USDA 532C), one or more *Rhizobium* extracts (e.g., an extract of media comprising *R. leguminosarum* S012A-2), one or more *Sinorhizobium* extracts (e.g., an extract of media comprising *S. fredii* CCBAU114 and/or *S. fredii* USDA 205), one or more *Penicillium* extracts (e.g., an extract of media comprising *P. bilaiae* ATCC 18309, *P. bilaiae* ATCC 20851, *P. bilaiae* ATCC 22348, *P. bilaiae* NRRL 50162, *P. bilaiae* NRRL 50169, *P. bilaiae* NRRL 50776, *P. bilaiae* NRRL 50777, *P. bilaiae* NRRL 50778, *P. bilaiae* NRRL 50777, *P. bilaiae* NRRL 50778, *P. bilaiae* NRRL 50779, *P. bilaiae* NRRL 50780, *P. bilaiae* NRRL 50781, *P. bilaiae* NRRL 50782, *P. bilaiae* NRRL 50783, *P. bilaiae* NRRL 50784, *P. bilaiae* NRRL 50785, *P. bilaiae* NRRL 50786, *P. bilaiae* NRRL 50787, *P. bilaiae* NRRL 50788, *P. bilaiae* RS7B-SD1, *P. brevicompactum* AgRF18, *P. canescens* ATCC 10419, *P. expansum* ATCC 24692, *P. expansum* YT02, *P. fellatanum* ATCC 48694, *P. gaestrivorus* NRRL 50170, *P. glabrum* DAOM 239074, *P. glabrum* CBS 229.28, *P. janthinellum* ATCC 10455, *P. lanosocoeruleum* ATCC 48919, *P. radicum* ATCC 201836, *P. radicum* FRR 4717, *P. radicum* FRR 4719, *P. radicum* N93/47267 and/or *P. raistrickii* ATCC 10490), one or more *Pseudomonas* extracts (e.g., an extract of media comprising *P. jessenii* PS06), one or more acaridical, insecticidal and/or nematicidal extracts (e.g., an extract of media comprising *Bacillus firmus* 1-1582, *Bacillus mycoides* AQ726, NRRL B-21664; *Beauveria bassiana* ATCC-74040, *Beauveria bassiana* ATCC-74250, *Burkholderia* sp. A396 sp. nov. *rinojensis*, NRRL B-50319, *Chromobacterium subtsugae* NRRL B-30655, *Chromobacterium vaccinii* NRRL B-50880, *Flavobacterium* H492, NRRL B-50584, Metarhizium anisopliae F52 (also known as Metarhizium anisopliae strain 52, Metarhizium anisopliae strain 7, Metarhizium anisopliae strain 43 and Metarhizium anisopliae BIO-1020, TAE-001;

deposited as DSM 3884, DSM 3885, ATCC 90448, SD 170 and ARSEF 7711) and/or *Paecilomyces fumosoroseus* FE991), and/or one or more fungicidal extracts (e.g., an extract of media comprising *Ampelomyces quisqualis* AQ 10® (Intrachem Bio GmbH & Co. KG, Germany), *Aspergillus flavus* AFLA-GUARD® (Syngenta Crop Protection, Inc., CH), *Aureobasidium pullulans* BOTECTOR® (bioferm GmbH, Germany), *Bacillus pumilus* AQ717 (NRRL B-21662), *Bacillus pumilus* NRRL B-30087, *Bacillus* AQ175 (ATCC 55608), *Bacillus* AQ177 (ATCC 55609), *Bacillus subtilis* AQ713 (NRRL B-21661), *Bacillus subtilis* AQ743 (NRRL B-21665), *Bacillus amyloliquefaciens* FZB24, *Bacillus amyloliquefaciens* NRRL B-50349, *Bacillus amyloliquefaciens* TJ1000 (also known as 1BE, isolate ATCC BAA-390), *Bacillus thuringiensis* AQ52 (NRRL B-21619), *Candida oleophila* 1-82 (e.g., ASPIRE® from Ecogen Inc., USA), *Candida saitoana* BIOCURE® (in mixture with lysozyme; BASF, USA) and BIOCOAT® (ArystaLife Science, Ltd., Cary, N.C.), *Clonostachys rosea* f. *catenulata* (also referred to as *Gliocladium catenulatum*) J1446 (PRESTOP®, Verdera, Finland), *Coniothyrium minitans* CONTANS® (Prophyta, Germany), *Cryphonectria parasitica* (CNICM, France), *Cryptococcus albidus* YIELD PLUS® (Anchor Bio-Technologies, South Africa), *Fusarium oxysporum* BIOFOX® (from S.I.A.P.A., Italy) and FUSACLEAN® (Natural Plant Protection, France), *Metschnikowia fructicola* SHEMER® (Agrogreen, Israel), *Microdochium dimerum* ANTIBOT® (Agrauxine, France), *Muscodor albus* NRRL 30547, *Muscodor roseus* NRRL 30548, *Phlebiopsis gigantea* ROTSOP® (Verdera, Finland), *Pseudozyma flocculosa* SPORODEX® (Plant Products Co. Ltd., Canada), *Pythium oligandrum* DV74 (POLYVERSUM®, Remeslo SSRO, Biopreparaty, Czech Rep.), *Reynoutria sachlinensis* (e.g., REGALIA® from Marrone BioInnovations, USA), *Streptomyces* NRRL B-30145, *Streptomyces* M1064, *Streptomyces galbus* NRRL 30232, *Streptomyces lydicus* WYEC 108 (ATCC 55445), *Streptomyces violaceusniger* YCED 9 (ATCC 55660; DE-THATCH-9®, DECOMP-9® and THATCH CONTROL®, Idaho Research Foundation, USA), *Streptomyces* WYE 53 (ATCC 55750; DE-THATCH-9®, DECOMP-9® and THATCH CONTROL®, Idaho Research Foundation, USA), *Talaromyces flavus* V117b (PROTUS®, Prophyta, Germany), *Trichoderma asperellum* SKT-1 (ECO-HOPE®, Kumiai Chemical Industry Co., Ltd., Japan), *Trichoderma atroviride* LC52 (SENTINEL®, Agrimm Technologies Ltd, NZ), *Trichoderma harzianum* T-22 (PLANTSHIELD®, der Firma BioWorks Inc., USA), *Trichoderma harzianum* TH-35 (ROOT PRO®, from Mycontrol Ltd., Israel), *Trichoderma harzianum* T-39 (TRICHODEX®, Mycontrol Ltd., Israel; TRICHODERMA 2000®, Makhteshim Ltd., Israel), *Trichoderma harzianum* ICC012 and *Trichoderma viride* TRICHOPEL (Agrimm Technologies Ltd, NZ), *Trichoderma harzianum* ICC012 and *Trichoderma viride* ICC080 (REMEDIER® WP, Isagro Ricerca, Italy), *Trichoderma polysporum* and *Trichoderma harzianum* (BINAB®, BINAB Bio-Innovation AB, Sweden), *Trichoderma stromaticum* TRICOVAB® (C.E.P.L.A.C., Brazil), *Trichoderma virens* GL-21 (SOILGARD®, Certis LLC, USA), *Trichoderma virens* G1-3, ATCC 57678, *Trichoderma virens* G1-21 (Thermo Trilogy Corporation, Wasco, Calif.), *Trichoderma virens* G1-3 and *Bacillus amyloliquefaciens* FZB2, *Trichoderma virens* G1-3 and *Bacillus amyloliquefaciens* NRRL B-50349, *Trichoderma virens* G1-3 and *Bacillus amyloliquefaciens* TJ1000, *Trichoderma virens* G1-21 and *Bacillus amyloliquefaciens* FZB24, *Trichoderma virens* G1-21 and *Bacillus amyloliquefaciens* NRRL B-50349, *Trichoderma virens* G1-21 and *Bacillus amyloliquefaciens* TJ1000, *Trichoderma viride* TRIECO® (Ecosense Labs. (India) Pvt. Ltd., Indien, BIO-CURE® F from T. Stanes & Co. Ltd., Indien), *Trichoderma viride* TV1 (Agribiotec srl, Italy), *Trichoderma viride* ICC080, and/or *Ulocladium oudemansii* HRU3 (BOTRY-ZEN®, Botry-Zen Ltd, NZ)).

Microbial extracts may be incorporated into inoculant compositions of the present disclosure in any suitable amount(s)/concentration(s). The absolute value of the amount/concentration/dosage of microbial extract(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

In some embodiments, the microbial extract(s) comprise(s) about 0.001 to about 5% (by weight) of the inoculant composition. For example, inoculant compositions of the present disclosure may comprise about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more microbial extracts. In some embodiments, the microbial extract(s) comprise(s) about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition.

Inoculant compositions of the present disclosure may comprise any suitable nutrient(s), including, but not limited to, organic acids (e.g., acetic acid, citric acid, lactic acid, malic acid, taurine, etc.), macrominerals (e.g., phosphorous, calcium, magnesium, potassium, sodium, iron, etc.), trace minerals (e.g., boron, cobalt, chloride, chromium, copper, fluoride, iodine, iron, manganese, molybdenum, selenium, zinc, etc.), vitamins, (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_3$, vitamin $B_9$, vitamin $B_{12}$, choline) vitamin C, vitamin D, vitamin E, vitamin K, carotenoids (α-carotene, β-carotene, cryptoxanthin, lutein, lycopene, zeaxanthin, etc.) and combinations thereof. In some embodiments, inoculant compositions of the present disclosure comprise phosphorous, boron, chlorine, copper, iron, manganese, molybdenum and/or zinc.

Nutrients may be incorporated into inoculant compositions of the present disclosure in any suitable amount(s)/concentration(s). The absolute value of the amount/concentration/dosage of nutrient(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

In some embodiments, the nutrient(s) comprise(s) about 0.001 to about 5% (by weight) of the inoculant composition. For example, inoculant compositions of the present disclosure may comprise about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more nutrients. In some embodiments, the nutrient(s) comprise(s) about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition.

Inoculant compositions of the present disclosure may comprise any suitable pesticide(s), including, but not limited to, acaricides, fungicides, herbicides, insecticides and nematicides. In some embodiments, inoculant compositions of the present disclosure comprise one or more biopesticides (e.g., one or more biofungicides, bio insecticides and/or bionematicides).

Inoculant compositions of the present disclosure may comprise any suitable fungicide(s), including, but not limited to, biological fungicides and chemical fungicides. Fungicides may be selected so as to provide effective control against a broad spectrum of phytopathogenic fungi (and fungus-like organisms), including, but not limited to, soilborne fungi from the classes Ascomycetes, Basidiomycetes, Chytridiomycetes, Deuteromycetes (syn. Fungi imperfecti), Peronosporomycetes (syn. Oomycetes), Plasmodiophoromycetes and Zygomycetes.

In some embodiments, inoculant compositions of the present disclosure comprise a fungicide (or combination of fungicides) that is toxic to one or more strains of *Albugo* (e.g., *A. candida*), *Alternaria* (e.g., *A. alternata*), *Aspergillus* (e.g., *A. candidus*, *A. clavatus*, *A. flavus*, *A. fumigatus*, *A. parasiticus*, *A. restrictus*, *A. sojae*, *A. solani*), *Blumeria* (e.g., *B. graminis*), *Botrytis* (e.g., *B. cinerea*), *Cladosporum* (e.g., *C. cladosporioides*), *Colletotrichum* (e.g., *C. acutatum*, *C. boninense*, *C. capsici*, *C. caudatum*, *C. coccodes*, *C. crassipes*, *C. dematium*, *C. destructivum*, *C. fragariae*, *C. gloeosporioides*, *C. graminicola*, *C. kehawee*, *C. lindemuthianum*, *C. musae*, *C. orbiculare*, *C. spinaceae*, *C. sublineolum*, *C. trifolii*, *C. truncatum*), *Fusarium* (e.g., *F. graminearum*, *F. moniliforme*, *F. oxysporum*, *F. roseum*, *F. tricinctum*), *Helminthosporium, Magnaporthe* (e.g., *M. grisea*, *M. oryzae*), *Melamspora* (e.g., *M. lini*), *Mycosphaerella* (e.g., *M. graminicola*), *Nematospora, Penicillium* (e.g., *P. rugulosum*, *P. verrucosum*), *Phakopsora* (e.g., *P. pachyrhizi*), *Phomopsis, Phytiphtoria* (e.g., *P. infestans*), *Puccinia* (e.g., *P. graminis*, *P. striiformis*, *P. tritici*, *P. triticina*), *Pucivinia* (e.g., *P. graministice*), *Pythium, Pytophthora, Rhizoctonia* (e.g., *R. solani*), *Scopulariopsis, Selerotinia, Thielaviopsis* and/or *Ustilago* (e.g., *U. maydis*).

Additional examples of fungi that may be targeted by inoculant compositions of the present disclosure may be found in Bradley, *Managing Diseases*, in ILLINOIS AGRONOMY HANDBOOK (2008).

As discussed above, inoculant compositions of the present disclosure may comprise one or more biological fungicides (i.e., one or more microorganisms the presence and/or output of which is toxic to a fungus).

In some embodiments, inoculant compositions of the present disclosure comprise one or more chemical fungicides. For example, in some embodiments, inoculant compositions of the present disclosure comprise one or more aromatic hydrocarbons, benzimidazoles, benzthiadiazole, carboxamides, carboxylic acid amides, morpholines, phenylamides, phosphonates, quinone outside inhibitors (e.g. strobilurins), thiazolidines, thiophanates, thiophene carboxamides and/or triazoles.

Non-limiting examples of chemical fungicides that may be useful in inoculant compositions of the present disclosure include strobilurins, such as azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide; carboxamides, such as carboxanilides (e.g., benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(4'-trifluoromethylthiobiphenyl-2-yl)-3-difluoromethyl-1-methyl-1H-pyra-zole-4-carboxamide, N-(2-(1,3,3-trimethylbutyl)-phenyl)-1,3-dimethyl-5-fluoro-1H-pyrazole-4-carboxamide), carboxylic morpholides (e.g., dimethomorph, flumorph, pyrimorph), benzoic acid amides (e.g., flumetover, fluopicolide, fluopyram, zoxamide), carpropamid, dicyclomet, mandipromamid, oxytetracyclin, silthiofam and N-(6-methoxy-pyridin-3-yl) cyclopropanecarboxylic acid amide; azoles, such as triazoles (e.g., azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole) and imidazoles (e.g., cyazofamid, imazalil, pefurazoate, prochloraz, triflumizol); heterocyclic compounds, such as pyridines (e.g., fluazinam, pyrifenox (cf. D1b), 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine), pyrimidines (e.g., bupirimate, cyprodinil, diflumetorim, fenarimol, ferimzone, mepanipyrim, nitrapyrin, nuarimol, pyrimethanil), piperazines (e.g., triforine), pirroles (e.g., fenpiclonil, fludioxonil), morpholines (e.g., aldimorph, dodemorph, dodemorph-acetate, fenpropimorph, tridemorph), piperidines (e.g., fenpropidin); dicarboximides (e.g., fluoroimid, iprodione, procymidone, vinclozolin), non-aromatic 5-membered heterocycles (e.g., famoxadone, fenamidone, flutianil, octhilinone, probenazole, 5-amino-2-isopropyl-3-oxo-4-ortho-tolyl-2,3-dihydropyrazole-1-carbothioic acid S-allyl ester), acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo-[1,5-a]pyrimidine; benzimidazoles, such as carbendazim; and other active substances, such as guanidines (e.g., guanidine, dodine, dodine free base, guazatine, guazatine-acetate, iminoctadine), iminoctadine-triacetate and iminoctadine-tris(albesilate); antibiotics (e.g., kasugamycin, kasugamycin hydrochloride-hydrate, streptomycin, polyoxine and validamycin A), nitrophenyl derivates (e.g., binapacryl, dicloran, dinobuton, dinocap, nitrothal-isopropyl, tecnazen). organometal compounds (e.g., fentin salts, such as fentin-acetate, fentin chloride, fentin hydroxide); sulfur-containing heterocyclyl compounds (e.g., dithianon, isoprothiolane), organophosphorus compounds (e.g., edifenphos, fosetyl, fosetyl-aluminum, iprobenfos, phosphorus acid and its salts, pyrazophos, tolclofos-methyl), organochlorine compounds (e.g., chlorothalonil, dichlofluanid, dichlorophen, flusulfamide, hexachlorobenzene, pencycuron, pentachlorphenole and its salts, phthalide, quintozene, thiophanate-methyl, thiophanate, tolylfluanid, N-(4-chloro-2-nitro-phenyl)-N-ethyl-4-methyl-benzenesulfonamide) and inorganic active substances (e.g., Bordeaux mixture, copper acetate, copper hydroxide, copper oxychloride, basic copper sulfate, sulfur) and combinations thereof. In some embodiments, inoculant compositions of the present disclosure comprise acibenzolar-S-methyl, azoxystrobin, benalaxyl, bixafen, boscalid, carbendazim, cyproconazole, dimethomorph, epoxiconazole, fludioxonil, fluopyram, fluoxastrobin, flutianil, flutolanil, fluxapyroxad, fosetyl-Al, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thiabendazole, thifluzamide, thiophanate, tolclofos-methyl, trifloxystrobin and triticonazole. In some embodiments, inoculant compositions of the present disclosure comprise azoxystrobin, pyraclostrobin, fluoxastrobin, trifloxystrobin, ipconazole, prothioconazole, sedaxane, fludioxonil, metalaxyl, mefenoxam, thiabendazole, fluxapyroxad and/or fluopyram.

Additional examples of fungicides that may be included in inoculant compositions of the present disclosure may be found in Bradley, Managing Diseases, in ILLINOIS AGRONOMY HANDBOOK (2008).

Inoculant compositions of the present disclosure may comprise any suitable herbicide(s), including, but not limited to, biological herbicides and chemical herbicides. Herbicides may be selected so as to provide effective control against a broad spectrum of plants, including, but not limited to, plants from the families Asteraceae, Caryophyllaceae, Poaceae and Polygonaceae.

In some embodiments, inoculant compositions of the present disclosure comprise an herbicide (or combination of herbicides) that is toxic to one or more strains of *Echinochloa* (e.g., *E. brevipedicellata, E. callopus, E. chacoensis, E. colona, E. crus-galli, E. crus-pavonis, E. elliptica, E. esculenta, E. frumentacea, E. glabrescens, E. haploclada, E. helodes, E. holciformis, E. inundata, E. jaliscana, E. Jubata, E. kimberleyensis, E. lacunaria, E. macrandra, E. muricata, E. obtusiflora, E. oplismenoides, E. orzyoides, E. paludigena, E. picta, E. pithopus, E. polystachya, E. praestans, E. pyramidalis, E. rotundiflora, E. stagnina, E. telmatophila, E. turneriana, E. ugandensis, E. walteri*), *Fallopia* (e.g., *F. baldschuanica, F. japonica, F. sachalinensis*), *Stellaria* (e.g., *S. media*) and/or *Taraxacum* (e.g., *T. albidum, T. aphrogenes, T. brevicorniculatum, T. californicum, T. centrasiatum, T. ceratophorum, T. erythrospermum, T. farinosum, T. holmboei, T. japonicum, T. kok-saghyz, T. laevigatum T. officinale, T. platycarpum*).

Additional species of plants that may be targeted by inoculant compositions of the present disclosure may be found in Hager, *Weed Management*, in ILLINOIS AGRONOMY HANDBOOK (2008) and LOUX ET AL., WEED CONTROL GUIDE FOR OHIO, INDIANA AND ILLINOIS (2015).

As discussed above, inoculant compositions of the present disclosure may comprise one or more biological herbicides (i.e., one or more microorganisms the presence and/or output of which is toxic to a plant).

In some embodiments, inoculant compositions of the present disclosure comprise one or more chemical herbicides. For example, in some embodiments, inoculant compositions of the present disclosure comprise one or more acetyl CoA carboxylase (ACCase) inhibitors, acetolactate synthase (ALS) inhibitors, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, nucleic acid inhibitors and/or one or more salts, esters, racemic mixtures and/or resolved isomers thereof. Non-limiting examples of chemical herbicides that may be useful in inoculant compositions of the present disclosure include 2,4-dichlorophenoxyacetic acid (2,4-D), 2,4,5-trichlorophenoxyacetic acid (2,4,5-T), ametryn, amicarbazone, aminocyclopyrachlor, acetochlor, acifluorfen, alachlor, atrazine, azafenidin, bentazon, benzofenap, bifenox, bromacil, bromoxynil, butachlor, butafenacil, butroxydim, carfentrazone-ethyl, chlorimuron, chlorotoluro, clethodim, clodinafop, clomazone, cyanazine, cycloxydim, cyhalofop, desmedipham, desmetryn, dicamba, diclofop, dimefuron, diuron, dithiopyr, fenoxaprop, fluazifop, fluazifop-P, fluometuron, flufenpyr-ethyl, flumiclorac-pentyl, flumioxazin, fluoroglycofen, fluthiacet-methyl, fomesafe, fomesafen, glyphosate, glufosinate, haloxyfop, hexazinone, imazamox, imazaquin, imazethapyr, ioxynil, isoproturon, isoxaflutole, lactofen, linuron, mecoprop, mecoprop-P, mesotrion, metamitron, metazochlor, methibenzuron, metolachlor (and S-metolachlor), metoxuron, metribuzin, monolinuron, oxadiargyl, oxadiazon, oxyfluorfen, phenmedipham, pretilachlor, profoxydim, prometon, prometry, propachlor, propanil, propaquizafop, propisochlor, pyraflufen-ethyl, pyrazon, pyrazolynate, pyrazoxyfen, pyridate, quizalofop, quizalofop-P (e.g., quizalofop-ethyl, quizalofop-P-ethyl, clodinafop-propargyl, cyhalofop-butyl, diclofop-methyl, fenoxaprop-P-ethyl, fluazifop-P-butyl, haloxyfop-methyl, haloxyfop-R-methyl), saflufenacil, sethoxydim, siduron, simazine, simetryn, sulcotrione, sulfentrazone, tebuthiuron, tembotrione, tepraloxydim, terbacil, terbumeton, terbuthylazine, thaxtomin (e.g., the thaxtomins described in U.S. Pat. No. 7,989,393), thenylchlor, tralkoxydim, triclopyr, trietazine, tropramezone, salts and esters thereof; racemic mixtures and resolved isomers thereof and combinations thereof. In some embodiments, inoculant compositions of the present disclosure comprise acetochlor, clethodim, dicamba, flumioxazin, fomesafen, glyphosate, glufosinate, mesotrione, quizalofop, saflufenacil, sulcotrione, S-3100 and/or 2,4-D. In some embodiments, inoculant compositions of the present disclosure comprise glyphosate, glufosinate, dicamba, 2,4-D, acetochlor, metolachlor, pyroxasulfone, flumioxazin, fomesafen, lactofen, metribuzin, mesotrione, and/or ethyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate.

Additional examples of herbicides that may be included in inoculant compositions of the present disclosure may be found in Hager, *Weed Management*, in ILLINOIS AGRONOMY HANDBOOK (2008) and LOUX ET AL., WEED CONTROL GUIDE FOR OHIO, INDIANA AND ILLINOIS (2015).

Inoculant compositions of the present disclosure may comprise any suitable insecticide(s), including, but not limited to, biological insecticides and chemical insecticides. Insecticides may be selected so as to provide effective control against a broad spectrum of insects, including, but not limited to, insects from the orders Coleoptera, Dermaptera, Diptera, Hemiptera, Homoptera, Hymenoptera, Lepidoptera, Orthoptera and Thysanoptera. For example, inoculant compositions of the present disclosure may comprise one or more insecticides toxic to insects from the families Acrididae, Aleytodidae, Anobiidae, Anthomyiidae, Aphididae, Bostrichidae, Bruchidae, Cecidomyiidae, Cerambycidae, Cercopidae, Chrysomelidae, Cicadellidae, Coccinellidae, Cryllotalpidae, Cucujidae, Curculionidae, Dermestidae, Elateridae, Gelechiidae, Lygaeidae, Meloidae, Membracidae, Miridae, Noctuidae, Pentatomidae, Pyralidae, Scarabaeidae, Silvanidae, Spingidae, Tenebrionidae and/or Thripidae.

In some embodiments, inoculant compositions of the present disclosure comprise an insecticide (or combination of insecticides) that is toxic to one or more species of *Acalymma, Acanthaoscelides* (e.g., *A. obtectus*), *Anasa* (e.g., *A. tristis*), *Anastrepha* (e.g., *A. ludens*), *Anoplophora* (e.g., *A. glabripennis*), *Anthonomus* (e.g., *A. eugenii*), *Acyrthosiphon* (e.g., *A. pisum*), *Bactrocera* (e.g., *B. dosalis*), *Bemisia* (e.g., *B. argentifolii, B. tabaci*), *Brevicoryne* (e.g., *B. brassicae*), *Bruchidius* (e.g., *B. atrolineatus*), *Bruchus* (e.g., *B. atomarius, B. dentipes, B. lentis, B. pisorum* and/or *B. rufipes*), *Callosobruchus* (e.g., *C. chinensis, C. maculatus, C. rhodesianus, C. subinnotatus, C. theobromae*), *Caryedon* (e.g., *C. serratus*), *Cassadinae, Ceratitis* (e.g., *C. capitata*), *Chrysomelinae, Circulifer* (e.g., *C. tenellus*), *Criocerinae, Cryptocephalinae, Cryptolestes* (e.g., *C. ferrugineus, C. pusillis, C. pussilloides*), *Cylas* (e.g., *C. formicarius*), *Delia* (e.g., *D. antiqua*), *Diabrotica, Diaphania* (e.g., *D. nitidalis*), *Diaphorina* (e.g., *D. citri*), *Donaciinae, Ephestia* (e.g, *E. cautella, E. elutella, E., keuhniella*), *Epilachna* (e.g., *E. varivestris*), *Epiphyas* (e.g., *E. postvittana*), *Eumolpinae, Galerucinae, Helicoverpa* (e.g., *H. zea*), *Heteroligus* (e.g., *H. meles*), *Iobesia* (e.g., *I. botrana*), *Lamprosomatinae, Lasioderma* (e.g., *L. serricorne*), *Leptinotarsa* (e.g., *L. decemlineata*), *Leptoglossus, Liriomyza* (e.g., *L. trifolii*), *Manducca, Melittia* (e.g., *M. cucurbitae*), *Myzus* (e.g., *M. persicae*), *Nezara* (e.g., *N. viridula*), *Orzaephilus* (e.g., *O. merator, O. surinamensis*), *Ostrinia* (e.g., *O. nubilalis*), *Phthorimaea* (e.g., *P. operculella*), *Pieris* (e.g., *P. rapae*), *Plodia* (e.g., *P. interpunctella*), *Plutella* (e.g., *P. xylostella*), *Popillia* (e.g., *P. japonica*), *Prostephanus* (e.g., *P. truncates*), *Psila, Rhizopertha* (e.g., *R. dominica*), *Rhopalosiphum* (e.g., *R. maidis*), *Sagrinae, Solenopsis* (e.g., *S. Invicta*), *Spilopyrinae, Sitophilus* (e.g., *S. granaries, S. oryzae* and/or *S. zeamais*), *Sitotroga* (e.g., *S. cerealella*), *Spodoptera* (e.g., *S. frugiperda*), *Stegobium* (e.g., *S. paniceum*), *Synetinae, Tenebrio* (e.g., *T. malens* and/or *T. molitor*), *Thrips* (e.g., *T. tabaci*), *Trialeurodes* (e.g., *T. vaporariorum*), *Tribolium* (e.g., *T. castaneum* and/or *T. confusum*), *Trichoplusia* (e.g., *T. ni*), *Trogoderma* (e.g., *T. granarium*) and *Trogossitidae* (e.g., *T. mauritanicus*).

Additional species of insects that may be targeted by inoculant compositions of the present disclosure may be found in Capinera, Handbook of Vegetable Pests (2001) and Steffey and Gray, *Managing Insect Pests*, in Illinois Agronomy Handbook (2008).

Inoculant compositions of the present disclosure may comprise any suitable nematicide(s) including, but not limited to, biological nematicides and chemical nematicides. Nematicides may be selected so as to provide effective control against a broad spectrum of nematodes, including, but not limited to, phytoparasitic nematodes from the classes Chromadorea and Enoplea.

In some embodiments, inoculant compositions of the present disclosure comprise a nematicide (or combination of nematicides) that is toxic to one or more strains of *Anguina, Aphelenchoides, Belonolaimus, Bursaphelenchus, Ditylenchus, Globodera, Helicotylenchus, Heterodera, Hirschmanniella, Meloidogyne, Naccobus, Pratylenchus, Radopholus, Rotylenshulus, Trichodorus, Tylenchulus* and/or *Xiphinema*.

Additional examples of nematodes that may be targeted by inoculant compositions of the present disclosure may be found in Capinera, Handbook of Vegetable Pests (2001) and Niblack, *Nematodes*, in Illinois Agronomy Handbook (2008).

As discussed above, inoculant compositions of the present disclosure may comprise one or more biological insecticides and/or nematicides (i.e., one or more microorganisms the presence and/or output of which is toxic to an insect and/or nematode).

In some embodiments, inoculant compositions of the present disclosure comprise one or more chemical insecticides and/or nematicides. For example, in some embodiments, inoculant compositions of the present disclosure comprise one or more carbamates, diamides, macrocyclic lactones, neonicotinoids, organophosphates, phenylpyrazoles, pyrethrins, spinosyns, synthetic pyrethroids, tetronic acids and/or tetramic acids.

Non-limiting examples of chemical insecticides and nematicides that may be useful in inoculant compositions of the present disclosure include acrinathrin, alpha-cypermethrin, betacyfluthrin, cyhalothrin, cypermethrin, deltamethrin, csfenvalcrate, etofenprox, fenpropathrin, fenvalerate, flucythrinate, fosthiazate, lambda-cyhalothrin, gamma-cyhalothrin, permethrin, tau-fluvalinate, transfluthrin, zeta-cypermethrin, cyfluthri, bifenthrin, tefluthrin, eflusilanat, fubfenprox, pyrethrin, resmethrin, imidacloprid, acetamiprid, thiamethoxam, nitenpyram, thiacloprid, dinotefuran, clothianidin, imidaclothiz, chlorfluazuron, diflubenzuron, lufenuron, teflubenzuron, triflumuron, novaluron, flufenoxuron, hexaflumuron, bistrifluoron, noviflumuron, buprofezin, cyromazine, methoxyfenozide, tebufenozide, halofenozide, chromafenozide, endosulfan, fipronil, ethiprole, pyrafluprole, pyriprole, flubendiamide, chlorantraniliprole (e.g., Rynaxypyr), cyazypyr, emamectin, emamectin benzoate, abamectin, ivermectin, milbemectin, lepimectin, tebufenpyrad, fenpyroximate, pyridaben, fenazaquin, pyrimidifen, tolfenpyrad, dicofol, cyenopyrafen, cyflumetofen, acequinocyl, fluacrypyrin, bifenazate, diafenthiuron, etoxazole, clofentezine, spinosad, triarathen, tetradifon, propargite, hexythiazox, bromopropylate, chinomethionat, amitraz, pyrifluquinazon, pymetrozine, flonicamid, pyriproxyfen, diofenolan, chlorfenapyr, metaflumizone, indoxacarb, chlorpyrifos, spirodiclofen, spiromesifen, spirotetramat, pyridalyl, spinctoram, acephate, triazophos, profenofos, oxamyl, spinetoram, fenamiphos, fenamipclothiahos, 4-{[(6-chloropyrid-3-yl)methyl](2,2-difluoroethyl)amino}furan-2(5H)-one, cadusaphos, carbaryl, carbofuran, ethoprophos, thiodicarb, aldicarb, aldoxycarb, metamidophos, methiocarb, sulfoxaflor, cyantraniliprole and tioxazofen and combinations thereof. In some embodiments, inoculant compositions of the present disclosure comprise abamectin, aldicarb, aldoxycarb, bifenthrin, carbofuran, chlorantraniliporle, chlothianidin, cyfluthrin, cyhalothrin, cypermethrin, cyantraniliprole, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam and/or thiodicarb. In some embodiments, inoculant compositions of the present disclosure comprise an insecticide selected from the group consisting of clothianidin, thiamethoxam, imidacloprid, cyantraniliprole, chlorantraniliprole, fluopyram and tioxazafen.

Additional examples of insecticides and nematicides that may be included in inoculant compositions of the present disclosure may be found in Steffey and Gray, *Managing Insect Pests*, in ILLINOIS AGRONOMY HANDBOOK (2008) and Niblack, *Nematodes*, in ILLINOIS AGRONOMY HANDBOOK (2008).

Pesticides may be incorporated into inoculant compositions of the present disclosure in any suitable amount(s)/concentration(s). The absolute value of the amount/concentration/dosage of pesticide(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

In some embodiments, inoculant compositions of the present disclosure comprise one or more commercial pesticides used in accordance with the manufacturer's recommended amounts/concentrations.

Inoculant compositions of the present disclosure may comprise any suitable plant signal molecule(s), including, but not limited to, lipo-chitooligosaccharides (LCOs), chitooligosaccharides (COs), chitinous compounds, flavonoids, jasmonic acid or derivatives thereof, linoleic acid or derivatives thereof, linolenic acid or derivatives thereof and karrikins.

Inoculant compositions of the present disclosure may comprise any suitable LCO(s).

LCOs, sometimes referred to as symbiotic nodulation (Nod) signals or Nod factors, consist of an oligosaccharide backbone of β-1,4-linked N-acetyl-D-glucosamine ("GlcNAc") residues with an N-linked fatty acyl chain condensed at the non-reducing end. LCOs differ in the number of GlcNAc residues in the backbone, in the length and degree of saturation of the fatty acyl chain and in the substitutions of reducing and non-reducing sugar residues. See, e.g., Denarie, et al., ANN. REV. BIOCHEM. 65:503 (1996); Hamel, et al., PLANTA 232:787 (2010); Prome, et al., PURE & APPL. CHEM. 70(1):55 (1998).

In some embodiments, inoculant compositions of the present disclosure comprise one or more LCOs represented by formula I:

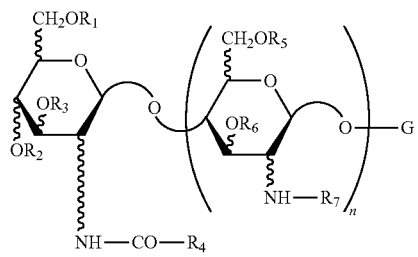

in which G is a hexosamine which can be substituted, for example, by an acetyl group on the nitrogen, a sulfate group, an acetyl group and/or an ether group on an oxygen; $R_1$, $R_2$, $R_3$, $R_5$, $R_8$ and $R_7$, which may be identical or different, represent H, $CH_3$ CO—, $C_x H_y$ CO— where x is an integer between 0 and 17 and y is an integer between 1 and 35, or any other acyl group such as, for example, a carbamoyl; $R_4$ represents a saturated or mono-, di- or tri-unsaturated aliphatic chain containing at least 12 carbon atoms; and n is an integer between 1 and 4.

In some embodiments, inoculant compositions of the present disclosure comprise one or more LCOs represented by formula II:

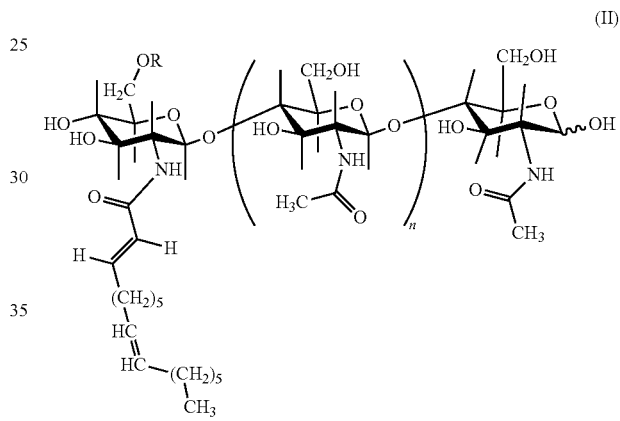

in which R represents H or $CH_3$ CO— and n is equal to 2 or 3. See, e.g., U.S. Pat. No. 5,549,718. A number of *Bradyrhizobium japonicum*-derived LCOs have also been described, including BjNod-V ($C_{18:1}$), BjNod-V (Ac, $C_{18:1}$), BjNod-V ($C_{16:1}$) and BjNod-V (Ac, $C_{16:0}$) (with "V" indicating the presence of five N-acetylglucosamines, "Ac" an acetylation, the number following the "C" indicating the number of carbons in the fatty acid side chain and the number following the ":" indicating the number of double bonds). See, e.g., U.S. Pat. Nos. 5,175,149 and 5,321,011. Additional LCOs obtained from bacterial strains include NodRM, NodRM-1, NodRM-3. When acetylated (the R=$CH_3$ CO—), they become AcNodRM-1 and AcNodRM-3, respectively (U.S. Pat. No. 5,545,718).

In some embodiments, inoculant compositions of the present disclosure comprise one or more LCOs represented by formula III:

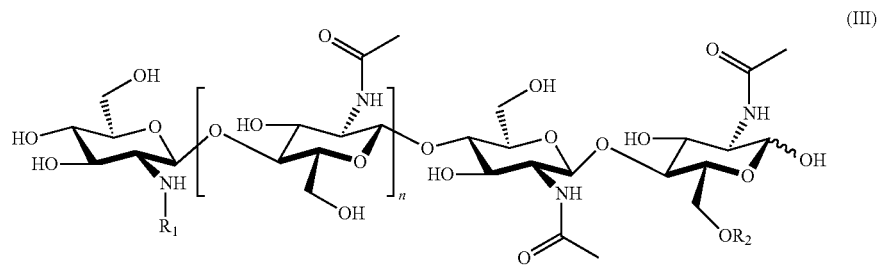

(III)

in which n=1 or 2; $R_1$ represents C16, C16:0, C16:1, C16:2, C18:0, C18:1Δ9Z or C18:1Δ11Z; and $R_2$ represents hydrogen or $SO_3H$.

LCOs included in compositions and methods of the present disclosure may be obtained from any suitable source.

In some embodiments, the LCO is obtained (i.e., isolated and/or purified) from a bacterial strain. For example, in some embodiments, inoculant compositions of the present disclosure comprise one or more LCOs obtained from a of *Azorhizobium, Bradyrhizobium* (e.g., *B. japonicum*), *Mesorhizobium, Rhizobium* (e.g., *R. leguminosarum*), or *Sinorhizobium* (e.g., *S. meliloti*).

In some embodiments, the LCO is obtained (i.e., isolated and/or purified) from a mycorrhizal fungus. For example, in some embodiments, inoculant compositions of the present disclosure comprise one or more LCOs obtained from a strain of Glomerocycota (e.g., *Glomus intraradicus*). See, e.g., WO 2010/049751 (in which the LCOs are referred to as "Myc factors").

In some embodiments, the LCO is synthetic. For example, in some embodiments, inoculant compositions of the present disclosure comprise one or more of the synthetic LCOs described in WO 2005/063784, WO 2007/117500 and/or WO 2008/071674. In some embodiments, the synthetic LCO contains one or more modifications or substitutions, such as those described in Spaink, Crit. Rev. Plant Sci. 54:257 (2000) and D'Haeze, supra. LCOs and precursors for the construction of LCOs (e.g., COs, which are themselves useful as plant signal molecules) may be synthesized by genetically engineered organisms. See, e.g., Samain et al., Carbohydrate Res. 302:35 (1997); Cottaz, et al., Meth. Eng. 7(4):311 (2005); and Samain, et al., J. Biotechnol. 72:33 (1999) (e.g., FIG. 1 therein, which shows structures of COs that can be made recombinantly in *E. coli* harboring different combinations of genes nodBCHL).

Further examples of LCOs (and derivatives thereof) that may be useful in compositions and methods of the present disclosure are provided below as formula IV:

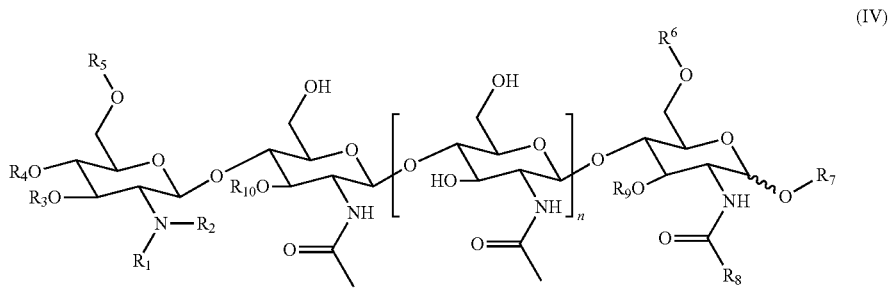

(IV)

in which $R_1$ represents C14:0, 3OH—C14:0, iso-C15:0, C16:0, 3-OH—C16:0, iso-C15:0, C16:1, C16:2, C16:3, iso-C17:0, iso-C17:1, C18:0, 3OH—C18:0, C18:0/3-OH, C18:1, OH—C18:1, C18:2, C18:3, C18:4, C19:1 carbamoyl, C20:0, C20:1, 3-OH—C20:1, C20:1/3-OH, C20:2, C20:3, C22:1 and C18-26(ω-1)-OH (which according to D'Haeze, et al., Glycobiology 12:79R-105R (2002), includes C18, C20, C22, C24 and C26 hydroxylated species and C16:1Δ9, C16:2 (Δ2,9) and C16:3 (Δ2,4,9)); $R_2$ represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, $SO_3H$, sulfate ester, 3-0-S-2-0-MeFuc, 2-0-MeFuc and 4-0-AcFuc; $R_7$ represents hydrogen, mannosyl or glycerol; $R_8$ represents hydrogen, methyl, or —$CH_2OH$; $R_9$ represents hydrogen, arabinosyl, or fucosyl; $R_{10}$ represents hydrogen, acetyl or fucosyl; and n represents 0, 1, 2 or 3. Naturally occurring LCOs embraced by this structure are described in D'Haeze, et al., supra.

Further examples of LCOs (and derivatives thereof) that may be useful in compositions and methods of the present disclosure are provided below as structures V-XXXIII:
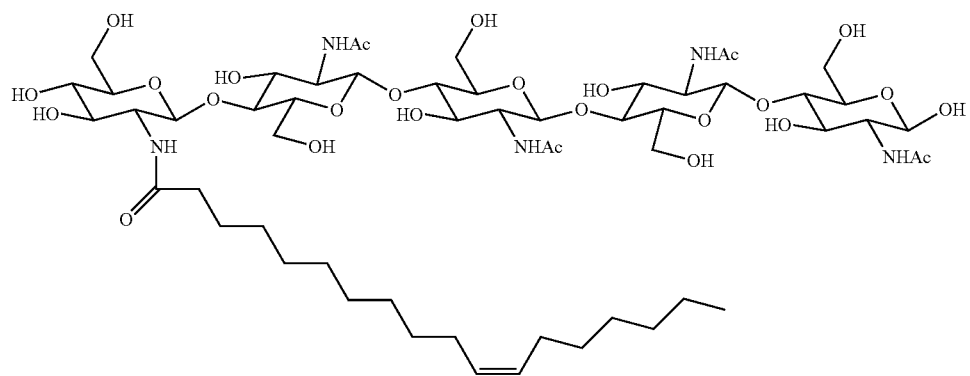
(V)
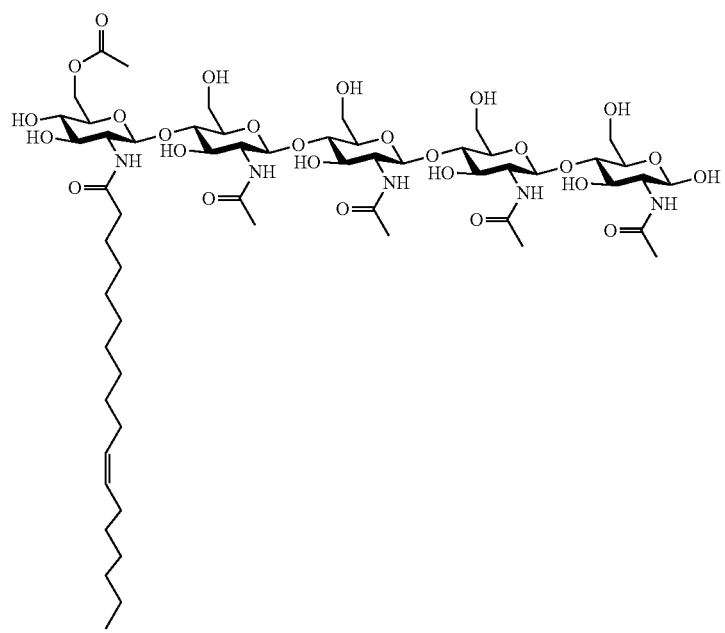
(VI)
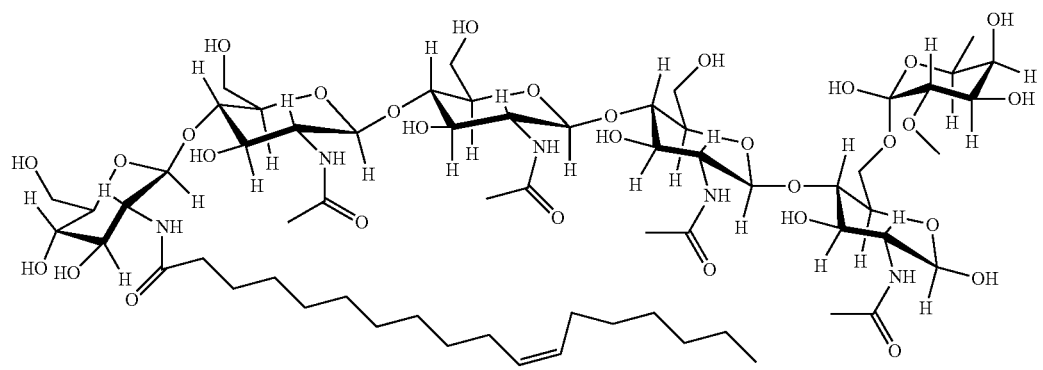
(VII)

-continued
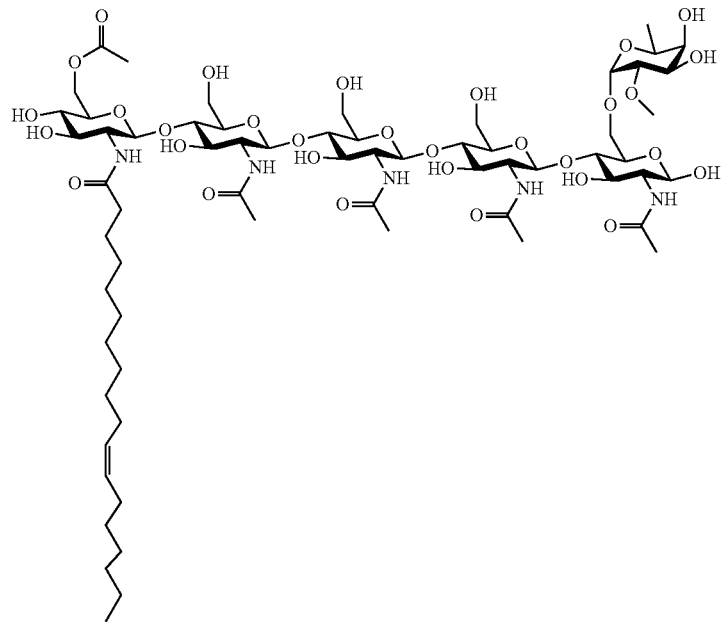
(VIII)
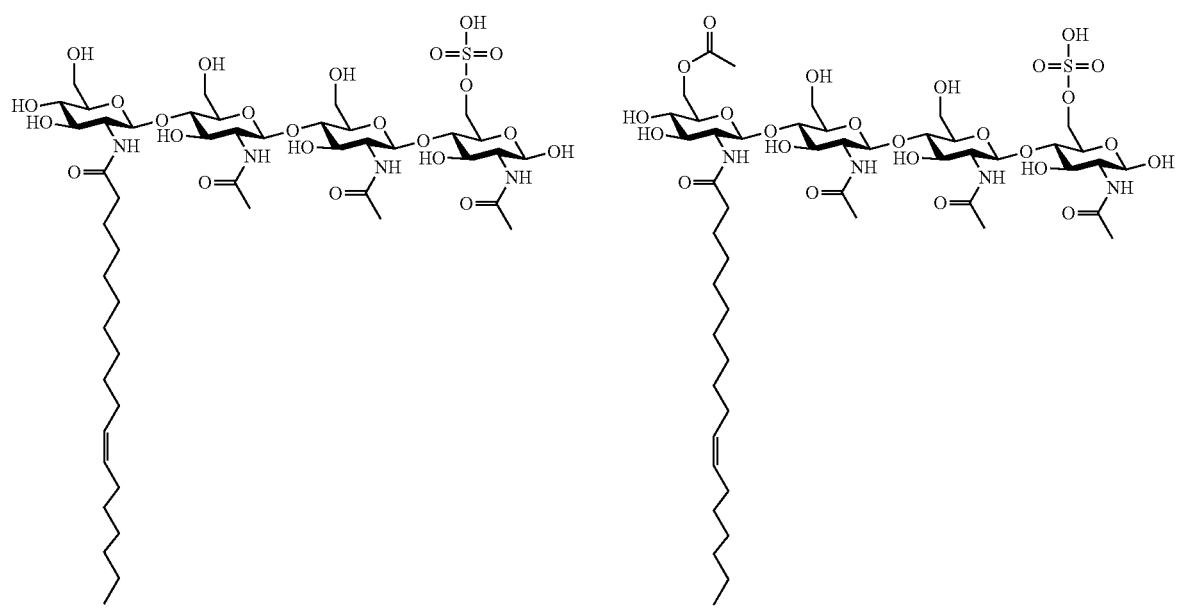
(IX) (X)
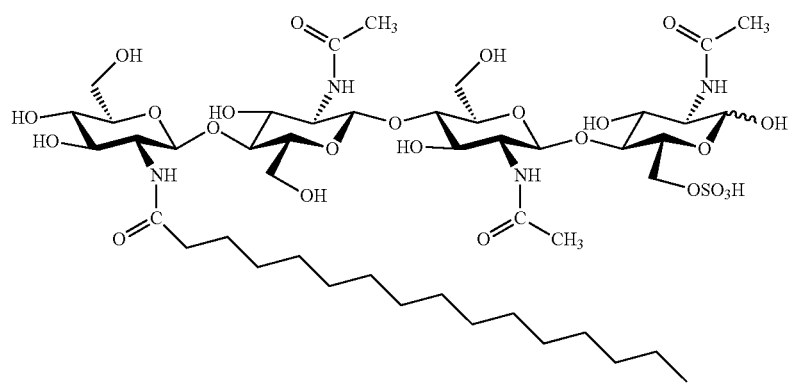
(XI)

-continued
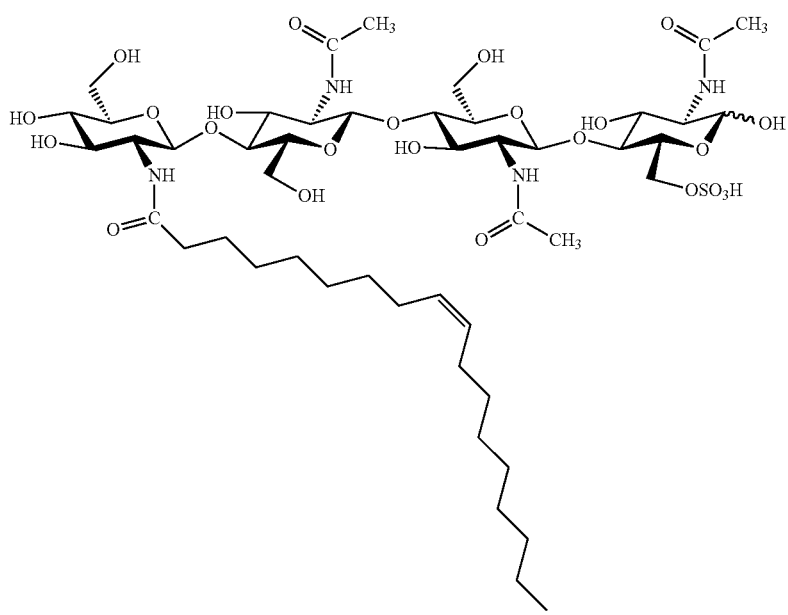
(XII)
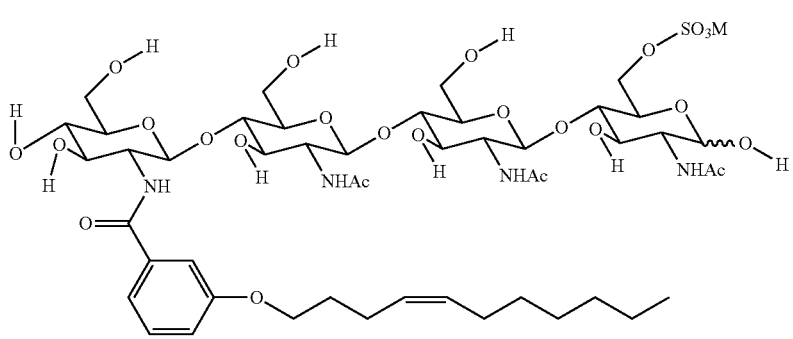
(XIII)
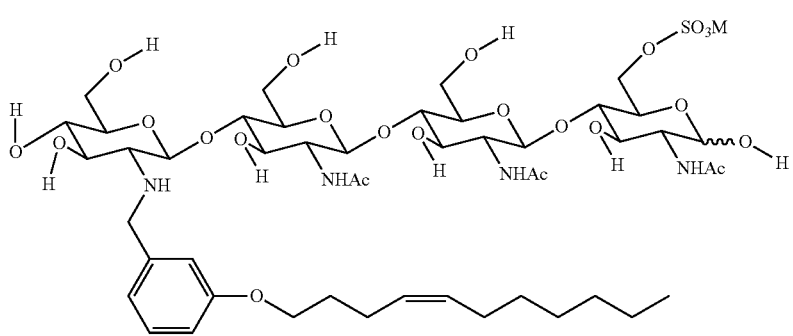
(XIV)
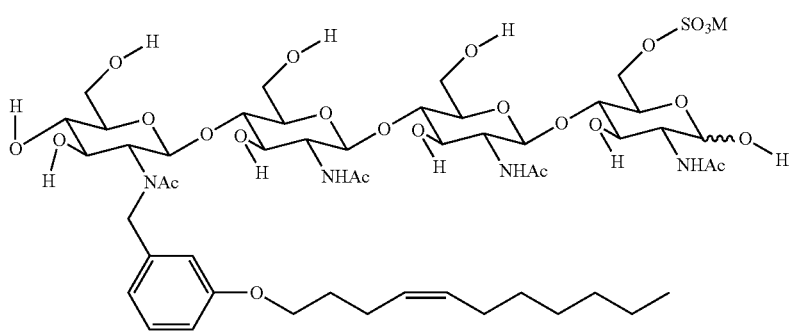
(XV)

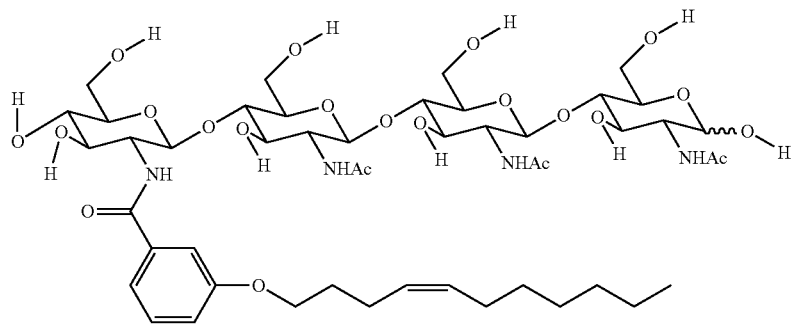
(XVI)
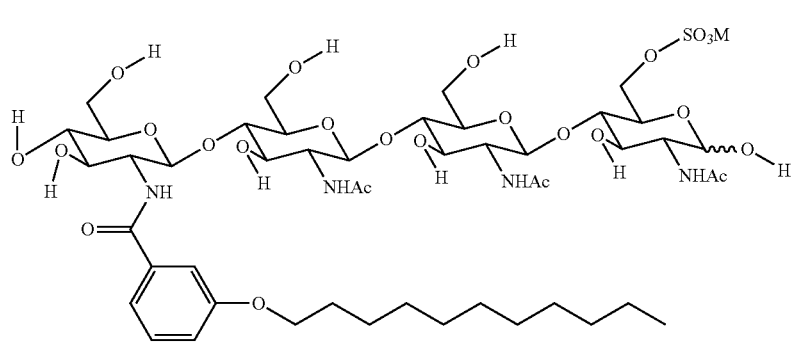
(XVII)
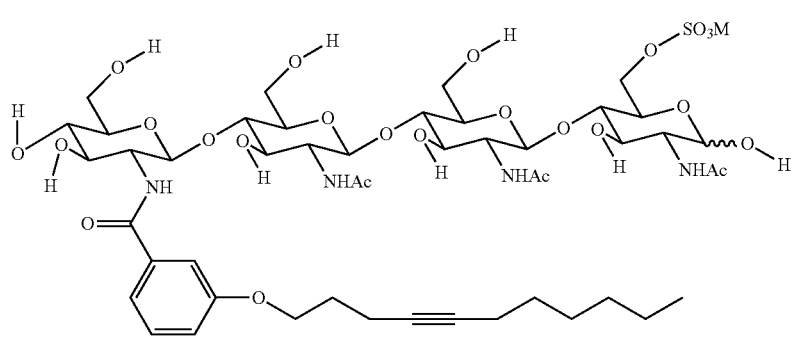
(XVIII)
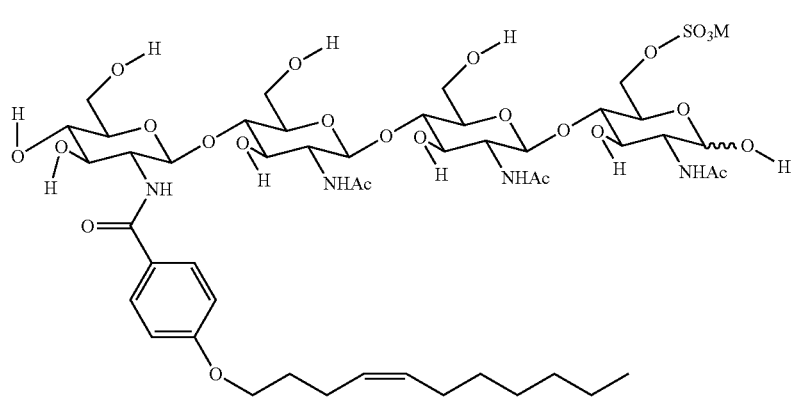
(XIX)

-continued
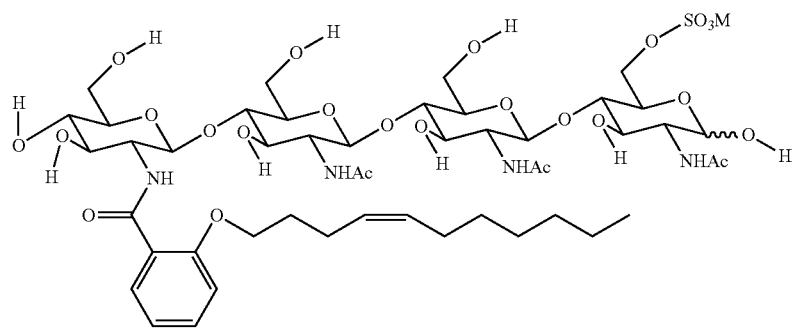
(XX)
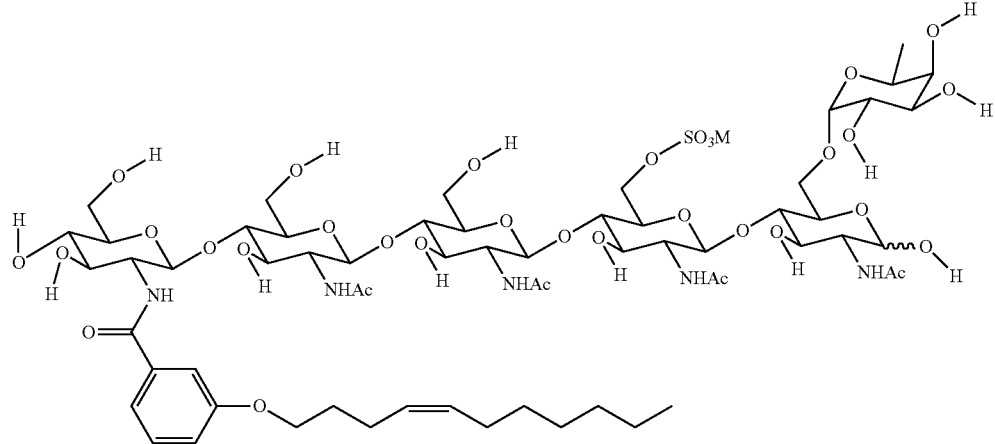
(XXI)
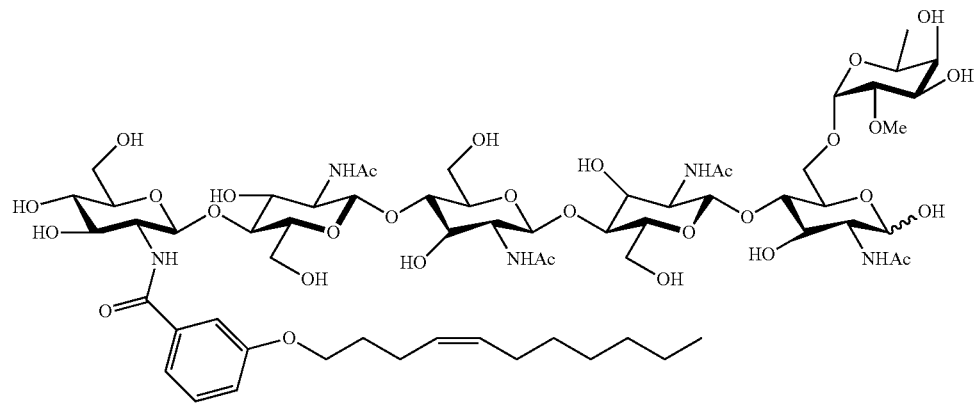
(XXII)
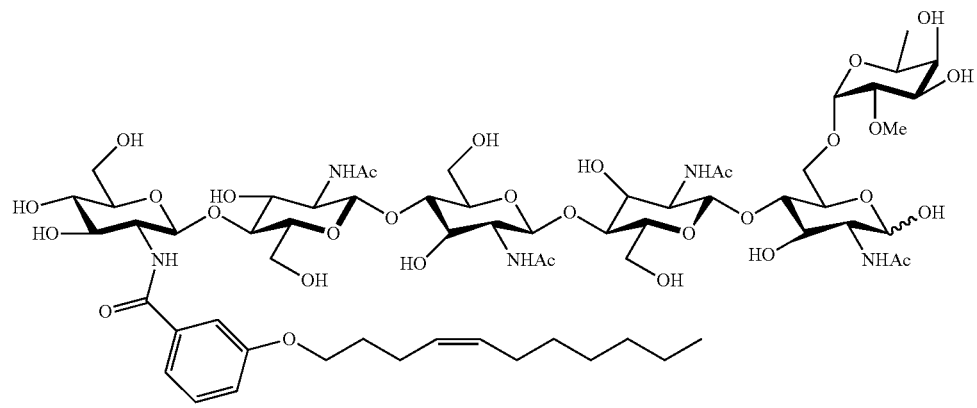
(XXIII)

-continued
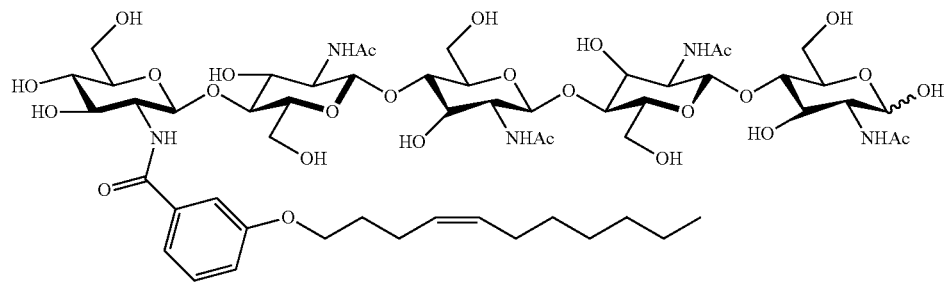
(XXIV)
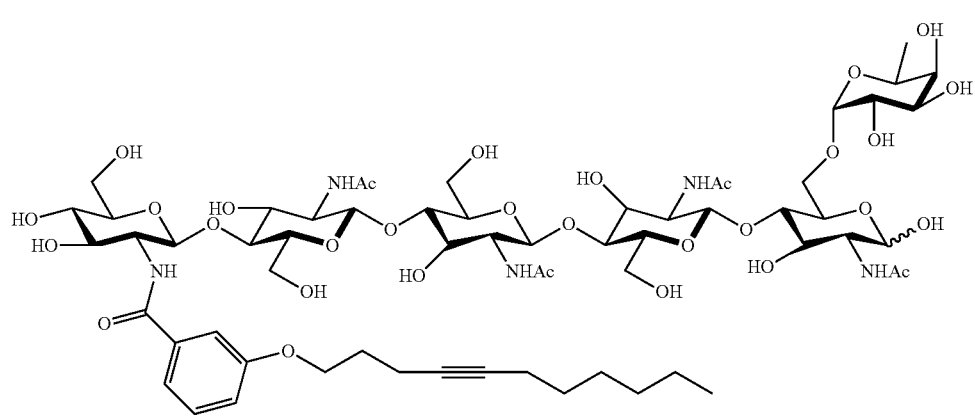
(XXV)
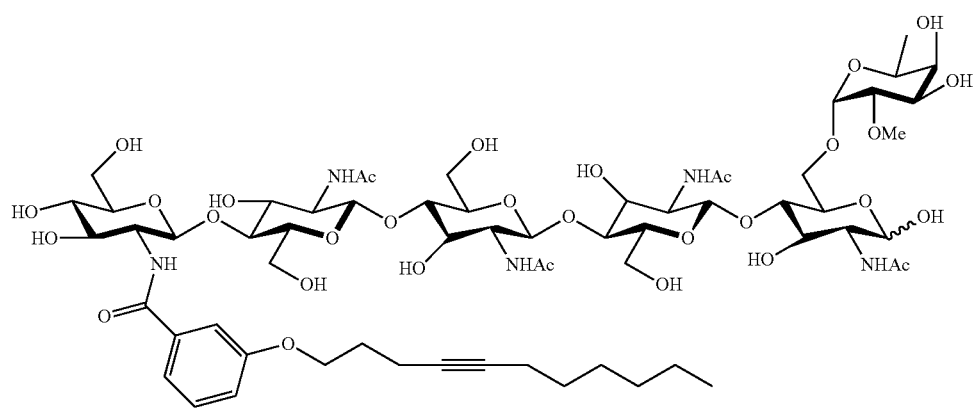
(XXVI)
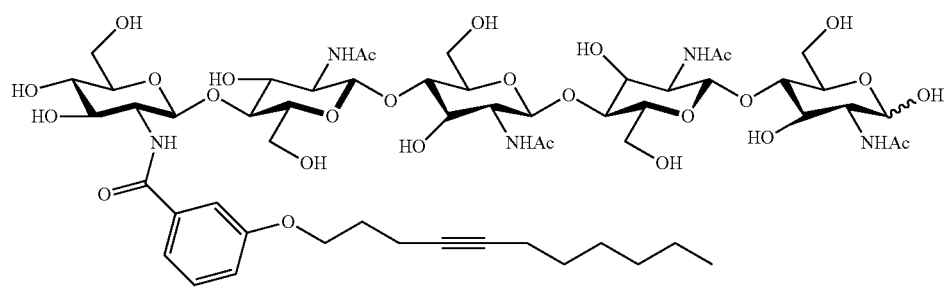
(XXVII)

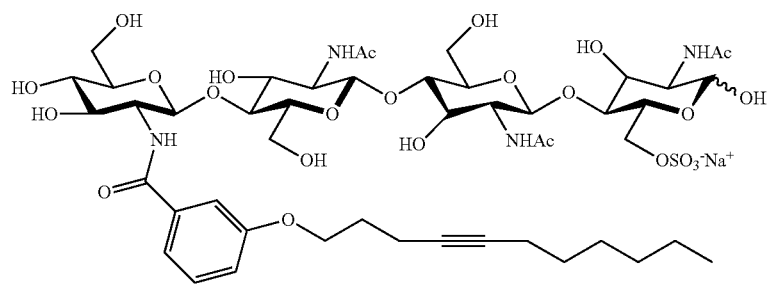
(XXVIII)
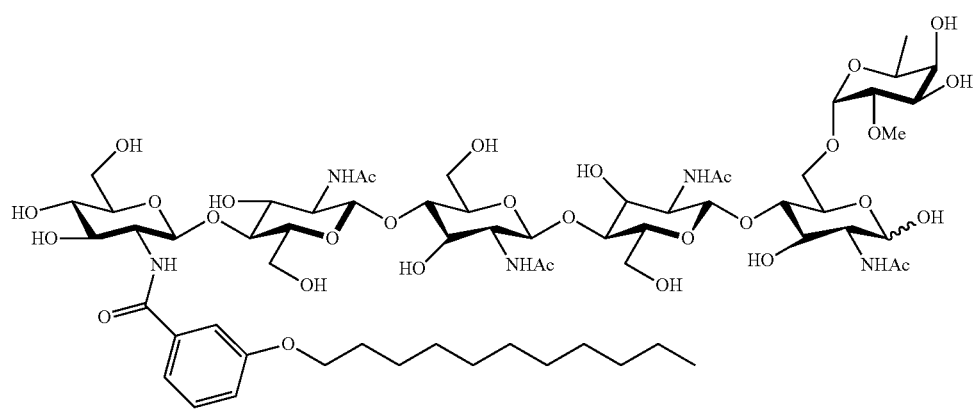
(XXIX)
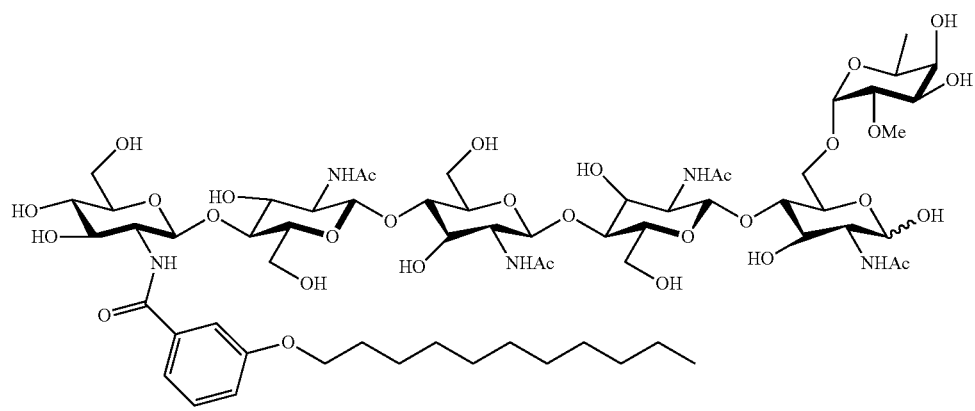
(XXX)
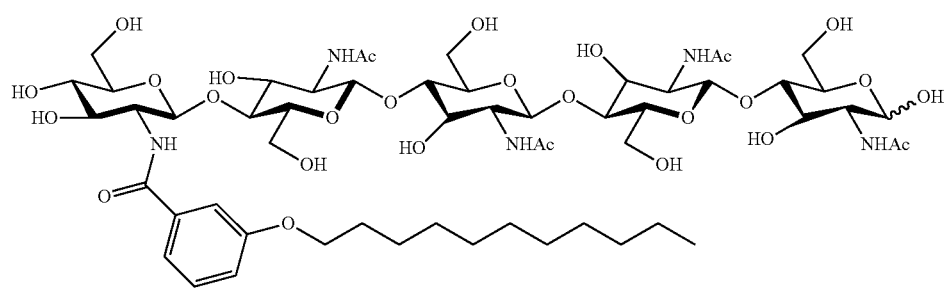
(XXXI)

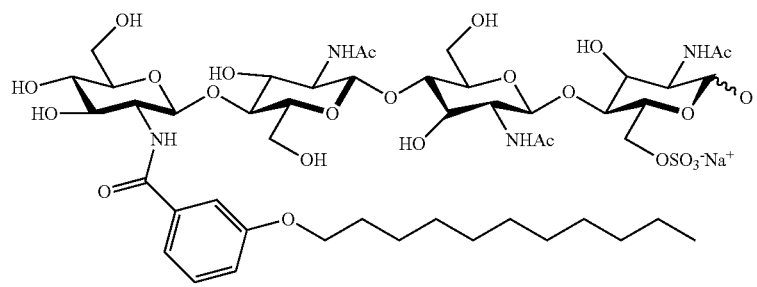

(XXXII)

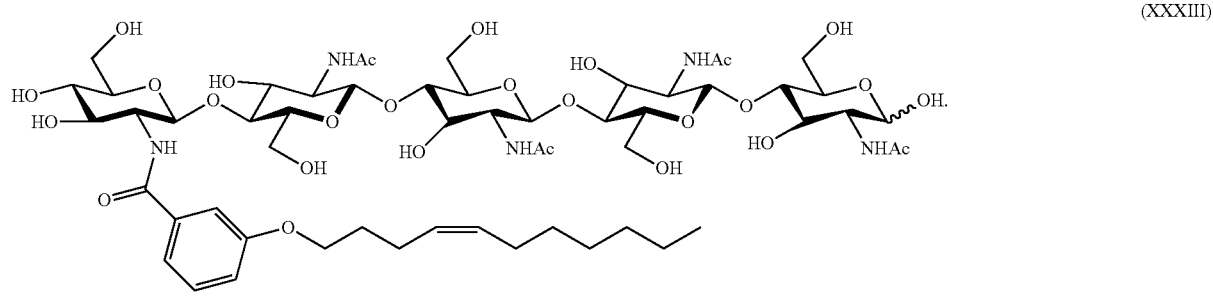

(XXXIII)

It is to be understood that compositions and methods of the present disclosure may comprise analogues, derivatives, hydrates, isomers, salts and/or solvates of LCOs.

Thus, in some embodiments, inoculant compositions of the present disclosure comprise one, two, three, four, five, six, seven, eight, nine, ten, or more LCOs represented by one or more of formulas I-IV and/or structures V-XXXIII and/or one, two, three, four, five, six, seven, eight, nine, ten, or more analogues, derivatives, hydrates, isomers, salts and/or solvates of LCOs represented by one or more of formulas I-IV and/or structures V-XXXIII.

LCOs may be incorporated into inoculant compositions of the present disclosure in any suitable amount(s)/concentration(s). The absolute value of the amount/concentration/dosage of LCO(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

In some embodiments, the inoculant compositions of the present disclosure comprise about $1\times10^{-20}$ M to about $1\times10^{-1}$ M LCO. For example, inoculant compositions of the present disclosure may comprise about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M of one or more LCOs.

In some embodiments, the LCO concentration is $1\times10^{-14}$ M to $1\times10^{-5}$ M, $1\times10^{-12}$ M to $1\times10^{-6}$ M, or $1\times10^{-10}$ M to $1\times10^{-7}$ M. In some embodiments, the LCO concentration is $1\times10^{-14}$ M to $1\times10^{-5}$ M, $1\times10^{-12}$ M to $1\times10^{-6}$ M, or $1\times10$ M to $1\times10^{-7}$ M.

Inoculant compositions of the present disclosure may comprise any suitable CO(s).

COs, sometimes referred to as N-acetylchitooligosaccharides, are also composed of GlcNAc residues but have side chain decorations that make them different from chitin molecules [$(C8-H_{13}NO_5)_n$, CAS No. 1398-61-4] and chitosan molecules [$(C_5H_{11}NO_4)_n$, CAS No. 9012-76-4]. See, e.g., D'Haeze et al., GLYCOBIOL. 12(6):79R (2002); Demont-Caulet et al., PLANT PHYSIOL. 120(1):83 (1999); Hanel et al., PLANTA 232:787 (2010); Muller et al., PLANT PHYSIOL. 124:733 (2000); Robina et al., TETRAHEDRON 58:521-530 (2002); Rouge et al., *Docking of Chitin Oligomers and Nod Factors on Lectin Domains of the LysM-RLK Receptors in the Medicago-Rhizobium Symbiosis*, in THE MOLECULAR IMMUNOLOGY OF COMPLEX CARBOHYDRATES-3 (Springer Science, 2011); Van der Holst et al., CURR. OPIN. STRUC. BIOL. 11:608 (2001); and Wan et al., PLANT CELL 21:1053 (2009); PCT/F100/00803 (2000). COs differ from LCOs in that they lack the pendant fatty acid chain that is characteristic of LCOs.

In some embodiments, inoculant compositions of the present disclosure comprise one or more COs represented by formula XXXIV:

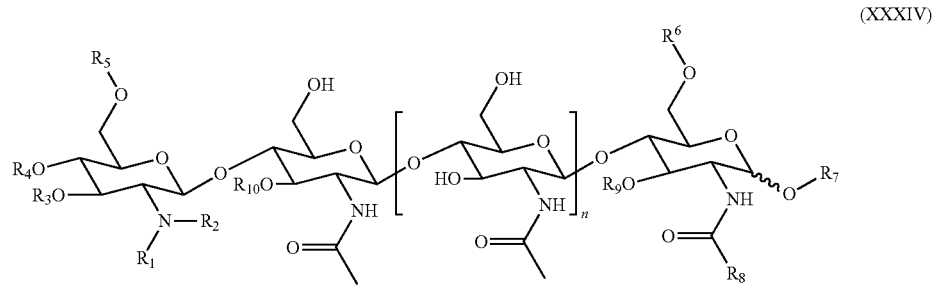

(XXXIV)

in which $R_1$ represents hydrogen or methyl; $R_2$ represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, sulfate ester, 3-O-S-2-O-MeFuc, 2-O-MeFuc and 4-O-AcFuc; $R_7$ represents hydrogen, mannosyl or glycerol; $R_8$ represents hydrogen, methyl, or —CH$_2$OH; $R_9$ represents hydrogen, arabinosyl, or fucosyl; $R_{10}$ represents hydrogen, acetyl or fucosyl; and n represents 0, 1, 2 or 3.

COs included in compositions and methods of the present disclosure may be obtained from any suitable source.

In some embodiments, the CO is derived from an LCO. For example, in some embodiments, inoculant compositions of the present disclosure comprise one or more COs derived from an LCO obtained (i.e., isolated and/or purified) from a strain of *Azorhizobium, Bradyrhizobium* (e.g., *B. japonicum*), *Mesorhizobium, Rhizobium* (e.g., *R. leguminosarum*), *Sinorhizobium* (e.g., *S. meliloti*), or mycorhizzal fungus (e.g., *Glomus intraradicus*). In some embodiments, the CO is derived from an LCO represented by one or more formulas I-IV and/or structures V-XXXIII. Thus, in some embodiments, inoculant compositions of the present disclosure may comprise one or more COs represented by one or more of formulas I-IV and/or structures V-XXXIII except that the pendant fatty acid is replaced with a hydrogen or methyl group.

In some embodiments, the CO is synthetic. Methods for the preparation of recombinant COs are known in the art. See, e.g., Cottaz et al., METH. ENG. 7(4):311 (2005); Samain et al., CARBOHYDRATE RES. 302:35 (1997.); and Samain et al., J. BIOTECHNOL. 72:33 (1999).

Examples of COs (and derivatives thereof) that may be useful in compositions and methods of the present disclosure are provided below as formula XXXV:

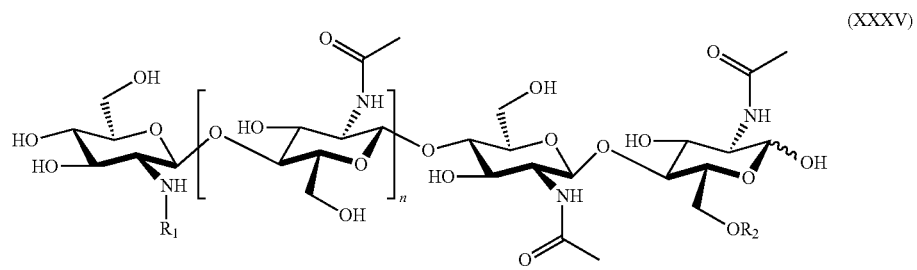

(XXXV)

in which n=1 or 2; $R_1$ represents hydrogen or methyl; and $R_2$ represents hydrogen or SO$_3$H.

Further examples of COs (and derivatives thereof) that may be useful in compositions and methods of the present disclosure are provided below as structures XXXVI-XXXIX:

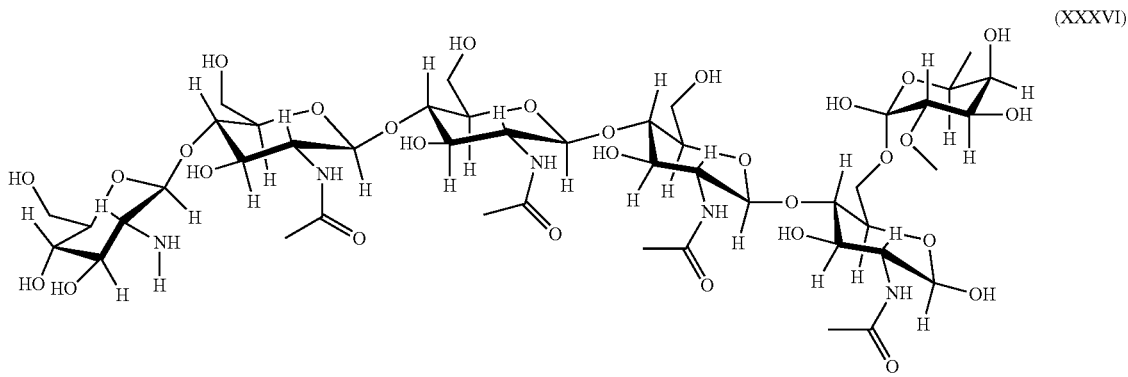

(XXXVI)

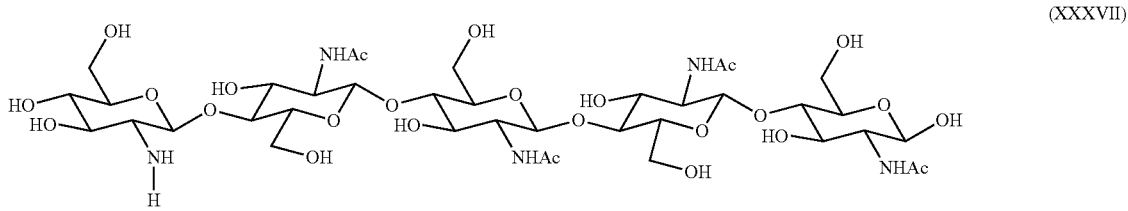

(XXXVII)

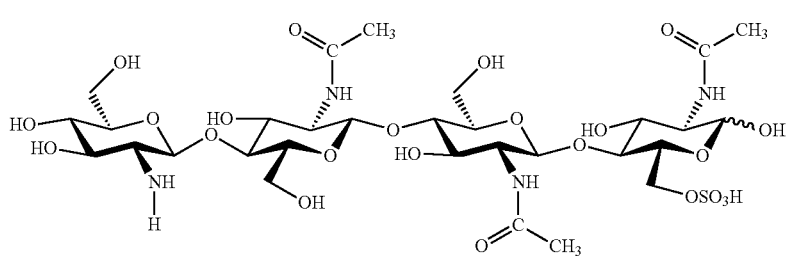

(XXXVIII)

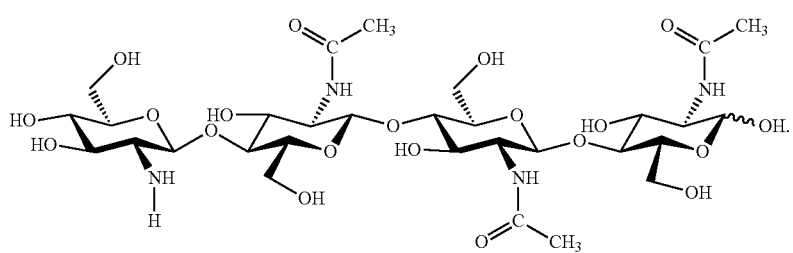

(XXXIX)

COs (and derivatives thereof) may be utilized in various forms of purity and may be used alone or in the form of a culture of CO-producing bacteria or fungi. In some embodiments, the CO(s) included in inoculant compositions of the present disclosure is/are at least 70%, 75%, 80%, 85%, 90%, 91%, 92%, 93%, 94%, 95%, 96%, 97%, 98%, 99%, 99.5% or more pure.

It is to be understood that compositions and methods of the present disclosure may comprise analogues, derivatives, hydrates, isomers, salts and/or solvates of COs.

Thus, in some embodiments, inoculant compositions of the present disclosure comprise one, two, three, four, five, six, seven, eight, nine, ten, or more COs represented by one or more of formulas XXXIV-XXXV and/or structures XXXVI-XXXIX and/or one, two, three, four, five, six, seven, eight, nine, ten, or more analogues, derivatives, hydrates, isomers, salts and/or solvates of COs represented by one or more of formulas XXXIV-XXXV and/or structures XXXVI-XXXIX.

COs may be incorporated into inoculant compositions of the present disclosure in any suitable amount(s)/concentration(s). The absolute value of the amount/concentration/dosage of CO(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

In some embodiments, the inoculant compositions of the present disclosure comprise about $1 \times 10^{-20}$ M to about $1 \times 10^{-1}$ M CO. For example, inoculant compositions of the present disclosure may comprise about $1 \times 10^{-20}$ M, $1 \times 10^{-19}$ M, $1 \times 10^{-18}$ M, $1 \times 10^{-17}$ M, $1 \times 10^{-16}$ M, $1 \times 10^{-15}$ M, $1 \times 10^{-14}$ M, $1 \times 10^{-13}$ M, $1 \times 10^{-12}$ M, $1 \times 10^{-11}$ M, $1 \times 10^{-10}$ M, $1 \times 10^{-9}$ M, $1 \times 10^{-8}$ M, $1 \times 10^{-7}$ M, $1 \times 10^{-6}$ M, $1 \times 10^{-5}$ M, $1 \times 10^{-4}$ M, $1 \times 10^{-3}$ M, $1 \times 10^{-2}$ M, $1 \times 10^{-1}$ M of one or more COs. In some embodiments, the CO concentration is $1 \times 10^{-14}$ M to $1 \times 10^{-5}$ M, $1 \times 10^{-12}$ M to $1 \times 10^{-6}$ M, or $1 \times 10^{-10}$ M to $1 \times 10^{-7}$ M. In some embodiments, the CO concentration is $1 \times 10^{-14}$ M to $1 \times 10^{-5}$ M, $1 \times 10^{-12}$ M to $1 \times 10^{-6}$ M, or $1 \times 10^{-10}$ M to $1 \times 10^{-7}$ M.

Inoculant compositions of the present disclosure may comprise any suitable chitinous compound(s), including, but not limited to, chitin (IUPAC: N-[5-[[3-acetylamino-4,5-dihydroxy-6-(hydroxymethyl)oxan-2yl]methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), chitosan (IUPAC: 5-amino-6-[5-amino-6-[5-amino-4,6-dihydroxy-2(hydroxymethyl)oxan-3-yl]oxy-4-hydroxy-2-(hydroxymethyl)oxan-3-yl]oxy-2 (hydroxymethyl)oxane-3,4-diol) and isomers, salts and solvates thereof.

Chitins and chitosans, which are major components of the cell walls of fungi and the exoskeletons of insects and crustaceans, are composed of GlcNAc residues.

Chitins and chitosans may be obtained commercially or prepared from insects, crustacean shells, or fungal cell walls. Methods for the preparation of chitin and chitosan are known in the art. See, e.g., U.S. Pat. No. 4,536,207 (preparation from crustacean shells) and U.S. Pat. No. 5,965,545 (preparation from crab shells and hydrolysis of commercial chitosan); Pochanavanich, et al., LETT. APPL. MICROBIOL. 35:17 (2002) (preparation from fungal cell walls).

Deacetylated chitins and chitosans may be obtained that range from less than 35% to greater than 90% deacetylation and cover a broad spectrum of molecular weights, e.g., low molecular weight chitosan oligomers of less than 15 kD and chitin oligomers of 0.5 to 2 kD; "practical grade" chitosan with a molecular weight of about 15 kD; and high molecular weight chitosan of up to 70 kD. Chitin and chitosan compositions formulated for seed treatment are commercially available. Commercial products include, for example, ELEXA® (Plant Defense Boosters, Inc.) and BEYOND™ (Agrihouse, Inc.).

Chitinous compounds may be incorporated into inoculant compositions of the present disclosure in any suitable amount(s)/concentration(s). The absolute value of the amount/concentration/dosage of chitinous compound(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

Inoculant compositions of the present disclosure may comprise any suitable flavonoid(s), including, but not limited to, anthocyanidins, anthoxanthins, chalcones, coumarins, flavanones, flavanonols, flavans and isoflavonoids, as well as analogues, derivatives, hydrates, isomers, polymers, salts and solvates thereof.

Flavonoids are phenolic compounds having the general structure of two aromatic rings connected by a three-carbon bridge. Classes of flavonoids include are known in the art. See, e.g., Jain et al., J. PLANT BIOCHEM. & BIOTECHNOL. 11:1 (2002); Shaw et al., ENVIRON. MICROBIOL. 11:1867 (2006). Flavonoid compounds are commercially available, e.g., from Novozymes BioAg, Saskatoon, Canada; Natland International Corp., Research Triangle Park, N.C.; MP Biomedicals, Irvine, Calif.; LC Laboratories, Woburn Mass. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast, as described in Ralston et al., PLANT PHYSIOL. 137:1375 (2005).

In some embodiments, inoculant compositions of the present disclosure comprise one or more anthocyanidins. For example, in some embodiments, inoculant compositions of the present disclosure comprise cyanidin, delphinidin, malvidin, pelargonidin, peonidin and/or petunidin.

In some embodiments, inoculant compositions of the present disclosure comprise one or more anthoxanthins. For example, in some embodiments, inoculant compositions of the present disclosure comprise one or more flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin).

In some embodiments, inoculant compositions of the present disclosure comprise one or more flavanones. For example, in some embodiments, inoculant compositions of the present disclosure comprise butin, eriodictyol, hesperetin, hesperidin, homoeriodictyol, isosakuranetin, naringenin, naringin, pinocembrin, poncirin, sakuranetin, sakuranin and/or sterubin.

In some embodiments, inoculant compositions of the present disclosure comprise one or more flavanonols. For example, in some embodiments, inoculant compositions of the present disclosure comprise dihydrokaempferol and/or taxifolin.

In some embodiments, inoculant compositions of the present disclosure comprise one or more flavans. For example, in some embodiments, inoculant compositions of the present disclosure comprise one or more flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin) and/or dimers, trimers, oligomers and/or polymers thereof (e.g., one or more proanthocyanidins).

In some embodiments, inoculant compositions of the present disclosure comprise one or more isoflavonoids. For example, in some embodiments, inoculant compositions of the present disclosure comprise one or more isoflavones (e.g, biochanin A, daidzein, formononetin, genistein and/or glycitein), isoflavanes (e.g., equol, ionchocarpane and/or laxifloorane), isoflavandiols, isoflavenes (e.g., glabrene, haginin D and/or 2-methoxyjudaicin), coumestans (e.g., coumestrol, plicadin and/or wedelolactone), pterocarpans and/or roetonoids.

Inoculant compositions of the present disclosure may comprise any suitable flavonoid derivative, including, but not limited to, neoflavonoids (e.g, calophyllolide, coutareagenin, dalbergichromene, dalbergin, nivetin) and pterocarpans (e.g., bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine, trifolirhizin).

Flavonoids and derivatives thereof may be incorporated into inoculant compositions of the present disclosure in any suitable form, including, but not limited to, polymorphic and crystalline forms.

Flavonoids may be incorporated into inoculant compositions of the present disclosure in any suitable amount(s)/concentration(s). The absolute value of the amount/concentration/dosage of flavonoid(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

Inoculant compositions of the present disclosure may comprise any suitable non-flavonoid node-gene inducer(s), including, but not limited to, jasmonic acid ([1R-[1a,2R(Z)]]-3-oxo-2-(pentenyl)cyclopentaneacetic acid; JA), linoleic acid ((Z,Z)-9,12-Octadecadienoic acid) and linolenic acid ((Z,Z,Z)-9,12,15-octadecatrienoic acid), as well as analogues, derivatives, hydrates, isomers, polymers, salts and solvates thereof.

Jasmonic acid and its methyl ester, methyl jasmonate (MeJA), collectively known as jasmonates, are octadecanoid-based compounds that occur naturally in some plants (e.g., wheat), fungi (e.g., *Botryodiplodia theobromae*, *Gibberella fujikuroi*), yeast (e.g., *Saccharomyces cerevisiae*) and bacteria (e.g., *Escherichia coli*). Linoleic acid and linolenic acid may be produced in the course of the biosynthesis of jasmonic acid. Jasmonates, linoleic acid and linolenic acid (and their derivatives) are reported to be inducers of nod gene expression or LCO production by rhizobacteria. See, e.g., Mabood, et al. PLANT PHYSIOL. BIOCHEM. 44(11):759 (2006); Mabood et al., AGR. J. 98(2):289 (2006); Mabood, et al., FIELD CROPS RES. 95(2-3):412 (2006); Mabood & Smith, *Linoleic and linolenic acid induce the expression of nod genes in Bradyrhizobium japonicum USDA* 3, PLANT BIOL. (2001).

Useful derivatives of jasmonic acid, linoleic acid, linolenic acid that may be useful in compositions of the present disclosure include esters, amides, glycosides and salts. Representative esters are compounds in which the carboxyl group of linoleic acid, linolenic acid, or jasmonic acid has been replaced with a —COR group, where R is an —OR$^1$ group, in which R$^1$ is: an alkyl group, such as a $C_1$-$C_3$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S.

Representative amides are compounds in which the carboxyl group of linoleic acid, linolenic acid, or jasmonic acid has been replaced with a —COR group, where R is an NR$^2$R$^3$ group, in which R$^2$ and R$^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium).

These salts may be readily prepared by mixing together a solution of linoleic acid, linolenic acid, or jasmonic acid with a solution of the base. The salts may be precipitated from solution and be collected by filtration or may be recovered by other means such as by evaporation of the solvent.

Non-flavonoid node-gene inducers may be incorporated into inoculant compositions of the present disclosure in any suitable amount(s)/concentration(s). The absolute value of the amount/concentration/dosage of non-flavonoid gene inducer(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

Inoculant compositions of the present disclosure may comprise any suitable karrakin(s), including, but not limited to, 2H-furo[2,3-c]pyran-2-ones, as well as analogues, derivatives, hydrates, isomers, polymers, salts and solvates thereof. In some embodiments, the inoculant composition comprises one or more karrakins represented by formula XXXX:

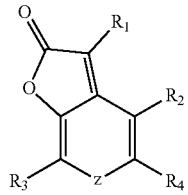

(XXXX)

in which Z is O, S or NR$_5$; R$_1$, R$_2$, R$_3$ and R$_4$ are each independently H, alkyl, alkenyl, alkynyl, phenyl, benzyl, hydroxy, hydroxyalkyl, alkoxy, phenyloxy, benzyloxy, CN, COR$_6$, COOR=, halogen, NR$_6$R$_7$, or NO$_2$; and R$_5$, R$_6$ and R$_7$ are each independently H, alkyl or alkenyl, or a biologically acceptable salt thereof.

Examples of biologically acceptable salts of karrakins may include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by formula XXXX and which may be suitable for use in the present disclosure include 3-methyl-2H-furo[2,3-c]pyran-2-one (where R$_1$=CH$_3$, R$_2$, R$_3$, R$_4$=H), 2H-furo[2,3-c]pyran-2-one (where R$_1$, R$_2$, R$_3$, R4=H), 7-methyl-2H-furo[2,3-c]pyran-2-one (where R$_1$, R$_2$, R$_4$=H, R$_3$=CH$_3$), 5-methyl-2H-furo[2,3-c]pyran-2-one (where R$_1$, R$_2$, R$_3$=H, R$_4$=CH$_3$), 3,7-dimethyl-2H-furo[2,3-c]pyran-2-one (where R$_1$, R$_3$=CH$_3$, R$_2$, R$_4$=H), 3,5-dimethyl-2H-furo[2,3-c]pyran-2-one (where R$_1$, R$_4$=CH$_3$, R$_2$, R$_3$=H), 3,5,7-trimethyl-2H-furo[2,3-c]pyran-2-one (where R$_1$, R$_3$, R$_4$=CH$_3$, R$_2$=H), 5-methoxymethyl-3-methyl-2H-furo[2,3-c]pyran-2-one (where R$_1$=CH$_3$, R$_2$, R$_3$=H, R$_4$=CH$_2$OCH$_3$), 4-bromo-3,7-dimethyl-2H-furo[2,3-c]pyran-2-one (where R$_1$, R$_3$=CH$_3$, R$_2$=Br, R$_4$=H), 3-methylfuro[2,3-c]pyridin-2(3H)-one (where Z=NH, R$_1$=CH$_3$, R$_2$, R$_3$, R$_4$=H) and 3,6-dimethylfuro[2,3-c]pyridin-2(6H)-one (where Z=N—CH$_3$, R$_1$=CH$_3$, R$_2$, R$_3$, R$_4$=H). See, e.g., U.S. Pat. No. 7,576,213; Halford, *Smoke Signals*, in CHEM. ENG. NEWS (Apr. 12, 2010) (reporting that karrikins or butenolides contained in smoke act as growth stimulants and spur seed germination after a forest fire and can invigorate seeds such as corn, tomatoes, lettuce and onions that had been stored).

Karrakins may be incorporated into inoculant compositions of the present disclosure in any suitable amount(s)/concentration(s). The absolute value of the amount/concentration/dosage of karrakin(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

Inoculant compositions of the present disclosure may comprise gluconolactone and/or one or more analogues, derivatives, hydrates, isomers, polymers, salts and/or solvates thereof.

Gluconolactone may be incorporated into inoculant compositions of the present disclosure in any suitable amount (s)/concentration(s). The absolute value of the amount/ concentration/dosage of gluconolactone(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/ concentration/dosage using routine dose-response experiments.

Inoculant compositions of the present disclosure may comprise any suitable excipient(s), including, but not limited to, dispersants, drying agents, anti-freezing agents, pH buffers and adhesives.

Inoculant compositions of the present disclosure may comprise any suitable agriculturally acceptable dispersant (s), including, but not limited to, surfactants and wetting agents.

In some embodiments, inoculant compositions of the present disclosure comprise one or more anionic surfactants. For example, in some embodiments, inoculant compositions of the present disclosure comprise one or more water-soluble anionic surfactants and/or one or more water-insoluble anionic surfactants, optionally one or more anionic surfactants selected from the group consisting of alkyl carboxylates (e.g., sodium stearate), alkyl sulfates (e.g., alkyl lauryl sulfate, sodium lauryl sulfate), alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and xylene sulfonates.

In some embodiments, inoculant compositions of the present disclosure comprise one or more cationic surfactants. For example, in some embodiments, inoculant compositions of the present disclosure comprise one or more pH-dependent amines and/or one or more quaternary ammonium cations, optionally one or more cationic surfactants selected from the group consisting of alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide and/or octenidine dihydrochloride.

In some embodiments, inoculant compositions of the present disclosure comprise one or more nonionic surfactants. For example, in some embodiments, inoculant compositions of the present disclosure comprise one or more water-soluble nonionic surfactants and/or one or more water-insoluble nonionic surfactants, optionally one or more nonionic surfactants selected from the group consisting of alcohol ethoxylates (e.g., TERGITOL™ 15-S surfactants, such as TERGITOL™15-S-9 (The Dow Chemical Company, Midland, Mich.)), alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers (e.g.), glycerol esters, glycol alkyl ethers (e.g., polyoxyethylene glycol alkyl ethers, polyoxypropylene glycol alkyl ethers), glycol alkylphenol ethers (e.g., polyoxyethylene glycol alkylphenol ethers), glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols.

In some embodiments, inoculant compositions of the present disclosure comprise at least at least one nonionic surfactant. In some embodiments, inoculant compositions of the present disclosure comprise at least one water insoluble nonionic surfactant and at least one water soluble nonionic surfactant. In some embodiments, inoculant compositions of the present disclosure comprise a combination of nonionic surfactants having hydrocarbon chains of substantially the same length.

In some embodiments, inoculant compositions of the present disclosure comprise one or more zwitterionic surfactants. For example, in some embodiments, inoculant compositions of the present disclosure comprise one or more betaines and/or one or more sultaines, optionally one or more zwitterionic surfactants selected from the group consisting of 3-[(3-Cholamidopropyl)dimethylammonio]-1-propanesulfonate, cocamidopropyl betaine, cocamidopropyl hydroxysultaine, phosphatidylserine, phosphatidylethanolamine, phosphatidylcholine and/or one or more sphingomyelins.

In some embodiments, inoculant compositions of the present disclosure comprise one or more soaps and/or organosilicone surfactants. For example, in some embodiments, inoculant compositions of the present disclosure comprise one or more alkali metal salts of fatty acids.

In some embodiments, inoculant compositions of the present disclosure comprise one or more wetting agents. For example, in some embodiments, inoculant compositions of the present disclosure comprise one or more naphthalene sulfonates, optionally one or more alkyl naphthalene sulfonates (e.g., sodium alkyl naphthalene sulfonate), one or more isopropyl naphthalene sulfonates (e.g., sodium isopropyl naphthalene sulfonate) and/or one or more butyl naphthalene sulfonates (e.g., sodium n-butyl naphthalene sulfonate).

Selection of appropriate dispersants will depend on the intended application(s) and the microorganism(s) present in the inoculant composition. In general, the dispersant(s) will have low toxicity for the microorganism(s) in the inoculant composition and for the plant part(s) to which the inoculant composition is to be applied. In some embodiments, the dispersant(s) will be selected to wet and/or emulsify one or more soils.

Non-limiting examples of dispersants that may be useful in compositions of the present disclosure include Atlox™ (e.g., 4916, 4991; Croda International PLC, Edison, N.J.), Atlox METASPERSE™ (Croda International PLC, Edison, N.J.), BIO-SOFT® (e.g., N series, such as N1-3, N1-7, N1-5, N1-9, N23-3, N2.3-6.5, N25-3, N25-7, N25-9, N91-2.5, N91-6, N91-8; Stepan Company, Northfield, Ill.), MAKON® nonionic surfactants (e.g., DA-4, DA-6 and DA-9; Stepan Company, Northfield, Ill.), MORWET® powders (Akzo Nobel Surface Chemistry LLC, Chicago, Ill.), MULTIWET™ surfactants (e.g., MO-85P-PW-(AP); Croda International PLC, Edison, N.J.), SILWET® L-77 (Helena Chemical Company, Collierville, Tenn.), SPAN™ surfactants (e.g., 20, 40, 60, 65, 80 and 85; Croda Inc., Edison N.J.), TAMOL™ dispersants (The Dow Chemical Company, Midland, Mich.), TERGITOL™ surfactants (e.g., TMN-6 and TMN-100X; The Dow Chemical Company, Midland, Mich.), TERSPERSE surfactants (e.g., 2001, 2020, 2100, 2105, 2158, 2700, 4894 and 4896; Hunstman Corp., The Woodlands, Tex.), TRITON™ surfactants (e.g., X-100; The Dow Chemical Company, Midland, Mich.), TWEEN® surfactants (e.g., TWEEN® 20, 21, 22, 23, 28, 40, 60, 61, 65, 80, 81 and 85; Croda International PLC, Edison, N.J.) and combinations thereof.

Dispersants may be incorporated into inoculant compositions of the present disclosure in any suitable amount(s)/concentration(s). The absolute value of the amount/concentration/dosage of dispersant(s) that is sufficient to cause the desired effect may be affected by factors such as the type, size and volume of material to which the composition will be applied, the type(s) of microorganisms in the composition, the number of microorganisms in the composition, the stability of the microorganisms in the composition and the storage conditions (e.g., temperature, relative humidity, duration). Those skilled in the art will understand how to select an effective amount/concentration/dosage using routine dose-response experiments.

In some embodiments, the dispersant(s) comprise(s) about 0.1 to about 25% (by weight) of the inoculant composition. For example, inoculant compositions of the present disclosure may comprise about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of one or more dispersants. In some embodiments, the dispersant (s) comprise(s) about 0.1, 0.2, 0.3, 0.4, 0.5, 0.6, 0.7, 0.8, 0.9 or 1 to about 1, 1.5, 2, 2.5, 3, 3.5, 4, 4.5, 5, 5.5, 6, 6.5, 7, 7.5, 8, 8.5, 9, 9.5 or 10% (by weight) of the inoculant composition.

In some embodiments, inoculant compositions of the present disclosure comprise one or more commercial wetting agents and/or one or more surfactants used in accordance with the manufacturer's recommended amounts/concentrations.

Additional examples of dispersants that may be included in inoculant compositions of the present disclosure may be found in BAIRD & ZUBLENA. 1993. SOIL FACTS: USING WETTING AGENTS (NONIONIC SURFACTANTS) ON SOIL (North Carolina Cooperative Extension Service Publication AG-439-25) (1993); BURGES, FORMULATION OF MICROBIAL BIOPESTICIDES: BENEFICIAL MICROORGANISMS, NEMATODES AND SEED TREATMENTS (Springer Science & Business Media) (2012); MCCARTY, WETTING AGENTS (Clemson University Cooperative Extension Service Publication) (2001).

Inoculant compositions of the present disclosure may comprise any suitable agriculturally acceptable drying agent (s), including, but not limited to, drying powders. For example, in some embodiments, inoculant compositions of the present disclosure comprise calcium stearate, clay (e.g., attapulgite clay, montmorillonite clay), graphite, magnesium stearate, magnesium sulfate, powdered milk, silica (e.g., fumed silica, hydrophobically-coated silica, precipitated silica), soy lecithin and/or talc.

Non-limiting examples of drying agents that may be useful in compositions of the present disclosure include AEROSIL® hydrophobic fumed silica powders (Evonik Corporation, Parsippany, N.J.), BENTOLITE® powders (BYK-Chemie GmbH, Wesel, Germany), INCOTEC® powders (INCOTEC Inc., Salinas, Calif.), SIPERNAT® silica powders (Evonik Corporation, Parsippany, N.J.) and combinations thereof.

Additional examples of drying agents that may be included in inoculant compositions of the present disclosure may be found in BURGES, FORMULATION OF MICROBIAL BIOPESTICIDES: BENEFICIAL MICROORGANISMS, NEMATODES AND SEED TREATMENTS (Springer Science & Business Media) (2012).

In some embodiments, inoculant compositions of the present disclosure comprise one or more commercial drying agents used in accordance with the manufacturer's recommended amounts/concentrations.

Drying agents may be incorporated into inoculant compositions of the present disclosure in any suitable amount (s)/concentration(s). The absolute value of the amount/concentration/dosage of drying agent(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

In some embodiments, the drying agent(s) comprise(s) about 1 to about 95% (by weight) of the inoculant composition. For example, inoculant compositions of the present disclosure may comprise about 5, 10, 15, 20, 25, 30, 35, 40, 45, 50, 55, 60, 65, 70, 75, 80, 85, 90, 95% or more (by weight) of one or more drying agents. In some embodiments, the drying agent amount/concentration is about 1 to about 65%, about 5% to about 20%, about 10% to about 25%, about 20% to about 50%, or about 30 to about 60% (by weight) of the inoculant composition.

In some embodiments, the inoculant compositions of the present disclosure comprise about 0.5 to about 10 grams of drying powder per liter of inoculant composition. For example, inoculant compositions of the present disclosure may comprise about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder per liter of inoculant composition.

Inoculant compositions of the present disclosure may comprise any suitable agriculturally acceptable anti-freezing agent(s), including, but not limited to, ethylene glycol, glycerin, propylene glycol and urea.

Anti-freezing agents may be incorporated into inoculant compositions of the present disclosure in any suitable amount(s)/concentration(s). The absolute value of the amount/concentration/dosage of anti-freezing agent(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

In some embodiments, inoculant compositions of the present disclosure comprise one or more commercial anti-freezing agents used in accordance with the manufacturer's recommended amounts/concentrations.

Inoculant compositions of the present disclosure may comprise any suitable pH buffer(s), including, but not limited to, potassium phosphate monobasic and potassium phosphate dibasic.

Buffers may be incorporated into inoculant compositions of the present disclosure in any suitable amount(s)/concentration(s). The absolute value of the amount/concentration/dosage of pH buffer(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

In some embodiments, the buffer(s) comprise(s) about 0.001 to about 5% (by weight) of the inoculant composition. For example, inoculant compositions of the present disclosure may comprise about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more buffers. In some embodiments, the buffer(s) comprise(s) about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition.

In some embodiments, inoculant compositions of the present disclosure have a pH of about 4.5 to about 9.5. In some embodiments, inoculant compositions of the present disclosure have a pH of about 6 to about 7.5. In some embodiments, inoculant compositions of the present disclosure have a pH of about 5, 5.5, 6, 6.5, 7, 7.5, 8 or 8.5.

Inoculant compositions of the present disclosure may comprise any suitable adhesive(s), including, but not limited to, adhesive compositions comprising, consisting essentially of or consisting of one or more disaccharides (e.g. maltose), gums (e.g., cellulose gum, guar gum, gum arabic, gum combretum, xantham gum), maltodextrins (e.g., one or more maltodextrins (each and/or collectively) having a DEV of about 10 to about 20), monosaccharides, oils (e.g., mineral oil, olive oil, peanut oil, soybean oil and/or sunflower oil) and/or oligosaccharides.

Adhesives may be incorporated into inoculant compositions of the present disclosure in any suitable amount(s)/concentration(s). The absolute value of the amount/concentration/dosage of adhesive(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

Inoculant compositions of the present disclosure may be formulated into any suitable type of composition, including, but not limited to, seed coatings, soil inoculants and foliar inoculants.

In some embodiments, inoculant compositions of the present disclosure are formulated as amorphous solids.

In some embodiments, inoculant compositions of the present disclosure are formulated as amorphous liquids.

In some embodiments, inoculant compositions of the present disclosure are formulated as wettable powders.

In some embodiments, inoculant compositions of the present disclosure are formulated as liquid compositions that are subsequently dried to produce a powder or granuale. For example, in some embodiments, liquid inoculant compositions of the present disclosure are drum dried, evaporation dried, fluidized bed dried, freeze dried, spray dried, spray-freeze dried, tray dried and/or vacuum dried to produce powders/granuales. Such powders/granuales may be further processed using any suitable method(s), including, but not limited to, flocculation, granulation and milling, to achieve a desired particle size or physical format. The precise method(s) and parameters of processing dried powders/granuales that are appropriate in a given situation may be affected by factors such as the desired particle size(s), the type, size and volume of material to which the composition will be applied, the type(s) of microorganisms in the composition, the number of microorganisms in the composition, the stability of the microorganisms in the composition and the storage conditions (e.g., temperature, relative humidity, duration). Those skilled in the art will understand how to select appropriate methods and parameters using routine experiments.

In some embodiments, inoculant compositions of the present disclosure are frozen for cryopreservation. For example, in some embodiments, liquid inoculant compositions of the present disclosure are flash-frozen and stored in a cryopreservation storage unit/facility. The precise method(s) and parameters of freezing and preserving inoculant compositions of the present disclosure that are appropriate in a given situation may be affected by factors such as the type(s) of microorganisms in the composition, the number of microorganisms in the composition, the stability of the microorganisms in the composition and the storage conditions (e.g., temperature, relative humidity, duration). Those skilled in the art will understand how to select appropriate methods and parameters using routine experiments.

Inoculant compositions of the present disclosure may be formulated for the treatment of any suitable plant type, including, but not limited to, row crops and vegetables. In some embodiments, inoculant compositions of the present disclosure are formulated for the treatment of one or more plants selected from the families listed in Appendix B. In some embodiments, inoculant compositions of the present disclosure are formulated for the treatment of one or more acaricide-, fungicide-, herbicide-, insecticide- and/or nematicide-resistant plants (e.g., one or more plants resistant to acetolactate synthase inhibitors.

Non-limiting examples of plants that may be treated with inoculant compositions of the present disclosure include plants sold by Monsanto Company (St. Louis, Mo.) under the BOLLGARD II®, DROUGHTGARD®, GENUITY®, RIB COMPLETE®, ROUNDUP READY®, ROUNDUP READY 2 YIELD®, ROUNDUP READY 2 EXTEND™, SMARTSTAX®, VT DOUBLE PRO®, VT TRIPLE PRO®, YIELDGARD®, YIELDGARD VT ROOTWORM/RR2®, YIELDGARD VT TRIPLE® and/or XTEND-FLEX™ tradenames.

Inoculant compositions of the present disclosure may be designed and formulated to improve not only the stability and survival of microorganisms therein, but also the dispersion of those microorganisms within the composition.

In some embodiments, inoculant compositions of the present disclosure improve one or more microbial stability characteristics of one or more microorganisms contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, inoculant compositions of the present disclosure may improve the ability of one or more of the microorganisms contained therein to germinate/propagate and/or to enhance plant yield by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the maltodextrins found in the inoculant composition and/or comprises a reduced amount of one or more of the maltodextrins found in the inoculant composition.

In some embodiments, inoculant compositions of the present disclosure improve the survival rate of one or more microorganisms contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, inoculant compositions of the present disclosure may improve the survival rate of one or more of the microorganisms contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the maltodextrins found in the inoculant composition and/or comprises a reduced amount of one or more of the maltodextrins found in the inoculant composition.

In some embodiments, inoculant compositions of the present disclosure improve the survival of one or more of the microorganisms contained therein to the extent that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microorganisms survive when the inoculant composition is stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, inoculant compositions of the present disclosure improve the survival of one or more of the microorganisms contained therein to the extent that at least about 5, 6, 7, 8, 9, 10, 11, 12, 13, 14, 15, 16, 17, 18, 19, 20, 25, 30, 35, 40, 45, 50, 55, 60, 65, 70% or more of the microorganisms survive when the inoculant composition is stored at 20, 21, 22, 23, 24, 25, 26, 27, 28, 29 and/or 30° C. and 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve the survival of one or more of the microorganisms contained therein to the extent that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microorganisms survive when the inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, inoculant compositions of the present disclosure improve the survival of one or more of the microorganisms contained therein to the extent that at least about 5, 6, 7, 8, 9, 10, 11, 12, 13, 14, 15, 16, 17, 18, 19, 20, 25, 30, 35, 40, 45, 50, 55, 60, 65, 70% or more of the microorganisms survive when the inoculant composition is coated of a seed, desiccated by 95% or more and stored at 20, 21, 22, 23, 24, 25, 26, 27, 28, 29 and/or 30° C. and 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve the survival of one or more of the microorganisms contained therein to the extent that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microorganisms survive when the inoculant composition is frozen and stored at or below −80° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve the survival of one or more of the microorganisms contained therein to the extent that at least $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ cfu/gram or milliliter or more of the microorganisms survive when the inoculant composition is stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, inoculant compositions of the present disclosure improve the survival of one or more of the microorganisms contained therein to the extent that at least $1 \times 10^4$, $1 \times 10^5$, $1 \times 10^6$, $1 \times 10^7$ cfu/seed or more of the microorganisms survive when the inoculant composition is stored at 20, 21, 22, 23, 24, 25, 26, 27, 28, 29 and/or 30° C. and 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve the survival of one or more of the microorganisms contained therein to the extent that at least $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ cfu/gram or milliliter or more of the microorganisms survive when the inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve the survival of one or more of the microorganisms contained therein to the extent that at least $1\times10^4$, $1\times10^5$, $1\times10^6$, $1\times10^7$ cfu/seed or more of the microorganisms survive when the inoculant composition is coated on a seed, desiccated by 95% or more and stored at 20, 21, 22, 23, 24, 25, 26, 27, 28, 29 and/or 30° C. and 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve the survival of one or more of the microorganisms contained therein to the extent that at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/gram or milliliter or more of the microorganisms survive when the inoculant composition is frozen and stored at or below −80° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve both the survival rate and one, two, three, four, five, six, seven, eight, nine, ten or more microbial stability characteristics of the microorganism(s) contained therein.

In some embodiments, microorganisms remain viable in inoculant compositions of the present disclosure for at least 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more (e.g., at least 12, 16, 20, 24, 28, 32, 36, 40, 44, 48, 52, 56, 60, 64, 68, 72, 76, 80, 84, 88, 92, 96, 100, 104 weeks or more when stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity).

In some embodiments, inoculant compositions of the present disclosure improve the dispersion of one or more microorganisms contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, inoculant compositions of the present disclosure may improve the dispersion of one or more of the microorganisms contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the protectants/dispersants found in the inoculant composition and/or comprises a reduced amount of one or more of the protectants/dispersants found in the inoculant composition.

In some embodiments, inoculant compositions of the present disclosure improve the dispersion of one or more of the microorganisms contained therein to the extent that at least about 50, 55, 60, 65, 70, 75, 80, 85, 90, 95% or more of the microorganisms are present as single cells/spores (rather than as members of a clump comprising two or more cells/spores).

In some embodiments, at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microorganisms remain in a fluid state and/or are surrounded by a composition that exists in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when the inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, at least about 5, 6, 7, 8, 9, 10, 11, 12, 13, 14, 15, 16, 17, 18, 19, 20, 25, 30, 35, 40, 45, 50, 55, 60, 65, 70% or more of the microorganisms remain in a fluid state surrounded by a composition that exists in a glassy and/or rubbery state at 20, 21, 22, 23, 24, 25, 26, 27, 28, 29 and/or 30° C. when the inoculant composition is coated of a seed, desiccated by 95% or more and stored at 20, 21, 22, 23, 24, 25, 26, 27, 28, 29 and/or 30° C. and 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microorganisms remain in a fluid state and/or are surrounded by a composition that exists in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when the inoculant composition is coated on a seed, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, at least $1\times10^4$, $1\times10^5$, $1\times10^6$, $1\times10^7$ cfu/seed or more of the microorganisms therein remain in a fluid state surrounded by a composition that exists in a glassy and/or rubbery state at 20, 21, 22, 23, 24, 25, 26, 27, 28, 29 and/or 30° C. when the inoculant composition is coated on a seed, desiccated by 95% or more and stored at 20, 21, 22, 23, 24, 25, 26, 27, 28, 29 and/or 30° C. and 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure exhibit enhanced flowability as compared to a control composition (e.g., a control composition that is identical to the inoculant composition of the present disclosure except that it lacks one or more of the components found in the inoculant composition and/or contains one or more components not found in the inoculant composition of the present disclosure). For example, the flowability of inoculant compositions of the present disclosure may be improved by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the stabilizers/dispersants found in the inoculant composition and/or comprises a reduced amount of one or more of the stabilizers/dispersants found in the inoculant composition.

The present disclosure extends to kits comprising, consisting essentially of, or consisting of an inoculant composition of the present disclosure and a container housing the inoculant composition. In some embodiments, the kit further comprises one or more oxygen scavengers, such as activated carbon, ascorbic acid, iron powder, mixtures of ferrous carbonate and metal halide catalysts, sodium chloride and/or sodium hydrogen carbonate.

The container may comprise any suitable material(s), including, but not limited to, materials that reduce the amount of light, moisture and/or oxygen that contact the inoculant composition when the container is sealed.

In some embodiments, the container comprises, consists essentially of, or consists of a material having light permeability of less than about 1, 2, 3, 4, 5, 6, 7, 8, 9, 10, 15, 20, 25, 30, 35, 40, 45, 50, 55, 60, 65, 70 or 75%.

In some embodiments, the container reduces the amount of ambient light that reaches the inoculant composition by about 5, 10, 15, 20, 25, 30, 35, 40, 45, 50, 55, 60, 65, 70, 75, 80, 85, 90, 95 or 100% when sealed.

In some embodiments, the container reduces the amount of ambient moisture that reaches the inoculant composition by about 5, 10, 15, 20, 25, 30, 35, 40, 45, 50, 55, 60, 65, 70, 75, 80, 85, 90, 95 or 100% when sealed.

In some embodiments, the container comprises, consists essentially of, or consists of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 $cm^3/m^2 \cdot day$ (as measured in accordance with ASTM D3985).

In some embodiments, the container reduces the amount of ambient oxygen that reaches the inoculant composition by about 5, 10, 15, 20, 25, 30, 35, 40, 45, 50, 55, 60, 65, 70, 75, 80, 85, 90, 95 or 100% when sealed.

In some embodiments, oxygen is actively removed from the container. Any suitable method(s) may be used to remove oxygen from the container, including, but not limited to, vacuum sealing and gas flushing methods. See generally WO2016/096821. In some embodiments, ambient air is evacuated from the container under vacuum and replaced with one or more inert gases (e.g., hydrogen, nitrogen, helium, neon, argon, krypton, xenon, radon, carbon dioxide, nitrous oxide, hydrogen sulfide, lower alkane and/or halo alkane).

In some embodiments, kits of the present disclosure comprise 1, 2, 3, 4, 5 or more additional containers. The additional containers may comprise any suitable component (s) or composition(s), including, but not limited to, agriculturally beneficial microorganisms, biostimulants, drying agents, nutrients, oxidation control components and pesticides. Examples of agriculturally beneficial microorganisms, biostimulants, drying agents, nutrients, oxidation control components and pesticides that may be included in the additional containers are described above.

The present disclosure extends to plant parts treated with an inoculant composition of the present disclosure (e.g., seeds coated with an inoculant composition of the present disclosure), plants grown from plant propagation materials treated with an inoculant composition of the present disclosure, plants treated with an inoculant composition of the present disclosure, plant parts harvested from plants grown from plant propagation materials treated with an inoculant composition of the present disclosure, plant parts harvested from plants treated with an inoculant composition of the present disclosure, processed products derived from plants grown from plant propagation materials treated with an inoculant composition of the present disclosure, processed products derived from plants treated with an inoculant composition of the present disclosure, crops comprising a plurality of plants grown from plant propagation materials treated with an inoculant composition of the present disclosure and crops comprising a plurality of plants treated with an inoculant composition of the present disclosure. Examples of methods that may be used to treat plants and plant parts with inoculant compositions of the present disclosure are discussed in further detail below.

In some embodiments, treated plant propagation materials comprise, consist essentially of or consist of a plant propagation material and a coating that covers at least a portion of the outer surface of the plant propagation material, said coating comprising, consisting essentially of, or consisting of an inoculant composition of the present disclosure.

The coating may cover any suitable portion of the plant propagation material. In some embodiments, the coating covers at least 20, 25, 30, 35, 40, 45, 50, 55, 60, 65, 70, 75, 80, 85, 90, 95% or more of the outer surface of the plant propagation material. In some embodiments, the coating completely covers the outer surface of the plant propagation material.

The coating may comprise one, two, three, four, five or more layers. In some embodiments, the coating comprises at least one layer that is free or substantially free of microorganisms. For example, in some embodiments, the coating comprises an inner layer that contains one or more microorganisms and one or more outer layers free or substantially free of microorganisms. In some embodiments, the coating comprises at least one layer that is free or substantially free of stabilizing compounds. For example, in some embodiments, the coating comprising an inner layer that contains one or more microorganisms but is free or substantially free of stabilizing compounds and an outer layer that is equivalent to an inoculant composition of the present disclosure except insofar as it lacks one or more microorganisms.

In some embodiments, coatings of the present disclosure comprise, consist essentially of or consist of an inner layer that comprises, consists essentially of or consists of an inoculant composition of the present disclosure and an outer layer that is equivalent to an inoculant composition of the present disclosure except insofar as it lacks one or more microorganisms.

For example, coated plant propagation materials of the present disclosure may comprise a seed that is coated with an inner layer comprising one or more maltodextrins (e.g., one or more maltodextrins having a DEV of about 15 to about 20) and one or more microorganisms (e.g., one or more strains of *Bradyrhizobium*, such as BRADY; and/or one or more strains of *Penicillium*, such as PENI) and an outer layer that comprises one or more maltodextrins (e.g., one or more maltodextrins having a DEV of about 15 to about 20) but is free of microorganisms.

In some embodiments, coatings of the present disclosure comprise, consist essentially of or consist of an inoculant composition of the present disclosure and a drying powder. For example, coated plant propagation materials of the present disclosure may comprise a seed that is coated with an inoculant composition comprising one or more maltodextrins (e.g., one or more maltodextrins having a DEV of about 15 to about 20) and one or more microorganisms (e.g., one or more strains of *Bradyrhizobium*, such as BRADY; and/or one or more strains of *Penicillium*, such as PENI) and then covered with a drying powder (e.g., a drying power that comprises calcium stearate, one or more clays, graphite, magnesium stearate, magnesium sulfate, powdered milk, silica, soy lecithin and/or talc).

The coating may have any suitable thickness. The absolute value of the thickness that is sufficient to cause the desired effect may be affected by factors such as the type, size and volume of material to which the composition will be applied, the type(s) of microorganisms in the composition, the number of microorganisms in the composition, the stability of the microorganisms in the composition and the storage conditions (e.g., temperature, relative humidity, duration). Those skilled in the art will understand how to select an effective amount/concentration/dosage using routine dose-response experiments. In some embodiments, the average thickness of the coating is at least 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5 µm or more. In some embodiments, the average thickness of the coating is about 1.5 to about 3.0 µm.

Plant propagation materials treated with inoculant compositions of the present disclosure may exhibit a high degree of flowability. In some embodiments, inoculant compositions of the present disclosure enhance the flowability of treated plant propagation material by at least 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition ((e.g., a control composition that is identical to the inoculant composition of the present disclosure except that it lacks one or more of the components found in the inoculant composition and/or contains one or more components not found in the inoculant composition of the present disclosure). In some embodiments, seeds coated with inoculant compositions of the present disclosure may exhibit a basic flowability energy of less than 5, 6, 7, 8, 9, 10, 20, 30, 40, 50, 60, 70, 80, 90, 100, 125, 150, 175, 200, 225, 2500, 275, 300, 325, 350, 375, 400, 425, 450, 475, 500, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000 mJ or less when measured at an airflow rate of 200, 300, 400, 500, 600, 700, 800, 900 and/or 1000 ml per minute using an FT4 Powder Rheometer® (Freeman Technology, Tewkesbury, UK).

Plant propagation materials treated with inoculant compositions of the present disclosure may exhibit a high degree of plantability. In some embodiments, inoculant compositions of the present disclosure enhance the plantability of treated plant propagation material by at least 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition ((e.g., a control composition that is identical to the inoculant composition of the present disclosure except that it lacks one or more of the components found in the inoculant composition and/or contains one or more components not found in the inoculant composition of the present disclosure). In some embodiments, seeds coated with inoculant compositions of the present disclosure may exhibit a plantability of at least 70, 75, 80, 85, 90, 91, 92, 93, 94, 95, 95.5, 96, 96.5, 97, 97.5, 98, 98.5, 99, 99.5% or more when measured using a brush-type seed meter, a vaccum seed meter and/or a finger pickup seed meter.

Plant propagation materials treated with inoculant compositions of the present disclosure may exhibit a low degree of dust-off. In some embodiments, inoculant compositions of the present disclosure enhance the dust-off of treated plant propagation material by at least 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition ((e.g., a control composition that is identical to the inoculant composition of the present disclosure except that it lacks one or more of the components found in the inoculant composition and/or contains one or more components not found in the inoculant composition of the present disclosure). In some embodiuments, seeds coated with inoculant compositions of the present disclosure exhibit a dust-off value of less than 0.01, 0.02, 0.03, 0.04, 0.05, 0.06, 0.07, 0.07, 0.08, 0.09, 0.1, 0.2, 0.3, 0.4, 0.5, 0.6, 0.7, 0.8, 0.9, 1 gram per 100 kilograms of seed when tested at room temperature (20-25° C.) and 30-50% relative humidity using a Type I HEUBACH DUSTMETER® (Heubach GmbH, Langelsheim, Germany) set to 30 rotations per minute, an air throughput of 20 liters per minute and total rotation time of 120 seconds. In some embodiments, seeds coated with inoculant compositions of the present disclosure may exhibit a Heubach dust value of less than about 0.01, 0.02, 0.03, 0.04, 0.05, 0.06, 0.07, 0.07, 0.08, 0.09, 0.1, 0.2, 0.3, 0.4, 0.5, 0.6, 0.7, 0.8, 0.9, 1 gram per 100 kilogram of treated seed when tested in accordance with the European Seed Association's Heubach Test ("Assessment of free floating dust and abrasion particles of treated seeds as a parameter of the quality of treated seeds" version 1.0).

Inoculant compositions of the present disclosure may be used to coat any suitable plant propagation materials, including, but not limited to, cuttings (e.g., leaves, stems), rhizomes, seeds and tubers. In some embodiments, the plant propagation material is a seed.

Inoculant compositions of the present disclosure may be used to coat plant propagation materials of any suitable plant type, including, but not limited to, row crops and vegetables. In some embodiments, inoculant compositions of the present disclosure are coated on propagation material derived from one or more plants selected from the families listed in Appendix B.

Non-limiting examples of plant propagation materials that may be coated with inoculant compositions of the present disclosure include seeds sold by Monsanto Company (St. Louis, Mo.) under the BOLLGARD II®, DROUGHTGARD®, GENUITY®, RIB COMPLETE®, ROUNDUP READY®, ROUNDUP READY 2 YIELD®, ROUNDUP READY 2 EXTEND™ SMARTSTAX®, VT DOUBLE PRO®, VT TRIPLE PRO®, YIELDGARD®, YIELDGARD VT ROOTWORM/RR2®, YIELDGARD VT TRIPLE® and/or XTENDFLEX™ tradenames.

The present disclosure extends to kits comprising, consisting essentially of, or consisting of a coated plant propagation material of the present disclosure and a container housing the coated plant propagation material. In some embodiments, the kit further comprises one or more oxygen scavengers, such as activated carbon, ascorbic acid, iron powder, mixtures of ferrous carbonate and metal halide catalysts, sodium chloride and/or sodium hydrogen carbonate.

The container may comprise any suitable material(s), including, but not limited to, materials that reduce the amount of light, moisture and/or oxygen that contact the coated plant propagation material when the container is sealed.

In some embodiments, the container comprises, consists essentially of, or consists of a material having light permeability of less than about 1, 2, 3, 4, 5, 6, 7, 8, 9, 10, 15, 20, 25, 30, 35, 40, 45, 50, 55, 60, 65, 70 or 75%.

In some embodiments, the container reduces the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

In some embodiments, the container reduces the amount of ambient moisture that reaches said plant propagation material by about 5, 10, 15, 20, 25, 30, 35, 40, 45, 50, 55, 60, 65, 70, 75, 80, 85, 90, 95 or 100% when sealed.

In some embodiments, the container comprises, consists essentially of, or consists of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 $cm^3/m^2 \cdot day$ (as measured in accordance with ASTM D3985).

In some embodiments, the container reduces the amount of ambient oxygen that reaches said plant propagation material by about 5, 10, 15, 20, 25, 30, 35, 40, 45, 50, 55, 60, 65, 70, 75, 80, 85, 90, 95 or 100% when sealed.

In some embodiments, oxygen is actively removed from the container. Any suitable method(s) may be used to remove oxygen from the container, including, but not limited to, vacuum sealing and gas flushing methods. See generally WO2016/096821. In some embodiments, ambient air is evacuated from the container under vacuum and replaced with one or more inert gases (e.g., hydrogen, nitrogen, helium, neon, argon, krypton, xenon, radon, carbon dioxide, nitrous oxide, hydrogen sulfide, lower alkane and/or halo alkane).

In some embodiments, kits of the present disclosure comprise 1, 2, 3, 4, 5 or more additional containers. The additional containers may comprise any suitable component(s) or composition(s), including, but not limited to, agriculturally beneficial microorganisms, biostimulants, drying agents, nutrients, oxidation control components and pesticides. Examples of agriculturally beneficial microorganisms, biostimulants, drying agents, nutrients, oxidation control components and pesticides that may be included in the additional containers are described above.

The present disclosure extends to methods of treating plants and plant parts with compositions of the present disclosure.

In some embodiments, methods of the present disclosure comprise, consist essentially of, or consist of applying an inoculant composition of the present disclosure to a plant or plant part.

Inoculant compositions of the present disclosure may be applied to plants and plant parts at any suitable time(s), including, but not limited to, prior to planting, at the time of planting and/or after planting. In some embodiments, plant propagation material is treated at least 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks prior to planting. In some embodiments, plant propagation material is treated less than 1, 2, 3, or 4 weeks prior to planting. In some embodiments, plant propagation material is treated at the time of planting. In some embodiments, plants are treated after germination (e.g., by soil amendment and/or foliar application).

Inoculant compositions of the present disclosure may be applied to plants and plant parts using any suitable method(s), including, but not limited to, on-seed application, in-furrow application, soil application and foliar application. The appropriate application method may be affected by factors such as the type, size and volume of material to which the inoculant composition will be applied, the timing of application, the type(s) of microorganisms in the composition, the number of microorganisms in the composition, the stability of the microorganisms in the inoculant composition and the storage conditions (e.g., temperature, relative humidity, duration). Those skilled in the art will understand how to select an effective method using routine dose-response experiments.

In some embodiments, inoculant compositions of the present disclosure are applied using a batch system in which predetermined batch sizes of plant material and inoculant composition are combined (e.g., by delivering both the plant material and inoculation composition into a mixer).

In some embodiments, inoculant compositions of the present disclosure are applied using a continuous treatment system calibrated to apply inoculant composition at a pre-defined rate in proportion to a continuous flow of plant material.

In some embodiments, plant propagation materials are soaked in a liquid inoculant composition of the present disclosure for at least 0.1, 0.2, 0.3, 0.4, 0.5, 0.6, 0.7, 0.8, 0.9, 1, 1.25, 1.5, 1.75, 2, 3, 4, 5, 6, 9, 12, 15, 18, 21, 24, 36, 48 hours or more.

In some embodiments, plant propagation materials are coated in an inoculant composition of the present disclosure. For example, in some embodiments, a liquid inoculant composition of the present disclosure is applied to the inside wall of a round container, seeds are added to the container, then the container is rotated such that the seeds come into contact with the composition, a process known in the art as "container coating."

In some embodiments, liquid inoculant compositions of the present disclosure are applied directly to plant materials. For example, in some embodiments, liquid inoculant compositions of the present disclosure are mixed with another liquid composition (e.g., a composition comprising one or more pesticides) to form a treatment composition, which is applied to plants or plant propagation materials.

In some embodiments, liquid inoculant compositions of the present disclosure are dried prior to application. For example, in some embodiments, liquid inoculant compositions of the present disclosure are dried to produce a powder or granuale, which is applied to plants or plant propagation materials.

Inoculant compositions of the present disclosure may be applied to plants and plant parts in any suitable amount(s)/concentration(s). The absolute value of the amount/concentration/dosage of inoculant composition that is sufficient to cause the desired effect may be affected by factors such as the type, size and volume of material to which the composition will be applied, the type(s) of microorganisms in the composition, the number of microorganisms in the composition, the stability of the microorganisms in the composition and the storage conditions (e.g., temperature, relative humidity, duration). Those skilled in the art will understand how to select an effective amount/concentration/dosage using routine dose-response experiments.

In some embodiments, the inoculant composition is applied in an amount ranging from about 0.5 to about 10 milliliters of inoculant composition per kilogram of plant material. For example, in some embodiments, about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 milliliters or more of inoculant composition is applied per kilogram of seed. In some embodiments, an inoculant composition comprising one or more maltodextrins (e.g., one or more maltodextrins having a DEV of about 15 to about 20) and one or more microorganisms (e.g., one or more strains of *Bradyrhizobium*, such as BRADY; and/or one or more strains of

*Penicillium*, such as PENI) is applied at a rate of about 2, 2.25, 2.5, 2.75, 3, 3.25, 3.5, 3.75, or 4 milliliters per kilogram of seed.

In some embodiments, methods of the present disclosure further comprise applying one or more drying powders to the plant or plant part.

Drying powders may be applied in any suitable amount (s)/concentration(s). The absolute value of the amount/concentration/dosage of drying powder(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

In some embodiments, the drying powder is applied in an amount ranging from about 0.5 to about 10 grams of drying powder per kilogram of plant propagation material. For example, in some embodiments, about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder (e.g., drying powder comprising magnesium stearate, magnesium sulfate, powdered milk, silica, soy lecithin and/or talc) is applied per kilogram of seed. In some embodiments, a drying powder comprising calcium stearate, attapulgite clay, montmorillonite clay, graphite, magnesium stearate, silica (e.g., fumed silica, hydrophobically-coated silica and/or precipitated silica) and/or talc is applied to seeds coated with an inoculant composition comprising one or more maltodextrins (e.g., one or more maltodextrins having a DEV of about 15 to about 20) and one or more microorganisms (e.g., one or more strains of *Bradyrhizobium*, such as BRADY; and/or one or more strains of *Penicillium*, such as PENI) at a rate of about 1, 1.25, 1.5, 1.75, 2, 2.25, 2.5, 2.75, or 3 grams per kilogram of seed.

In some embodiments, methods of the present disclosure further comprise applying one or more additional agriculturally beneficial components (e.g., one or more biostimulants, microbial extracts, nutrients, pesticides and/or plant signal molecules) to the plant or plant part. For example, in some embodiments, an inoculant composition of the present disclosure is applied to a seed and a second composition comprising one or more pesticides is applied to the seed and/or to the plant that grows from the seed.

Additional agriculturally beneficial components may be applied in any suitable amount(s)/concentration(s). The absolute value of the amount/concentration/dosage of drying powder(s) that is sufficient to cause the desired effect may be affected by factors such as the type, size and volume of material to which the composition will be applied, the stability of the microorganisms in the composition and the storage conditions (e.g., temperature, relative humidity, duration). Those skilled in the art will understand how to select an effective amount/concentration/dosage using routine dose-response experiments.

The present disclosure extends to methods comprising, consisting essentially of, or consisting of growing a plant from a plant propagation material that has been treated with a composition of the present disclosure. In some embodiments, the plant is grown from a plant propagation material planted in a soil.

As noted above, inoculant compositions of the present disclosure may comprise myriad agriculturally beneficial constituents in addition to any agriculturally beneficial microorganisms contained therein, including, but not limited to, biostimulants, microbial extracts, nutrients, pesticides and plant signal molecules. It is to be understood that such agriculturally beneficial constituents may also be used in conjunction with inoculant compositions of the present disclosure (rather than incorporated into inoculant compositions of the present disclosure). Thus, the present disclosure extends to systems and methods of using inoculant compositions of the present disclosure in conjunction with additional compositions comprising one or more agriculturally beneficial constituents. The additional composition(s) may comprise any suitable agriculturally beneficial constituent(s), including, but not limited to, the agriculturally beneficial constituents described above.

In some embodiments, inoculant compositions of the present disclosure are used in conjunction with one or more on-seed compositions, one or more in-furrow compositions, one or more soil-applied compositions and/or one or more foliar-applied compositions.

In some embodiments, inoculant compositions of the present disclosure are used as part of an integrated disease and/or pest management system.

The present disclosure extends to animal feed compositions comprising, consisting essentially of, or consisting of a food component and a microbial component, said microbial component comprising, consisting essentially of, or consisting of an inoculant composition of the present disclosure.

Animal feed compositions of the present disclosure may comprise any suitable food component, including, but not limited to, fodder (e.g., grains, hay, legumes, silage and/or straw) and forage (e.g., grass).

Animal feed compositions of the present disclosure may be fed to any suitable animal, including, but not limited to, farm animals, zoo animals, laboratory animals and/or companion animals. In some embodiments, the animal feed composition is formulated to meet the dietary needs of birds (e.g., chickens, ducks, quails and/or turkeys), bovids (e.g., antelopes, bison, cattle, gazelles, goats, impala, oxen, sheep and/or wildebeests), canines, cervids (e.g., caribou, deer, elk and/or moose), equines (e.g., donkeys, horses and/or zebras), felines, fish, pigs, rabbits, rodents (e.g., guinea pigs, hamsters, mice and/or rats) and the like.

The present disclosure also provides methods of enhancing the survival and/or stability of microorganisms in a composition, said methods comprising, consisting essentially of, or consisting of adding an effective amount of one or more stabilizing compounds to said composition.

Any suitable stabilizing compound may be added to the composition, including, but not limited to, maltodextrins, monosaccharides, disaccharides, oligosaccharides, malt extracts, peat extracts, betaines, prolines, sarcosines, peptones, skim milks, oxidation control components and hygroscopic polymers.

In some embodiments, one or more maltodextrins is/are added to the composition.

In some embodiments, one or more disaccharides is/are added to the composition.

In some embodiments, one or more maltodextrins and one or more disaccharides are added to the composition.

Any suitable maltodextrin(s) may be added to the composition, including, but not limited to, maltodextrins having a DEV of about 3, 4, 5, 6, 7, 8, 9, 10, 11, 12, 13, 14, 15, 16, 17, 18, 19, 20, 21, 22, 23, 24, or 25.

In some embodiments, one or more maltodextrins having a DEV of about 10 to about 20 (e.g., one or more maltodextrins having a DEV of about 15 to about 20) is added to the composition. In some embodiments, a combination of maltodextrins having a DEV of about 10 to about 20 (e.g., a combination of maltodextrins having a DEV of about 15 to about 20) is added to the composition.

In some embodiments, one or more maltodextrins having a glass transition temperature (Tg) of at least 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity is added to the composition. In some embodiments, a combination of maltodextrins having a glass transition temperature (Tg) of at least 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity is added to the composition.

In some embodiments, one or more maltodextrins that raise the Tg of the composition until it is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity is added to the composition. In some embodiments, a combination of maltodextrins that raises the Tg of the composition until it is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity is added to the composition.

In some embodiments, one or more maltodextrins that raise the Tg of the composition at the relative humidity at which the inoculant composition is to be stored until it is at least 5, 10, 15, 20, 25, 30, 35, 40, 45, 50° C. or more higher than the temperature at which the inoculant composition is to be stored is added to the composition. In some embodiments, a combination of maltodextrins that raises the Tg of the composition at the relative humidity at which the inoculant composition is to be stored until it is at least 5, 10, 15, 20, 25, 30, 35, 40, 45, 50° C. or more higher than the temperature at which the inoculant composition is to be stored is added to the composition.

In some embodiments, one or more maltodextrins having an onset temperature of at least 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity is added to the composition. In some embodiments, a combination of maltodextrins having an onset temperature of at least 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity is added to the composition.

In some embodiments, one or more maltodextrins that raise the onset temperature of the composition until it is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity is added to the composition. In some embodiments, a combination of maltodextrins that raises the onset temperature of the composition until it is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45° C. or more at 52% relative humidity is added to the composition.

In some embodiments, one or more maltodextrins that raise the onset temperature of the composition at the relative humidity at which the inoculant composition is to be stored until it is at least 5, 10, 15, 20, 25, 30, 35, 40, 45, 50° C. or more higher than the temperature at which the inoculant composition is to be stored is added to the composition. In some embodiments, a combination of maltodextrins that raises the onset temperature of the composition at the relative humidity at which the inoculant composition is to be stored until it is at least 5, 10, 15, 20, 25, 30, 35, 40, 45, 50° C. or more higher than the temperature at which the inoculant composition is to be stored is added to the composition.

Non-limiting examples of maltodextrins that may be useful in methods of the present disclosure include MALTRIN® M040 (DEV=5; molecular weight=3600; Grain Processing Corporation, Muscatine, Iowa), MALTRIN® M100 (DEV=10; molecular weight=1800; Grain Processing Corporation, Muscatine, Iowa), MALTRIN® M150 (DEV=15; molecular weight=1200; Grain Processing Corporation, Muscatine, Iowa), MALTRIN® M200 (DEV=20; molecular weight=900; Grain Processing Corporation, Muscatine, Iowa), MALTRIN® M250 (DEV=25; molecular weight=720; Grain Processing Corporation, Muscatine, Iowa); GLOBE® Plus 15 DE (Ingredion Inc., Westchester, Ill.); and combinations thereof. In some embodiments, the maltodextrin (or combination of maltodextrins) has a DEV of 15 to 20 and/or a Tg and/or onset temperature at the relative humidity at which the inoculant composition is to be stored that is at least 20, 25, 30, 35, 40, 45, or 50° C. higher than the temperature at which the inoculant composition is to be stored.

Maltodextrins may be added to the composition in any suitable form. In some embodiments, the maltodextrin(s) added to the composition is/are at least 70, 75, 80, 85, 90, 91, 92, 93, 94, 95, 96, 97, 98, 99, 99.5% or more pure.

Any suitable monosaccharide(s) may be added to the composition, including, but not limited to, allose, altrose, arabinose, fructose, galactose, glucose, gulose, iodose, lyxose, mannose, ribose, talose, threose and/or xylose. In some embodiments, gluscose is added to the composition. In some embodiments, a monosaccharide other than glucose is added to the composition.

Any suitable disaccharide(s) may be added to the composition, including, but not limited to, cellobiose, chitobiose, gentiobiose, gentiobiulose, isomaltose, kojibiose, lactose, lactulose, laminaribiose, maltose (e.g., maltose monohydrate, anhydrous maltose), maltulose, mannobiose, melibiose, melibiulose, nigerose, palatinose, rutinose, rutinulose, sophorose, sucrose, trehalose, turanose and/or xylobiose. In some embodiments, maltose is added to the composition. In some embodiments, a disaccharide other than maltose is added to the composition. In some embodiments, trehalose is added to the composition. In some embodiments, a disaccharide other than trehalose is added to the composition.

Any suitable oligosaccharide(s) may be added to the composition, including, but not limited to, fructo-oligosaccharides, galacto-oligosaccharides, mannon-oligosaccharides and/or raffinose.

Mono-, di- and/or oligosaccharides may be added to the composition in any suitable form. In some embodiments, the mono-, di- and/or oligosaccharide(s) added to the composition is/are at least 70, 75, 80, 85, 90, 91, 92, 93, 94, 95, 96, 97, 98, 99, 99.5% or more pure.

Any suitable betaine(s) may be added to the composition, including, but not limited to, trimethylglycine.

Betaines may be added to the composition in any suitable form. In some embodiments, the betaine(s) added to the composition is/are at least 70, 75, 80, 85, 90, 91, 92, 93, 94, 95, 96, 97, 98, 99, 99.5% or more pure.

Proline may be added to the composition in any suitable form. In some embodiments, the proline(s) added to the composition is/are at least 70, 75, 80, 85, 90, 91, 92, 93, 94, 95, 96, 97, 98, 99, 99.5% or more pure.

Sarcosine may be added to the composition in any suitable form. In some embodiments, the sarcosine(s) added to the composition is/are at least 70, 75, 80, 85, 90, 91, 92, 93, 94, 95, 96, 97, 98, 99, 99.5% or more pure.

Any suitable peptone(s) may be added to the composition, including, but not limited to, bacterial peptones, meat peptones, milk peptones, vegetable peptones and yeast peptones.

Peptones may be added to the composition in any suitable form. In some embodiments, the peptone(s) added to the composition is/are at least 70, 75, 80, 85, 90, 91, 92, 93, 94, 95, 96, 97, 98, 99, 99.5% or more pure.

Any suitable oxidation control component(s) may be added to the composition, including, but not limited to, antioxidants and/or oxygen scavengers.

In some embodiments, one or more antioxidants is added to the composition. For example, in some embodiments, ascorbic acid, ascorbyl palmitate, ascorbyl stearate, calcium ascorbate, carotenoids, lipoic acid, phenolic compounds (e.g., flavonoids, flavones, flavonols), potassium ascorbate, sodium ascorbate, thiols (e.g., glutathione, lipoic acid, N-acetyl cysteine), tocopherols, tocotrienols, ubiquinone and/or uric acid is/are added to the composition.

Non-limiting examples of antioxidants that may be added to the composition include those that are soluble in the cell membrane (e.g., alpha tocopherol (vitamin E), ascorbyl palmitate) and those that are soluble in water (e.g., ascorbic acid and isomers or ascorbic acid, sodium or potassium salts of ascorbic acid or isomers or ascorbic acid, glutathione, sodium or potassium salts of glutathione). In some embodiments, use of a membrane-soluble antioxidant necessitates the addition of one or more surfactants to adequately disperse the antioxidant within the inoculant composition.

In some embodiments, one or more commercial antioxidants is added to the composition in accordance with the manufacturer's recommended amounts/concentrations.

In some embodiments, one or more oxygen scavengers is added to the composition. For example, in some embodiments, ascorbic acid, ascorbate salts, catechol and/or sodium hydrogen carbonate is/are added to the composition.

Any suitable hygroscopic polymer may be added to the composition, including, but not limited to, hygroscopic agars, albumins, alginates, carrageenans, celluloses, gums (e.g., cellulose gum, guar gum, gum arabic, gum combretum, xantham gum), methyl celluloses, nylons, pectins, polyacrylic acids, polycaprolactones, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches.

Non-limiting examples of polymers that may be added to the composition include AGRIMER™ polymers (e.g., 30, AL-10 LC, AL-22, AT/ATF, VA 3E, VA 31, VA 5E, VA 51, VA 6, VA 6E, VA 7E, VA 71, VEMA AN-216, VEMA AN-990, VEMA AN-1200, VEMA AN-1980, VEMA H-815MS; Ashland Specialty Ingredients, Wilmington, Del.), EASYSPERSE™ polymers (Ashland Specialty Ingredients, Wilmington, Del.); DISCO™ AG polymers (e.g., L-250, L-280, L-285, L-286, L-320, L-323, L-517, L-519, L-520, L800; Incotec Inc., Salinas, Calif.), KELZAN® polymers (Bri-Chem Supply Ltd., Calgary, Alberta, CA), SEEDWORX™ polymers (e.g., Bio 200; Aginnovation, LLC, Walnut Groove, Calif.), TICAXAN® xanthan powders, such as PRE-HYDRATED® TICAXAN® Rapid-3 Powder (TIC Gums, White Marsh, Md.) and combinations thereof.

Additional examples of polymers that may be added to the composition may be found in Pouci, et al. AM. J. AGRIC. BIOL. SCI. 3(1):299 (2008).

Hygroscopic polymers may be added to the composition in any suitable form. In some embodiments, the hygroscopic polymer(s) added to the composition is/are at least 70, 75, 80, 85, 90, 91, 92, 93, 94, 95, 96, 97, 98, 99, 99.5% or more pure.

Stabilizing compounds, such as maltodextrins, monosaccharides, disaccharides, oligosaccharides, malt extracts, peat extracts, betaines, prolines, sarcosines, peptones, skim milks, oxidation control components and hygroscopic polymers, may be added to the composition in any suitable amount(s)/concentration(s)/dosage(s). The absolute value of the amount/concentration/dosage of stabilizing compound (s) that is/are sufficient to cause the desired effect(s) may be affected by factors such as the type, size and volume of material to which the composition will be applied, the type(s) of microorganisms in the composition, the number of microorganisms in the composition, the stability of the microorganisms in the composition and storage conditions (e.g., temperature, relative humidity, duration). Those skilled in the art will understand how to select an effective amount/concentration/dosage using routine dose-response experiments.

In some embodiments, the stabilizing compound(s) is/are added to the composition until it/they are present in the amount/concentration/dosage described above with respect to inoculant compositions of the present disclosure. For example, one or more maltodextrins (each and/or collectively) having a DEV value of about 15 to about 20 and/or one or more disaccharides (e.g., maltose) may be added to the composition until it/they comprise(s) about 1 to about 95% or more (by weight), optionally about 5, 10, 15, 20, 25, 30, 35, 40, 45, 50, 55, 60, 65, 70, 75, 80, 85, 90, 95% (by weight), of the composition.

In some embodiments, the stabilizing compound(s) is/are added in an amount/concentration sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microorganisms in the composition remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when the composition is desiccated by about 5, 10, 15, 20, 25, 30, 35, 40, 45, 50, 55, 60, 65, 70, 75, 80, 85, 90, 95% or more.

In some embodiments, the stabilizing compound(s) is/are added in an amount/concentration sufficient to ensure that microorganisms remain viable in compositions of the present disclosure for at least 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more (e.g., at least 12, 16, 20, 24, 28, 32, 36, 40, 44, 48, 52, 56, 60, 64, 68, 72, 76, 80, 84, 88, 92, 96, 100, 104 weeks or more when stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity).

In some embodiments, the stabilizing compound(s) is/are added in an amount/concentration sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microorganisms in the composition survive following storage at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are added in an amount/concentration sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microorganisms in the composition survive following desiccation (of about 5, 10, 15, 20, 25, 30, 35, 40, 45, 50, 55, 60, 65, 70, 75, 80, 85, 90, 95% or more) and storage at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are added in an amount/concentration sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microorganisms in the composition survive following cryopreservation at or below −80° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are added in an amount/concentration sufficient to ensure that at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microbial spores therein survive when the composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are present in an amount/concentration sufficient to ensure that at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microbial spores therein survive when the composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are present in an amount/concentration sufficient to ensure that at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microbial spores therein survive when the composition is desiccated (by about 5, 10, 15, 20, 25, 30, 35, 40, 45, 50, 55, 60, 65, 70, 75, 80, 85, 90, 95% or more) stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are present in an amount/concentration sufficient to ensure that at least $1\times10^1$, $1\times10^2$, $1\times10^3$, $1\times10^4$, $1\times10^5$, $1\times10^6$, $1\times10$, $1\times10^8$, $1\times10^1$, $1\times10^{10}$, $1\times10^{11}$, $1\times10^{12}$ cfu/seed or more of the microbial spores therein survive following cryopreservation at or below −80° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the stabilizing compound(s) is/are present in an amount/concentration sufficient to ensure that at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microbial spores therein survive when the composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

Stablizing compounds may be added to the composition in any suitable ratio(s). In some embodiments, one or more maltodextrins and one or more additional stabilizing compounds are added to the composition at a maltodextrin: additional stabilizing compound ratio of about 1:99 to about 99:1 (by weight, based upon the respective weight percentages of the maltodextrin(s) and the additional stabilizing compound(s) in the inoculant composition). For example, one or more maltodextrins and one or more additional stabilizing compounds are added to the composition at a maltodextrin:additional stabilizing compound ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more, preferably about 45:55, 50:50, 55:45, 60:40, 65:35, 70:30, 75:25, 80:20, 85:15, 90:10, 95:5 or more. In some embodiments, one or more maltodextrins and one or more additional stabilizing compounds are added to the composition at a maltodextrin:additional stabilizing compound ratio of about 15:85 to about 85:15, optionally about 65:35. In some embodiments, one or more maltodextrins (e.g., one or more maltodextrins (each and/or collectively) having a DEV of about 15 to about 20) and one or more disaccharides (e.g., maltose) are added to the composition at a maltodextrin:disaccharide ratio of about 15:85, about 35:65, about 65:35 or about 85:15.

Particular embodiments of the present disclosure are described in the following numbered paragraphs:

1. An inoculant composition, comprising, consisting essentially of, or consisting of: one or more maltodextrins, one or more monosaccharides and/or one or more disaccharides; and one or more microorganisms.

2. The inoculant composition of paragraph 1, wherein said one or more maltodextrins, one or more monosaccharides and/or one or more disaccharides comprises, consists essentially of, or consists of one or more maltodextrins having a dextrose equivalent value of about 3, 4, 5, 6, 7, 8, 9, 10, 11, 12, 13, 14, 15, 16, 17, 18, 19, 20.

3. The inoculant composition of paragraph 1, wherein said one or more maltodextrins, one or more monosaccharides and/or one or more disaccharides comprises, consists essentially of, or consists of one or more maltodextrins having a dextrose equivalent value of about 10 to about 20, optionally about 15 to about 20.

4. The inoculant composition of paragraph 1, wherein said one or more maltodextrins, one or more monosaccharides and/or one or more disaccharides comprise(s) about 5, 10, 15, 20, 25, 30, 35, 40, 45, 50, 55, 60, 65, 70, 75, 80, 85, 90, 95% or more (by weight) of said inoculant composition.

5. The inoculant composition of paragraph 1, wherein said one or more maltodextrins, one or more monosaccharides and/or one or more disaccharides comprise(s) about 5 to about 95% (by weight), optionally about 1 to about 65%, about 10% to about 30%, about 20% to about 40%, about 20% to about 50%, or about 30 to about 60% (by weight), of said inoculant composition.

6. The inoculant composition of any one of the preceding paragraphs, wherein said one or more maltodextrins, one or more monosaccharides and/or one or more disaccharides is/are present in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms survive when said inoculant composition is desiccated by about 5, 10, 15, 20, 25, 30, 35, 40, 45, 50, 55, 60, 65, 70, 75, 80, 85, 90, 95% or more.

7. The inoculant composition of any one of the preceding paragraphs, wherein said one or more maltodextrins, one or more monosaccharides and/or one or more disaccharides is/are present in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms survive when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

8. The inoculant composition of any one of the preceding paragraphs, wherein said one or more maltodextrins, one or more monosaccharides and/or one or more disaccharides is/are present in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms survive when said inoculant composition is coated on a plant propagation material and desiccated by about 5, 10, 15, 20, 25, 30, 35, 40, 45, 50, 55, 60, 65, 70, 75, 80, 85, 90, 95% or more.

9. The inoculant composition of any one of the preceding paragraphs, wherein said one or more maltodextrins, one or more monosaccharides and/or one or more disaccharides is/are present in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms survive when said inoculant composition is coated on a plant propagation material, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

10. The inoculant composition of any one of the preceding paragraphs, wherein said one or more maltodextrins, one or more monosaccharides and/or one or more disaccharides is/are present in an amount sufficient to ensure that at least about $1\times10^1$ to about $1\times10^{10}$ colony-forming units of said one or more microorganisms per gram and/or milliliter of said inoculant composition survive when said inoculant composition is desiccated by about 5, 10, 15, 20, 25, 30, 35, 40, 45, 50, 55, 60, 65, 70, 75, 80, 85, 90, 95% or more.

11. The inoculant composition of any one of the preceding paragraphs, wherein said one or more maltodextrins, one or more monosaccharides and/or one or more disaccharides is/are present in an amount sufficient to ensure that at least about $1\times10^1$ to about $1\times10^{10}$ colony-forming units of said one or more microorganisms per gram and/or milliliter of said inoculant composition survive when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally at least $1\times10^4$, $1\times10^5$, $1\times10^6$, $1\times10^7$ or more colony-forming units per gram and/or milliliter of said inoculant composition.

12. The inoculant composition of any one of the preceding paragraphs, wherein said one or more maltodextrins, one or more monosaccharides and/or one or more disaccharides is/are present in an amount sufficient to ensure that at least about $1\times10^1$ to about $1\times10^{10}$ colony-forming units of said one or more microorganisms per seed survive when said inoculant composition is coated on a seed and desiccated by about 5, 10, 15, 20, 25, 30, 35, 40, 45, 50, 55, 60, 65, 70, 75, 80, 85, 90, 95% or more.

13. The inoculant composition of any one of the preceding paragraphs, wherein said one or more maltodextrins, one or more monosaccharides and/or one or more disaccharides is/are present in an amount sufficient to ensure that at least about $1\times10^1$ to about $1\times10^{10}$ colony-forming units of said one or more microorganisms per seed survive when said inoculant composition is coated on a seed, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1\times10^4$, $1\times10^5$, $1\times10^6$, $1\times10^7$ or more colony-forming units per seed.

14. The inoculant composition of any one of the preceding paragraphs, wherein said one or more maltodextrins, one or more monosaccharides and/or one or more disaccharides is/are present in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is desiccated by about 5, 10, 15, 20, 25, 30, 35, 40, 45, 50, 55, 60, 65, 70, 75, 80, 85, 90, 95% or more.

15. The inoculant composition of any one of the preceding paragraphs, wherein said one or more maltodextrins, one or more monosaccharides and/or one or more disaccharides is/are present in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

16. The inoculant composition of any one of the preceding paragraphs, wherein said one or more maltodextrins, one or more monosaccharides and/or one or more disaccharides is/are present in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is coated on a plant propagation material and desiccated by about 5, 10, 15, 20, 25, 30, 35, 40, 45, 50, 55, 60, 65, 70, 75, 80, 85, 90, 95% or more.

17. The inoculant composition of any one of the preceding paragraphs, wherein said one or more maltodextrins, one or more monosaccharides and/or one or more disaccharides is/are present in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is coated on a plant propagation material, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

18. The inoculant composition of any one of the preceding paragraphs, wherein said one or more maltodextrins, one or more monosaccharides and/or one or more disaccharides is/are present in an amount sufficient to ensure that at least about $1\times10^1$ to about $1\times10^{10}$ colony-forming units of said one or more microorganisms per gram and/or milliliter of said inoculant composition remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is desiccated by about 5, 10, 15, 20, 25, 30, 35, 40, 45, 50, 55, 60, 65, 70, 75, 80, 85, 90, 95% or more.

19. The inoculant composition of any one of the preceding paragraphs, wherein said one or more maltodextrins, one or more monosaccharides and/or one or more disaccharides is/are present in an amount sufficient to ensure that at least about $1\times10^1$ to about $1\times10^{10}$ colony-forming units of said one or more microorganisms per gram and/or milliliter of said inoculant composition remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1\times10^4$, $1\times10^5$, $1\times10^6$, $1\times10^7$ or more colony-forming units per gram and/or milliliter of said inoculant composition.

20. The inoculant composition of any one of the preceding paragraphs, wherein said one or more maltodextrins, one or more monosaccharides and/or one or more disaccharides is/are present in an amount sufficient to ensure that at least about $1\times10^1$ to about $1\times10^{10}$ colony-forming units of said one or more microorganisms per seed remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is coated on a seed and desiccated by about 5, 10, 15, 20, 25, 30, 35, 40, 45, 50, 55, 60, 65, 70, 75, 80, 85, 90, 95% or more.

21. The inoculant composition of any one of the preceding paragraphs, wherein said one or more maltodextrins, one or more monosaccharides and/or one or more disaccharides is/are present in an amount sufficient to ensure that at least about $1\times10^1$ to about $1\times10^{10}$ colony-forming units of said one or more microorganisms per seed remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is coated on a seed, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1\times10^4$, $1\times10^5$, $1\times10^6$, $1\times10^7$ or more colony-forming units per seed.

22. The inoculant composition of any one of the preceding paragraphs, wherein said one or more microorganisms is present in said inoculant composition in a concentration ranging from about $1\times10^1$ to about $1\times10^{15}$ colony-forming units of said one or more microorganisms per gram and/or milliliter of said inoculant composition, optionally $1\times10^4$, $1\times10^5$, $1\times10^6$, $1\times10^7$, $1\times10^8$, $1\times10^9$, $1\times10^{10}$ or more colony-forming units per gram and/or milliliter of said inoculant composition.

23. The inoculant composition of any one of the preceding paragraphs, wherein said one or more microorganisms comprises, consists essentially of, or consists of one or more microorganisms that improve the availability of a soil nutrient.

24. The inoculant composition of any one of the preceding paragraphs, wherein said one or more microorganisms comprises, consists essentially of, or consists of one or more diazotrophs.

25. The inoculant composition of any one of the preceding paragraphs, wherein said one or more microorganisms comprises, consists essentially of, or consists of one or more rhizobacteria.

26. The inoculant composition of any one of the preceding paragraphs, wherein said one or more microorganisms comprises, consists essentially of, or consists of one or more strains of *Bradyrhizobium*, optionally one or more strains of *Bradyrhizobium japonicum*.

27. The inoculant composition of any one of the preceding paragraphs, wherein said one or more microorganisms comprises, consists essentially of, or consists of one or more strains of *Rhizobium*, optionally one or more strains of *Rhizobium leguminosarum*.

28. The composition of any one of the preceding paragraphs, wherein said one or more microorganisms comprises, consists essentially of, or consists of one or more strains of *Sinorhizobium*, optionally one or more strains of *Sinorhizobium* meliloti.

29. The composition of any one of the preceding paragraphs, wherein said one or more microorganisms comprises, consists essentially of, or consists of one or more strains of *Mesorhizobium*.

30. The inoculant composition of any one of the preceding paragraphs, wherein said one or more microorganisms comprises, consists essentially of, or consists of one or more strains of *Azorhizobium*.

31. The inoculant composition of any one of the preceding paragraphs, wherein said one or more microorganisms comprises, consists essentially of, or consists of *Azospirillum brasilense* INTA Az-39, *Bradyrhizobium elkanii* SEMIA 501, *Bradyrhizobium elkanii* SEMIA 587, *Bradyrhizobium elkanii* SEMIA 5019, *Bradyrhizobium japonicum* NRRL B-50586 (also deposited as NRRL B-59565), *Bradyrhizobium japonicum* NRRL B-50587 (also deposited as NRRL B-59566), *Bradyrhizobium japonicum* NRRL B-50588 (also deposited as NRRL B-59567), *Bradyrhizobium japonicum* NRRL B-50589 (also deposited as NRRL B-59568), *Bradyrhizobium japonicum* NRRL B-50590 (also deposited as NRRL B-59569), *Bradyrhizobium japonicum* NRRL B-50591 (also deposited as NRRL B-59570), *Bradyrhizobium japonicum* NRRL B-50592 (also deposited as NRRL B-59571), *Bradyrhizobium japonicum* NRRL B-50593 (also deposited as NRRL B-59572), *Bradyrhizobium japonicum* NRRL B-50594 (also deposited as NRRL B-50493), *Bradyrhizobium japonicum* NRRL B-50608, *Bradyrhizobium japonicum* NRRL B-50609, *Bradyrhizobium japonicum* NRRL B-50610, *Bradyrhizobium japonicum* NRRL B-50611, *Bradyrhizobium japonicum* NRRL B-50612, *Bradyrhizobium japonicum* NRRL B-50726, *Bradyrhizobium japonicum* NRRL B-50727, *Bradyrhizobium japonicum* NRRL B-50728, *Bradyrhizobium japonicum* NRRL B-50729, *Bradyrhizobium japonicum* NRRL B-50730, *Bradyrhizobium japonicum* SEMIA 566, *Bradyrhizobium japonicum* SEMIA 5079, *Bradyrhizobium japonicum* SEMIA 5080, *Bradyrhizobium japonicum* USDA 6, *Bradyrhizobium japonicum* USDA 110, *Bradyrhizobium japonicum* USDA 122, *Bradyrhizobium japonicum* USDA 123, *Bradyrhizobium japonicum* USDA 127, *Bradyrhizobium japonicum* USDA 129, *Bradyrhizobium japonicum* USDA 532C, *Rhizobium leguminosarum* S012A-2 (IDAC 080305-01), *Sinorhizobium fredii* CCBAU114 and/or *Sinorhizobium fredii* USDA 205.

32. The inoculant composition of any one of the preceding paragraphs, wherein said one or more microorganisms comprises, consists essentially of, or consists of one or more strains having a genomic sequence that is at least 75, 80, 85, 90, 95, 96, 97, 98, 99% or more identical to any of the strains recited in paragraph 14 on the basis of 16S rDNA sequence identity.

33. The inoculant composition of any one of the preceding paragraphs, wherein said one or more microorganisms comprises, consists essentially of, or consists of one or more phosphate-solubilizing microorganisms.

34. The inoculant composition of any one of the preceding paragraphs, wherein said one or more microorganisms comprises, consists essentially of, or consists of one or more strains of *Penicillium*, optionally one or more strains of *P. bilaiae* and/or one or more strains of *P. gaestrivorus*.

35. The inoculant composition of any one of the preceding paragraphs, wherein said one or more microorganisms comprises, consists essentially of, or consists of *Penicillium bilaiae* (formerly known as *P. bilaii* and *P. bilaji*) ATCC 18309, *Penicillium bilaiae* ATCC 20851, *Penicillium bilaiae* ATCC 22348, *Penicillium bilaiae* NRRL 50162, *Penicillium bilaiae* NRRL 50169, *Penicillium bilaiae* NRRL 50776, *Penicillium bilaiae* NRRL 50777, *Penicillium bilaiae* NRRL 50778, *Penicillium bilaiae* NRRL 50777, *Penicillium bilaiae* NRRL 50778, *Penicillium bilaiae* NRRL 50779, *Penicillium bilaiae* NRRL 50780, *Penicillium bilaiae* NRRL 50781, *Penicillium bilaiae* NRRL 50782, *Penicillium bilaiae* NRRL 50783, *Penicillium bilaiae* NRRL 50784, *Penicillium bilaiae* NRRL 50785, *Penicillium bilaiae* NRRL 50786, *Penicillium bilaiae* NRRL 50787, *Penicillium bilaiae* NRRL 50788, *Penicillium bilaiae* RS7B-SD1, *Penicillium brevicompactum* AgRF18, *Penicillium canescens* ATCC 10419, *Penicillium expansum* ATCC 24692, *Penicillium expansum* YT02, *Penicillium fellatanum* ATCC 48694, *Penicillium gaestrivorus* NRRL 50170, *Penicillium glabrum* DAOM 239074, *Penicillium glabrum* CBS 229.28, *Penicillium janthinellum* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* N93/47267, *Penicillium raistrickii* ATCC 10490 and/or *Pseudomonas jessenii* PS06.

36. The inoculant composition of any one of the preceding paragraphs, wherein said one or more microorganisms comprises, consists essentially of, or consists of one or more strains having a genomic sequence that is at least 75, 80, 85, 90, 95, 96, 97, 98, 99% or more identical to any of the strains recited in paragraph 18 above on the basis of 16S rDNA sequence identity.

37. The inoculant composition of any one of the preceding paragraphs, wherein said one or more microorganisms comprises, consists essentially of, or consists of one or more mycorrhizal fungi.

38. The inoculant composition of any one of the preceding paragraphs, wherein said one or more microorganisms comprises, consists essentially of, or consists of one or more biopesticides, optionally one or more acaricides, one or more biofungicides, one or more bioinsecticides and/or one or more bionematicides.

39. The inoculant composition of any one of the preceding paragraphs, wherein said one or more maltodextrins, one or more monosaccharides and/or one or more disaccharides comprises, consists essentially of, or consists of one or more disaccharides, optionally maltose, trehalose, lactose, sucrose and/or cellobiose.

40. The inoculant composition of paragraph 39, wherein said one or more disaccharides comprise about 5, 10, 15, 20, 25, 30, 35, 40, 45, 50, 55, 60, 65, 70, 75, 80, 85, 90% or more (by weight) of said inoculant composition.

41. The inoculant composition of paragraph 39, wherein said one or more disaccharides comprises about 5 to about 90% (by weight), optionally about 1 to about 65%, about 5% to about 20%, about 10% to about 25%, about 20% to about 50%, or about 30 to about 60% (by weight), of said inoculant composition.

42. The inoculant composition of paragraph 39, wherein said one or more disaccharides constitutes about 10, 11, 12, 13, 14, 15, 16, 17, 18, 19, 20, 21, 22, 23, 24, 25, 26, 27, 28, 29, 30, 31, 32, 33, 34 35, 36 37, 38, 39 40, 41, 42, 43, 44, 45% of the said inoculant composition (by weight).

43. The inoculant composition of any one of paragraphs 39 to 42, wherein said one or more maltodextrins and said one or more disaccharides collectively comprise about 5, 10, 15, 20, 25, 30, 35, 40, 45, 50, 55, 60, 65, 70, 75, 80, 85, 90, 95% or more (by weight) of said inoculant composition.

44. The inoculant composition of any one of paragraphs 39 to 42, wherein said one or more maltodextrins and said one or more disaccharides collectively comprise about 5 to about 95% (by weight), optionally about 1 to about 65%, about 5% to about 20%, about 10% to about 25%, about 10% to about 30%, about 20% to about 40%, about 20% to about 50%, or about 30 to about 60% (by weight), of said inoculant composition.

45. The inoculant composition of any one of paragraphs 39 to 44, wherein said one or more maltodextrins and said one or more disaccharides are present in said inoculant composition in a maltodextrin:disaccharide ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more, optionally about 45:55, 50:50, 55:45, 60:40, 65:35, 70:30, 75:25, 80:20, 85:15, 90:10, 95:5 or more.

46. The inoculant composition of any one of the preceding paragraphs, wherein said inoculant composition comprises one or more biostimulants, optionally one or more seaweed extracts, one or more humic acids, one or more fulvic acids, myo-inositol and/or glycine.

47. The inoculant composition of any one of the preceding paragraphs, wherein said inoculant composition comprises one or more nutrients, optionally one or more vitamins (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids (α-carotene, β-carotene, cryptoxanthin, lutein, lycopene and/or zeaxanthin), macro-minerals (e.g., calcium, iron, magnesium, nitrogen, phosphorous, potassium and/or sodium), trace minerals (e.g., boron, cobalt, chloride, chromium, copper, fluoride, iodine, iron, manganese, molybdenum, selenium and/or zinc) and/or organic acids (e.g., acetic acid, citric acid, lactic acid, malic acid and/or taurine).

48. The inoculant composition of any one of the preceding paragraphs, wherein said inoculant composition comprises one or more pesticides, optionally:

one or more fungicides, optionally one or more of the fungicides disclosed on pages 26-28 above;

one or more herbicides, optionally one or more of the herbicides disclosed on page 28-29 above;

one or more insecticides, optionally one or more of the insecticides disclosed on page 29-31 above; and/or one or more nematicides, optionally one or more of the nematicides disclosed on page 29-31 above.

49. The inoculant composition of any one of the preceding paragraphs, wherein said inoculant composition comprises one or more plant signal molecules 50. The inoculant composition of any one of the preceding paragraphs, wherein said inoculant composition comprises one or more lipo-chitooligosaccharides, optionally one or more of the lipo-chitooligosaccharides represented by formulas I-IV.

51. The inoculant composition of any one of the preceding paragraphs, wherein said inoculant composition comprises one or more of the lipo-chitooligosaccharides represented by structures V-XXXIII.

52. The inoculant composition of any one of the preceding paragraphs, wherein said inoculant composition comprises one or more chitooligosaccharides, optionally one or more of the chitooligosaccharides represented by formulas XXXIV-XXXV.

53. The inoculant composition of any one of the preceding paragraphs, wherein said inoculant composition comprises one or more of the chitooligosaccharides represented by structures XXXVI-XXXIX.

54. The inoculant composition of any one of the preceding paragraphs, wherein said inoculant composition comprises one or more chitinous compounds, optionally one or more chitins and/or one or more chitosans.

55. The inoculant composition of any one of the preceding paragraphs, wherein said inoculant composition comprises one or more flavonoids, optionally one or more anthocyanidins, such as cyanidin, delphinidin, malvidin, pelargonidin, peonidin and/or petunidin; anthoxanthins, such as flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin); flavanones, such as butin, eriodictyol, hesperetin, hesperidin, homoeriodictyol, isosakuranetin, naringenin, naringin, pinocembrin, poncirin, sakuranetin, sakuranin and/or sterubin; flavanonols, such as dihydrokaempferol and/or taxifolin; flavans, such as flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol)

and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin); and/or isoflavonoids, such as isoflavones (e.g, biochanin A, daidzein, formononetin, genistein and/or glycitein), isoflavanes (e.g., equol, ionchocarpane and/or laxifloorane), isoflavandiols, isoflavenes (e.g., glabrene, haginin D and/or 2-methoxyjudaicin), coumestans (e.g., coumestrol, plicadin and/or wedelolactone), pterocarpans and/or roetonoids; and/or one or more analogues, derivatives, hydrates, isomers, polymers, salts and solvates thereof, such as neoflavonoids (e.g, calophyllolide, coutareagenin, dalbergichromene, dalbergin and/or nivetin) and/or pterocarpans (e.g., bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine and/or trifolirhizin).

56. The inoculant composition of any one of the preceding paragraphs, wherein said inoculant composition comprises jasmonic acid and/or one or more derivatives thereof.

57. The inoculant composition of any one of the preceding paragraphs, wherein said inoculant composition comprises linoleic acid and/or one or more derivatives thereof.

58. The inoculant composition of any one of the preceding paragraphs, wherein said inoculant composition comprises linolenic acid and/or one or more derivatives thereof.

59. The inoculant composition of any one of the preceding paragraphs, wherein said inoculant composition comprises one or more karrakins, optionally one or more karrakins represented by formula XXXX.

60. The inoculant composition of any one of the preceding paragraphs, wherein said inoculant composition comprises gluconolactone.

61. The inoculant composition of any one of the preceding paragraphs, wherein said inoculant composition comprises one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate.

62. The inoculant composition of any one of the preceding paragraphs, wherein said inoculant composition comprises one or more agriculturally acceptable carriers, optionally one or more soil-compatible carriers, seed-compatible carriers and/or foliar-compatible carriers.

63. The inoculant composition of any one of the preceding paragraphs, wherein said inoculant composition comprises one or more non-aqueous solvents.

64. The inoculant composition of any one of the preceding paragraphs, wherein said inoculant composition comprises one or more inorganic solvents, optionally decane, dodecane, hexylether and/or nonane.

65. The inoculant composition of any one of the preceding paragraphs, wherein said inoculant composition comprises one or more organic solvents.

66. The inoculant composition of any one of the preceding paragraphs, wherein said inoculant composition comprises water.

67. The inoculant composition of any one of the preceding paragraphs, wherein said inoculant composition comprises one or more growth media, optionally YEM media, mannitol yeast extract, glycerol yeast extract, Czapek-Dox media and/or potato dextrose broth.

68. The inoculant composition of any one of the preceding paragraphs, wherein said inoculant composition comprises one or more agriculturally acceptable polymers, optionally agar, alginate, carrageenan, cellulose, guar gum, locust bean gum, methylcellulose, pectin, polycaprolactone, polylactide, polyvinyl alcohol, polyvinyl pyrrolidone, sodium carboxymethyl cellulose, starch and/or xanthan gum.

69. The inoculant composition of any one of the preceding paragraphs, wherein said inoculant composition comprises one or more agriculturally acceptable wetting agents, optionally one or more naphthalene sulfonates, optionally one or more alkyl naphthalene sulfonates (e.g., sodium alkyl naphthalene sulfonate), one or more isopropyl naphthalene sulfonates (e.g., sodium isopropyl naphthalene sulfonate) and/or one or more butyl naphthalene sulfonates (e.g., sodium n-butyl naphthalene sulfonate).

70. The inoculant composition of any one of the preceding paragraphs, wherein said inoculant composition comprises one or more agriculturally acceptable drying agents, optionally calcium stearate, attapulgite clay, montmorillonite clay, graphite, magnesium stearate, silica (e.g., fumed silica, hydrophobically-coated silica and/or precipitated silica) and/or talc.

71. The inoculant composition of any one of the preceding paragraphs, wherein said inoculant composition comprises one or more agriculturally acceptable surfactants, optionally one or more anionic surfactants (e.g., one or more anionic surfactants selected from the group consisting of alkyl carboxylates (e.g., sodium stearate), alkyl sulfates (e.g., alkyl lauryl sulfate, sodium lauryl sulfate), alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and xylene sulfonates), cationic surfactants (e.g., one or more cationic surfactants selected from the group consisting of alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide and octenidine dihydrochloride), ionic surfactants (e.g., one or more ionic surfactants selected from the group consisting of ethers, glycol ethers, ethanolamides, sulfoanylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, polyoxyethylenated polyoxyproylene glycols, sorbitan fatty esters, sorbitan fatty acid alcohol ethoxylates and sorbitan fatty acid ester ethoxylates), nonionic surfactants (e.g., one or more nonionic surfactants selected from the group consisting of alcohol ethoxylates, alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers (e.g.), glycerol esters, glycol alkyl ethers (e.g., polyoxyethylene glycol alkyl ethers, polyoxypropylene glycol alkyl ethers), glycol alkylphenol ethers (e.g., polyoxyethylene glycol alkylphenol ethers), glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and tertiary acetylenic glycols), styrene acrylic polymers, modified styrene acrylic polymers and/or zwitterionic surfactants (e.g., one or more zwitterionic surfactants selected from the group consisting of 3-[(3-Cholamidopropyl)dimethylammonio]-1-propanesulfonate, cocamidopropyl betaine, cocamidopropyl hydroxysultaine, phosphatidylserine, phosphatidylethanolamine, phosphatidylcholine and sphingomyelins).

72. The inoculant composition of any one of the preceding paragraphs, wherein said inoculant composition comprises one or more agriculturally acceptable soaps and/or organosilicone surfactants, optionally one or more alkali metal salts of fatty acids.

73. The inoculant composition of any one of the preceding paragraphs, wherein said inoculant composition comprises one or more agriculturally acceptable anti-freezing agents, optionally ethylene glycol, glycerin, propylene glycol and/or urea.

74. The composition of any one of the preceding paragraphs, wherein said inoculant composition comprises, consists essentially of or is an amorphous liquid.

75. The inoculant composition of any one of the preceding paragraphs, wherein said inoculant composition comprises, consists essentially of or is an amorphous solid.

76. The inoculant composition of any one of the preceding paragraphs, wherein said inoculant composition comprises, consists essentially of or is a powder or granuale, optionally a spray-dried powder, freeze-dried powder, spray-freeze-dried powder or fluidized bed-dried granuale.

77. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms survive when said inoculant composition is desiccated by about 5, 10, 15, 20, 25, 30, 35, 40, 45, 50, 55, 60, 65, 70, 75, 80, 85, 90, 95% or more.

78. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms survive when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

79. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms survive when said inoculant composition is coated on a plant propagation material and desiccated by about 5, 10, 15, 20, 25, 30, 35, 40, 45, 50, 55, 60, 65, 70, 75, 80, 85, 90, 95% or more.

80. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms survive when said inoculant composition is coated on a plant propagation material, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

81. The inoculant composition of any one of the preceding paragraphs, wherein at least about $1\times10^1$ to about $1\times10^{10}$ colony-forming units of said one or more microorganisms per gram and/or milliliter of said inoculant composition survive when said inoculant composition is desiccated by about 5, 10, 15, 20, 25, 30, 35, 40, 45, 50, 55, 60, 65, 70, 75, 80, 85, 90, 95% or more.

82. The inoculant composition of any one of the preceding paragraphs, wherein at least about $1\times10^1$ to about $1\times10^{10}$ colony-forming units of said one or more microorganisms per gram and/or milliliter of said inoculant composition survive when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally at least $1\times10^4$, $1\times10^5$, $1\times10^6$, $1\times10^7$ or more colony-forming units per gram and/or milliliter of said inoculant composition.

83. The inoculant composition of any one of the preceding paragraphs, wherein at least about $1\times10^1$ to about $1\times10^{10}$ colony-forming units of said one or more microorganisms per seed survive when said inoculant composition is coated on a seed and desiccated by about 5, 10, 15, 20, 25, 30, 35, 40, 45, 50, 55, 60, 65, 70, 75, 80, 85, 90, 95% or more.

84. The inoculant composition of any one of the preceding paragraphs, wherein at least about $1\times10^1$ to about $1\times10^{10}$ colony-forming units of said one or more microorganisms per seed survive when said inoculant composition is coated on a seed, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1\times10^4$, $1\times10^5$, $1\times10^6$, $1\times10^7$ or more colony-forming units per seed.

85. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms remain in a fluid state and/or that at least about 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is desiccated by about 5, 10, 15, 20, 25, 30, 35, 40, 45, 50, 55, 60, 65, 70, 75, 80, 85, 90, 95% or more.

86. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

87. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is coated on a plant propagation material and desiccated by about 5, 10, 15, 20, 25, 30, 35, 40, 45, 50, 55, 60, 65, 70, 75, 80, 85, 90, 95% or more.

88. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is coated on a plant propagation material, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

89. The inoculant composition of any one of the preceding paragraphs, wherein at least about $1\times10^1$ to about $1\times10^{10}$ colony-forming units of said one or more microorganisms per gram and/or milliliter of said inoculant composition remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is desiccated by about 5, 10, 15, 20, 25, 30, 35, 40, 45, 50, 55, 60, 65, 70, 75, 80, 85, 90, 95% or more.

90. The inoculant composition of any one of the preceding paragraphs, wherein at least about $1\times10^1$ to about $1\times10^{10}$ colony-forming units of said one or more microorganisms per gram and/or milliliter of said inoculant composition remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1\times10^4$, $1\times10^5$, $1\times10^6$, $1\times10^7$ or more colony-forming units per gram and/or milliliter of said inoculant composition.

91. The inoculant composition of any one of the preceding paragraphs, wherein at least about $1\times10^1$ to about $1\times10^{10}$ colony-forming units of said one or more microorganisms per seed remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is coated on a seed and desiccated by about 5, 10, 15, 20, 25, 30, 35, 40, 45, 50, 55, 60, 65, 70, 75, 80, 85, 90, 95% or more.

92. The inoculant composition of any one of the preceding paragraphs, wherein at least about $1\times10^1$ to about $1\times10^{10}$ colony-forming units of said one or more microorganisms per seed remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is coated on a seed, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1\times10^4$, $1\times10^5$, $1\times10^6$, $1\times10^7$ or more colony-forming units per seed.

93. A coated plant propagation material, comprising, consisting essentially of, or consisting of:
a plant propagation material; and
a coating that covers at least a portion of the outer surface of said plant propagation material, said coating comprising, consisting essentially of, or consisting of the inoculation composition of any one of paragraphs 1-92.

94. The coated plant propagation material paragraph 93, wherein said coating comprises, consists essentially of, or consists of an inner coating layer that comprises said one or more microorganisms and an outer coating layer that is devoid of said one or more microorganisms.

95. The coated plant propagation material of any one of paragraphs 93-94, wherein said coating comprises, consists essentially of or is an amorphous liquid.

96. The coated plant propagation material of any one of paragraphs 93-94, wherein said coating comprises, consists essentially of or is an amorphous solid.

97. The coated plant propagation material of any one of paragraphs 93-94, wherein said coating comprises, consists essentially of or is a powder or granuale, optionally a spray-dried powder, freeze-dried powder, spray-freeze-dried powder or fluidized bed-dried granuale.

98. The coated plant propagation material of any one of paragraphs 93-97, wherein said coating comprises about $1 \times 10^1$ to about $1 \times 10^{15}$ colony-forming units of said one or more microorganisms, optionally $1 \times 10^4$, $1 \times 10^5$, $1 \times 10^6$, $1 \times 10^7$ or more colony-forming units.

99. The coated plant propagation material any one of paragraphs 93-98, wherein said plant propagation material is a seed.

100. The coated plant propagation material of paragraph 99, wherein said seed is a monocot seed.

101. The coated plant propagation material of paragraph 99, wherein said seed is a dicot seed.

102. The coated plant propagation material of paragraph 99, wherein said seed is a leguminous seed.

103. The coated plant propagation material of paragraph 99, wherein said seed is a non-leguminous seed.

104. The coated plant propagation material of paragraph 99, wherein said plant propagation material is of the family Amaranthaceae, optionally chard, spinach, sugar beet, or quinoa.

105. The coated plant propagation material of paragraph 99, wherein said plant propagation material is of the family Asteraceae, optionally artichoke, asters, chamomile, chicory, chrysanthemums, dahlias, daisies, echinacea, goldenrod, guayule, lettuce, marigolds, safflower, sunflowers, or zinnias.

106. The coated plant propagation material of paragraph 99, wherein said plant propagation material is of the family Brassicaceae, optionally arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, or *Arabidopsis thaliana*.

107. The coated plant propagation material of paragraph 99, wherein said plant propagation material is of the family Cucurbitaceae, optionally cantaloupe, cucumber, honeydew, melon, pumpkin, squash (e.g., acorn squash, butternut squash, summer squash), watermelon, or zucchini.

108. The coated plant propagation material of paragraph 99, wherein said plant propagation material is of the family Fabaceae, optionally alfalfa, beans, carob, clover, guar, lentils, mesquite, peas, peanuts, soybeans, tamarind, tragacanth, or vetch.

109. The coated plant propagation material of paragraph 99, wherein said plant propagation material is of the family Malvaceae, optionally cacao, cotton, durian, hibiscus, kenaf, kola, or okra.

110. The coated plant propagation material of paragraph 99, wherein said plant propagation material is of the family Poaceae, optionally bamboo, barley, corn, fonio, lawn grass (e.g., Bahia grass, Bermudagrass, bluegrass, Buffalograss, Centipede grass, Fescue, or *Zoysia*), millet, oats, ornamental grasses, rice, rye, sorghum, sugar cane, triticale, or wheat.

111. The coated plant propagation material of paragraph 99, wherein said plant propagation material is of the family Polygonaceae, optionally buckwheat.

112. The coated plant propagation material of paragraph 99, wherein said plant propagation material is of the family Rosaceae, optionally almonds, apples, apricots, blackberry, blueberry, cherries, peaches, plums, quinces, raspberries, roses, or strawberries.

113. The coated plant propagation material of paragraph 99, wherein said plant propagation material is of the family Solanaceae, optionally bell peppers, chili peppers, eggplant, *petunia*, potato, tobacco, or tomato.

114. The coated plant propagation material of paragraph 99, wherein said plant propagation material is of the family Vitaceae, optionally grape.

115. A kit, comprising: the inoculant composition of any one of paragraphs 1 to 92 or the coated plant propagation material of any one of paragraphs 93 to 114; and a container housing said inoculant composition or coated plant propagation material.

116. The kit of claim 115, wherein said container reduces the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

117. The kit of any one of paragraphs 115-116, wherein said container reduces the amount of ambient oxygen that reaches said plant propagation material by about 5, 10, 15, 20, 25, 30, 35, 40, 45, 50, 55, 60, 65, 70, 75, 80, 85, 90, 95 or 100% when sealed.

118. The kit of any one of paragraphs 115-117, wherein said container comprises, consists essentially of, or consists of a material having light permeability of less than about 1, 2, 3, 4, 5, 6, 7, 8, 9, 10, 15, 20, 25, 30, 35, 40, 45, 50, 55, 60, 65, 70 or 75%.

119. The kit of any one of paragraphs 115-118, wherein said container comprises, consists essentially of, or consists of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 cm$^3$/m$^2$ day (as measured in accordance with ASTM D3985).

120. The kit of any one of paragraphs 115-119, wherein said kit further comprises one or more oxygen-absorbing compound, optionally activated carbon, iron powder, sodium chloride, ferrous carbonate, one or more metal halide catalysts and/or sodium hydrogen carbonate.

121. A plant treated with the inoculant composition of any one of paragraphs 1-92.

122. A plant germinated from the coated plant propagation material of any one of paragraphs 93-114.

123. A plant part harvested from the plant of any one of paragraphs 121-122.

124. A processed product produced from the plant part of paragraph 123.

125. A crop comprising, consisting essentially of, or consisting of a plurality of the plant or plant part of any one of paragraphs 121-124.

126. A method, comprising, consisting essentially of, or consisting of: applying the inoculant composition of any one of paragraphs 1-92 to a plant propagation material, optionally: drying the inoculant composition of any one of paragraphs 1-92; and applying the dried inoculant composition of any one of claims 1-92 to the plant propagation material.

127. The method of paragraph 126, further comprising planting said plant propagation material in a growth medium, optionally soil.

128. The method of paragraph 127, wherein said plant propagation material is planted in soil in which plants of the same genus were cultivated in at least one of the three years prior to said planting, optionally in each of the one, two or three years immediately preceding said planting.

129. The method of any one of paragraphs 126-128, wherein said inoculant composition is applied to the plant propagation material at the time of planting.

130. The method of any one of paragraphs 126-128, wherein said inoculant composition is applied to the plant propagation material at least 1, 2, 3, 4, 5, 6, 7, 8, 9, 10, 11, 12, 15, 18, 21, 24, 27, 30, 33, 36, 39, 42, 45, 48 hours or more prior to planting.

131. The method of any one of paragraphs 126-128, wherein said inoculant composition is applied to the plant propagation material at least 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more prior to planting.

132. The method of any one of paragraphs 126-128, wherein said inoculant composition is applied to the plant propagation material about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months or more prior to planting.

133. The method of any one of paragraphs 126-132, wherein said plant propagation material is a seed.

134. The method of any one of paragraphs 126-132, wherein said plant propagation material is a monocot seed.

135. The method of any one of paragraphs 126-132, wherein said plant propagation material is a dicot seed.

136. The method of any one of paragraphs 126-132, wherein said plant propagation material is a leguminous seed.

137. The method of any one of paragraphs 126-132, wherein said plant propagation material is a non-leguminous seed.

138. The method of any one of paragraphs 126-132, wherein said plant propagation material is of the family Amaranthaceae, optionally chard, spinach, sugar beet, or quinoa.

139. The method of any one of paragraphs 126-132, wherein said plant propagation material is of the family Asteraceae, optionally artichoke, asters, chamomile, chicory, chrysanthemums, dahlias, daisies, echinacea, goldenrod, guayule, lettuce, marigolds, safflower, sunflowers, or zinnias.

140. The method of any one of paragraphs 126-132, wherein said plant propagation material is of the family Brassicaceae, optionally arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, or *Arabidopsis thaliana*.

141. The method of any one of paragraphs 126-132, wherein said plant propagation material is of the family Cucurbitaceae, optionally cantaloupe, cucumber, honeydew, melon, pumpkin, squash (e.g., acorn squash, butternut squash, summer squash), watermelon, or zucchini.

142. The method of any one of paragraphs 126-132, wherein said plant propagation material is of the family Fabaceae, optionally alfalfa, beans, carob, clover, guar, lentils, mesquite, peas, peanuts, soybeans, tamarind, tragacanth, or vetch.

143. The method of any one of paragraphs 126-132, wherein said plant propagation material is of the family Malvaceae, optionally cacao, cotton, durian, hibiscus, kenaf, kola, or okra.

144. The method of any one of paragraphs 126-132, wherein said plant propagation material is of the family Poaceae, optionally bamboo, barley, corn, fonio, lawn grass (e.g., Bahia grass, Bermudagrass, bluegrass, Buffalograss, Centipede grass, Fescue, or *Zoysia*), millet, oats, ornamental grasses, rice, rye, sorghum, sugar cane, triticale, or wheat.

145. The method of any one of paragraphs 126-132, wherein said plant propagation material is of the family Polygonaceae, optionally buckwheat.

146. The method of any one of paragraphs 126-132, wherein said plant propagation material is of the family Rosaceae, optionally almonds, apples, apricots, blackberry, blueberry, cherries, peaches, plums, quinces, raspberries, roses, or strawberries.

147. The method of any one of paragraphs 126-132, wherein said plant propagation material is of the family Solanaceae, optionally bell peppers, chili peppers, eggplant, *petunia*, potato, tobacco, or tomato.

148. The method of any one of paragraphs 126-132, wherein plant propagation material seed is of the family Vitaceae, optionally grape.

149. A method comprising, consisting essentially of, or consisting of: planting the coated plant propagation material of any one of paragraphs 93-114 in a growth medium, optionally soil.

150. The method of any one of paragraphs 127-149, further comprising applying the inoculant composition of any one of paragraphs 1-92 to the plant that grows from the plant propagation material.

151. A method of enhancing the stability and/or survivability of one or more microorganisms in a composition, comprising, consisting essentially of, or consisting of: adding one or more maltodextrins, one or more monosaccharides and/or one or more disaccharides to said composition.

152. The method of paragraph 151, wherein said one or more maltodextrins, one or more monosaccharides and/or one or more disaccharides comprises, consists essentially of, or consists of one or more maltodextrins having a dextrose equivalent value of about 3, 4, 5, 6, 7, 8, 9, 10, 11, 12, 13, 14, 15, 16, 17, 18, 19, 20.

153. The method of paragraph 151, wherein said one or more maltodextrins, one or more monosaccharides and/or one or more disaccharides comprises, consists essentially of, or consists of one or more maltodextrins having a dextrose equivalent value of about 10 to about 20, optionally about 15 to about 20.

154. The method of any one of paragraphs 151-153, wherein said one or more maltodextrins, one or more monosaccharides and/or one or more disaccharides is added until it comprises about 5, 10, 15, 20, 25, 30, 35, 40, 45, 50, 55, 60, 65, 70, 75, 80, 85, 90, 95% or more (by weight) of said composition.

155. The method of any one of paragraphs 151-153, wherein said one or more maltodextrins, one or more monosaccharides and/or one or more disaccharides is added until it comprises about 5 to about 95% (by weight), optionally about 1 to about 65%, about 10% to about 30%, about 20% to about 40%, about 20% to about 50%, or about 30 to about 60% (by weight), of said composition.

156. The method of any one of paragraphs 151-155, wherein said one or more maltodextrins, one or more monosaccharides and/or one or more disaccharides s added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms survive when said inoculant composition is desiccated by about 5, 10, 15, 20, 25, 30, 35, 40, 45, 50, 55, 60, 65, 70, 75, 80, 85, 90, 95% or more.

157. The method of any one of paragraphs 151-156, wherein said one or more maltodextrins, one or more monosaccharides and/or one or more disaccharides is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms survive when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

158. The method of any one of paragraphs 151-157, wherein said one or more maltodextrins, one or more monosaccharides and/or one or more disaccharides is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms survive when said inoculant composition is coated on a plant propagation material and desiccated by about 5, 10, 15, 20, 25, 30, 35, 40, 45, 50, 55, 60, 65, 70, 75, 80, 85, 90, 95% or more.

159. The method of any one of paragraphs 151-158, wherein said one or more maltodextrins, one or more monosaccharides and/or one or more disaccharides is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms survive when said inoculant composition is coated on a plant propagation material, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

160. The method of any one of paragraphs 151-159, wherein said one or more maltodextrins, one or more monosaccharides and/or one or more disaccharides is added in an amount sufficient to ensure that at least about $1 \times 10^1$ to about $1 \times 10^{10}$ colony-forming units of said one or more microorganisms per gram and/or milliliter of said inoculant composition survive when said inoculant composition is desiccated by about 5, 10, 15, 20, 25, 30, 35, 40, 45, 50, 55, 60, 65, 70, 75, 80, 85, 90, 95% or more.

161. The method of any one of paragraphs 151-160, wherein said one or more maltodextrins, one or more monosaccharides and/or one or more disaccharides is added in an amount sufficient to ensure that at least about $1 \times 10^1$ to about $1 \times 10^{10}$ colony-forming units of said one or more microorganisms per gram and/or milliliter of said inoculant composition survive when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally at least $1 \times 10^4$, $1 \times 10^5$, $1 \times 10^6$, $1 \times 10^7$ or more colony-forming units per gram and/or milliliter of said inoculant composition.

162. The method of any one of paragraphs 151-161, wherein said one or more maltodextrins, one or more monosaccharides and/or one or more disaccharides is added in an amount sufficient to ensure that at least about $1 \times 10^1$ to about $1 \times 10^{10}$ colony-forming units of said one or more microorganisms per seed survive when said inoculant composition is coated on a seed and desiccated by about 5, 10, 15, 20, 25, 30, 35, 40, 45, 50, 55, 60, 65, 70, 75, 80, 85, 90, 95% or more.

163. The method of any one of paragraphs 151-162, wherein said one or more maltodextrins, one or more monosaccharides and/or one or more disaccharides is added in an amount sufficient to ensure that at least about $1 \times 10^1$ to about $1 \times 10^{10}$ colony-forming units of said one or more microorganisms per seed survive when said inoculant composition is coated on a seed, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1 \times 10^4$, $1 \times 10^5$, $1 \times 10^6$, $1 \times 10^7$ or more colony-forming units per seed.

164. The method of any one of paragraphs 151-163, wherein said one or more maltodextrins, one or more monosaccharides and/or one or more disaccharides is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is desiccated by about 5, 10, 15, 20, 25, 30, 35, 40, 45, 50, 55, 60, 65, 70, 75, 80, 85, 90, 95% or more.

165. The method of any one of paragraphs 151-164, wherein said one or more maltodextrins, one or more monosaccharides and/or one or more disaccharides is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

166. The method of any one of paragraphs 151-165, wherein said one or more maltodextrins, one or more monosaccharides and/or one or more disaccharides s added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is coated on a plant propagation material and desiccated by about 5, 10, 15, 20, 25, 30, 35, 40, 45, 50, 55, 60, 65, 70, 75, 80, 85, 90, 95% or more.

167. The method of any one of paragraphs 151-166, wherein said one or more maltodextrins, one or more monosaccharides and/or one or more disaccharides is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microorganisms remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is coated on a plant propagation material, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

168. The method of any one of paragraphs 151-167, wherein said one or more maltodextrins, one or more monosaccharides and/or one or more disaccharides is added in an amount sufficient to ensure that at least about $1 \times 10^1$ to about $1 \times 10^{10}$ colony-forming units of said one or more microorganisms per gram and/or milliliter of said inoculant composition remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is desiccated by about 5, 10, 15, 20, 25, 30, 35, 40, 45, 50, 55, 60, 65, 70, 75, 80, 85, 90, 95% or more.

169. The method of any one of paragraphs 151-168, wherein said one or more maltodextrins, one or more monosaccharides and/or one or more disaccharides is added in an amount sufficient to ensure that at least about $1 \times 10^1$ to about $1 \times 10^{10}$ colony-forming units of said one or more microorganisms per gram and/or milliliter of said inoculant composition remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1 \times 10^4$, $1 \times 10^5$, $1 \times 10^6$, $1 \times 10^7$ or more colony-forming units per gram and/or milliliter of said inoculant composition.

170. The method of any one of paragraphs 151-169, wherein said one or more maltodextrins, one or more monosaccharides and/or one or more disaccharides is added in an amount sufficient to ensure that at least about $1 \times 10^1$ to about $1 \times 10^{10}$ colony-forming units of said one or more microorganisms per seed remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is coated on a seed and desiccated by about 5, 10, 15, 20, 25, 30, 35, 40, 45, 50, 55, 60, 65, 70, 75, 80, 85, 90, 95% or more.

171. The method of any one of paragraphs 151-170, wherein said one or more maltodextrins, one or more monosaccharides and/or one or more disaccharides is added in an amount sufficient to ensure that at least about $1 \times 10^1$ to about $1 \times 10^{10}$ colony-forming units of said one or more microorganisms per seed remain in a fluid state and/or that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the composition surrounding the microorganisms remains in a glassy and/or rubbery state at 4, 5, 6, 7, 8, 9, 10, 11, 12, 13, 14, 15, 16, 17, 18, 19, 20, 21, 22, 23, 24, 25, 26, 27, 28, 29 and/or 30° C. when said inoculant composition is coated on a seed, desiccated by about 5, 10, 15, 20, 25, 30, 35, 40, 45, 50, 55, 60, 65, 70, 75, 80, 85, 90, 95% or more and stored at 4, 5, 6, 7, 8, 9, 10, 11, 12, 13, 14, 15, 16, 17, 18, 19, 20, 21, 22, 23, 24, 25, 26, 27, 28, 29 and/or 30° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1 \times 10^4$, $1 \times 10^5$, $1 \times 10^6$, $1 \times 10^7$ or more colony-forming units per seed.

172. The method of any of paragraphs 151-171, comprising adding one or more disaccharides to said composition.

173. The method of paragraph 172, wherein said one or more disaccharides is added until it comprises about 10, 11, 12, 13, 14, 15, 16, 17, 18, 19, 20, 21, 22, 23, 24, 25, 26, 27, 28, 29, 30, 31, 32, 33, 34 35, 36 37, 38, 39 40, 41, 42, 43, 44, 45% (by weight) of the said composition.

174. The method of paragraph 172, wherein said one or more disaccharides is added until it comprises about 5 to about 90% (by weight), optionally about 1 to about 65%, about 5% to about 20%, about 10% to about 25%, about 20% to about 50%, or about 30 to about 60% (by weight), of said composition.

175. The method of any of paragraphs 172-174, wherein said one or more maltodextrins and said one or more disaccharides are added until they collectively comprise about 5, 10, 15, 20, 25, 30, 35, 40, 45, 50, 55, 60, 65, 70, 75, 80, 85, 90, 95% or more (by weight) of said composition.

176. The method of any of paragraphs 172-174, wherein said one or more maltodextrins and said one or more disaccharides are added until they collectively comprise about 5 to about 95% (by weight), optionally about 1 to about 65%, about 5% to about 20%, about 10% to about 25%, about 10% to about 30%, about 20% to about 40%, about 20% to about 50%, or about 30 to about 60% (by weight), of said inoculant composition.

177. The method of any of paragraphs 172-176, wherein said one or more maltodextrins and said one or more disaccharides are added to said composition in a maltodextrin:disaccharide ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more, optionally about 50:50, 55:45, 60:40, 65:35, 70:30, 75:25, 80:20, 85:15, 90:10, 95:5 or more.

178. The method of any of paragraphs 151-177, further comprising adding one or more drying agents to said composition.

179. The method of paragraph 178, wherein said one or more drying agents comprises calcium stearate, one or more clays, graphite, magnesium stearate, magnesium sulfate, powdered milk, one or more silica powders, soy lecithin and/or talc.

180. The method of any one of claims 151-179 further comprising adding one or more microbial extracts to said composition.

181. The method of paragraph 180, wherein said one or more microbial extracts comprises: one or more *Bacillus* extracts, optionally an extract of media comprising *B. amyloliquefaciens* D747, *B. amyloliquefaciens* NRRL B-50349, *B. amyloliquefaciens* TJ1000, *B. amyloliquefaciens* FZB24, *B. amyloliquefaciens* FZB42, *B. amyloliquefaciens* IN937a, *B. amyloliquefaciens* IT-45, *B. amyloliquefaciens* TJ 1000, *B. amyloliquefaciens* M1B1600, *B. amyloliquefaciens* BS27 (deposited as NRRL B-5015), *B. amyloliquefaciens* BS2084 (deposited as NRRL B-50013), *B. amyloliquefaciens* 15AP4 (deposited as ATCC PTA-6507), *B. amyloliquefaciens* 3AP4 (deposited as ATCC PTA-6506), *B. amyloliquefaciens* LSSA01 (deposited as NRRL B-50104), *B. amyloliquefaciens* ABP278 (deposited as NRRL B-50634), *B. amyloliquefaciens* 1013 (deposited as NRRL B-50509), *B. amyloliquefaciens* 918 (deposited as NRRL B-50508), *B. amyloliquefaciens* 22CP1 (deposited as ATCC PTA-6508) and *B. amyloliquefaciens* BS18 (deposited as NRRL B-50633), *B. cereus* 1-1562, *B. firmus* 1-1582, *B. licheniformis* BA842 (deposited as NRRL B-50516), *B. licheniformis* BL21 (deposited as NRRL B-50134), *B. mycoides* NRRL B-21664, *B. pumilus* NRRL B-21662, *B. pumilus* NRRL B-30087, *B. pumilus* ATCC 55608, *B. pumilus* ATCC 55609, *B. pumilus* GB34, *B. pumilus* KFP9F, *B. pumilus* QST 2808, *B. subtilis* ATCC 55078, *B. subtilis* ATCC 55079, *B. subtilis* MBI 600, *B. subtilis* NRRL B-21661, *B. subtilis* NRRL B-21665, *B. subtilis* CX-9060, *B. subtilis* GB03, *B. subtilis* GB07, *B. subtilis* QST-713, *B. subtilis* FZB24, *B. subtilis* D747, *B. subtilis* 3BP5 (deposited as NRRL B-50510), *B. thuringiensis* ATCC 13367, *B. thuringiensis* GC-91, *B. thuringiensis* NRRL B-21619, *B. thuringiensis* ABTS-1857, *B. thuringiensis* SAN 4011, *B. thuringiensis* ABG-6305, *B. thuringiensis* ABG-6346, *B. thuringiensis* AM65-52, *B. thuringiensis* SA-12, *B. thuringiensis* SB4, *B. thuringiensis* ABTS-351, *B. thuringiensis* HD-1, *B. thuringiensis* EG 2348, *B. thuringiensis* EG 7826, *B. thuringiensis* EG 7841, *B. thuringiensis* DSM 2803, *B. thuringiensis* NB-125 and/or *B. thuringiensis* NB-176;

one or more *Bradyrhizobium* extracts, optionally an extract of media comprising *B. elkanii* SEMIA 501, *B. elkanii* SEMIA 587, *B. elkanii* SEMIA 5019, *B. japonicum* NRRL B-50586 (also deposited as NRRL B-59565), *B. japonicum* NRRL B-50587 (also deposited as NRRL B-59566), *B. japonicum* NRRL B-50588 (also deposited as NRRL B-59567), *B. japonicum* NRRL B-50589 (also deposited as NRRL B-59568), *B. japonicum* NRRL B-50590 (also deposited as NRRL B-59569), *B. japonicum* NRRL B-50591 (also deposited as NRRL B-59570), *B. japonicum* NRRL B-50592 (also deposited as NRRL B-59571), *B. japonicum* NRRL B-50593 (also deposited as NRRL B-59572), *B. japonicum* NRRL B-50594 (also deposited as NRRL B-50493), *B. japonicum* NRRL B-50608, *B. japonicum* NRRL B-50609, *B. japonicum* NRRL B-50610, *B. japonicum* NRRL B-50611, *B. japonicum* NRRL B-50612, *B. japonicum* NRRL B-50726, *B. japonicum* NRRL B-50727, *B. japonicum* NRRL B-50728, *B. japonicum* NRRL B-50729, *B. japonicum* NRRL B-50730, *B. japonicum* SEMIA 566, *B. japonicum* SEMIA 5079, *B. japonicum* SEMIA 5080, *B. japonicum* USDA 6, *B. japonicum* USDA 110, *B. japonicum* USDA 122, *B. japonicum* USDA 123, *B. japonicum* USDA 127, *B. japonicum* USDA 129 and/or *B. japonicum* USDA 532C;

one or more *Rhizobium* extracts, optionally an extract of media comprising *R. leguminosarum* SO12A-2;

one or more *Sinorhizobium* extracts, optionally an extract of media comprising *S. fredii* CCBAU114 and/or *S. fredii* USDA 205;

one or more *Penicillium* extracts, optionally an extract of media comprising *P. bilaiae* ATCC 18309, *P. bilaiae* ATCC 20851, *P. bilaiae* ATCC 22348, *P. bilaiae* NRRL 50162, *P. bilaiae* NRRL 50169, *P. bilaiae* NRRL 50776, *P. bilaiae* NRRL 50777, *P. bilaiae* NRRL 50778, *P. bilaiae* NRRL 50777, *P. bilaiae* NRRL 50778, *P. bilaiae* NRRL 50779, *P. bilaiae* NRRL 50780, *P. bilaiae* NRRL 50781, *P. bilaiae* NRRL 50782, *P. bilaiae* NRRL 50783, *P. bilaiae* NRRL 50784, *P. bilaiae* NRRL 50785, *P. bilaiae* NRRL 50786, *P. bilaiae* NRRL 50787, *P. bilaiae* NRRL 50788, *P. bilaiae* RS7B-SD1, *P. brevicompactum* AgRF18, *P. canescens* ATCC 10419, *P. expansum* ATCC 24692, *P. expansum* YT02, *P. fellatanum* ATCC 48694, *P. gaestrivorus* NRRL 50170, *P. glabrum* DAOM 239074, *P. glabrum* CBS 229.28, *P. janthinellum* ATCC 10455, *P. lanosocoeruleum* ATCC 48919, *P. radicum* ATCC 201836, *P. radicum* FRR 4717, *P. radicum* FRR 4719, *P. radicum* N93/47267 and/or *P. raistrickii* ATCC 10490; one or more *Streptomyces* extracts, optionally an extract of media comprising *Streptomyces* NRRL B-30145, *Streptomyces* M1064, *S. galbus* NRRL 30232, *S. lydicus* WYEC 108 (ATCC 55445), *S. violaceusniger* YCED 9 (ATCC 55660) and/or *Streptomyces* WYE 53 (ATCC 55750); and/or one or more *Trichoderma* extracts, optionally an extract of media comprising *T. asperellum* SKT-1 (ECO-HOPE®, Kumiai Chemical Industry Co., Ltd., Japan), *T. atroviride* LC52 (SENTINEL®, Agrimm Technologies Ltd, NZ), *T. harzianum* T-22 (PLANTSHIELD®, der Firma BioWorks Inc., USA), *T. harzianum* TH-35 (ROOT PRO®, from Mycontrol Ltd., Israel), *T. harzianum* T-39 (TRICHODEX®, Mycontrol Ltd., Israel; T. 2000®, Makhteshim Ltd., Israel), *T. harzianum* ICC012 and *T. viride* TRICHOPEL (Agrimm Technologies Ltd, NZ), *T. harzianum* ICC012 and *T. viride* ICC080 (REMEDIER® WP, Isagro Ricerca, Italy), *T. polysporum* and *T. harzianum* (BINAB®, BINAB Bio-Innovation AB, Sweden), *T. stromaticum* TRICOVAB® (C.E.P.L.A.C., Brazil), *T. virens* GL-21 (SOILGARD®, Certis LLC, USA), *T. virens* G1-3, ATCC 57678, *T. virens* G1-21 (Thermo Trilogy Corporation, Wasco, Calif.), *T. virens* G1-3 and *Bacillus amyloliquefaciens* FZB2, *T. virens* G1-3 and *Bacillus amyloliquefaciens* NRRL B-50349, *T. virens* G1-3 and *Bacillus amyloliquefaciens* TJ1000, *T. virens* G1-21 and *Bacillus amyloliquefaciens* FZB24, *T. virens* G1-21 and *Bacillus amyloliquefaciens* NRRL B-50349, *T. virens* G1-21 and *Bacillus amyloliquefaciens* TJ1000, *T. viride* TRIECO® (Ecosense Labs. (India) Pvt. Ltd., Indien, BIO-CURE® F from T. Stanes & Co. Ltd., Indien), *T. viride* TV1 (Agribiotec srl, Italy), *T. viride* ICC080.

182. The inoculant composition of any one of paragraphs 180-181, wherein said one or more microbial extracts comprises less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5% water by weight, based upon the total weight of the composition.

183. The method of any one of paragraphs 180-182, wherein said one or more microbial extracts is added until it comprises about 0.1 to about 5% (by weight) of said composition, optionally about 0.1 to about 2% (by weight) of said composition, optionally about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of said composition.

184. A method, comprising, consisting essentially of or consisting of:
applying the inoculant composition of any one of paragraphs 1-92 to a seed and/or to the plant that grows from said seed;
applying a second composition to said seed and/or to the plant that grows from said seed, said second composition comprising:
one or more agriculturally beneficial microorganisms, optionally one or more diazotrophs, one or more phosphate-solubilizing microorganisms, one or more mycorrhizal fungi and/or one or more biopesticides, optionally one or more bioacaricides, one or more biofungicides, one or more bioinsecticides and/or one or more bionematicides;
one or more biostimulants, optionally one or more seaweed extracts, one or more humic acids, one or more fulvic acids, myo-inositol and/or glycine;
one or more nutrients, optionally one or more vitamins (e.g., vitamin A, vitamin B complex (i.e., vitamin B1, vitamin B2, vitamin B3, vitamin B5, vitamin B6, vitamin B7, vitamin B8, vitamin B9, vitamin B12, choline) vitamin C, vitamin D, vitamin E, vitamin K, carotenoids (α-carotene, β-carotene, cryptoxanthin, lutein, lycopene and/or zeaxanthin), macrominerals (e.g., calcium, iron, magnesium, nitrogen, phosphorous, potassium and/or sodium), trace minerals (e.g., boron, cobalt, chloride, chromium, copper, fluoride, iodine, iron, manganese, molybdenum, selenium and/or zinc) and/or organic acids (e.g., acetic acid, citric acid, lactic acid, malic acid and/or taurine);
one or more fungicides, optionally one or more of the fungicides disclosed on pages 26-28 above;
one or more herbicides, optionally one or more of the herbicides disclosed on page 28-29 above;
one or more insecticides, optionally one or more of the insecticides disclosed on page 29-31 above;
one or more nematicides, optionally one or more of the nematicides disclosed on page 29-31 above;
one or more lipo-chitooligosaccharides, optionally one or more of the lipo-chitooligosaccharides represented by formulas I-IV and/or one or more of the lipo-chitooligosaccharides represented by structures V-XXXIII;
one or more chitooligosaccharides, optionally one or more of the chitooligosaccharides represented by formulas XXXIV-XXXV and/or one or more of the chitooligosaccharides represented by structures XXXVI-XXXIX,
one or more chitinous compounds, optionally one or more chitins and/or one or more chitosans;
one or more flavonoids, optionally one or more anthocyanidins, such as cyanidin, delphinidin, malvidin, pelargonidin, peonidin and/or petunidin; anthoxanthins, such as flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin); flavanones, such as butin, eriodictyol, hesperetin, hesperidin, homoeriodictyol, isosakuranetin, naringenin, naringin, pinocembrin, poncirin, sakuranetin, sakuranin and/or sterubin; flavanonols, such as dihydrokaempferol and/or taxifolin; flavans, such as flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin); and/or isoflavonoids, such as isoflavones (e.g, biochanin A, daidzein, formononetin, genistein and/or glycitein), isoflavanes (e.g., equol, ionchocarpane and/or laxifloorane), isoflavandiols, isoflavenes (e.g., glabrene, haginin D and/or 2-methoxyjudaicin), coumestans (e.g., coumestrol, plicadin and/or wedelolactone), pterocarpans and/or roetonoids; and/or one or more analogues, derivatives, hydrates, isomers, polymers, salts and solvates thereof, such as neoflavonoids (e.g, calophyllolide, coutareagenin, dalbergichromene, dalbergin and/or nivetin) and/or pterocarpans (e.g., bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine and/or trifolirhizin);
jasmonic acid and/or one or more derivatives thereof;
linoleic acid and/or one or more derivatives thereof;
linolenic acid and/or one or more derivatives thereof;

one or more karrakins, optionally one or more karrakins represented by formula XXXX; gluconolactone; and/or one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate.

EXAMPLES

The following examples are not intended to be a detailed catalogue of all the different ways in which the present disclosure may be implemented or of all the features that may be added to the present disclosure. Subjects skilled in the art will appreciate that numerous variations and additions to the various embodiments may be made without departing from the present disclosure. Hence, the following descriptions are intended to illustrate some particular embodiments of the invention and not to exhaustively specify all permutations, combinations and variations thereof.

Unless otherwise stated, the percentages described in the following examples are weight percentages based on the total weight of the composition being described.

Unless otherwise stated, the microbial suspensions described in the following examples comprise microbes that were grown to stationary phase prior to use.

Unless otherwise stated, seeds were coated in the following examples in accordance with Seed Coating Protocol 1 or Seed Coating Protocol 2:

Seed Coating Protocol 1: Desired volumes of seeds and coating material were placed in a gallon-size plastic bag. The bag was inflated until the seeds/coating material occupy approximately one-third of the volume contained within the bag, then sealed. The sealed bag was shaken for one minute, then opened to allow the seeds to dry at room temperature (21-23° C.) for four hours. In experiments comprising multiple coatings, each subsequent coating material was added to the bag immediately upon opening, the bag was re-inflated and sealed, and the seeds were shaken with the outer coating material for one minute prior to the drying step.

Seed Coating Protocol 2: Seeds were coated with the desired volume of coating material using a laboratory-scale liquid seed treater (HEGE 11, Wintersteger, Inc., Salt Lake City, Utah), then placed in an open gallon-size plastic pag and allowed to dry at room temperature (21-23° C.) for four hours. In double-coating experiments, the outer coating material was added to the system after the first coating step.

Unless otherwise stated, the on-seed survivability assays described in the following examples were carried out in accordance with Survivability Protocol 1 or Survivability Protocol 2:

Survivability Protocol 1: At each designated time point, 50 seeds were placed in a 250 ml Erlenmeyer flask with 50 ml 0.85% NaCl buffer, then shaken on an orbital shaker at 200 rpm for 15 minutes at 21-24° C. Flask buffer was serially diluted into 0.85% NaCl buffer (using 10-fold dilutions), vortexed and plated on Yeast Extract Mannitol Agar+Polymixin B in triplicate (100 µl per plate). Plates were incubated for approximately seven days at 30° C. Colonies were counted, and plates containing between 30 and 300 colonies were selected for recordation.

Survivability Protocol 2: At each designated time point, 100 seeds were placed in a 250 ml Erlenmeyer flask with 100 ml 0.85% NaCl buffer, 0.4 ml TWEEN® 80 and a one-inch magnetic stir bar, then shaken on a magnetic stir plate at 800 rpm for 15 minutes at 21-24° C. Flask buffer was serially diluted into 0.85% NaCl buffer (using 10-fold dilutions), vortexed and plated on Yeast Extract Mannitol Agar+Vancomycin+Cycloheximide in triplicate (100 µl per plate). Plates were sealed in gallon-size plastic bags and incubated for approximately seven days at 30° C. at 65% relative humidity. Colonies were counted, and plates containing between 30 and 300 colonies were selected for recordation.

Example 1

Maltose Enhanced the Survivability of Desiccated *Bradyrhizobium*

Untreated soybean seeds (ASGROW®; Monsanto Company, St. Louis, Mo.) were weighed out into 100 g allotments. Each allotment of seeds was coated according to Seed Coating Protocol 1 with one of the double-layer coatings set forth in Table 1:

TABLE 1

| Inner Coating (300 µl per 100 g seed) | Outer Coating (300 µl per 100 g seed) |
|---|---|
| *Bradyrhizobium japonicum* NRRL B-50626 suspension | none |
| *Bradyrhizobium japonicum* NRRL B-50626 suspension | deionized water containing 30% maltose monohydrate |
| *Bradyrhizobium japonicum* NRRL B-50626 suspension containing 30% maltose monohydrate | deionized water containing 30% maltose monohydrate |

Figure 2:
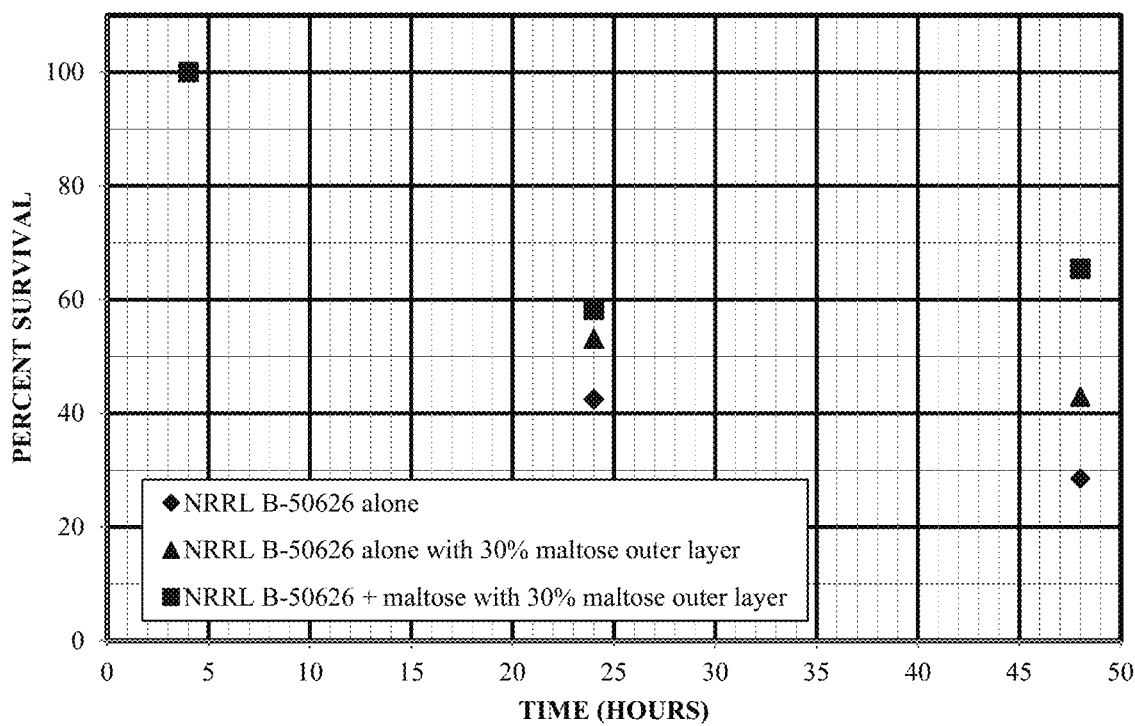
Figure 3:
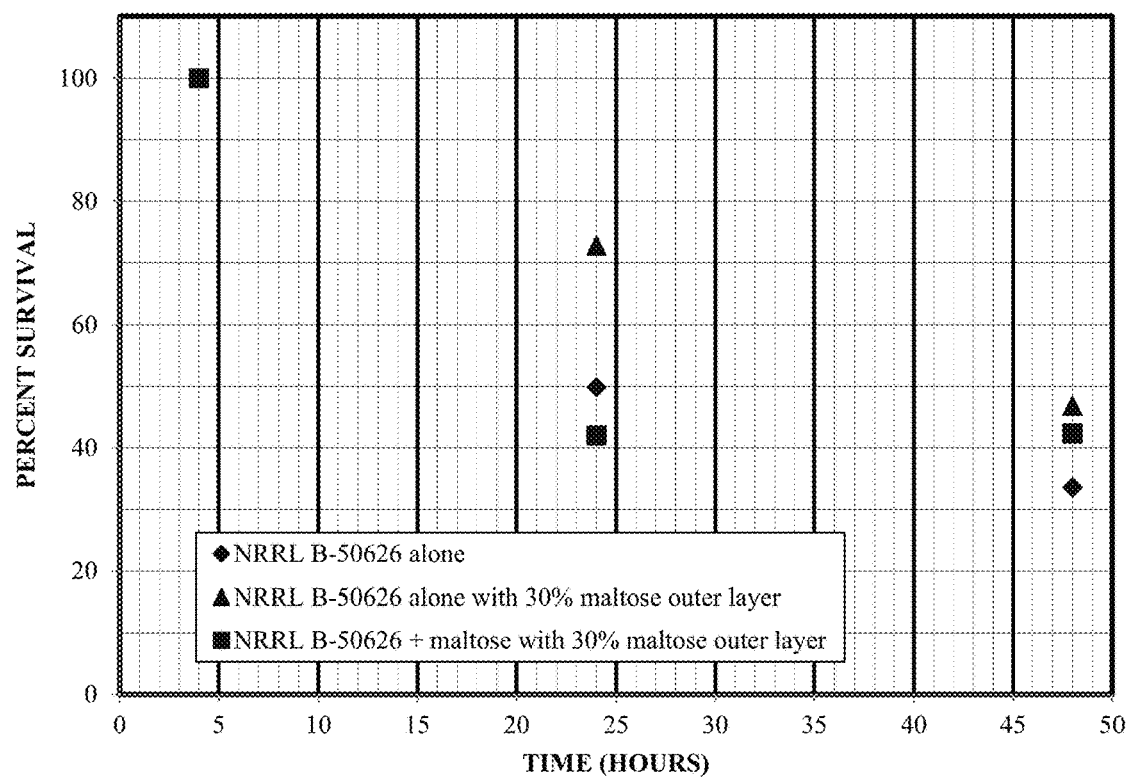

Coated seeds were stored at room temperature and less than 20%, 35-40% or 70-75% relative humidity and then assayed for on-seed survivability. FIGS. 1-3.

Example 2

Maltose Enhanced the Survivability of Desiccated *Bradyrhizobium*

Untreated soybean seeds (ASGROW®; Monsanto Company, St. Louis, Mo.) were weighed out into 100 g allotments. Each allotment of seeds was coated according to Seed Coating Protocol 1 with one of the double-layer coatings set forth in Table 2:

TABLE 2

| Innermost Coating (per 100 g seed) | Inner Coating (per 100 g seed) | Outer Coating (per 100 g seed) |
|---|---|---|
| none | 300 µl *Bradyrhizobium japonicum* SEMIA 5079 suspension | none |
| none | 300 µl *Bradyrhizobium japonicum* SEMIA 5079 suspension containing 30% maltose monohydrate | 400 µl deionized water containing 50% maltose monohydrate |
| none | 300 µl *Bradyrhizobium japonicum* SEMIA 5079 suspension containing 30% maltose monohydrate | 400 µl deionized water containing 30% maltose monohydrate |
| none | 400 µl *Bradyrhizobium japonicum* SEMIA 5079 suspension containing 30% maltose monohydrate | 300 µl deionized water containing 30% maltose monohydrate |
| 200 µl deionized water containing 30% maltose monohydrate | 300 µl *Bradyrhizobium japonicum* SEMIA 5079 suspension containing 30% maltose monohydrate | 200 µl deionized water containing 30% maltose monohydrate |
| 200 µl deionized water containing 50% maltose monohydrate | 300 µl *Bradyrhizobium japonicum* SEMIA 5079 suspension containing 30% maltose monohydrate | 200 µl deionized water containing 50% maltose monohydrate |

Figure 4:
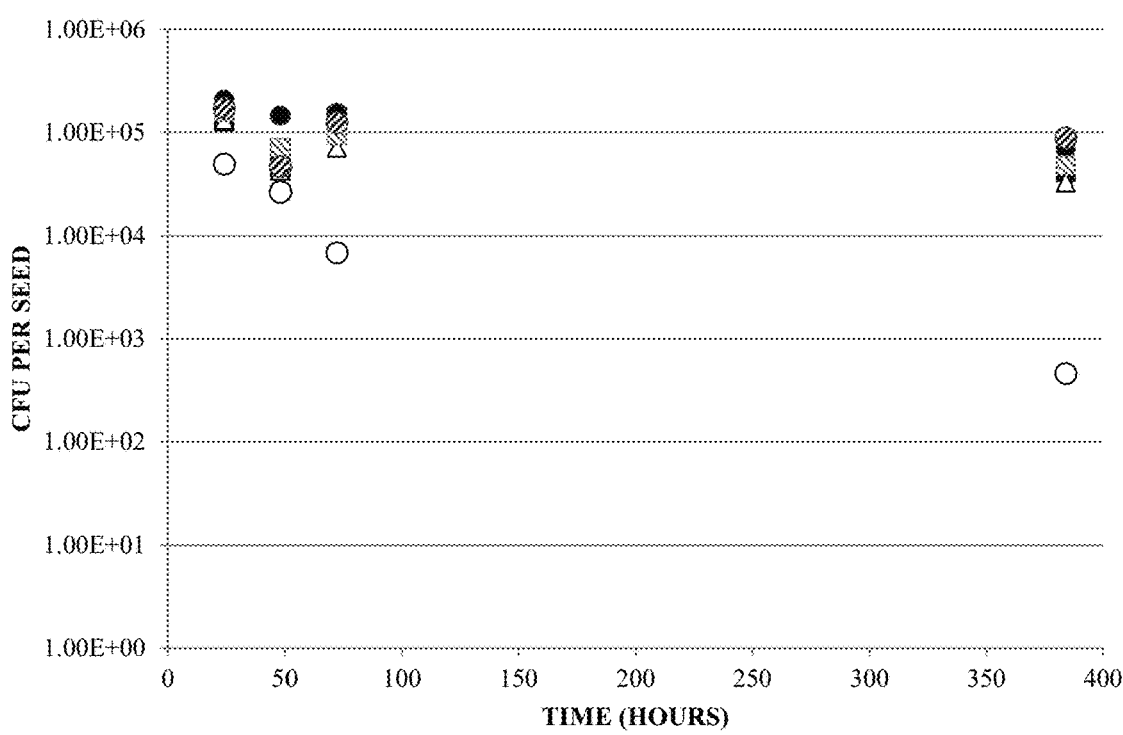
FIGS. 4-6 are graphs showing the survivability of desiccated *Bradyrhizobium japonicum* SEMIA 5079 on soybean seeds stored at 30° C. and 11%, 32% or 54% relative humidity, respectively. Open circles=seeds coated with 300 µl *Bradyrhizobium japonicum* SEMIA 5079 suspension. Solid squares=seeds coated with 300 µl *Bradyrhizobium japonicum* SEMIA 5079 suspension containing maltose monohydrate (30% w/w); 400 µl deionized water containing maltose monohydrate (50% w/w). Open triangles=seeds coated with seeds coated with 300 µl *Bradyrhizobium japonicum* SEMIA 5079 suspension containing maltose monohydrate (30% w/w); 400 µl deionized water containing maltose monohydrate (30% w/w). Solid circles=seeds coated with seeds coated with 400 µl *Bradyrhizobium japonicum* SEMIA 5079 suspension containing maltose monohydrate (30% w/w); 300 µl deionized water containing maltose monohydrate (30% w/w). Striped squares=seeds coated with 200 µl deionized water containing maltose monohydrate (30% w/w); 300 µl *Bradyrhizobium japonicum* SEMIA 5079 suspension containing maltose monohydrate (30% w/w); 200 µl deionized water containing maltose monohydrate (30% w/w). Striped circles=seeds coated with 200 µl deionized water containing maltose monohydrate (30% w/w); 300 µl *Bradyrhizobium japonicum* SEMIA 5079 suspension containing maltose monohydrate (30% w/w); 200 µl deionized water containing 50% maltose monohydrate (50% w/w).
Figure 5:
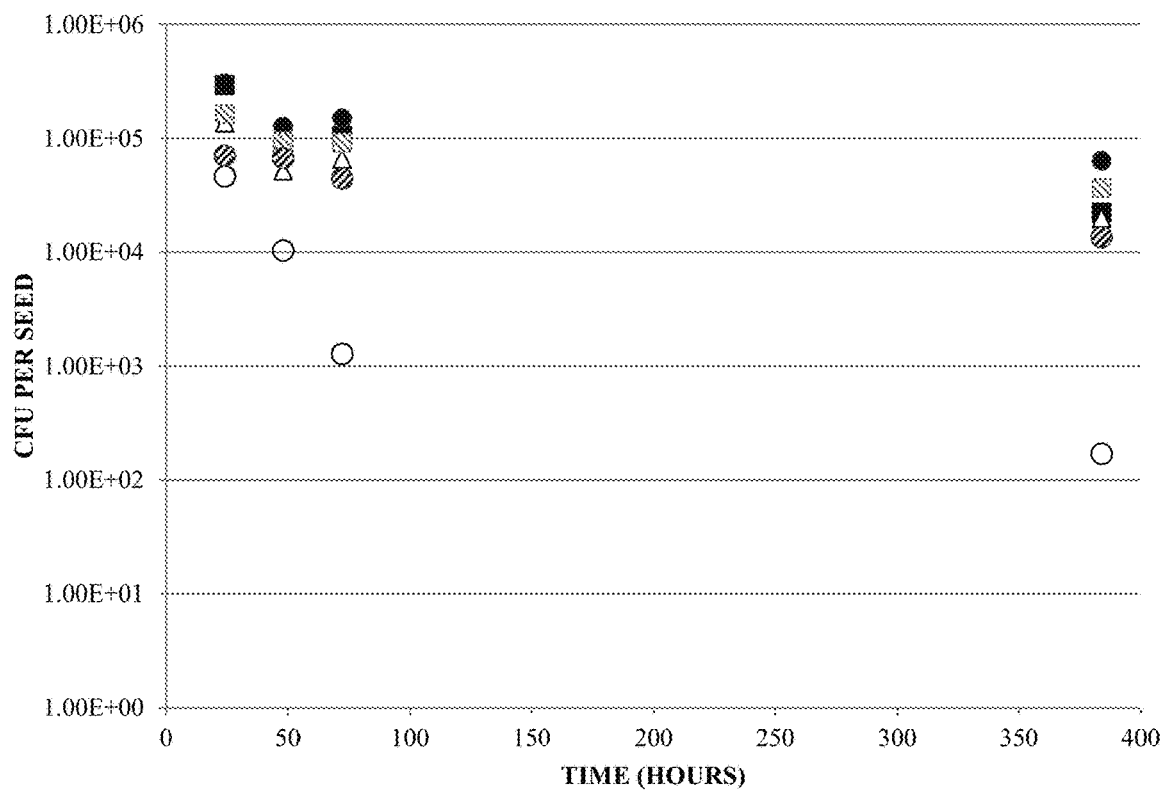
Figure 6:
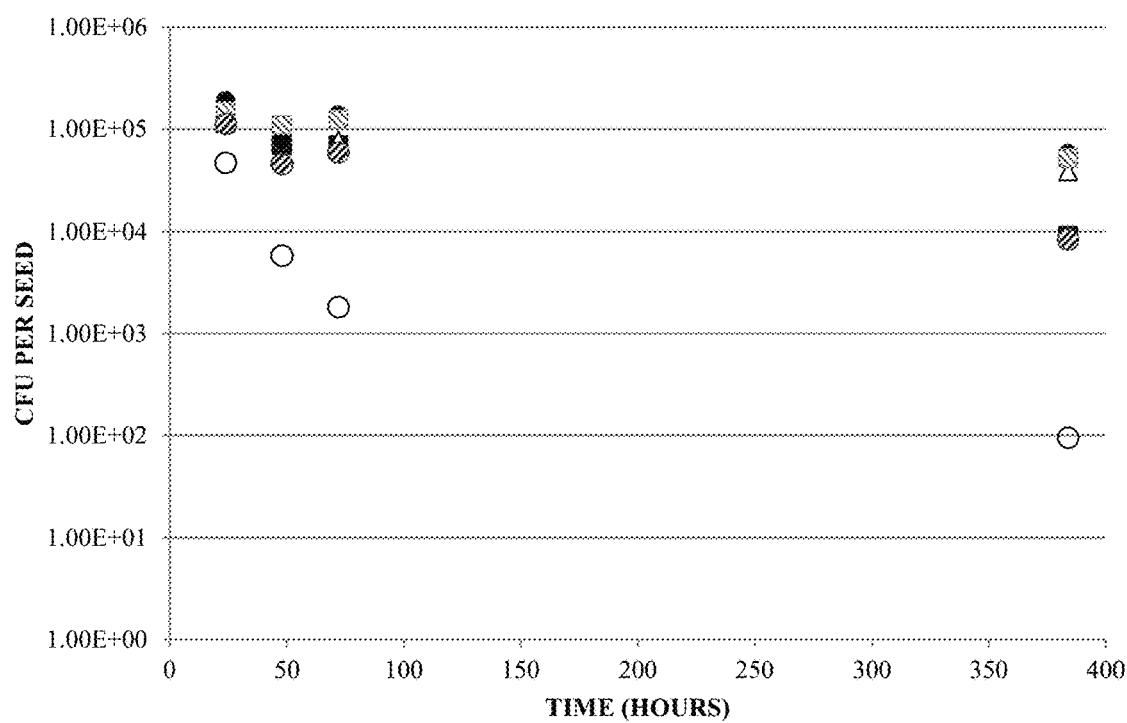

Coated seeds were stored at 30° C. and 11%, 32% or 54% relative humidity and then assayed for on-seed survivability. FIGS. 4-6.

Example 3

Maltose and Trehalose Enhanced the Survivability of Desiccated *Bradyrhizobium*

Untreated soybean seeds (ASGROW®; Monsanto Company, St. Louis, Mo.) were weighed out into 100 g allotments. Each allotment of seeds was coated according to Seed Coating Protocol 1 with one of the double-layer coatings set forth in Table 3:

TABLE 3

| Inner Coating (per 100 g seed) | Outer Coating (per 100 g seed) |
|---|---|
| 300 µl *Bradyrhizobium japonicum* SEMIA 5079 suspension | none |
| 400 µl *Bradyrhizobium japonicum* SEMIA 5079 suspension containing 30% maltose monohydrate | 300 µl deionized water containing 30% maltose monohydrate |
| 400 µl *Bradyrhizobium japonicum* SEMIA 5079 suspension containing 30% maltose monohydrate | 300 µl deionized water containing 30% trehalose dihydrate |

Figure 7:
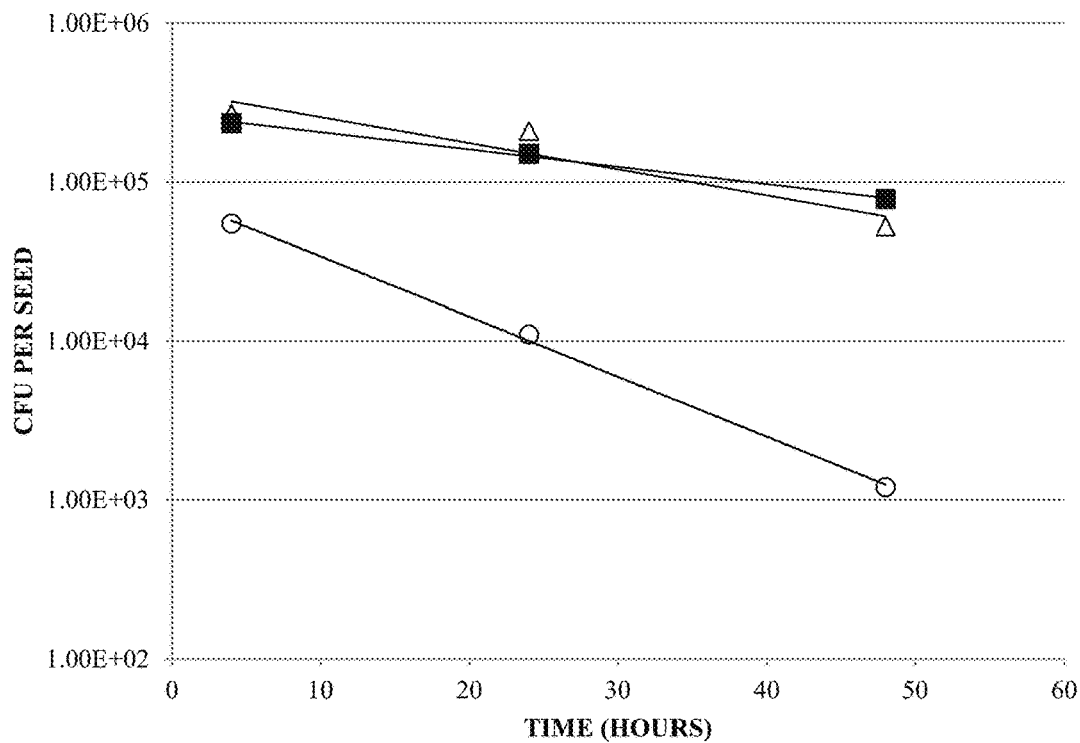
FIGS. 7-9 are graphs showing the survivability of desiccated *Bradyrhizobium japonicum* SEMIA 5079 on soybean seeds stored at 30° C. and 11%, 32% or 54% relative humidity, respectively. Circles=seeds coated with 300 µl *Bradyrhizobium japonicum* SEMIA 5079 suspension. Squares=seeds coated with 400 µl *Bradyrhizobium japonicum* SEMIA 5079 suspension containing maltose monohydrate (30% w/w); 300 µl deionized water containing maltose monohydrate (30% w/w). Triangles=seeds coated with seeds coated with 400 µl *Bradyrhizobium japonicum* SEMIA 5079 suspension containing maltose monohydrate (30% w/w); 400 µl deionized water containing trehalose dehydrate (30% w/w).
Figure 8:
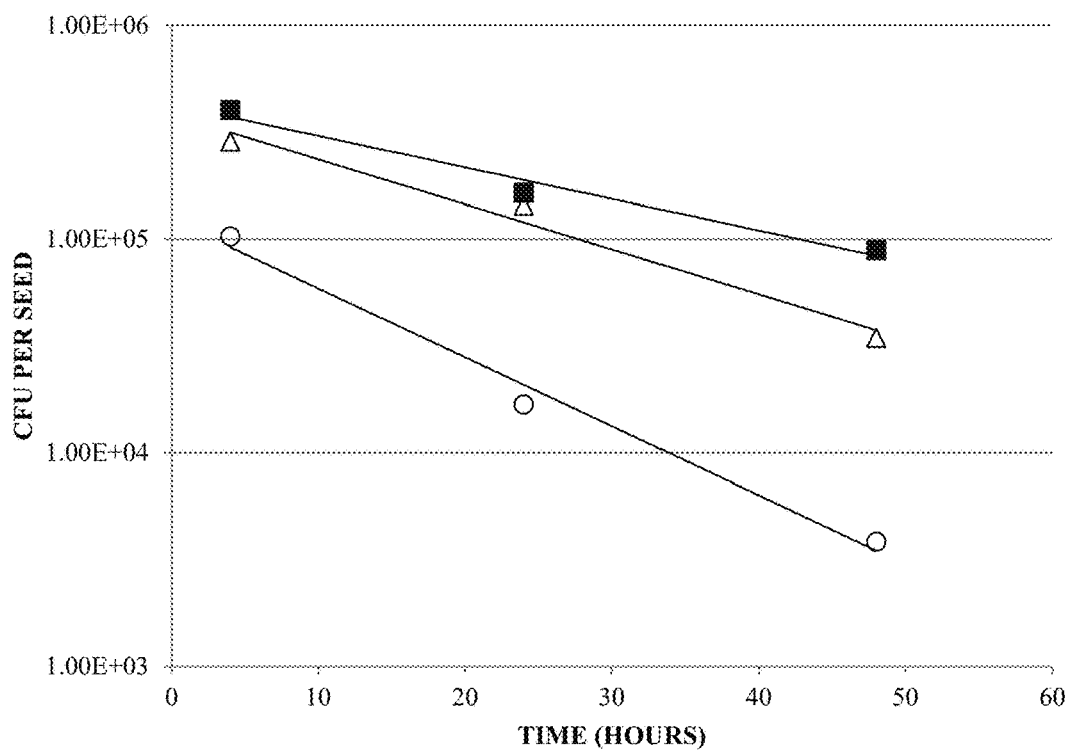
Figure 9:
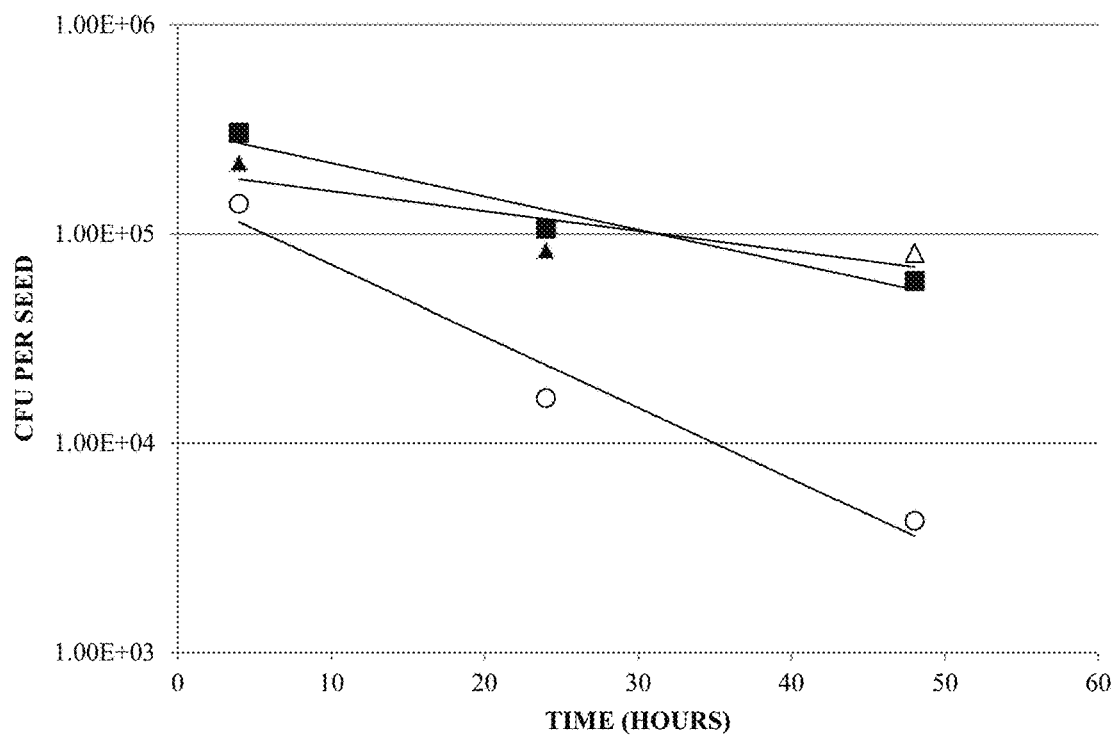
Figure 10:
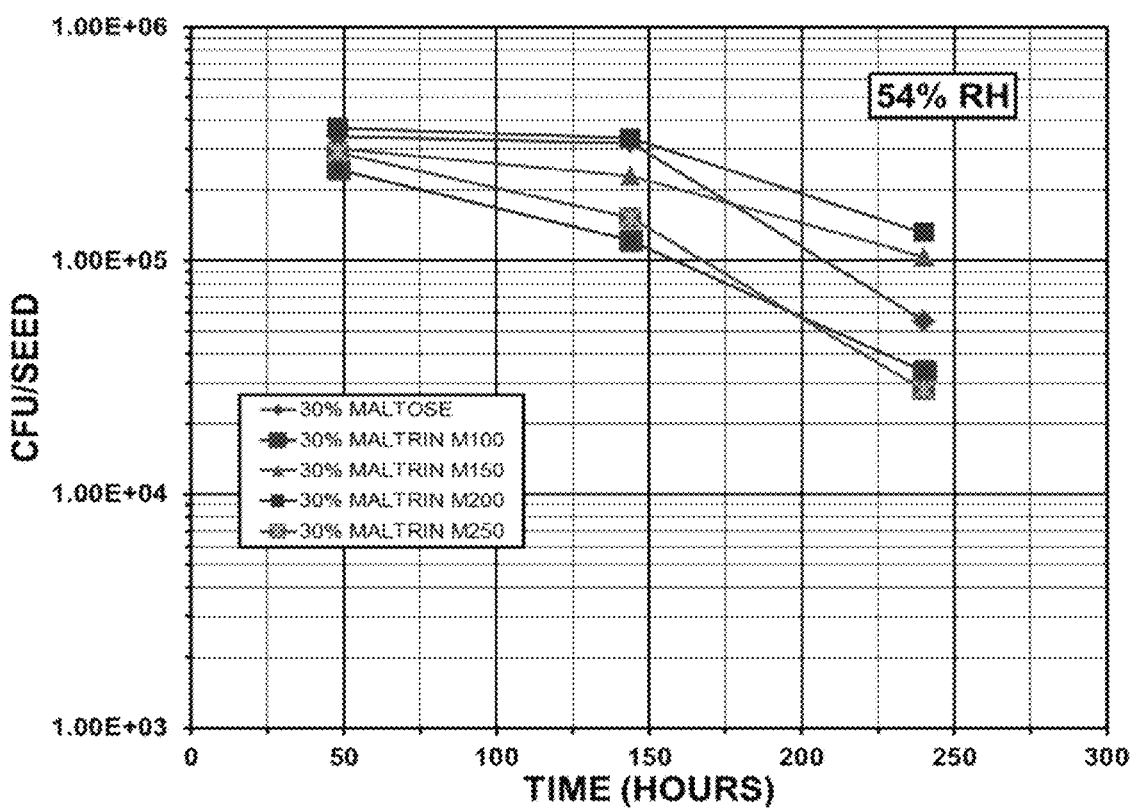
FIGS. 10-13 are figures showing the survivability of desiccated *Bradyrhizobium japonicum* SEMIA 5079 on soybean seeds stored at 30° C. and 54% or 76% relative humidity.
Figure 11:
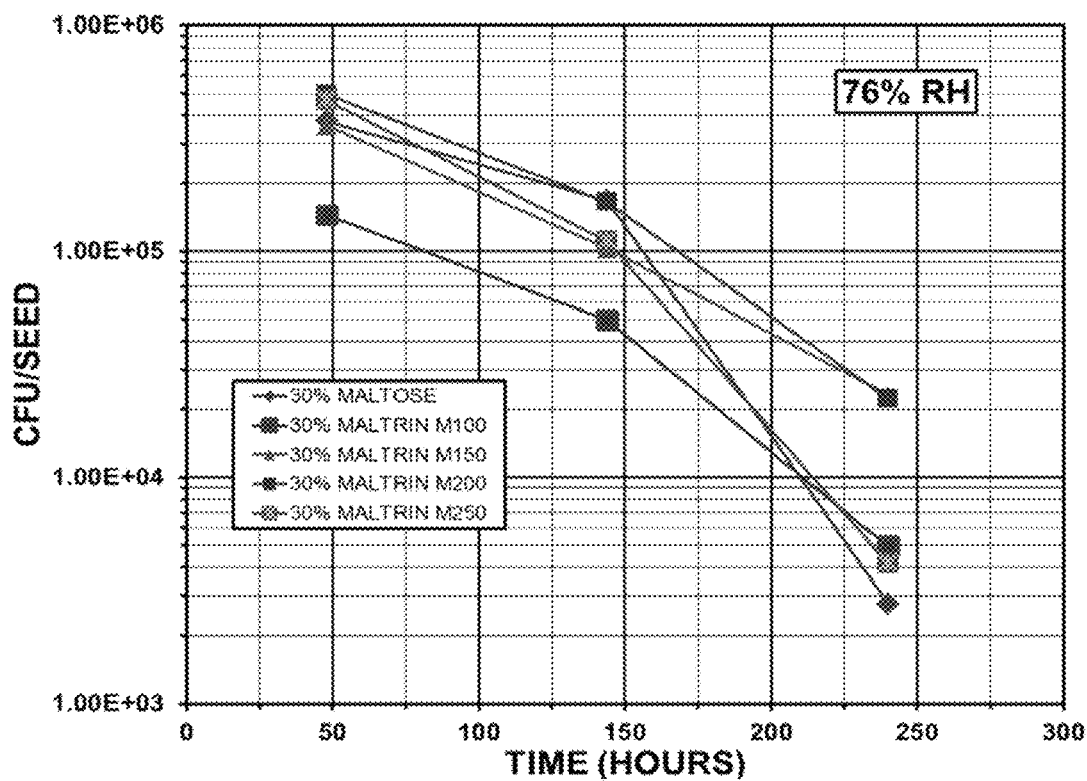
Figure 12:
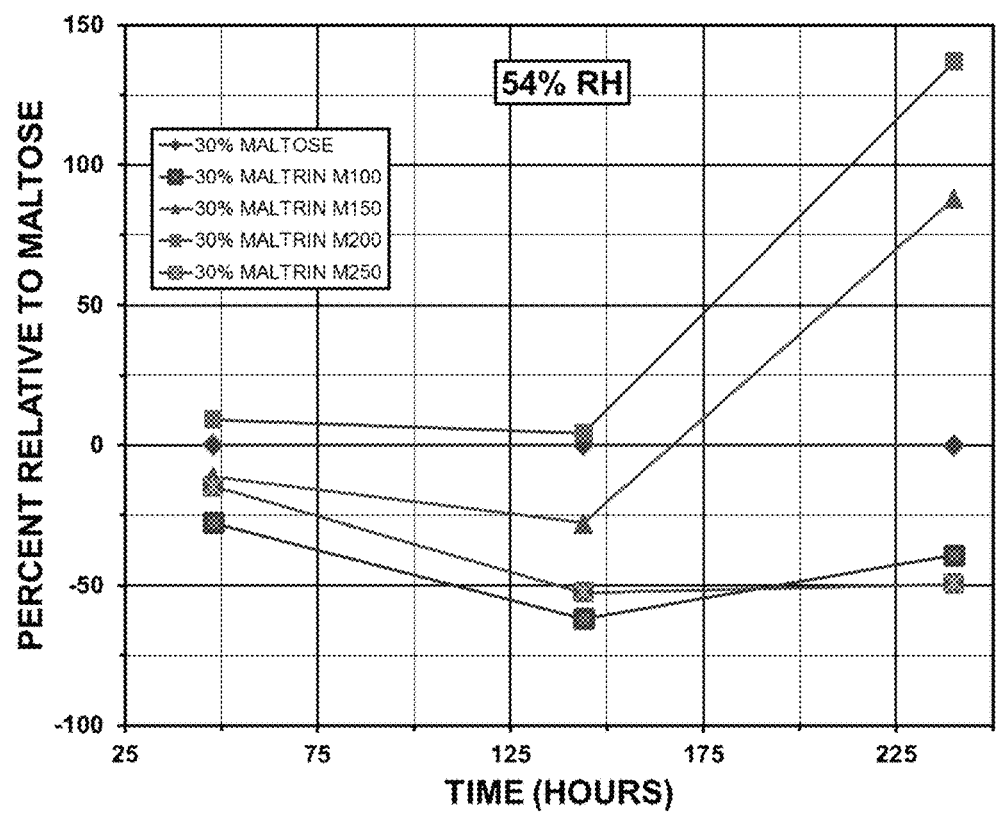
Figure 13:
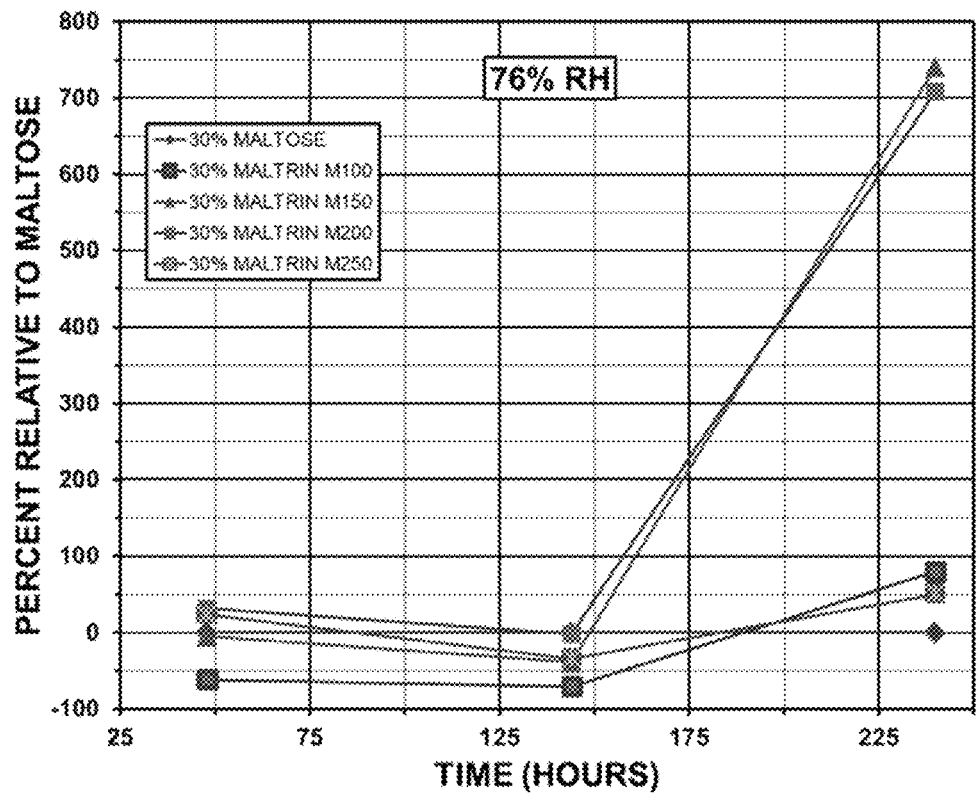

Coated seeds were stored at 30° C. and 11%, 32% or 54% relative humidity and then assayed for on-seed survivability. FIGS. 7-9.

Example 4

Maltodextrins enhanced the survivability of desiccated *Bradyrhizobium* Untreated soybean seeds (ASGROW® AG2733; Monsanto Company, St. Louis, Mo.) were weighed out into 100 g allotments. Each allotment of seeds was coated according to Seed Coating Protocol 1 with one of the double-layer coatings set forth in Table 4:

TABLE 4

| Inner Coating (400 µl per 100 g seed) | Outer Coating (300 µl per 100 g seed) |
|---|---|
| *Bradyrhizobium japonicum* SEMIA 5079 suspension containing 30% maltose monohydrate | deionized water containing 30% maltose monohydrate |
| *Bradyrhizobium japonicum* SEMIA 5079 suspension containing 30% MALTRIN® M100 | deionized water containing 30% MALTRIN® M100 |
| *Bradyrhizobium japonicum* SEMIA 5079 suspension containing 30% MALTRIN® M150 | deionized water containing 30% MALTRIN® M150 |
| *Bradyrhizobium japonicum* SEMIA 5079 suspension containing 30% MALTRIN® M200 | deionized water containing 30% MALTRIN® M200 |
| *Bradyrhizobium japonicum* SEMIA 5079 suspension containing 30% MALTRIN® M250 | deionized water containing 30% MALTRIN® M250 |

Coated seeds were stored at 30° C. and 54% or 76% relative humidity and then assayed for on-seed survivability. FIGS. 10-13. The on-seed survivability of *Bradyrhizobium japonicum* SEMIA 5079 at 54% relative humidity was increased by both MALTRIN® M150 (88%) and M200 (137%), as compared to maltose monohydrate. The on-seed viability of *Bradyrhizobium japonicum* SEMIA 5079 at 76% relative humidity was increased by both MALTRIN® M150 (741%) and M200 (709%), as compared to maltose monohydrate.

Example 5

Combinations of Maltodextrins Enhanced the Survivability of Desiccated *Bradyrhizobium*

Untreated soybean seeds (ASGROW® AG3433; Monsanto Company, St. Louis, Mo.) were weighed out into 100 g allotments. Each allotment of seeds was coated according to Seed Coating Protocol 1 with one of the double-layer coatings set forth in Table 5:

TABLE 5

| Inner Coating (400 µl per 100 g seed) | Outer Coating (300 µl per 100 g seed) |
|---|---|
| *Bradyrhizobium japonicum* SEMIA 5079 suspension containing 22.5% MALTRIN® M150 + 7.5% MALTRIN® M200 | deionized water containing 22.5% MALTRIN® M150 + 7.5% MALTRIN® M200 |
| *Bradyrhizobium japonicum* SEMIA 5079 suspension containing 15% MALTRIN® M150 + 15% MALTRIN® M200 | deionized water containing 15% MALTRIN® M150 + 15% MALTRIN® M200 |
| *Bradyrhizobium japonicum* SEMIA 5079 suspension containing 7.5% MALTRIN® M150 + 22.5% MALTRIN® M200 | deionized water containing 7.5% MALTRIN® M150 + 22.5% MALTRIN® M200 |
| *Bradyrhizobium japonicum* SEMIA 5079 suspension containing 22.5% MALTRIN® M100 + 7.5% MALTRIN® M200 | deionized water containing 22.5% MALTRIN® M100 + 7.5% MALTRIN® M200 |
| *Bradyrhizobium japonicum* SEMIA 5079 suspension containing 15% MALTRIN® M100 + 15% MALTRIN® M200 | deionized water containing 15% MALTRIN® M100 + 15% MALTRIN® M200 |
| *Bradyrhizobium japonicum* SEMIA 5079 suspension containing 30% Maltose monohydrate | deionized water containing 30% Maltose monohydrate |

Figure 14:
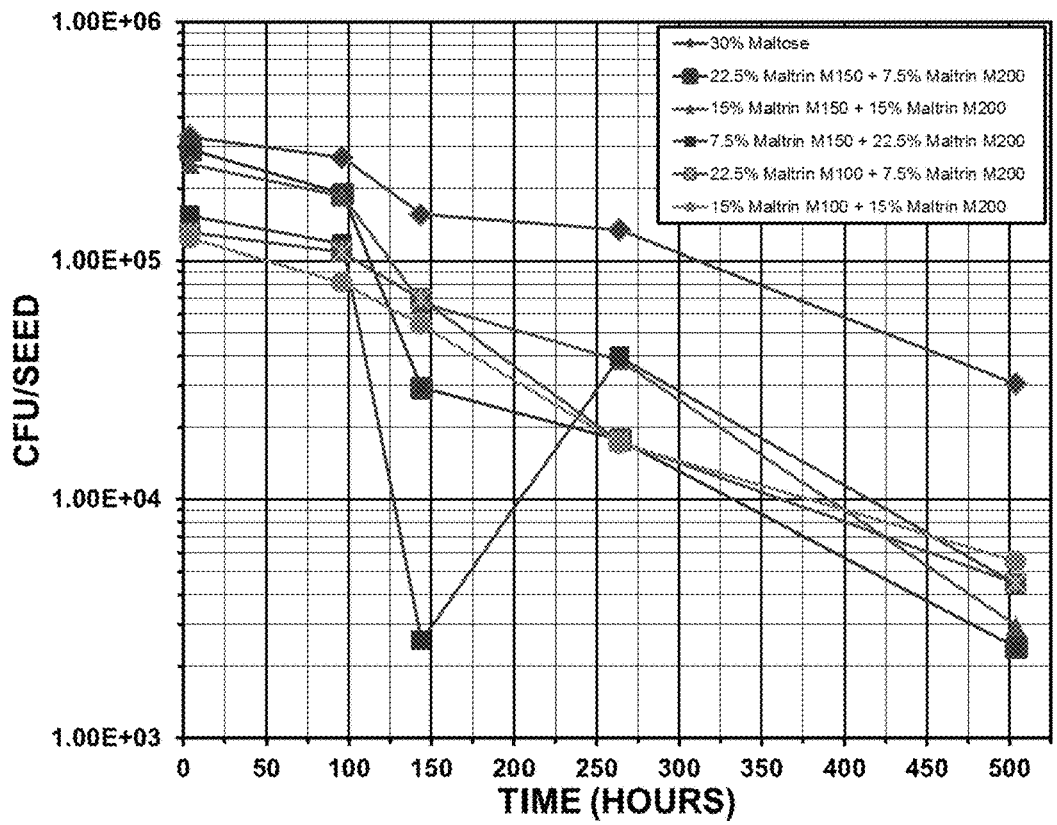
FIGS. 14-16 are graphs showing the survivability of desiccated *Bradyrhizobium japonicum* SEMIA 5079 on soybean seeds stored at 30° C. and 11%, 54% or 76% relative humidity, respectively.
Figure 15:
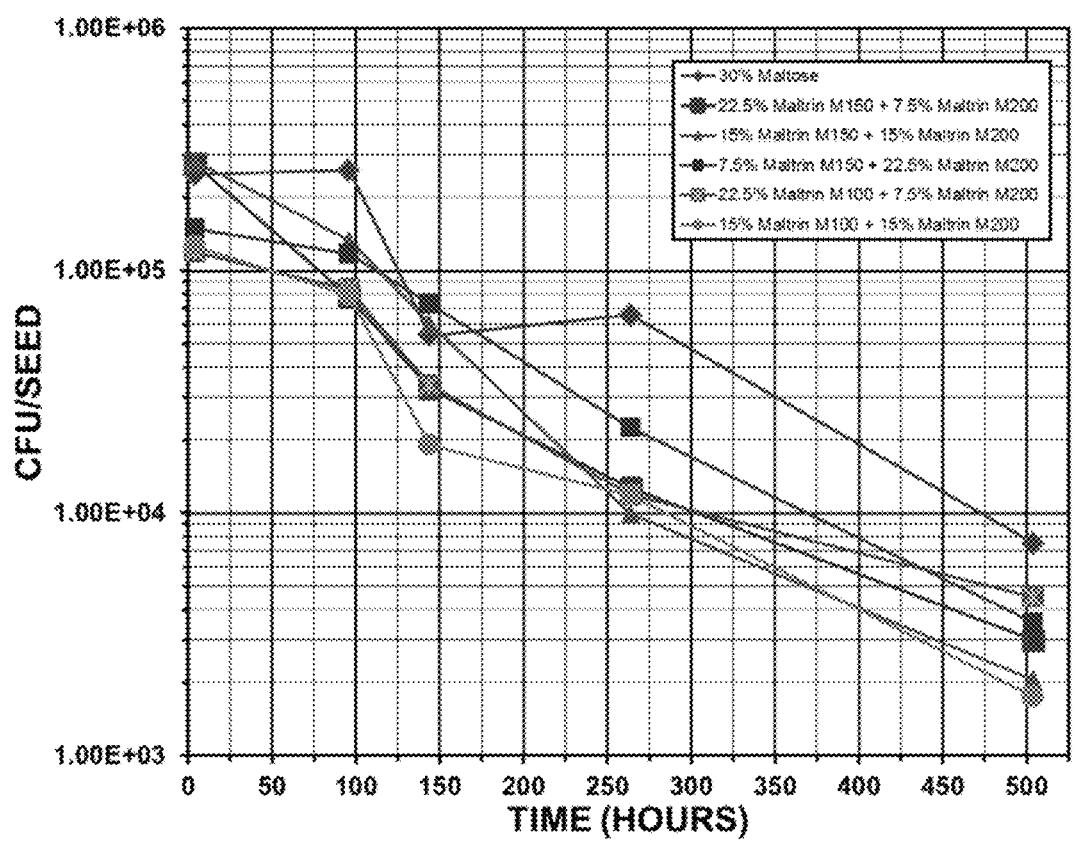
Figure 16:
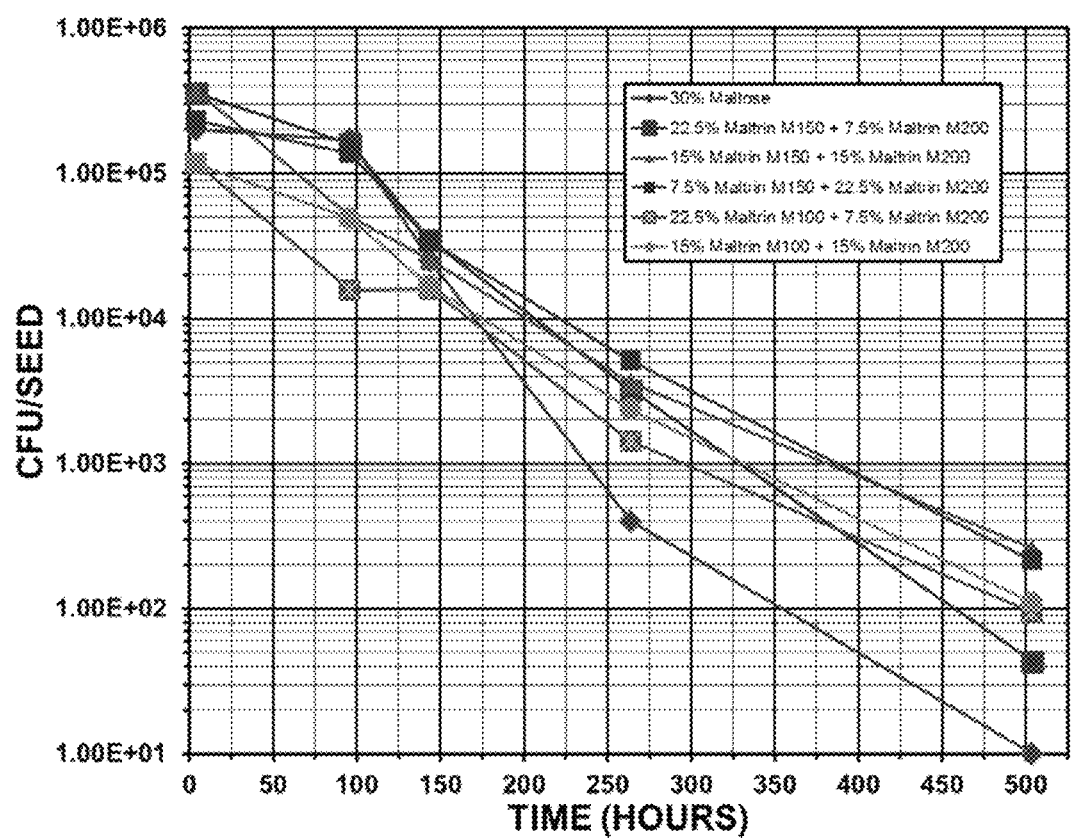

Coated seeds were stored at 30° C. at 11%, 54% or 76% relative humidity and then assayed for on-seed survivability. FIGS. 14-16.

Example 6

Combinations of Maltodextrins and Sucrose Enhanced the Survivability of Desiccated *Bradyrhizobium*

Untreated soybean seeds (ASGROW® AG3433; Monsanto Company, St. Louis, Mo.) were weighed out into 100 g allotments. Each allotment of seeds was coated according to Seed Coating Protocol 1 with one of the double-layer coatings set forth in Table 6:

TABLE 6

| Inner Coating (400 µl per 100 g seed) | Outer Coating (300 µl per 100 g seed) |
|---|---|
| *Bradyrhizobium japonicum* SEMIA 5079 suspension containing 30% MALTRIN® M100 (circles in the graphs below) | deionized water containing 30% MALTRIN® M100 |
| *Bradyrhizobium japonicum* SEMIA 5079 suspension containing 26% MALTRIN® M100 + 4% Sucrose (triangles in the graphs below) | deionized water containing 26% MALTRIN® M100 + 4% Sucrose |
| *Bradyrhizobium japonicum* SEMIA 5079 suspension containing 22% MALTRIN® M100 + 8% Sucrose (squares in the graphs below) | deionized water containing 22% MALTRIN® M100 + 8% Sucrose |

Figure 17:
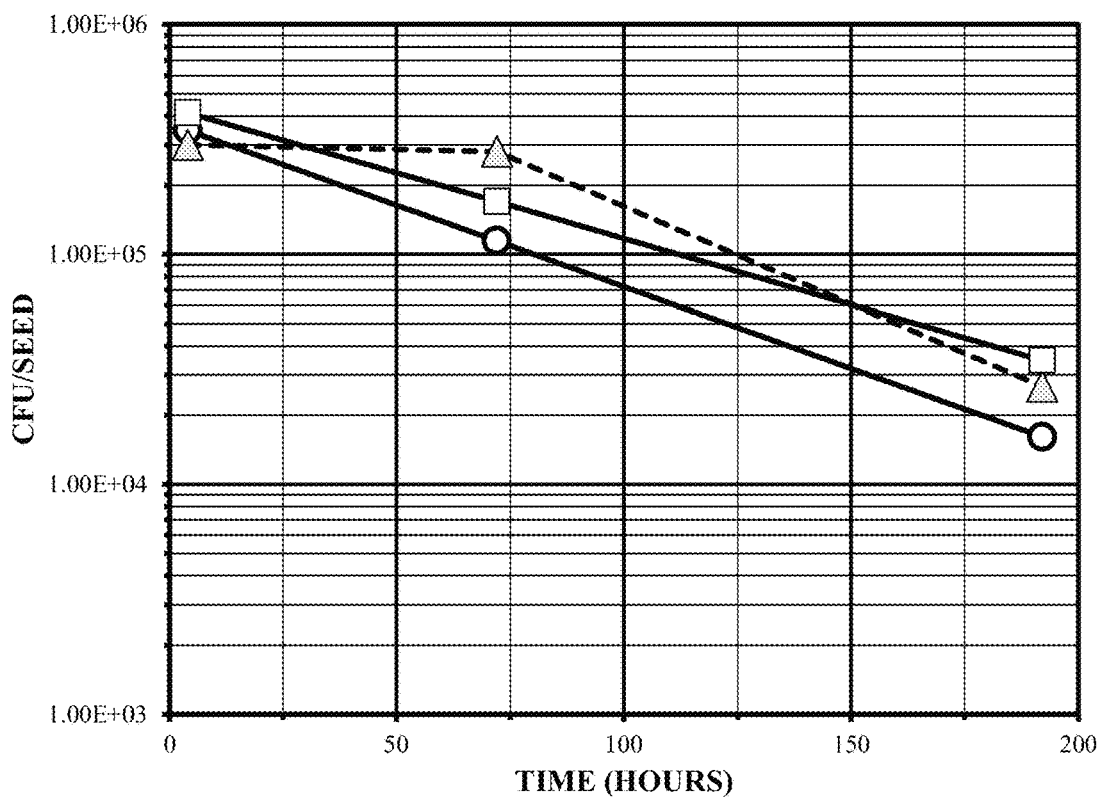
FIGS. 17-19 are graphs showing the survivability of desiccated *Bradyrhizobium japonicum* SEMIA 5079 on soybean seeds stored at 30° C. and 11%, 54% or 76% relative humidity, respectively.
Figure 18:
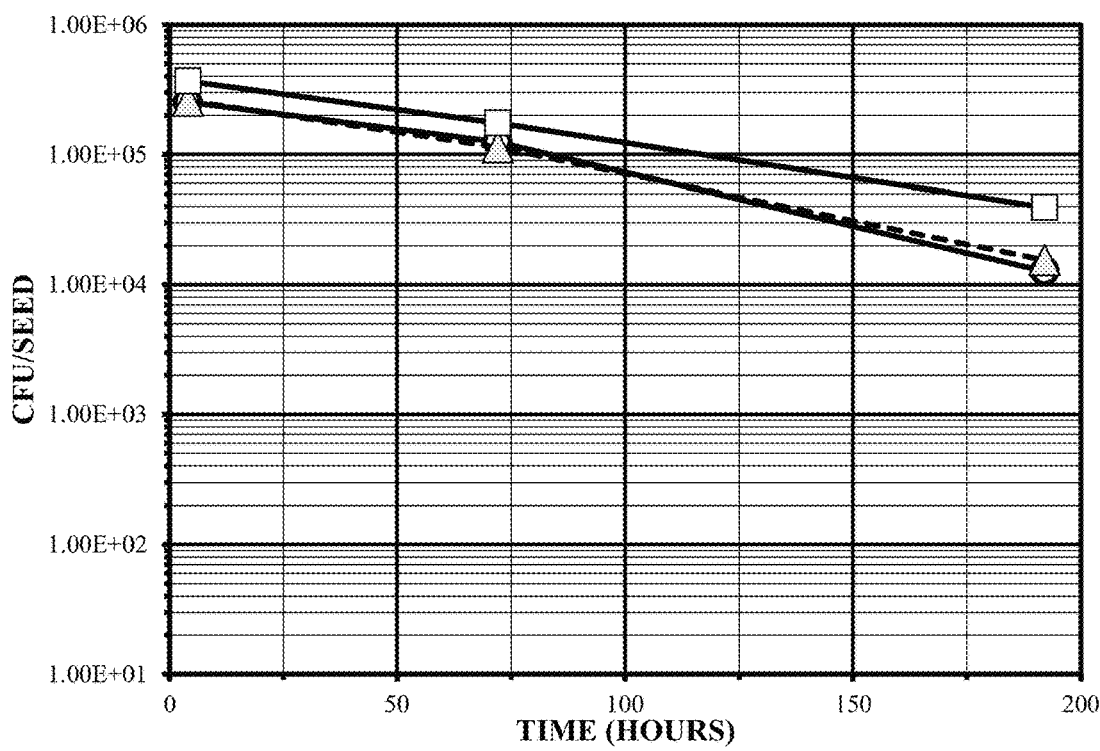
Figure 19:
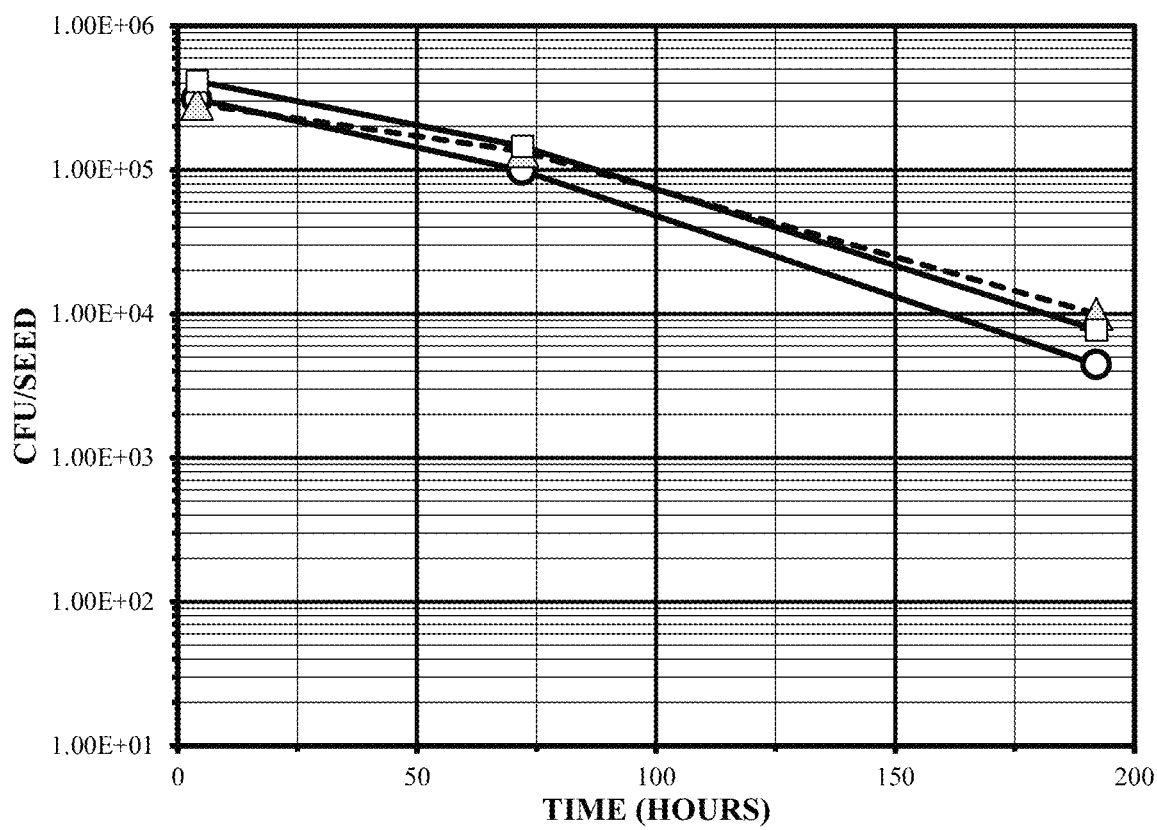

Coated seeds were stored at 30° C. at 11%, 54% or 76% relative humidity and then assayed for on-seed survivability. FIGS. 17-19.

Example 7

Combinations of Maltodextrin and Maltose Enhanced On-Seed Survivability of *Bradyrhizobium*

Untreated soybean seeds (ASGROW® AG4831; Monsanto Company, St. Louis, Mo.) were weighed out into 100 g allotments. Each allotment of seeds was coated according to Seed Coating Protocol 2 with 400 µl of one of the coatings set forth in Table 7:

TABLE 7

| Single Coating |
|---|
| *Bradyrhizobium japonicum* SEMIA 5079 suspension containing 17.5% (65% GLOBE® Plus 15 DE + 35% Maltose monohydrate) |
| *Bradyrhizobium japonicum* SEMIA 5079 suspension containing 26.3% (65% GLOBE® Plus 15 DE + 35% Maltose monohydrate) |
| *Bradyrhizobium japonicum* SEMIA 5079 suspension containing 32.4% (65% GLOBE® Plus 15 DE + 35% Maltose monohydrate) |
| *Bradyrhizobium japonicum* SEMIA 5079 suspension containing 35.0% (65% GLOBE® Plus 15 DE + 35% Maltose monohydrate) |
| *Bradyrhizobium japonicum* SEMIA 5079 suspension containing 39.4% (65% GLOBE® Plus 15 DE + 35% Maltose monohydrate) |
| *Bradyrhizobium japonicum* SEMIA 5079 suspension containing 43.8% (65% GLOBE® Plus 15 DE + 35% Maltose monohydrate) |
| *Bradyrhizobium japonicum* SEMIA 5079 suspension containing 48.1% (65% GLOBE® Plus 15 DE + 35% Maltose monohydrate) |
| *Bradyrhizobium japonicum* SEMIA 5079 suspension containing 52.5% (65% GLOBE® Plus 15 DE + 35% Maltose monohydrate) |
| *Bradyrhizobium japonicum* SEMIA 5079 suspension containing 56.9% (65% GLOBE® Plus 15 DE + 35% Maltose monohydrate) |
| *Bradyrhizobium japonicum* SEMIA 5079 suspension containing 61.3% (65% GLOBE® Plus 15 DE + 35% Maltose monohydrate) |

Figure 20:
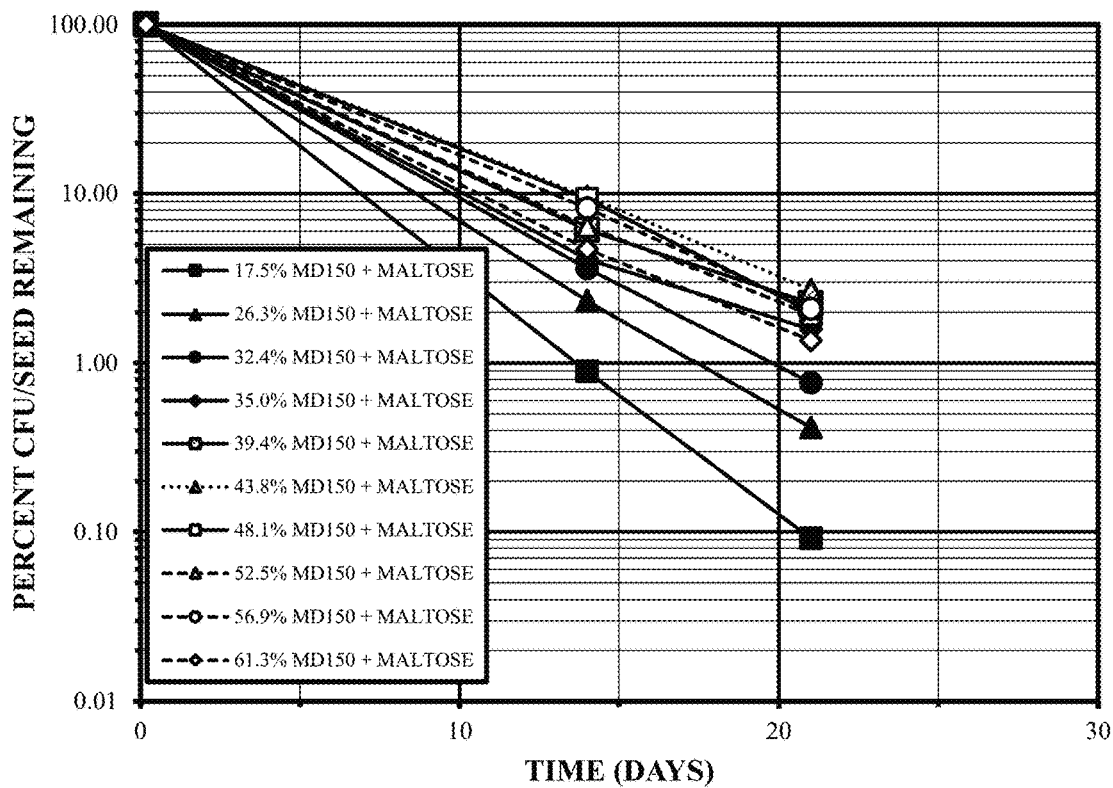
FIG. 20 is a graph showing the survivability of desiccated *Bradyrhizobium japonicum* SEMIA 5079 on soybean seeds stored at 25° C. and 65% relative humidity.

Coated seeds were stored at 25° C. at 65% relative humidity and then assayed for on-seed survivability. FIG. 20.

Example 8

Combinations of Maltodextrins and Maltose/Trehalose Enhanced the Survivability of Desiccated *Bradyrhizobium*

Untreated soybean seeds (ASGROW® AG2031; Monsanto Company, St. Louis, Mo.) were weighed out into 100 g allotments. Each allotment of seeds was coated with one of the following according to Seed Coating Protocol 1 with one of the double-layer coatings set forth in Table 8:

TABLE 8

| | Inner Coating (350 µl per 100 g seed) | Outer Coating (350 µl per 100 g seed) |
|---|---|---|
| A | *Bradyrhizobium japonicum* SEMIA 5079 suspension containing 9.750% MALTRIN® M150 + 9.75% MALTRIN® M200 + 10.500% Maltose monohydrate | deionized water containing 9.750% MALTRIN® M150 + 9.75% MALTRIN® M200 + 10.500% Maltose monohydrate |
| B | *Bradyrhizobium japonicum* SEMIA 5079 suspension containing | deionized water containing 14.625% MALTRIN® M150 + |

TABLE 8-continued

| Inner Coating (350 μl per 100 g seed) | Outer Coating (350 μl per 100 g seed) |
|---|---|
| 14.625% MALTRIN® M150 + 4.875% MALTRIN® M200 + 10.500% Maltose monohydrate | 4.875% MALTRIN® M200 + 10.500% Maltose monohydrate |
| C  *Bradyrhizobium japonicum* SEMIA 5079 suspension containing 19.500% MALTRIN® M150 + 10.500% Maltose monohydrate | deionized water containing 19.500% MALTRIN® M150 + 10.500% Maltose monohydrate |
| D  *Bradyrhizobium japonicum* SEMIA 5079 suspension containing 4.500% MALTRIN® M150 + 13.500% MALTRIN® M200 + 12.000% Trehalose dihydrate | deionized water containing 4.500% MALTRIN® M150 + 13.500% MALTRIN® M200 + 12.000% Trehalose dihydrate |
| E  *Bradyrhizobium japonicum* SEMIA 5079 suspension containing 10.800% MALTRIN® M150 + 7.200% MALTRIN® M200 + 12.000% Trehalose dihydrate | deionized water containing 10.800% MALTRIN® M150 + 7.200% MALTRIN® M200 + 12.000% Trehalose dihydrate |
| F  *Bradyrhizobium japonicum* SEMIA 5079 suspension containing 18.000% MALTRIN® M150 + 12.000% Trehalose dihydrate | deionized water containing 18.000% MALTRIN® M150 + 12.000% Trehalose dihydrate |
| G  *Bradyrhizobium japonicum* SEMIA 5079 suspension containing 3.750% MALTRIN® M150 + 11.250% MALTRIN® M200 + 15.000% Trehalose dihydrate | deionized water containing 3.750% MALTRIN® M150 + 11.250% MALTRIN® M200 + 15.000% Trehalose dihydrate |
| H  *Bradyrhizobium japonicum* SEMIA 5079 suspension containing 9.000% MALTRIN® M150 + 6.000% MALTRIN® M200 + 15.000% Trehalose dihydrate | deionized water containing 9.000% MALTRIN® M150 + 6.000% MALTRIN® M200 + 15.000% Trehalose dihydrate |
| I  *Bradyrhizobium japonicum* SEMIA 5079 suspension containing 15.000% MALTRIN® M150 + 15.000% Trehalose dihydrate | deionized water containing 15.000% MALTRIN® M150 + 15.000% Trehalose dihydrate |

Figure 21:
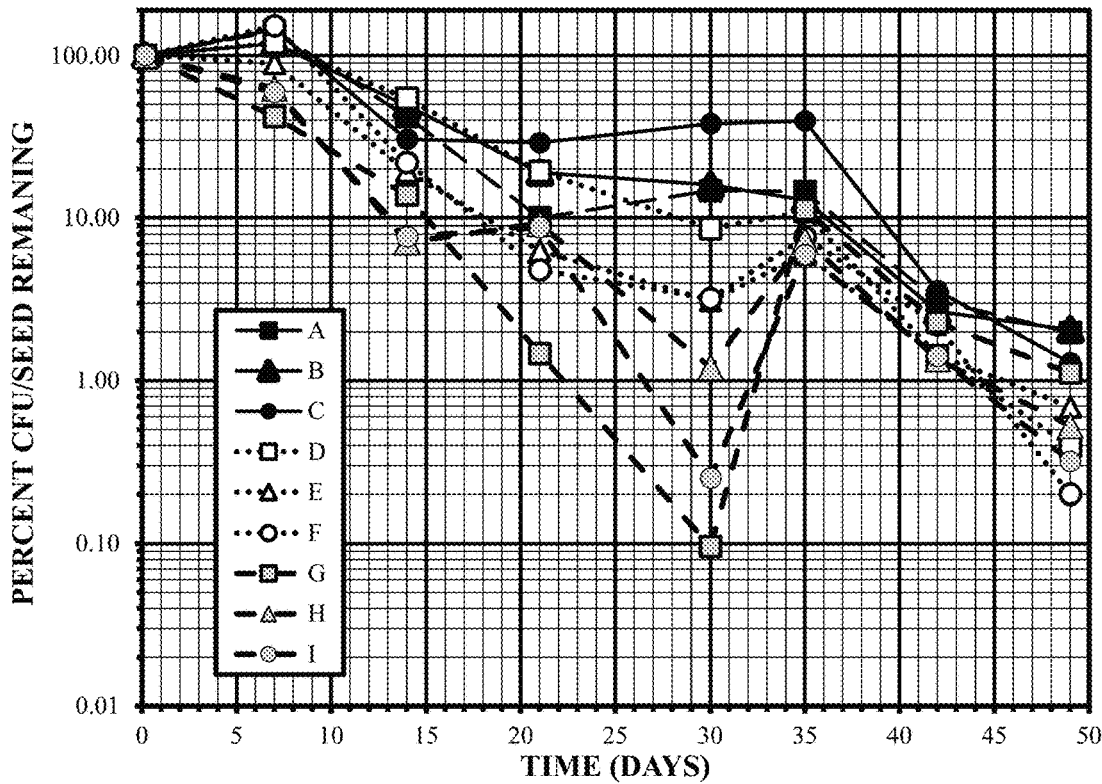
FIG. 21 is a graph showing the survivability of desiccated *Bradyrhizobium japonicum* SEMIA 5079 on soybean seeds stored at room temperature and 65% relative humidity, expressed as percent remaining relative to the initial 4 hour time point.

Coated seeds were stored at room temperature at 65% relative humidity and then assayed for on-seed survivability. FIG. 21.

Example 9

Mixtures of Maltodextrin and Trehalose Enhanced the Survivability of Desiccated *Bradyrhizobium*

Untreated soybean seeds (ASGROW® AG2031; Monsanto Company, St. Louis, Mo.) were weighed out into 100 g allotments. Each allotment of seeds was coated according to Seed Coating Protocol 1 with one of the double-layer coatings set forth in Table 9 or one of the single-layer coatings set forth in Table 10:

TABLE 9

| Inner Coating (350 μl per 100 g seed) | Outer Coating (350 μl per 100 g seed) |
|---|---|
| *Bradyrhizobium japonicum* SEMIA 5079 suspension containing | deionized water containing 12% MALTRIN® M150 + |

TABLE 9-continued

| Inner Coating (350 μl per 100 g seed) | Outer Coating (350 μl per 100 g seed) |
|---|---|
| 12% MALTRIN® M150 + 8% Trehalose dihydrate | 8% Trehalose dihydrate |
| *Bradyrhizobium japonicum* SEMIA 5079 suspension containing 12% MALTRIN® M150 + 8% Trehalose dihydrate | *Bradyrhizobium japonicum* SEMIA 5079 suspension containing 12% MALTRIN® M150 + 8% Trehalose dihydrate |
| *Bradyrhizobium japonicum* SEMIA 5079 suspension containing 15% MALTRIN® M150 + 10% Trehalose dihydrate | deionized water containing 15% MALTRIN® M150 + 10% Trehalose dihydrate |
| *Bradyrhizobium japonicum* SEMIA 5079 suspension containing 15% MALTRIN® M150 + 10% Trehalose dihydrate | *Bradyrhizobium japonicum* SEMIA 5079 suspension containing 15% MALTRIN® M150 + 10% Trehalose dihydrate |
| *Bradyrhizobium japonicum* SEMIA 5079 suspension containing 18% MALTRIN® M150 + 12% Trehalose dihydrate | deionized water containing 18% MALTRIN® M150 + 12% Trehalose dihydrate |
| *Bradyrhizobium japonicum* SEMIA 5079 suspension containing 18% MALTRIN® M150 + 12% Trehalose dihydrate | *Bradyrhizobium japonicum* SEMIA 5079 suspension containing 18% MALTRIN® M150 + 12% Trehalose dihydrate |

TABLE 10

| Single Coating (700 μl per 100 g seed) |
|---|
| *Bradyrhizobium japonicum* SEMIA 5079 suspension containing 24% MALTRIN® M150 + 16% Trehalose dihydrate |
| *Bradyrhizobium japonicum* SEMIA 5079 suspension containing 30% MALTRIN® M150 + 20% Trehalose dihydrate |
| *Bradyrhizobium japonicum* SEMIA 5079 suspension containing 36% MALTRIN® M150 + 24% Trehalose dihydrate |

Figure 22:
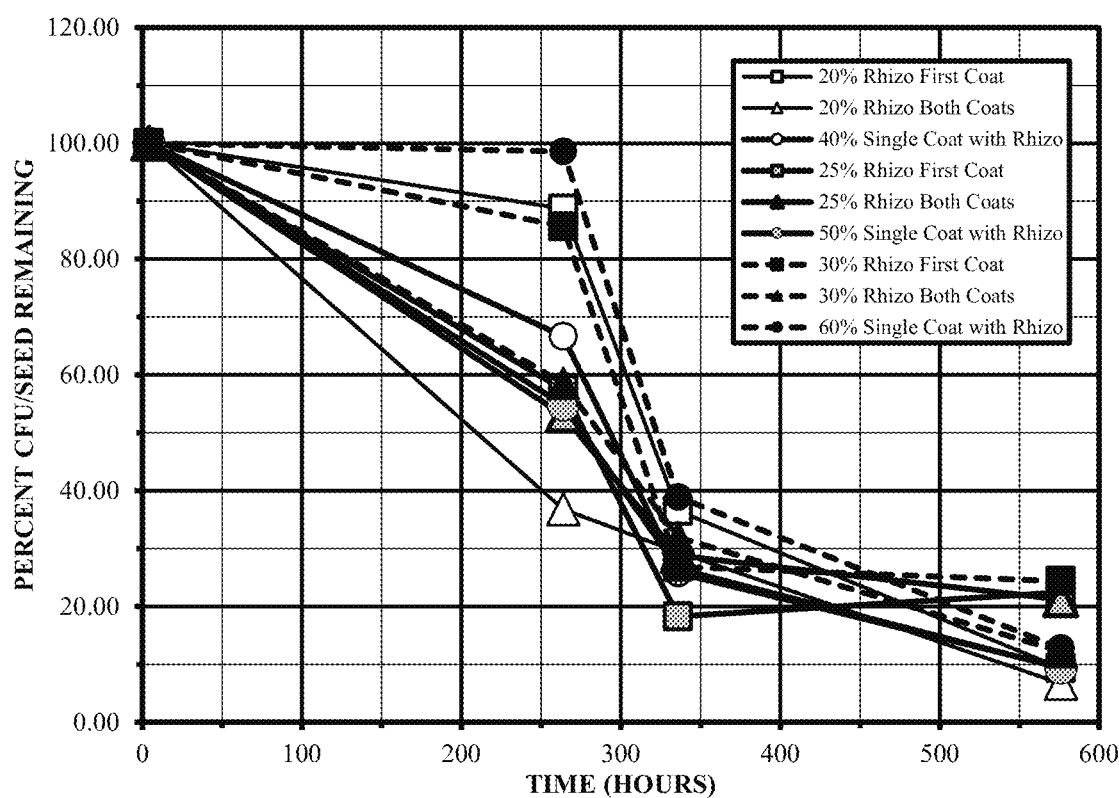
FIG. 22 is a graph showing the survivability of desiccated *Bradyrhizobium japonicum* SEMIA 5079 on soybean seeds stored at room temperature at 65% relative humidity, expressed as percent remaining relative to the initial 4 hour time point.

Coated seeds were stored at room temperature at 65% relative humidity and then assayed for on-seed survivability. FIG. 22.

Example 10

Ascorbic Acid and Glutathione Reduced the Adverse Effects of Light on the Survivability of Desiccated *Bradyrhizobium* in Maltodextrin-Containing Inoculant Compositions Untreated soybean seeds (ASGROW® AG2031; Monsanto Company, St. Louis, Mo.) were weighed out into 100 g allotments. Each allotment of seeds was coated according to Seed Coating Protocol 1 with one of the double-layer coatings set forth in Table 11:

TABLE 11

|  | Inner Coating (350 μl per 100 g seed) | Outer Coating (350 μl per 100 g seed) |
|---|---|---|
| Light 1 | *Bradyrhizobium japonicum* SEMIA 5079 suspension containing 16.90% MALTRIN® M150 + 9.1% Maltose monohydrate | *Bradyrhizobium japonicum* SEMIA 5079 suspension containing 16.90% MALTRIN® M150 + 9.1% Maltose monohydrate |
| Light 2 | *Bradyrhizobium japonicum* SEMIA 5079 suspension containing 16.90% MALTRIN® M150 + | *Bradyrhizobium japonicum* SEMIA 5079 suspension containing 16.90% MALTRIN® M150 + |

TABLE 11-continued

| | Inner Coating (350 μl per 100 g seed) | Outer Coating (350 μl per 100 g seed) |
|---|---|---|
| | 9.1% Maltose monohydrate + 0.10% Ascorbic acid + 0.15% glutathione | 9.1% Maltose monohydrate + 0.10% Ascorbic acid + 0.15% glutathione |
| Light 3 | *Bradyrhizobium japonicum* SEMIA 5079 suspension containing 16.90% MALTRIN ® M150 + 9.1% Maltose monohydrate + 0.20% Ascorbic acid + 0.30% glutathione | *Bradyrhizobium japonicum* SEMIA 5079 suspension containing 16.90% MALTRIN ® M150 + 9.1% Maltose monohydrate + 0.20% Ascorbic acid + 0.30% glutathione |
| Dark | *Bradyrhizobium japonicum* SEMIA 5079 suspension containing 16.90% MALTRIN ® M150 + 9.1% Maltose monohydrate | *Bradyrhizobium japonicum* SEMIA 5079 suspension containing 16.90% MALTRIN ® M150 + 9.1% Maltose monohydrate |

Figure 23:
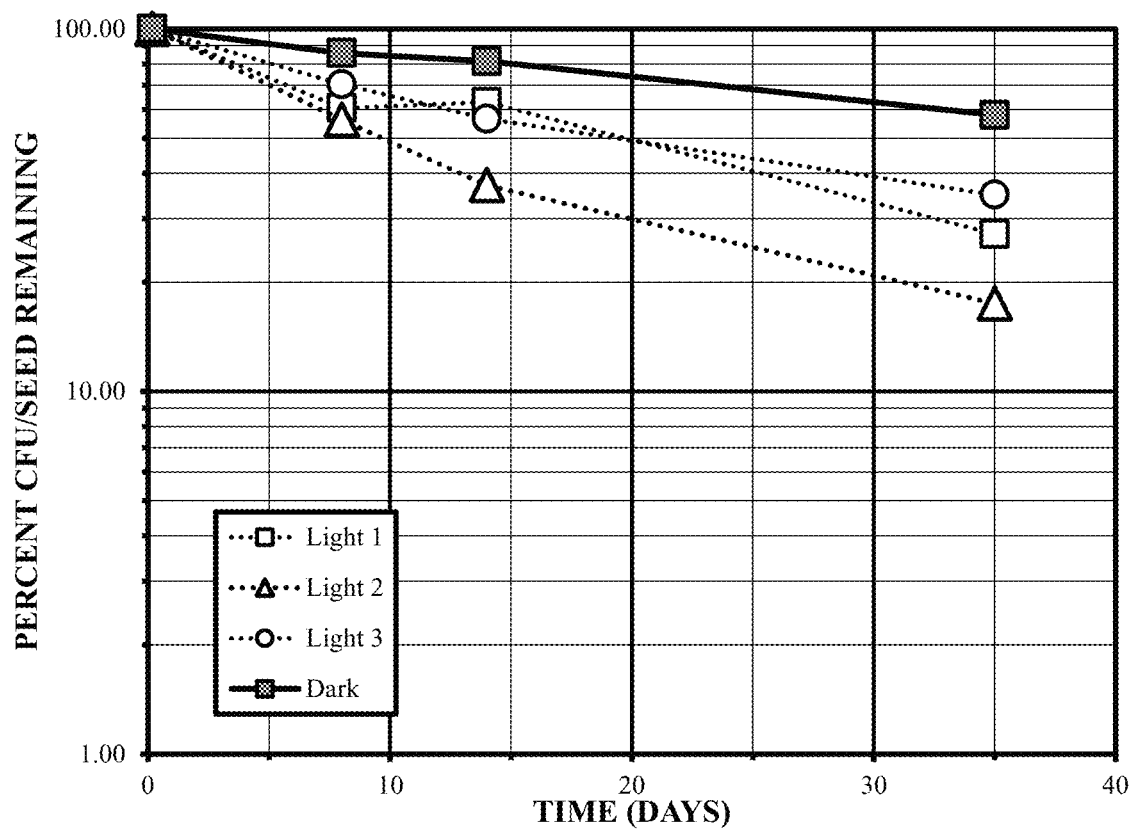
FIG. 23 is a graph showing the survivability of desiccated *Bradyrhizobium japonicum* SEMIA 5079 on soybean seeds stored at room temperature and 65% relative humidity, expressed as percent remaining relative to the initial 4 hour time point.

Coated seeds were stored at room temperature in a light or dark desiccator at 65% relative humidity and then assayed for on-seed survivability. FIG. 23.

Example 11

Combinations of Maltodextrin and Maltose Enhanced the Survivability of Desiccated *Pseudomonas*

Figure 24:
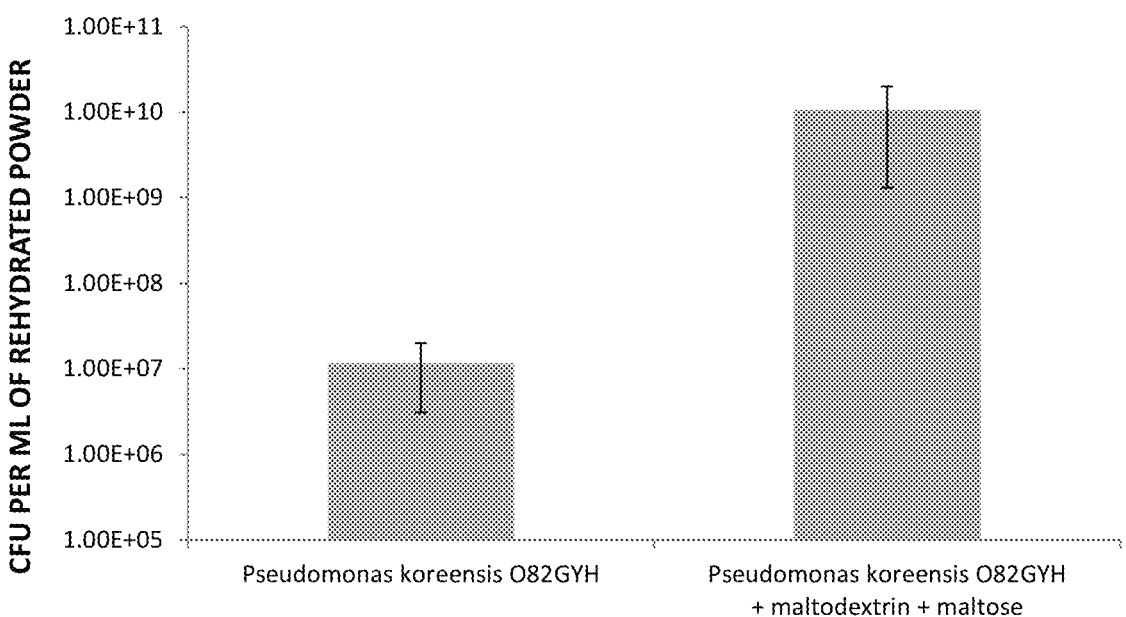
FIG. 24 is a graph showing the survivability of *Pseudomonas koreensis* 082GYH after fluidized bed drying with calcium carbonate and rehydration with phosphate buffered saline.

An aqueous suspension comprising *Pseudomonas koreensis* 082GYH ($1\times10^{11}$ CFU per ml) was split into aliquots. MALTRIN® M150 and maltose monohydrate were added to half of the aliquots to final concentrations of 26% and 14%, respectively. Each aliquot was dried in a Freund-Vector VFC-Lab 1 Flo-Coater® fluidized bed dryer (Freund-Vector Corporation, Marion, Iowa), top spray only, using calcium carbonate as the carrier. The resultant powders were packaged and sealed in plastic bags and stored at room temperature and ambient relative humidity for 48 hours prior to rehydration with phosphate buffered saline comprising 0.85% sodium chloride on a Wrist Action® Shaker (Burrell Scientific LLC, Pittsburgh, Pa.) for 30 minutes. The rehydrated samples were assayed for survivability. FIG. 24.

Example 12

Combinations of Maltodextrin, Maltose, Ascorbic Acid and Glutathione Enhanced the Survivability of Desiccated *Bradyrhizobium*

Untreated soybean seeds (ASGROW® AG2031; Monsanto Company, St. Louis, Mo.) were weighed out into 100 g allotments. Each allotment of seeds was coated according to Seed Coating Protocol 1 with 540 μl of one of the single-layer coatings set forth in Table 12:

TABLE 12

| | Single Coating |
|---|---|
| Light 85/15 | *Bradyrhizobium japonicum* SEMIA 5079 suspension containing 27.54% MALTRIN ® M150 + 4.86% Maltose monohydrate + 0.0007% Ascorbic acid + 0.00105% glutathione |
| Light 75/25 | *Bradyrhizobium japonicum* SEMIA 5079 suspension containing 24.30% MALTRIN ® M150 + 8.10% Maltose monohydrate + 0.0007% Ascorbic acid + 0.00105% glutathione |
| Light 65/35 | *Bradyrhizobium japonicum* SEMIA 5079 suspension containing 21.06% MALTRIN ® M150 + 11.34% Maltose monohydrate + 0.0007% Ascorbic acid + 0.00105% glutathione |
| Light 55/45 | *Bradyrhizobium japonicum* SEMIA 5079 suspension containing 17.82% MALTRIN ® M150 + 14.58% Maltose monohydrate + 0.0007% Ascorbic acid + 0.00105% glutathione |
| Light 45/55 | *Bradyrhizobium japonicum* SEMIA 5079 suspension containing 14.58% MALTRIN ® M150 + 17.82% Maltose monohydrate + 0.0007% Ascorbic acid + 0.00105% glutathione |
| Light Biopower | *Bradyrhizobium japonicum* SEMIA 5079 suspension containing 25.93% Nitragin Biopower ® |
| Dark 85/15 | *Bradyrhizobium japonicum* SEMIA 5079 suspension containing 27.54% MALTRIN ® M150 + 4.86% Maltose monohydrate + 0.0007% Ascorbic acid + 0.00105% glutathione |
| Dark 75/25 | *Bradyrhizobium japonicum* SEMIA 5079 suspension containing 24.30% MALTRIN ® M150 + 8.10% Maltose monohydrate + 0.0007% Ascorbic acid + 0.00105% glutathione |
| Dark 65/35 | *Bradyrhizobium japonicum* SEMIA 5079 suspension containing 21.06% MALTRIN ® M150 + 11.34% Maltose monohydrate + 0.0007% Ascorbic acid + 0.00105% glutathione |
| Dark 55/45 | *Bradyrhizobium japonicum* SEMIA 5079 suspension containing 17.82% MALTRIN ® M150 + 14.58% Maltose monohydrate + 0.0007% Ascorbic acid + 0.00105% glutathione |
| Dark 45/55 | *Bradyrhizobium japonicum* SEMIA 5079 suspension containing 14.58% MALTRIN ® M150 + 17.82% Maltose monohydrate + 0.0007% Ascorbic acid + 0.00105% glutathione |
| Dark Biopower | *Bradyrhizobium japonicum* SEMIA 5079 suspension containing 25.93% Nitragin Biopower ® |

Figure 25:
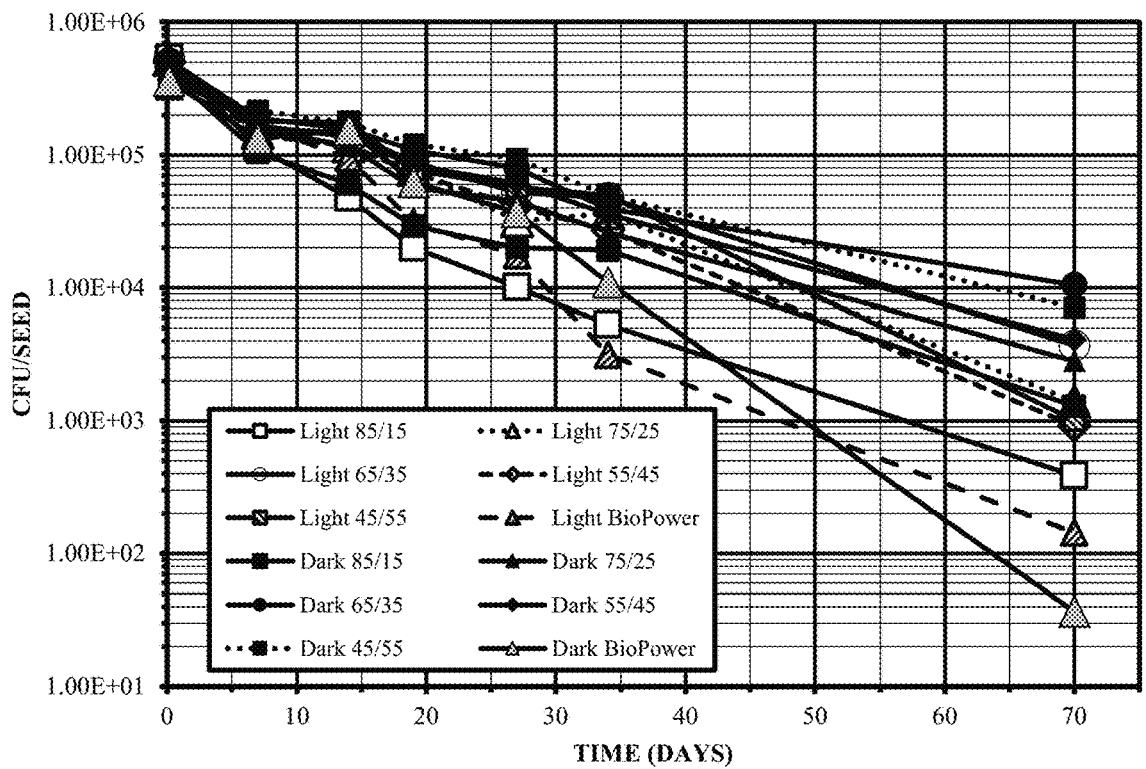
FIGS. 25-26 are graphs showing the survivability of desiccated *Bradyrhizobium japonicum* SEMIA 5079 on soybean seeds stored at room temperature and 65% relative humidity.
Figure 26:
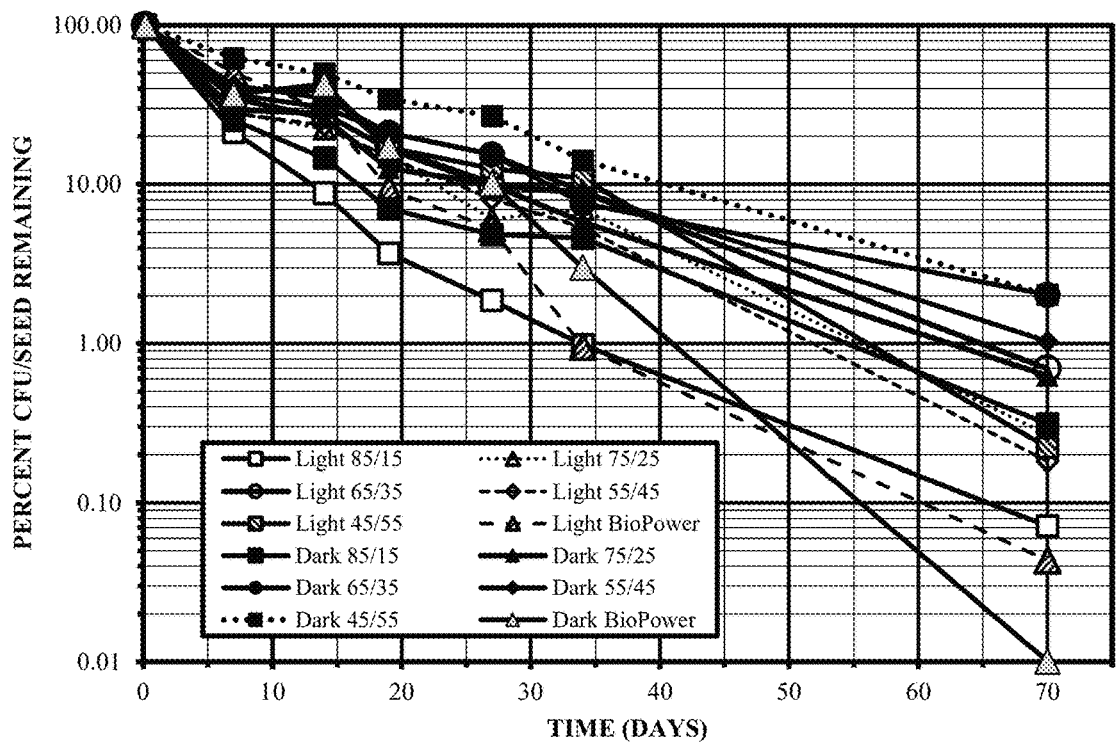

Coated seeds were stored at room temperature in a light or dark desiccator at 65% relative humidity and then assayed for on-seed survivability. FIGS. 25-26.

Example 13

Maltodextrin-Based Stabilizer Enhanced the Survivability of Spray-Dried *Bradyrhizobium*

Figure 27:
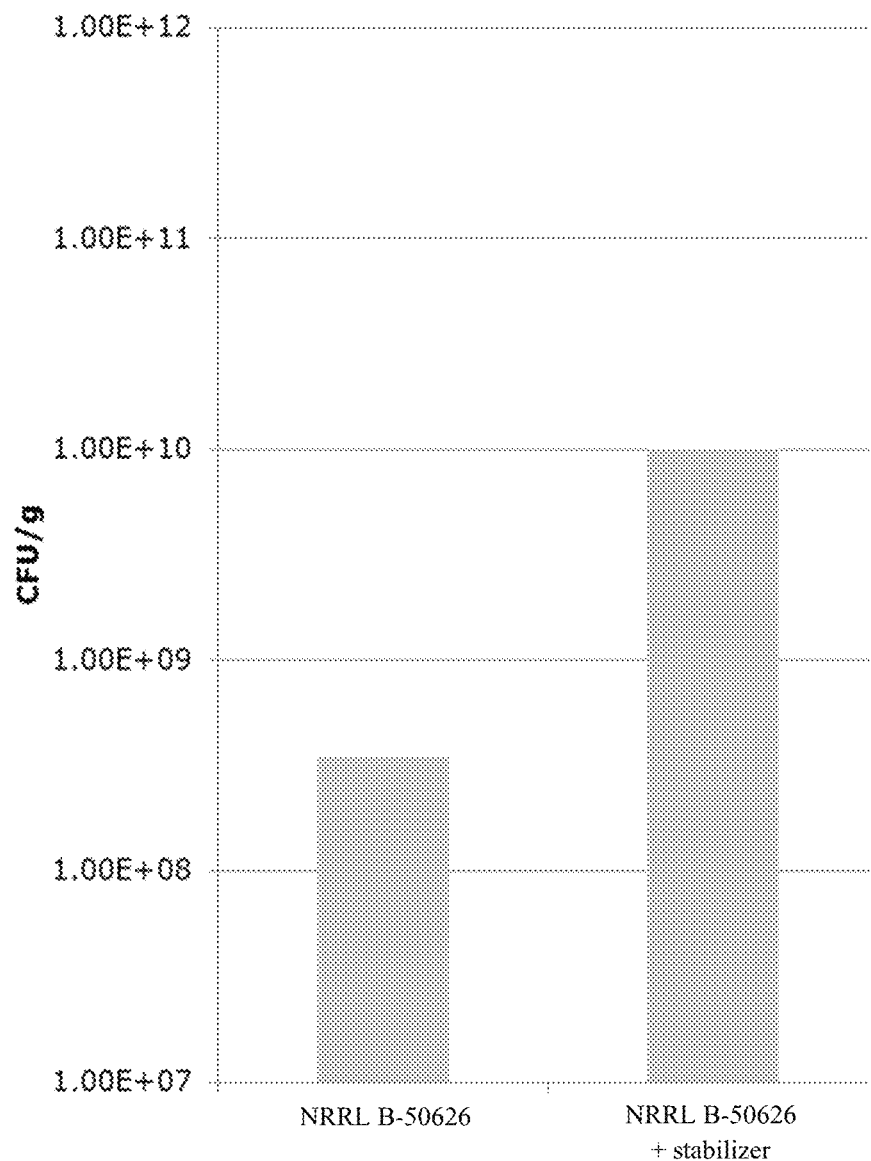
FIG. 27 is a graph showing the survivability of *Bradyrhizobium japonicum* NRRL B-50626 after spray drying with and without a maltodextrins-based stabilizer.

Aqueous liquid inoculant compositions comprising *Bradyrhizobium japonicum* NRRL B-50626 with or without a maltodextrin-based stabilizer (28% MALTRIN® M150+ 12% maltose monohydrate+0.074% potassium phosphate monobasic+0.08% potassium phosphate dibasic in deionized water) were spray-dried using a BUCHI Mini Spray Dryer B-290 (BUCHI Corp., New Castle, Del.) equipped with a three-fluid nozzle. The inner fluid-*Bradyrhizobium japonicum* NRRL B-50626 suspension or *Bradyrhizobium japonicum* NRRL B-50626 suspension containing the maltodextrin-based stabilizer (10% w/w)-contained $1\times10^{10}$ cfu per ml. Deionized water containing the maltodextrin-based stabilizer (10% w/w) was used as the outer fluid. The flow rates of the inner and outer fluids were equalized and run at a 15% pump speed (4.5 ml per minute). Inlet temperature was 135° C. Outlet temperature was 67° C. The aspirator and regulator were both run at the maximum setting using room air at ambient temperature and humidity. As shown FIG. 27, the maltodextin-based stabilizer significantly increased the survivability of *Bradyrhizobium japonicum* NRRL B-50626 during the spray-drying process.

Example 14

Maltodextrin-Based Stabilizer Enhanced the Survivability of Spray-Dried *Bradyrhizobium*

Four grams of water was added to 100 grams of soybean seeds (ASGROW® AG2035; Monsanto Company, St. Louis, Mo.). The wet seeds were then coated with 0.2 grams of a mixture (Table 13) comprising *Bradyrhizobium japonicum* NRRL B-50626 that were spray-dried with a maltodextrin stabilizer as described in Example 19 above.

TABLE 13

Seed-Coating Mixture

Figure 28:
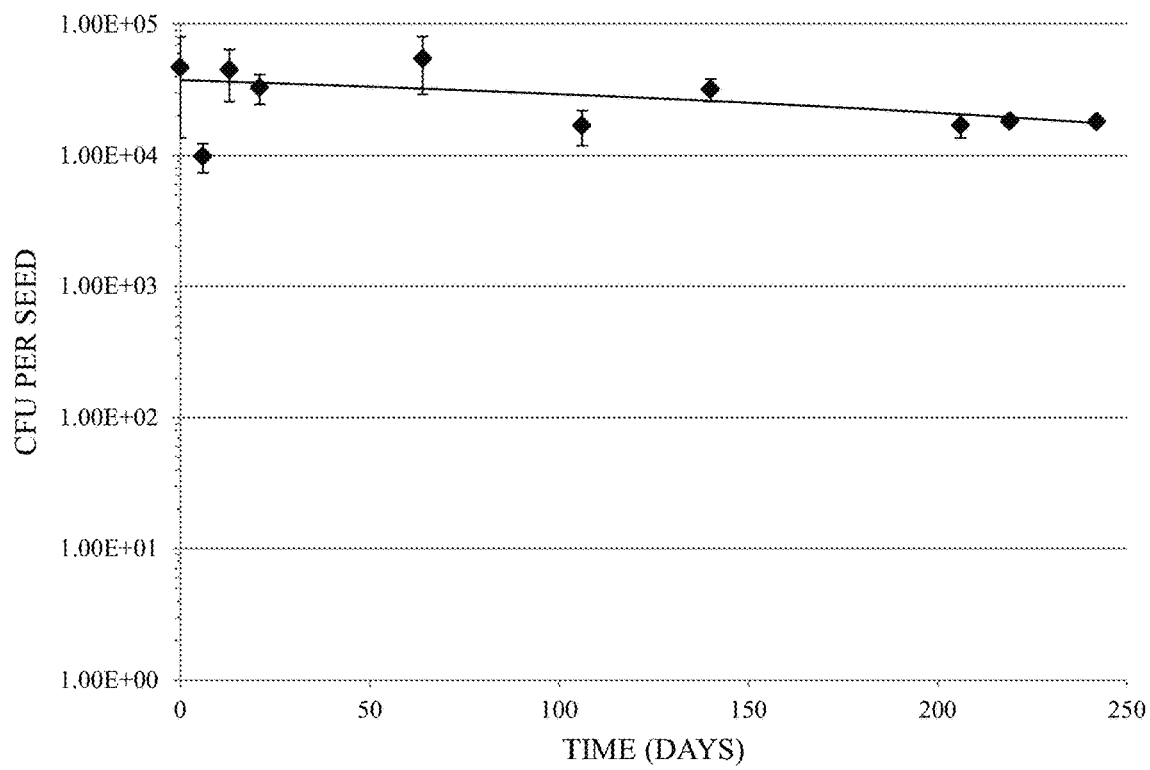
FIG. 28 is a graph showing the survivability of spray-dried *Bradyrhizobium japonicum* NRRL B-50626 on soybean seeds stored at 10° C. and 50% relative humidity.

25% (w/w) spray-dried *Bradyrhizobium japonicum* NRRL B-50626
25% (w/w) adhesive powder consisting of 64.93% MALTRIN ® M150 + 34.96% maltose monohydrate + 0.022% potassium phosphate monobasic + 0.089% potassium phosphate dibasic
50% (w/w) drying agent consisting of 61% INCOTEC ® F028 drying powder + 39% linoleic acid Coated seeds were stored at 10° C. and 50% relative humidity and then assayed for on-seed survivability. As shown in FIG. 28, the spray-dried *Bradyrhizobium* remained stable on the seed for at least 249 days.

Example 15

Maltodextrin-Based Stabilizer Enhanced the Survivability of Spray-Dried *Bradyrhizobium*

Four grams of water was added to 100 grams of untreated soybean seeds (ASGROW® AG2035; Monsanto Company, St. Louis, Mo.) or soybean seeds (ASGROW® AG2035; Monsanto Company, St. Louis, Mo.) pre-treated with ACCELERON® seed treatment product (Monsanto Company, St. Louis, Mo.). The wet seeds were then coated with 0.2 grams of a mixture (Table 14) comprising *Bradyrhizobium japonicum* NRRL B-50626 that were spray-dried with a maltodextrin stabilizer as described in Example 19 above.

TABLE 14

Seed-Coating Mixture

Figure 29:
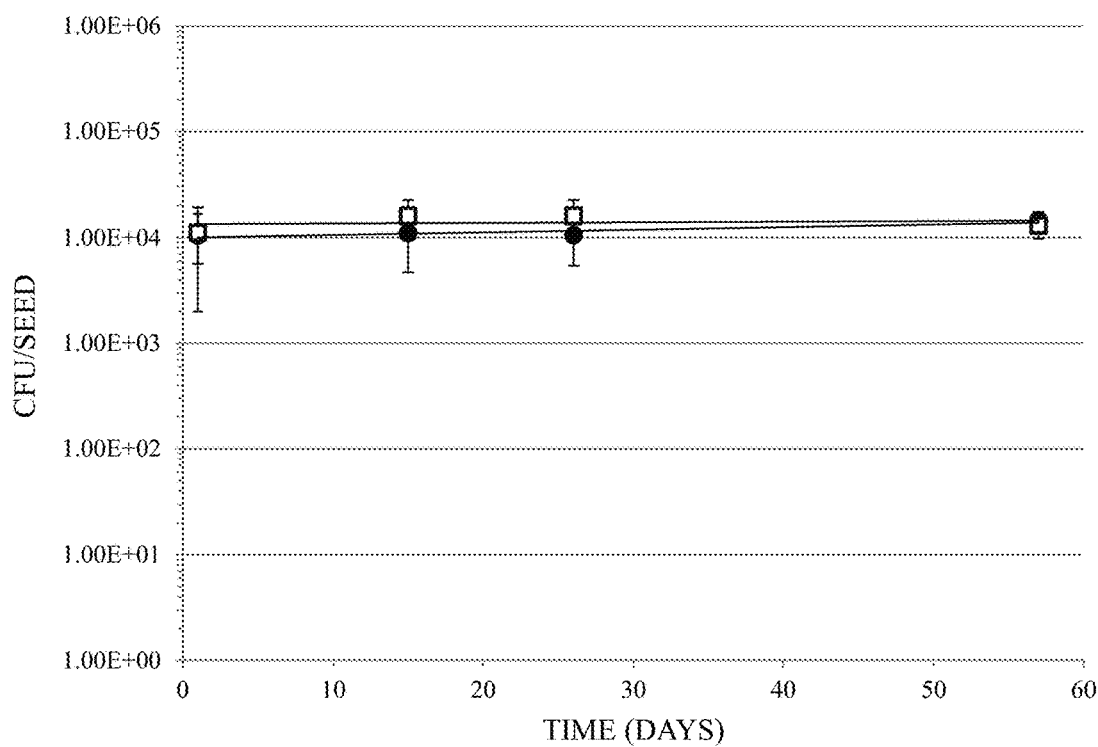
FIG. 29 is a graph showing the survivability of spray-dried *Bradyrhizobium japonicum* NRRL B-50626 on untreated (solid circles) and treated (open squares) soybean seeds stored at 10° C. and 50% relative humidity.
Figure 30:
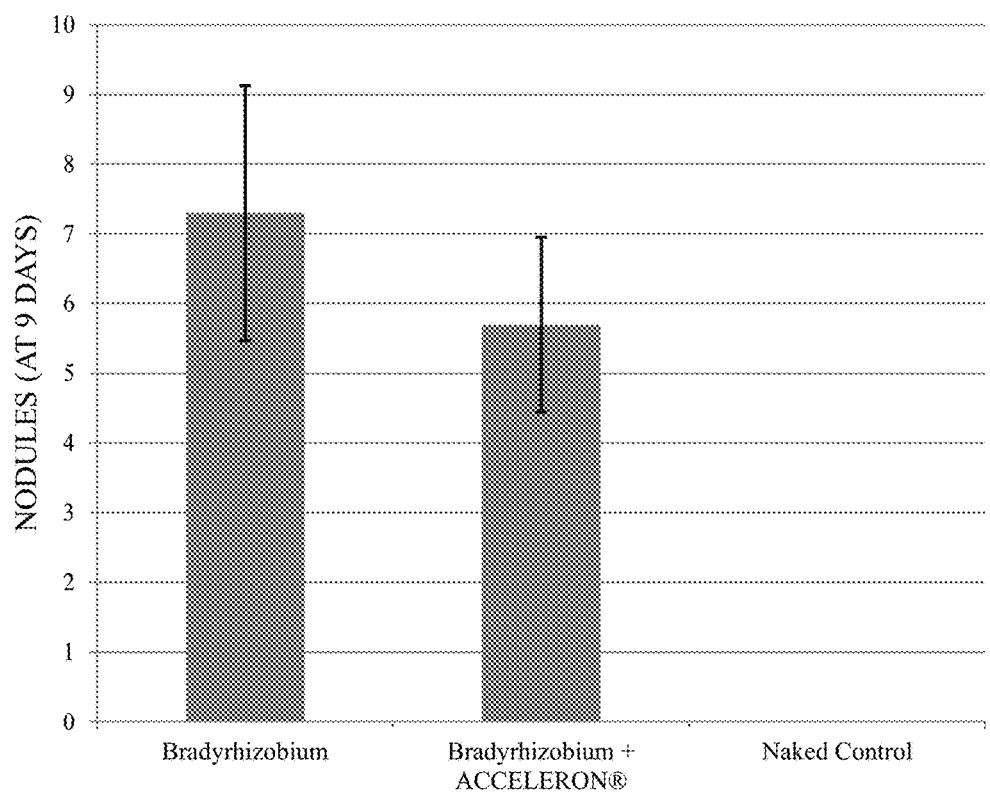
FIG. 30 is a graph showing the root modulation of plants grown for 9 days from untreated soybean seeds coated with spray-dried *Bradyrhizobium japonicum* NRRL B-50626, ACCELERON®-treated soybean seeds coated with spray-dried *Bradyrhizobium japonicum* NRRL B-50626 and naked control seeds.
Figure 31:
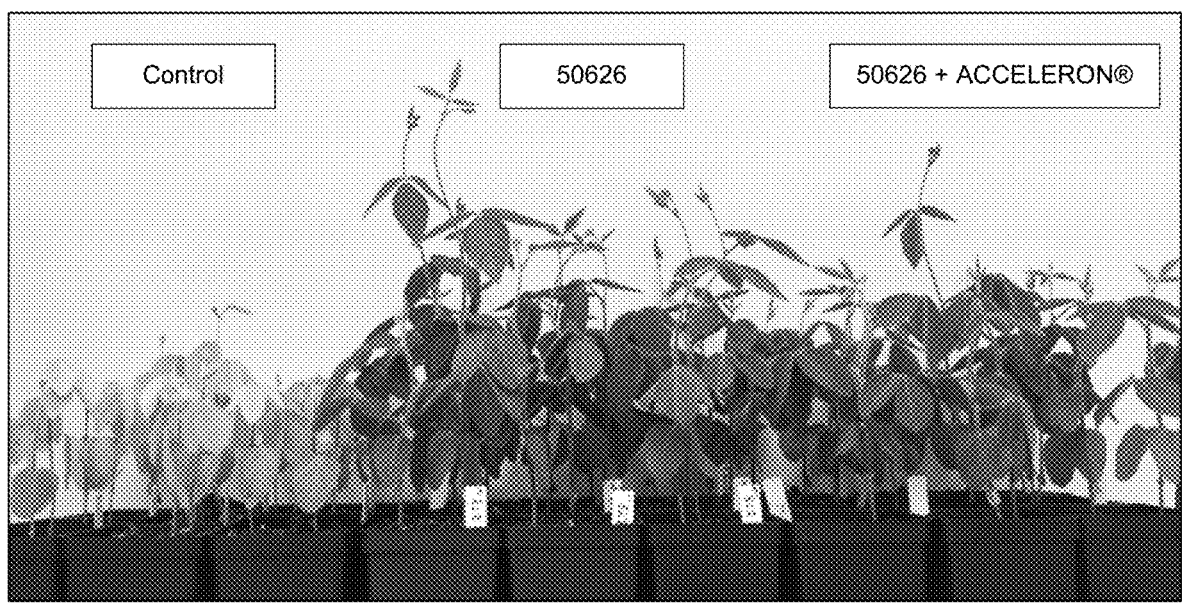
FIG. 31 is a photograph showing plants grown for 25 days from untreated soybean seeds coated with spray-dried *Bradyrhizobium japonicum* NRRL B-50626 (middle), ACCELERON®-treated soybean seeds coated with spray-dried *Bradyrhizobium japonicum* NRRL B-50626 (right) and naked control seeds (left).

25% (w/w) spray-dried *Bradyrhizobium japonicum* NRRL B-50626
25% (w/w) adhesive powder consisting of 64.93% GLOBE ® Plus 15 DE + 34.96% maltose monohydrate + 0.022% potassium phosphate monobasic + 0.089% (w/w) potassium phosphate dibasic
50% (w/w) drying agent consisting of 61% INCOTEC ® F028 drying powder + 39% linoleic acid Coated seeds were stored at 10° C. and 50% relative humidity and then assayed for on-seed survivability. As shown in FIG. 29, the spray-dried *Bradyrhizobium* remained stable on both untreated and treated seeds for at least 57 days. When planted alongside naked control seeds in autoclaved soil, the coated seeds exhibited earlier root nodulation (FIG. 30) and a significant increase in both plant size and chlorophyll content (FIG. 31).

Example 16

Maltodextrin-Based Stabilizer Enhanced the Survivability and Dispersion of *Penicillium* Spores Solid non-aqueous inoculant compositions of the present disclosure comprising *Penicillium bilaiae* spores (ATCC 20851 and/or RS7B-SD1) were stored for four weeks at 40° C. or for twenty weeks at 20% C alongside a commercially available wettable powder comprising *Penicillium bilaiae* spores (ATCC 20851 and RS7B-SD1). The survival rate of *Penicillium* spores was greater in each of the solid non-aqueous inoculant compositions of the present disclosure than in the commercially available wettable powder. Table 15.

TABLE 15

|   | Inoculant Composition | Viable spores after 20 weeks at 20° C.[1] | Viable spores after 4 weeks at 40° C.[1] |
|---|---|---|---|
| A | *P. bilaiae* spores (10% w/w) + MALTRIN QD ® M580 (74.879% w/w) + maltose monohydrate (8.320% w/w) + MULTIWET MO-85P-PW-(AP) (2.750% w/w) + SUNSPRAY ® 6N (4.051% w/w) | 51% | 11% |
| B | *P. bilaiae* spores (10% w/w) + MALTRIN QD ® M580 (62.40% w/w) + maltose monohydrate (20.80% w/w) + MULTIWET MO-85P-PW-(AP) (2.75% w/w) + SUNSPRAY ® 6N (4.05% w/w) | 54% | 13% |
| C | *P. bilaiae* spores (10% w/w) + MALTRIN QD ® M580 (49.92% w/w) + maltose monohydrate (33.28% w/w) + MULTIWET MO-85P-PW-(AP) (2.5% w/w) + SUNSPRAY ® 6N (4.05% w/w) | 40% | 12% |
| D | *P. bilaiae* spores (10% w/w) + MALTRIN QD ® M580 (52.31% w/w) + maltose monohydrate (34.88% w/w) + BIOSOFT ® N23-3 (2.81% w/w) | 79% | 28% |

TABLE 15-continued

| | Inoculant Composition | Viable spores after 20 weeks at 20° C.[1] | Viable spores after 4 weeks at 40° C.[1] |
|---|---|---|---|
| E | *P. bilaiae* spores (10% w/w) + MALTRIN QD ® M580 (65.39% w/w) + maltose monohydrate (21.80% w/w) + BIOSOFT ® N23-3 (2.81% w/w) | 93% | 32% |
| F | *P. bilaiae* spores (10% w/w) + MALTRIN QD ® M580 (78.469% w/w) + maltose monohydrate (8.719% w/w) + BIOSOFT ® N23-3 (2.813% w/w) | 68% | 34% |
| Control | Commercially available wettable powder comprising *P. bilaiae* spores | 52% | 4% |

[1]Expressed as a percentage of the spore content (cfu per gram of inoculant composition) measured at time zero.

The abilities of the aforementioned inoculant compositions to disperse *Penicillium bilaiae* spores are tested by measuring the ease with which each inoculant composition can be mixed into 100 ml of water in a 250 ml Erlenmeyer flask at 130 rpm on an orbital shaker. As a follow up to this qualitative testing, the percentage of single spores (compared to clumps of >2 spores) in each inoculant composition is calculated by observing the spores under a microscope at 200× magnification. Each of the solid non-aqueous inoculant compositions of the present disclosure exhibits greater spore dispersion than the commercially available wettable powder.

Example 17

Figure 32:
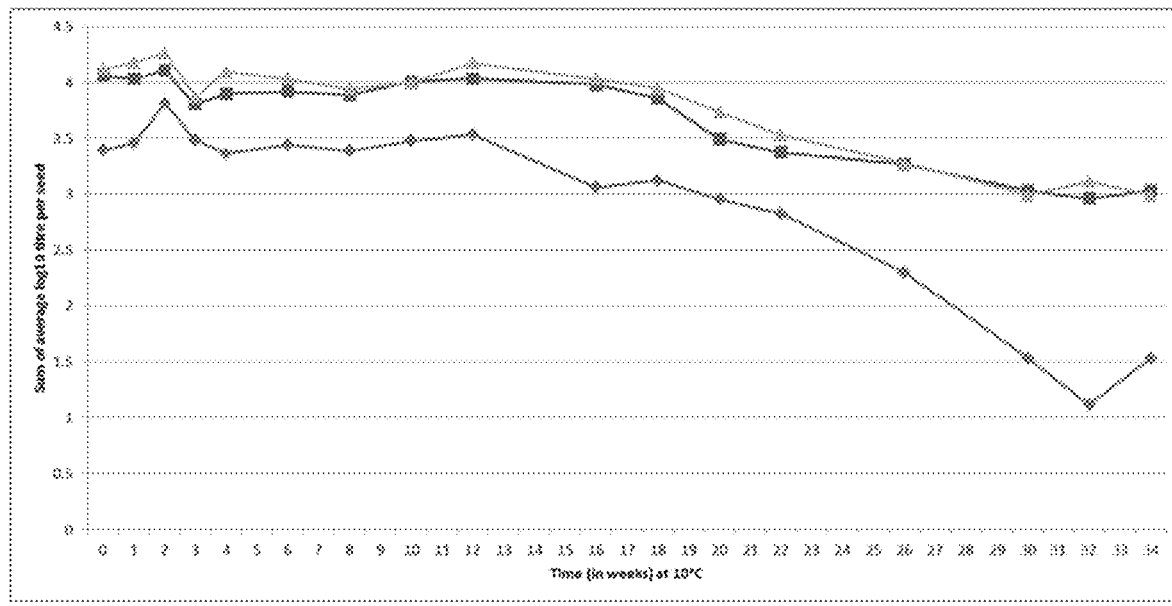
FIGS. 32-34 are graphs showing the survivability of spray-dried *Penicillium bilaiae* on corn seeds and 50% relative humidity and 10° C., 20° C. or 30° C., respectively. Triangles=corn seeds coated with a spray-dried composition comprising *Penicillium bilaiae* spores (10% w/w), MALTRIN QDO M580 (78.469% w/w), maltose monohydrate (8.719% w/w) and BIOSOFT® N23-3 (2.813% w/w). Squares=corn seeds coated with a spray-dried composition comprising *Penicillium bilaiae* spores (10% w/w), MALTRIN QDO M580 (74.879% w/w), maltose monohydrate (8.320% w/w), MULTIWET® MO-85P-PW-(AP) (2.750% w/w) and SUNSPRAY® 6N (4.051% w/w). Diamonds=corn seeds coated with a commercially available wettable powder comprising *Penicillium bilaiae* spores.
Figure 33:
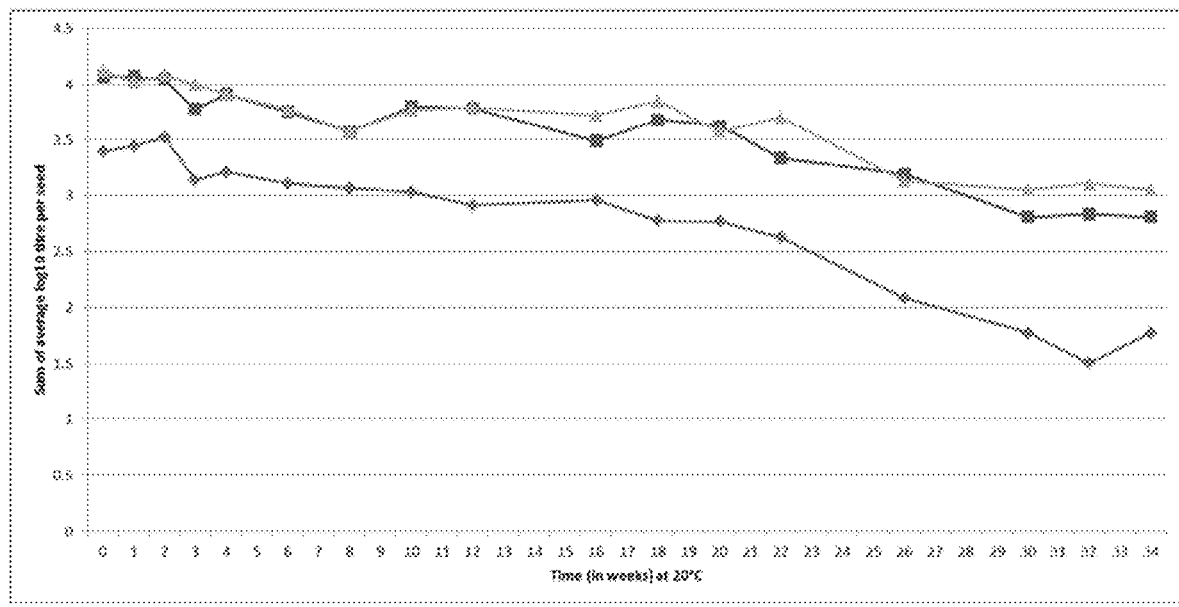
Figure 34:
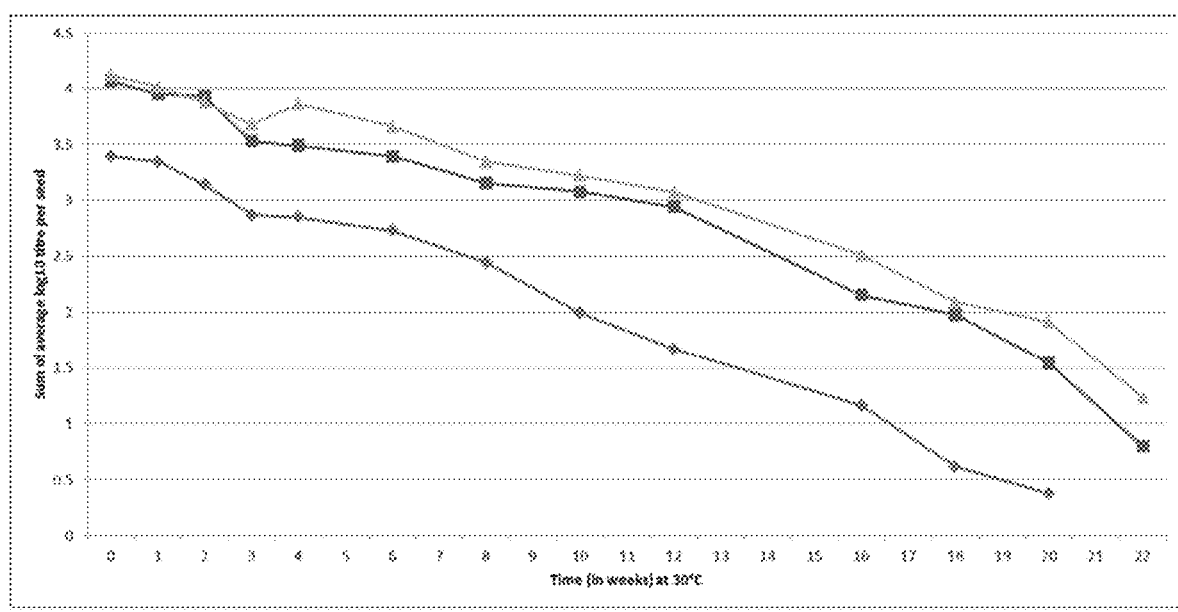

Maltodextrin-Based Stabilizer Enhanced the Survivability of *Penicillium* Spores Solid non-aqueous inoculant compositions of the present disclosure comprising spores of *Penicillium bilaiae* and a commercially available wettable powder comprising corresponding spores were coated on corn seeds treated with a commercially available pesticide. The coated seeds were stored at 10, 20 or 30° C. and 50% relative humidity for 1, 2, 3, 4, 6, 8, 10, 12, 16, 18, 20, 22, 26, 30, 32, 34 or 42 weeks and then assayed for on-seed survivability. As indicated in Table 16 and FIGS. 32-34, the survival rate of *Penicillium* spores was greater on seeds coated with the solid non-aqueous inoculant compositions of the present disclosure than on seeds coated with the commercially available wettable powder.

TABLE 16

| | Inoculant Composition | Viable spores after 42 weeks at 10° C.[1] | Viable spores after 20 weeks at 20° C.[1] | Viable spores after 12 weeks at 30° C.[1] |
|---|---|---|---|---|
| F | *P. bilaiae* spores (10% w/w) + MALTRIN QD ® M580 (78.469% w/w) + maltose monohydrate (8.719% w/w) + BIOSOFT ® N23-3 (2.813% w/w) | 8% | 28% | 11% |
| A | *P. bilaiae* spores (10% w/w) + MALTRIN QD ® M580 (74.879% w/w) + maltose monohydrate (8.320% w/w) + MULTIWET MO-85P-PW-(AP) (2.750% w/w) + SUNSPRAY ® 6N (4.051% w/w) | 7% | 23% | 17% |
| Control | Commercially available wettable powder comprising *P. bilaiae* spores | 2% | 14% | 2% |

[1]Expressed as a percentage of the spore content (cfu per seed) measured at time zero.

Example 18

Maltodextrin-Based Stabilizer Enhanced the Survivability of *Penicillium* Spores Solid non-aqueous inoculant compositions of the present disclosure comprising spores of *Penicillium bilaiae* and a commercially available wettable powder comprising corresponding spores were coated on corn seeds treated with a commercially available pesticide. The coated seeds were stored at 20 or 30° C. and 50% relative humidity for 12 weeks and then assayed for on-seed survivability. As indicated Table 17, the survival rate of *Penicillium* spores was greater on seeds coated with the solid non-aqueous inoculant compositions of the present disclosure than on seeds coated with the commercially available wettable powder.

TABLE 17

| | Inoculant Composition | Viable spores after 12 weeks at 20° C.[1] | Viable spores after 12 weeks at 30° C.[1] |
|---|---|---|---|
| E | *P. bilaiae* spores (10% w/w) + MALTRIN QD ® M580 (65.39% w/w) + maltose monohydrate (21.80% w/w) + BIOSOFT ® N23-3 (2.81% w/w) | 58% | 8% |
| D | *P. bilaiae* spores (10% w/w) + MALTRIN QD ® M580 (52.31% w/w) + maltose monohydrate (34.88% w/w) + BIOSOFT ® N23-3 (2.81% w/w) | 55% | 5% |
| B | *P. bilaiae* spores (10% w/w) + MALTRIN QD ® M580 (62.40% w/w) + maltose monohydrate (20.80% w/w) + MULTIWET MO-85P-PW-(AP) (2.75% w/w) + SUNSPRAY ® 6N (4.05% w/w) | 38% | 8% |
| C | *P. bilaiae* spores (10% w/w) + MALTRIN QD ® M580 (49.92% w/w) + maltose monohydrate (33.28% w/w) + MULTIWET MO-85P-PW-(AP) (2.5% w/w) + SUNSPRAY ® 6N (4.05% w/w) | 41% | 6% |
| Control | Commercially available wettable powder comprising *P. bilaiae* spores | 33% | 2% |

[1]Expressed as a percentage of the spore content (cfu per seed) measured at time zero.

APPENDIX A

*Acinetobacter*, *Actinomycetes*, *Aegerita*, *Agrobacterium* (e.g., *A. radiobacter* strains such as K1026 and K84), *Akanthomyces*, *Alcaligenes*, *Alternaria*, *Aminobacter* (e.g., *A. aganoensis*, *A. aminovorans*, *A. anthyllidis*, *A. ciceronei*, *A. lissarensis*, *A. niigataensis*), *Ampelomyces* (e.g., *A. quisqualis* strains such as M-10), *Anabaena* (e.g., *A. aequalis*, *A. affinis*, *A. angstumalis angstumalis*, *A. angstumalis marchita*, *A. aphanizomendoides*, *A. azollae*, *A. bornetiana*, *A. catenula*, *A. cedrorum*, *A. circinalis*, *A. confervoides*, *A. constricta*, *A. cyanobacterium*, *A. cycadeae*, *A. cylindrica*, *A. echinispora*, *A. felisii*, *A. flos-aquae flos-aquae*, *A. flos-aquae minor*, *A. flos-aquae treleasei*, *A. helicoidea*, *A. inaequalis*, *A. lapponica*, *A. laxa*, *A. lemmermannii*, *A. levanderi*, *A. limnetica*, *A. macrospora macrospora*, *A. macrospora robusta*, *A. monticulosa*, *A. nostoc*, *A. ascillarioides*, *A. planctonica*, *A. raciborski*, *A. scheremetievi*, *A. sphaerica*, *A. spiroides crassa*, *A. spiroides sprroides*, *A. subcylindrica*, *A. torulosa*, *A. unispora*, *A. variabilis*, *A. verrucosa*, *A. viguieri*, *A. wisconsinense*, *A. zierlingii*), *Arthrobacter*, *Arthrobotrys* (e.g., *A. aggregata*, *A. alaskana*, *A. ameropora*, *A. anomala*, *A. apscheronica*, *A. arthrobotryoides*, *A. azerbaijanica*, *A. bakunika*, *A. botryospora*, *A. brochopaga*, *A. chazarica*, *A. chilensis*, *A. cladodes*, *A. calvispora*, *A. compacta*, *A. conoides*, *A. constringens*, *A. cylindrospora*, *A. dactyloides*, *A. deflectans*, *A. dendroides*, *A. doliiformis*, *A. drechsleri*, *A. elegans*, *A. ellipsospora*, *A. entomopaga*, *A. ferox*, *A. foliicola*, *A. fruticulosa*, *A. globospora*, *A. hatospora*, *A. hertziana*, *A. indica*, *A. irregularis*, *A. javanica*, *A. kirghizica*, *A. longa*, *A. longiphora*, *A. longiramulifera*, *A. longispora*, *A. mangrovispora*, *A. megaspora*, *A. microscaphoides*, *A. microspora*, *A. multisecundaria*, *A. musiformis*, *A. nematopaga*, *A. nonseptata*, *A. oligospora*, *A. oudemansii*, *A. oviformis*, *A. perpasta*, *A. polycephala*, *A. pseudoclavata*, *A. pyriformis*, *A. recta*, *A. robusta*, *A. rosea*, *A. scaphoides*, *A. sclerohypha*, *A. shahriari*, *A. shizishanna*, *A. sinensis*, *A. soprunovii*, *A. stilbacea*, *A. straminicola*, *A. superba*, *A. tabrizica*, *A. venusta*, *A. vermicola*, *A. yunnanensis*), *Aschersonia*, *Ascophaera*, *Aspergillus* (e.g., *A. flavus* strains such as NRRL 21882, *A. parasiticus*), *Aulosira* (e.g., *A. aenigmatica*, *A. africana*, *A. bohemensis*, *A. bombayensis*, *A. confluens*, *A. fertilissima*, *A. fertilissma* var. *tenius*, *A. fritschii*, *A. godoyana*, *A. implexa*, *A. laxa*, *A. plantonica*, *A. prolifica*, *A. pseuodoramosa*, *A. schauinslandii*, *A. striata*, *A. terrestris*, *A. thermalis*), *Aureobacterium*, *Aureobasidium* (e.g., *A. pullulans* strains such as DSM 14940 and DSM 14941), *Azobacter*, *Azorhizobium* (e.g., *A. caulinodans*, *A. doebereinerae*, *A. oxalatiphilum*), *Azospirillum* (e.g., *A. amazonense* strains such as BR 11140 (SpY2T), *A. brasilense* strains such as INTA Az-39, AZ39, XOH, BR 11002, BR 11005, Ab-V5 and Ab-V6, *A. canadense*, *A. doebereinerae*, *A. formosense*, *A. halopraeferans*, *A. irakense*, *A. largimobile*, *A. lipoferum* strains such as BR 11646, *A. melinis*, *A. oryzae*, *A. picis*, *A. rugosum*, *A. thiophilum*, *A. zeae*), *Azotobacter* (e.g., *A. agilis*, *A. armeniacus*, A. sp. AR, *A. beijerinckii*, *A. chroococcum*, A. DCU26, A. FA8, *A. nigricans*, *A. paspali*, *A. salinestris*, *A. tropicalis*, *A. vinelandii*), *Bacillus* (e.g., *B. amyloliquefaciens* strains such as D747, NRRL B-50349, TJ1000 (also known as 1BE, isolate ATCC BAA-390), FZB24, FZB42, IN937a, IT-45, TJ1000, MBI600, BS27 (deposited as NRRL B-5015), BS2084 (deposited as NRRL B-50013), 15AP4 (deposited as ATCC PTA-6507), 3AP4 (deposited as ATCC PTA-6506), LSSA01 (deposited as NRRL B-50104), ABP278 (deposited as NRRL B-50634), 1013 (deposited as NRRL B-50509), 918 (deposited as NRRL B-50508), 22CP1 (deposited as ATCC PTA-6508) and BS18 (deposited as NRRL B-50633), *B. cereus* strains such as 1-1562, *B. firmus* strains such as 1-1582, *B. laevolacticus*, *B. licheniformis* strains such as BA842 (deposited as NRRL B-50516) and BL21 (deposited as NRRL B-50134), *B. macerns*, *B. firmus*, *B. mycoides* strains such as NRRL B-21664, *B. pasteurii*, *B. pumilus* strains such as NRRL B-21662, NRRL B-30087, ATCC 55608, ATCC 55609, GB34, KFP9F and QST 2808, *B. sphaericus*, *B. subtilis* strains such as ATCC 55078, ATCC 55079, MBI 600, NRRL B-21661, NRRL B-21665, CX-9060, GB03, GB07, QST-713, FZB24, D747 and 3BP5 (deposited as NRRL B-50510), *B. thuringiensis* strains such as ATCC 13367, GC-91, NRRL B-21619, ABTS-1857, SAN 4011, ABG-6305, ABG-6346, AM65-52, SA-12, SB4, ABTS-351, HD-1, EG 2348, EG 7826, EG 7841, DSM 2803, NB-125 and NB-176), *Beijerinckia*, *Beauveria* (e.g., *B. bassiana* strains such as ATCC 26851, ATCC 48023, ATCC 48585, ATCC 74040, ATCC-74250, DSM 12256 and PPRI 5339), *Beijerinckia*, *Blastodendrion*, *Bosea* (e.g., *B. eneae*, *B. lathyri*, *B. lupini*, *B. massiliensis*, *B. minatitlanensis*, *B. robiniae*, *B. thiooxidans*, *B. vestrisi*), *Bradyrhizobium* (e.g., *B. arachidis*, *B. bete*, *B. canariense*, *B. cytisi*, *B. daqingense*, *B. denitrificans*, *B. diazoefficiens*, *B. elkanii* strains such as SEMIA 501, SEMIA 587 and SEMIA 5019, *B. ganzhouense*, *B. huanghuauhaiense*, *B. icense*, *B. ingae*, *B. iriomotense*, *B. japonicum* strains such as NRRL B-50586 (also deposited as NRRL B-59565), NRRL B-50587 (also deposited as NRRL B-59566), NRRL B-50588 (also deposited as NRRL B-59567), NRRL B-50589 (also deposited as NRRL B-59568), NRRL B-50590 (also deposited as NRRL B-59569), NRRL B-50591 (also deposited as NRRL B-59570), NRRL B-50592 (also deposited as NRRL B-59571), NRRL B-50593 (also deposited as NRRL B-59572), NRRL B-50594 (also deposited as NRRL B-50493), NRRL B-50608, NRRL B-50609, NRRL B-50610, NRRL B-50611, NRRL B-50612, NRRL B-50726, NRRL B-50727, NRRL B-50728, NRRL B-50729, NRRL B-50730, SEMIA 566, SEMIA 5079, SEMIA 5080, USDA 6, USDA 110, USDA 122, USDA 123, USDA 127, USDA 129 and USDA 532C, *B. jicamae*, *B. lablabi*, *B. liaoningense*, *B. manausense*, *B. neotropicale*, *B. oligotrophicum*, *B. ottawaense*, *B. pachyrhizi*, *B. paxilaeri*, *B. retamae*, *B. rifense*, *B. valentinum*, *B. yuanmingense*), *Burkholderia* (e.g., *B. acidipaludis*, *B. ambifaria*, *B. andropogonis*, *B. anthina*, *B. arboris*, *B. bannensis*, *B. bryophila*, *B. caledonica*, *B. caribensis*, *B. caryophylli*, *B. cenocepacua*, *B. choica*, *B. cocovenenans*, *B. contaminans*, *B. denitrificans*, *B. diazotrophica*, *B. diffusa*, *B. dilworthii*, *B. dolosa*, *B. eburnea*, *B. endofungorum*, *B. ferrariae*, *B. fungorum*, *B. ginsengisoli*, *B. gladioli*, *B. glathei*, *B. glumae*, *B. graminis*, *B. grimmiae*, *B. heleia*, *B. hospital*, *B. humi*, *B. kururiensis*, *B. lata*, *B. latens*, *B. mallei*, *B. megapolitana*, *B. metallica*, *B. mimosarum*, *B. multivorans*, *B. nodosa*, *B. norimbergensis*, *B. oklahomensis*, *B. phenazinium*, *B. phenoliruptrix*, *B. phymatum*, *B. phytofirmans*, *B. pickettii*, *B. plantarii*, *B. pseudomallei*, *B. pseudomultivorans*, *B. pyrrocinia*, *B. rhizoxinica*, *B. rhynchosiae*, *B. sabiae*, *B. sacchari*, *B. sartisoli*, *B. sediminicola*, *B. seminalis*, *B. silvatlantica*, *B. singaporensis*, *B. soli*, *B. sordidcola*, *B.* sp. strains such as A396, *B. sprentiae*, *B. stabilis*, *B. symbiotica*, *B. telluris*, *B. terrae*, *B. terrestris*, *B. terricola*, *B. thailandensis*, *B. tropica*, *B. tuberum*, *B. ubonensis*, *B. udeis*, *B. unamae*, *B. vandii*, *B. vietnamiensis*, *B. xenovorans*, *B. zhejiangensis*), *Brevibacillus*, *Burkholderia* (e.g., *B.* sp. nov. *rinojensis*), *Calonectria*, *Candida* (e.g., *C. oleophila* such 1-182, *C. saitoana*), *Candidatus* (e.g., *C. Burkholderia calva*, *C. Burkholderia crenata*, *C. Burkholderia hispidae*, *C. Burkholderia kirkii*, *C. Burkholderia mamillata*, *C. Burkholderia nigropunctata*, *C. Burkholderia rigidae*, *C. Burkholderia schumannianae*, *C. Burkholderia verschuerenii*, *C. Burkholderia virens*, *C. Phytoplasma allocasuarinae*, *C. Phytoplasma americanum*, *C. Phytoplasma asteris*, *C. Phytoplasma aurantifolia*, *C. Phytoplasma australiense*, *C. Phytoplasma balanitae*, *C. Phytoplasma brasiliense*, *C. Phytoplasma caricae*, *C. Phytoplasma castaneae*, *C. Phytoplasma cocosnigeriae*, *C. Phytoplasma cocostanzaniae*, *C. Phytoplasma convolvuli*, *C. Phytoplasma costaricanum*, *C. Phytoplasma cynodontis*, *C. Phytoplasma fragariae*, *C. Phytoplasma fraxini*, *C. Phytoplasma graminis*, *C. Phytoplasma japonicum*, *C. Phytoplasma luffae*, *C. Phytoplasma lycopersici*, *C. Phytoplasma malasianum*, *C. Phytoplasma mali*, *C. Phytoplasma omanense*, *C. Phytoplasma oryzae*, *C. Phytoplasma palmae*, *C. Phytoplasma palmicola*, *C. Phytoplasma phoenicium*, *C. Phytoplasma pini*, *C. Phytoplasma pruni*, *C. Phytoplasma prunorum*, *C. Phytoplasma pyri*, *C. Phytoplasma rhamni*, *C. Phytoplasma rubi*, *C. Phytoplasma solani*, *C. Phytoplasma spartii*, *C. Phytoplasma sudamericanum*, *C. Phytoplasma tamaricis*, *C. Phytoplasma trifolii*, *C. Phytoplasma ulmi*, *C. Phytoplasma vitis*, *C. Phytoplasma ziziphi*), *Chromobacterium* (e.g., *C. subtsugae* NRRL B-30655 and PRAA4-1, *C. vaccinia* strains such as NRRL B-50880, *C. violaceum*), *Chryseomonas*, *Clavibacter*, *Clonostachys* (e.g., *C. rosea* f. *catenulata* (also referred to as *Gliocladium catenulatum*) strains such as J1446), *Clostridium*, *Coelemomyces*, *Coelomycidium*, *Colletotrichum* (e.g., *C. gloeosporioides* strains such as ATCC 52634), *Comomonas*, *Conidiobolus*, *Coniothyrium* (e.g., *C. minitans* strains such as CON/M/91-08), *Cordyceps*, *Corynebacterium*, *Couchia*, *Cryphonectria* (e.g., *C. parasitica*), *Cryptococcus* (e.g., *C. albidus*), *Cryptophlebia* (e.g., *C. leucotreta*), *Culicinomyces*, *Cupriavidus* (e.g., *C. alkaliphilus*, *C. basilensis*, *C. campinensis*, *C. gilardii*, *C. laharis*, *C. metallidurans*, *C. numazuensis*, *C. oxalaticus*, *C. pampae*, *C. pauculus*, *C. pinatubonensis*, *C. respiraculi*, *C. taiwanensis*), *Curtobacterium*, *Cydia* (e.g., *C. pomonella* strains such as V03 and V22), *Dactylaria* (e.g., *D. candida*), *Delftia* (e.g., *D. acidovorans* strains such as RAY209), *Desulforibtio*, *Desulfovibrio*, *Devosia* (e.g., *D. neptuniae*), *Dilophosphora* (e.g., *D. alopecuri*), *Engyodontium*, *Enterobacter*, *Entomophaga*, *Entomophthora*, *Erynia*, *Escherichia* (e.g., *E. intermedia*), *Eupenicillium*, *Exiguobacterium*, *Filariomyces*, *Filobasidiella*, *Flavobacterium* (e.g., F. H492), *Frankia* (e.g., *F. alni*), *Fusarium* (e.g., *F. laterium*, *F. oxysporum*, *F. solani*), *Gibellula*, *Gigaspora* (e.g., *G. margarita*), *Gliocladium* (e.g., *G. virens* strains such as ATCC 52045), *Glomus* (e.g., *G. aggregatum*, *G. brasilianum*, *G. clarum*, *G. deserticola*, *G. etunicatum*, *G. fasciculatum*, *G. intraradices* strains such as RTI-801, *G. monosporum*, *G. mosseae*), *Gluconobacter*, *Halospirulina*, *Harposporium* (e.g., *H. anguillulae*), *Hesperomyces*, *Hirsutella* (e.g., *H. minnesotensis*, *H. rhossiliensis*, *H. thomsonii* strains such as ATCC 24874), *Hydrogenophage*, *Hymenoscyphous* (e.g., *H. ericae*), *Hymenostilbe*, *Hypocrella*, *Isaria* (e.g., *I. fumosorosea* strains such as Apopka-97 (deposited as ATCC 20874)), *Klebsiella* (e.g., *K. pneumoniae*, *K. oxytoca*), *Kluyvera*, *Laccaria* (e.g., *L. bicolor*, *L. laccata*), *Lactobacillus*, *Lagenidium*, *Lecanicillium* (e.g., *L. lecanii* strains such as KV01, *L. longisporum* strains such as KV42 and KV71), *Leptolegnia*, *Lysobacter*(e.g., *L. antibioticus* strains such as 13-1 and HS124, *L. enzymogenes* strains such as 3.1T8), *Massospora*, *Meristacrum* (e.g., *M. asterospermum*), *Mesorhizobium* (e.g., *M. abyssinicae*, *M. albiziae*, *M. alhagi*, *M. amorphae*, *M. australicum*, *M. camelthorni*, *M. caraganae*, *M. chacoense*, *M. ciceri*, *M. gobiense*, *M. hawassense*, *M. huakuii*, *M. loti*, *M. mediterraneum*, *M. metallidurans*, *M. muleiense*, *M. opportunistum*, *M. plurifarium*, *M. qingshengii*, *M. robiniae*, *M. sangaii*, *M. septentrionale*, *M. shangrilense*, *M. shonense*, *M. silamurunense*, *M. tamadayense*, *M. tarimense*, *M. temperatum*, *M. thiogangeticum*, *M. tianshanense*), *Metarhizium* (e.g., *M. anisopliae* (also referred to as *M. brunneum*, *Metarrhizium*

*anisopliae*, and green muscadine) strains such as IMI 330189, FI-985, FI-1045, F52 (deposited as DSM 3884, DSM 3885, ATCC 90448, SD 170 and ARSEF 7711) and ICIPE 69), M. flavoviride strains such as ATCC 32969), *Methylobacterium* (e.g., *M. adhaesivum, M. aerolatum, M. aminovorans, M. aquaticum, M. brachiatum, M. brachythecii, M. bullatum, M. cerastii, M. chloromethanicum, M. dankookense, M. dichloromethanicum, M. extorquens, M. fujisawaense, M. gnaphalii, M. goesingense, M. gossipiicola, M. gregans, M. haplocladii, M. hispanicum, M. iners, M. isbiliense, M. jeotgali, M. komagatae, M. longum, M. lusitanum, M. marchantiae, M. mesophilicum, M. nodulans, M. organophilum, M. oryzae, M. oxalidis, M. persicinum, M. phyllosphaerae, M. platani, M. podarium, M. populi, M. radiotolerans, M. rhodesianum, M. rhodinum, M. salsuginis, M. soli, M. suomiense, M. tardum, M. tarhaniae, M. thiocyanatum, M. thurigiense, M. trifolii, M. variabile, M. zatmanii*), *Metschnikowia* (e.g., *M. fructicola*), *Microbacterium* (e.g., *M. laevaniformans*), *Microdochium* (e.g., *M. dimerum*), *Microsphaeropsis* (e.g., *M. ochracea* P130A), *Microvirga* (e.g., *M. aerilata, M. aerophila, M. flocculans, M. guangxiensis, M. lotononidis, M. lupini, M. subterranea, M. vignae, M. zambiensis*), *Monacrosporium* (e.g., *M. cionopagum*), *Mucor, Muscodor* (e.g., *M. albus* such NRRL 30547, QST 20799 and SA-13, *M. roseus* strains such as NRRL 30548), *Mycoderma, Myiophagus, Myriangium, Myrothecium* (e.g., *M. verrucaria*), *Nectria, Nematoctonus* (e.g., *N. geogenius, N. leiosporus*), *Neozygites, Nomuraea* (e.g., *N. rileyi* strains such as SA86101, GU87401, SR86151, CG128 and VA9101), *Nostoc* (e.g., *N. azollae, N. caeruleum, N. carneum, N. comminutum, N. commune, N. ellipsosporum, N. flagelliforme, N. linckia, N. longstaffi, N. microscopicum, N. muscorum, N. paludosum, N. pruniforme, N. punctifrome, N. sphaericum, N. sphaeroides, N. spongiaeforme, N. verrucosum*), *Ochrobactrum* (e.g., *O. anthropi, O. cicero, O. cytisi, O. daejeonense, O. gallinifaecis, O. grigonense, O. guangzhouense, O. haematophilum, O. intermedium, O. lupini, O. oryzae, O. pectoris, O. pituitosum, O. pseudointermedium, O. pseudogrignonense, O. rhizosphaerae, O. thiophenivorans, O. tritici*), *Oidiodendron, Paecilomyces* (e.g., *P. fumosoroseus* strains such as FE991 and FE 9901, *P. lilacinus* strains such as 251, DSM 15169 and BCP2), *Paenibacillus* (e.g., *P. alvei* strains such as NAS6G6, *P. azotofixans, P. polymyxa* strains such as ABP166 (deposited as NRRL B-50211)), *Pandora, Pantoea* (e.g., *P. agglomerans* strains such as NRRL B-21856, *P. vagans* strains such as C9-1), *Paraglomus* (e.g., *P. brazilianum*), *Paraisaria, Pasteria, Pasteuria* (e.g., *P. nishizawae* strains such as Pn1, *P. penetrans, P. ramose, P.* sp. strains such as ATCC PTA-9643 and ATCC SD-5832, *P. thornea, P. usage*), *Penicillium* (e.g., *P. albidum, P. aurantiogriseum, P. bilaiae* (formerly known as *P. bilaii* and *P. bilaji*) strains such as ATCC 18309, ATCC 20851, ATCC 22348, NRRL 50162, NRRL 50169, NRRL 50776, NRRL 50777, NRRL 50778, NRRL 50777, NRRL 50778, NRRL 50779, NRRL 50780, NRRL 50781, NRRL 50782, NRRL 50783, NRRL 50784, NRRL 50785, NRRL 50786, NRRL 50787, NRRL 50788 and RS7B-SD1, *P. brevicompactum* strains such as AgRF18, *P. canescens* strains such as ATCC 10419, *P. chyrsogenum, P. citreonigrum, P. citrinum, P. digitatum, P. expansum* strains such as ATCC 24692 and YT02, *P. fellatanum* strains such as ATCC 48694, *P. frequentas, P. fuscum, P. fussiporus, P. gaestrivorus* strains such as NRRL 50170, *P. glabrum* strains such as DAOM 239074 and CBS 229.28, *P. glaucum, P. griseofulvum, P. implicatum, P. janthinellum* strains such as ATCC 10455, *P. lanosocoeruleum* strains such as ATCC 48919, *P. lilacinum, P. minioluteum, P. montanense, P. nigricans, P. oxalicum, P. pinetorum, P. pinophilum, P. purpurogenum, P. radicum* strains such as ATCC 201836, FRR 4717, FRR 4719 and N93/47267, *P. raistrickii* strains such as ATCC 10490, *P. rugulosum, P. simplicissimum, P. solitum, P. variabile, P. velutinum, P. viridicatum*), *Phingobacterium, Phlebiopsis* (e.g., *P. gigantea*), *Photorhabdus, Phyllobacterium* (e.g., *P. bourgognense, P. brassicacearum, P. catacumbae, P. endophyticum, P. ifriqiyense, P. leguminum, P. loti, P. myrsinacearum, P. sophorae, P. trifoli*), *Pichia* (e.g., *P. anomala* strains such as WRL-076), *Pisolithus* (e.g., *P. tinctorius*), *Planktothricoides, Plectonema, Pleurodesmospora, Pochonia* (e.g., *P. chlamydopora*), *Podonectria, Polycephalomyces, Prochlorocoous* (e.g., *P. marinus*), *Prochloron* (e.g., *P. didemni*), *Prochlorothrix, Pseudogibellula, Pseudomonas* (e.g., *P. agarici, P. antartica, P. aurantiaca, P. aureofaciens, P. azotifigens, P. azotoformans, P. balearica, P. blatchfordae, P. brassicacearum, P. brenneri, P. cannabina, P. cedrina, P. cepacia, P. chlororaphis* strains such as MA 342, *P. congelans, P. corrugata, P. costantinii, P. denitrificans, P. entomophila, P. fluorescens* strains such as ATCC 27663, CL 145A and A506, *P. fragii, P. fuscovaginae, P. fulva, P. gessardii, P. jessenii* strains such as PS06, *P. kilonensis, P. koreensis, P. libanensis, P. lil, P. lundensis, P. lutea, P. luteola, P. mandelii, P. marginalis, P. meditrranea, P. meridana, P. migulae, P. moraviensis, P. mucidolens, P. orientalis, P. oryzihabitans, P. palleroniana, P. panacis, P. parafulva, P. peli, P. pertucinogena, P. plecoglossicida, P. protogens, P. proteolytica, P. putida, P. pyrocina* strains such as ATCC 15958, *P. rhodesiae, P.* sp. strains such as DSM 13134, *P. striata, P. stutzeri, P. syringae, P. synxantha, P. taetrolens, P. thisvervalensis, P. tolaasii, P. veronii*), *Pseudozyma* (e.g., *P. flocculosa* strains such as PF-A22 UL), *Pythium* (e.g., *P. oligandrum* strains such as DV 74), *Rhizobium* (e.g., *R. aggregatum, R. alamii, R. alkalisoli, P. alvei, P. azibense, P. borbori, R. calliandrae, R. cauense, R. cellulosilyticum, R. daejeonense, R. endolithicum, R. endophyticum, R. etli, R. fabae, R. flavum, R. fredii, R. freirei, R. galegae, R. gallicum, R. giardinii, R. grahamii, R. hainanense, R. halophytocola, R. halotolerans, R. helanshanense, R. herbae, R. huautlense, R. indigoferae, R. jaguaris, R. kunmingense, R. laguerreae, R. larrymoorei, R. leguminosarum* strains such as SO12A-2 (IDAC 080305-01), *R. lemnae, R. leucaenae, R. loessense, R. lupini, R. lusitanum, R. mayense, R. mesoamericanum, R. mesosinicum, R. milu- onense, R. mongolense, R. multihospitium, R. naphthalenivorans, R. nepotum, R. oryzae, R. pakistanensis, R. paknamense, R. paranaense, R. petrolearium, R. phaseoli, R. phenanthrenilyticum, R. pisi, R. pongamiae, R. populi, R. pseudoryzae, R. pusense, R. qilianshanese, r. radiobacter, R. rhizogenes, R. rhizoryzae, R. rozettiformans, R. rubi, R. selenitireeducens, R. skierneiwicense, R. smilacinae, R. soli, R. sophorae, R. sophoriradicis, R. sphaerophysae, R. straminoryzae, R. subbaraonis, R. sullae, R. taibaishanense, R. tarimense, R. tibeticum, R. trifolii* strains such as RP113-7, *R. tropici* strains such as SEMIA 4080, *R. tubonense, R. undicola, R. vallis, R. viciae* strains such as P1 NP3Cst, SU303 and WSM 1455, *R. vignae, R. vitis, R. yanglingense, R. yantingense*), *Rhizoctonia, Rhizopogon* (e.g., *R. amylopogon, R. fulvigleba, R. luteolus, R. villosuli*), *Rhodococcus, Saccharopolyspora* (e.g., *S. spinosa*), *Scleroderma* (e.g., *S. cepa S. citrinum*), *Septobasidium, Serratia, Shinella* (e.g., *S. kummerowiae*), *Sinorhizoium* (e.g., *S. abri, S. adhaerens, S. americanum, S. arboris, S. chiapanecum, S. fredii* strains such as CCBAU114 and USDA 205, *S. garamanticus, S. indiaense, S. kostiense, S. kummerowiae, S. medicae, S. meliloti* strains such as MSDJ0848, *S. mexica-* nus, *S. numidicus, S. psoraleae, S. saheli, S. sesbaniae, S. sojae, S. terangae, S. xinjiangense*), *Sorosporella, Sphaerodes* (e.g., *S. mycoparasitica* strains such as IDAC 301008-01), *Spodoptera* (e.g., *S. littoralis*), *Sporodiniella, Steinernema* (e.g., *S. carpocapsae, S. feltiae, S. kraussei* strains such as L137), *Stenotrophomonas, Streptomyces* (e.g., *S. cacaoi* strains such as ATCC 19093, *S. galbus* strains such as NRRL 30232, *S. griseoviridis* strains such as K61, *S. lydicus* strains such as WYEC 108, *S. violaceusniger* strains such as YCED-9 (deposited as ATCC 55660)), *Streptosporangium, Stillbella, Swaminathania, Talaromyces* (e.g., *T. aculeatus, T. flavus* strains such as V117b), *Tetranacrium, Thiobacillus, Tilachlidium, Tolypocladium, Tolypothrix, Torrubiella, Torulospora, Trenomyces, Trichoderma* (e.g. *T. asperellum* strains such as SKT-1 and ICC 012, *T. atroviride* strains such as LC52 and CNCM 1-1237, *T. fertile* strains such as JM41R, *T. gamsii* strains such as ICC 080, *T. hamatum* strains such as ATCC 52198, *T. harzianum* strains such as ATCC 52445, KRL-AG2, T-22, TH-35, T-39 and l00012, *T. polysporum, T. reesi* strains such as ATCC 28217 *T. stromaticum, T. virens* strains such as ATCC 57678, G1-3, GL-21 and G-41, *T. viridae* strains such as ATCC 52440, ICC080 and TV1), *Typhula, Ulocladium* (e.g., *U. oudemansii* strains such as HRU3), *Uredinella, Variovorax, Verticillium* (e.g., *V. chlamydosporum, V. lecanii* strains such as ATCC 46578), *Vibrio, Xanthobacter, Xanthomonas, Xenorhabdus, Yersinia* (e.g., *Y. entomophaga*), *Zoophthora*

APPENDIX B

Amaranthaceae (e.g., chard, spinach, sugar beet, quinoa), Asteraceae (e.g., artichoke, asters, chamomile, chicory, chrysanthemums, dahlias, daisies, echinacea, goldenrod, guayule, lettuce, marigolds, safflower, sunflowers, zinnias), Brassicaceae (e.g., arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, *Arabidopsis thaliana*), Cucurbitaceae (e.g., cantaloupe, cucumber, honeydew, melon, pumpkin, squash (e.g., acorn squash, butternut squash, summer squash), watermelon, zucchini), Fabaceae (e.g., alfalfa, beans, carob, clover, guar, lentils, mesquite, peas, peanuts, soybeans, tamarind, tragacanth, vetch), Malvaceae (e.g., cacao, cotton, durian, hibiscus, kenaf, kola, okra), Poaceae (e.g., bamboo, barley, corn, fonio, lawn grass (e.g., Bahia grass, Bermudagrass, bluegrass, Buffalograss, Centipede grass, Fescue, or *Zoysia*), millet, oats, ornamental grasses, rice, rye, sorghum, sugar cane, triticale, wheat), Polygonaceae (e.g., buckwheat), Rosaceae (e.g., almonds, apples, apricots, blackberry, blueberry, cherries, peaches, plums, quinces, raspberries, roses, strawberries), Solanaceae (e.g., bell peppers, chili peppers, eggplant, *petunia*, potato, tobacco, tomato), Vitaceae (e.g., grape)

That which is claimed:

1. An aqueous inoculant composition comprising:
  one or more maltodextrins having a dextrose equivalent value of about 15 to about 20;
  one or more disaccharides;
  one or more hygroscopic polymers selected from the group consisting of carboxymethyl celluloses, gums and polyvinyl alcohols; and
  one or more strains of Gram-negative bacteria, in which one or more of the following is true:
    said one or more maltodextrins and said one or more disaccharides are present in a maltodextrin: disaccharide ratio of about 35:65 to about 65:35;
    said one or more disaccharides comprises maltose;
    said one or more strains of Gram-negative bacteria is/are present in a concentration ranging from about $1\times10^4$ to about $1\times10^{11}$ colony-forming units per gram of said aqueous inoculant composition.

2. The aqueous inoculant composition of claim 1, in which said one or more maltodextrins and said one or more disaccharides are present in a maltodextrin: disaccharide ratio of about 35:65 to about 65:35.

3. The aqueous inoculant composition of claim 1, in which said one or more disaccharides comprises maltose.

4. The aqueous inoculant composition of claim 1, in which said one or more hygroscopic polymers comprises a carboxymethyl cellulose.

5. The aqueous inoculant composition of claim 1, in which said one or more hygroscopic polymers comprises one or more gums.

6. The aqueous inoculant composition of claim 1, in which said one or more hygroscopic polymers comprises xantham gum.

7. The aqueous inoculant composition of claim 1, in which said one or more hygroscopic polymers comprises a polyvinyl alcohol.

8. The aqueous inoculant composition of claim 1, in which said one or more hygroscopic polymers comprises a carboxymethyl cellulose and a polyvinyl alcohol.

9. The aqueous inoculant composition of claim 1, in which said one or more hygroscopic polymers comprises about 0.1 to about 5% of said aqueous inoculant composition, by weight, based upon the total weight of said aqueous inoculant composition.

10. The aqueous inoculant composition of claim 1, in which said one or more hygroscopic polymers comprises about 0.1 to about 1% of said aqueous inoculant composition, by weight, based upon the total weight of said aqueous inoculant composition.

11. The aqueous inoculant composition of claim 1, in which said one or more strains of Gram-negative bacteria is/are present in a concentration of at least $1\times10^5$ colony-forming units per gram of said inoculant composition.

12. The aqueous inoculant composition of claim 1, in which said one or more Gram-negative bacteria is/are present at a concentration of at least $1\times10^7$ colony-forming units per gram of said inoculant composition.

13. The aqueous inoculant composition of claim 1, further comprising one or more surfactants.

14. The aqueous inoculant composition of claim 13, in which said one or more surfactants comprises one or more siloxanes.

15. The aqueous inoculant composition of claim 13, in which said one or more surfactants comprises one or more trisiloxanes.

16. A method comprising applying an aqueous inoculant composition to a plant or plant part, said aqueous inoculant composition comprising:
  one or more maltodextrins having a dextrose equivalent value of about 15 to about 20;
  one or more disaccharides;
  one or more hygroscopic polymers; and
  one or more strains of Gram-negative bacteria.

17. A method comprising introducing an aqueous inoculant composition into a plant growth medium comprising soil, said aqueous inoculant composition comprising:
  one or more maltodextrins having a dextrose equivalent value of about 15 to about 20;
  one or more disaccharides;
  one or more hygroscopic polymers; and
  one or more strains of Gram-negative bacteria.

18. A coated plant seed, comprising:
a plant seed; and
a coating that covers at least a portion of an outer surface of said plant seed, said coating comprising an aqueous inoculant composition that comprises:
one or more maltodextrins having a dextrose equivalent value of about 15 to about 20;
one or more disaccharides;
one or more hygroscopic polymers; and
one or more strains of Gram-negative bacteria.

19. A kit comprising a plurality of plant seeds that have been treated with an aqueous inoculant composition that comprises:
one or more maltodextrins having a dextrose equivalent value of about 15 to about 20;
one or more disaccharides;
one or more hygroscopic polymers; and
one or more strains of Gram-negative bacteria.

20. A method of improving the stability of a Gram-negative bacteria in an aqueous composition, said method comprising introducing into said composition:
one or more maltodextrins having a dextrose equivalent value of about 15 to about 20;
one or more disaccharides; and
one or more hygroscopic polymers selected from the group consisting of carboxymethyl celluloses, gums and polyvinyl alcohols, in which one or more of the following is true:
said one or more maltodextrins and said one or more disaccharides are introduced into said composition in a maltodextrin: disaccharide ratio of about 35:65 to about 65:35;
said one or more disaccharides comprises maltose.

* * * * *